(12) United States Patent
Haurand et al.

(10) Patent No.: US 8,318,774 B2
(45) Date of Patent: *Nov. 27, 2012

(54) COMPOUNDS INVOLVING MGLUR5 RECEPTOR REGULATION AND METHODS OF MAKING THE COMPOUNDS

(75) Inventors: Michael Haurand, Aachen (DE); Klaus Schiene, Juchen (DE); Sven Kühnert, Düren (DE); Melanie Reich, Aachen (DE)

(73) Assignee: Gruenenthal GmbH, Aachen (DE)

( * ) Notice: Subject to any disclaimer, the term of this patent is extended or adjusted under 35 U.S.C. 154(b) by 966 days.

This patent is subject to a terminal disclaimer.

(21) Appl. No.: 12/147,203

(22) Filed: Jun. 26, 2008

(65) Prior Publication Data

US 2008/0269295 A1 Oct. 30, 2008

Related U.S. Application Data

(63) Continuation of application No. PCT/EP2006/012483, filed on Dec. 22, 2006.

(51) Int. Cl.
*A01N 43/40* (2006.01)
*A61K 31/445* (2006.01)

(52) U.S. Cl. ........ 514/326; 514/370; 546/209; 548/181; 548/195

(58) Field of Classification Search .......... 514/326, 514/370; 546/209; 548/181, 195
See application file for complete search history.

(56) References Cited

U.S. PATENT DOCUMENTS

| | | | |
|---|---|---|---|
| 5,843,988 | A | 12/1998 | Annoura et al. |
| 7,067,533 | B2 | 6/2006 | Takemoto et al. |
| 7,871,999 | B2 * | 1/2011 | Haurand et al. ........... 514/210.2 |
| 2002/0165223 | A1 | 11/2002 | Greenlee et al. |
| 2003/0139447 | A1 | 7/2003 | Takemoto et al. |
| 2005/0101595 | A1 | 5/2005 | Chu et al. |
| 2006/0178401 | A1 | 8/2006 | Takemoto et al. |

FOREIGN PATENT DOCUMENTS

| | | |
|---|---|---|
| DE | 10 2004 032 567 | 3/2006 |
| EP | 15 77 301 | 9/2005 |
| JP | 8 169884 A | 7/1996 |
| JP | 2004 501079 A | 1/2004 |
| JP | 2004 509108 A | 3/2004 |
| WO | 2004 014903 | 2/2004 |
| WO | 2004 029044 | 4/2004 |
| WO | WO 2004 074283 A1 | 9/2004 |
| WO | WO 2004 078749 A1 | 9/2004 |
| WO | 2005 007641 | 1/2005 |
| WO | 2005 035500 | 4/2005 |
| WO | WO 2005 044797 A1 | 5/2005 |

OTHER PUBLICATIONS

Vippagunta et al. Advanced Drug Delivery Reviews 2001, 48, 3-26, abstract).*
Morissette et al. Advanced Drug Delivery Reviews 2004, 56, 275-300).*
Souillac et al., Characterization of Delivery Systems, Differential Scanning Calorimetry, pp. 217-218 (in Encyclopedia of Controlled Drug Delivery, 1999, John Wiley & Sons, pp. 212-227.*
Gennaro edition; Remmington's Pharmaceutical Sciences, 17th Edition, Mack Publishing Company, Easton, PA 1985, in particular in part 8, chapters 76 to 93.
Dubuisson, D et al; "The formalin test: a quantitative study of the analgesic effects of morphine, meperidine, and brain stem stimulation in rats and cats"; Pain, 4, 1977, pp. 161-174.

* cited by examiner

*Primary Examiner* — Andrew D Kosar
*Assistant Examiner* — Valerie Rodriguez-Garcia
(74) *Attorney, Agent, or Firm* — Norris McLaughlin & Marcus. P.A.

(57) ABSTRACT

3-((Thiazol-2-yl)amino)propylproiolamide compounds of the formula I:

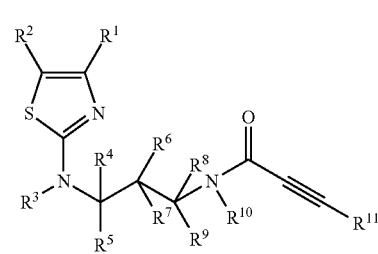

wherein the variables are as defined herein, are useful to prevent or treat a disease or disorder involving mGluR5 receptor regulation. Also disclosed are pharmaceutical compositions containing the compounds and methods of making the compounds.

29 Claims, No Drawings

COMPOUNDS INVOLVING MGLUR5 RECEPTOR REGULATION AND METHODS OF MAKING THE COMPOUNDS

This application is a continuation of PCT/EP2006/012483, filed on Dec. 22, 2006, which, in turn, claims priority of German Patent Application No. DE 10 2005 062 990.3, filed on Dec. 28, 2005.

The present invention relates to substituted thiazoles, to methods for their production, to drugs containing these compounds and to the use of said compounds for producing drugs.

Pain is a fundamental clinical symptom. There is a worldwide need for effective methods of treating pain. The urgent need for action for patient-oriented and purposeful treatment of chronic and non-chronic pain conditions, this being taken to mean the successful and satisfactory treatment of pain for the patient, is also documented in the large number of scientific papers which have recently appeared in the field of applied analgesics and fundamental research work on nociception.

Conventional opioids, such as morphine, are effective in the treatment of severe to very severe pains, but often lead to undesired side effects such as respiratory depression, vomiting, sedation, constipation or the development of tolerance. In addition, they are often not sufficiently effective against neuropathic pain, from which tumour patients in particular suffer.

An object of the present invention was thus to provide new compounds which are suitable in particular as active pharmaceutical ingredients in drugs, preferably in drugs for treating pain.

It has now surprisingly been found that the substituted thiazoles of the following general formula I are suitable for mGluR5 receptor regulation and thus can be used in particular as active pharmaceutical ingredients in drugs for the prophylaxis and/or treatment of disorders or diseases connected with these receptors and/or processes.

The invention thus relates to substituted thiazoles of general formula I,
in which

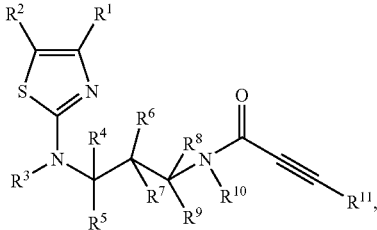

I $R^1$ and $R^2$ independently of one another each represent H; F; Cl; Br; I; —$NO_2$; —CN; —$NH_2$; —OH; —SH; —C(=O)—OH; —C(=O)—H; —NH—C(=O)—H; —NH—$R^{33}$; —$NR^{34}R^{35}$; —C(=O)—$R^{36}$; —C(=O)—O—$R^{37}$; —O—C(=O)—$R^{38}$; —NH—C(=O)—$R^{39}$; —$NR^{40}$—C(=O)—$R^{41}$; —C(=O)—$NH_2$; —C(=O)—NH—$R^{42}$; —C(=O)—$NR^{43}R^{44}$; —O—$R^{45}$; —S—$R^{46}$; —S(=O)—$R^{47}$; —S(=O)$_2$—$R^{48}$; —NH—C(=O)—NH—$R^{49}$; —NH—C(=S)—NH—$R^{50}$; —NH—S(=O)$_2$—$R^{51}$; —$NR^{52}$—S(=O)$_2$—$R^{53}$; alkyl, alkenyl or alkynyl which is unsubstituted or substituted at least once; heteroalkyl, heteroalkenyl or heteroalkynyl which is unsubstituted or substituted at least once; cycloalkyl or cycloalkenyl which is unsubstituted or substituted at least once; heterocycloalkyl or heterocycloalkenyl which is unsubstituted or substituted at least once; -(alkylene)-cycloalkyl, -(alkenylene)-cycloalkyl, -(alkynylene)-cycloalkyl, -(alkylene)-cycloalkenyl, -(alkenylene)-cycloalkenyl or -(alkynylene)-cycloalkenyl which is unsubstituted or substituted at least once; -(heteroalkylene)-cycloalkyl, -(heteroalkenylene)-cycloalkyl, -(heteroalkylene)-cycloalkenyl or -(heteroalkenylene)-cycloalkenyl which is unsubstituted or substituted at least once; -(alkylene)-heterocycloalkyl, -(alkenylene)-heterocycloalkyl, -(alkynylene)-heterocycloalkyl, -(alkylene)-heterocycloalkenyl, -(alkenylene)-heterocycloalkenyl or -(alkynylene)-heterocycloalkenyl which is unsubstituted or substituted at least once; -(heteroalkylene)-heterocycloalkyl, -(heteroalkenylene)-heterocycloalkyl, -(heteroalkylene)-heterocycloalkenyl or -(heteroalkenylene)-heterocycloalkenyl which is unsubstituted or substituted at least once; aryl which is unsubstituted or substituted at least once; heteroaryl which is unsubstituted or substituted at least once; -(alkylene)-aryl, -(alkenylene)-aryl, -(alkynylene)-aryl, -(heteroalkylene)-aryl or -(heteroalkenylene)-aryl which is unsubstituted or substituted at least once; or -(alkylene)-heteroaryl, -(alkenylene)-heteroaryl, -(alkynylene)-heteroaryl, -(heteroalkylene)-heteroaryl or -(heteroalkenylene)-heteroaryl which is unsubstituted or substituted at least once;

or $R^1$ and $R^2$ together with the carbon atoms linking them form a phenylene radical which is unsubstituted or substituted at least once;

$R^3$ and $R^{10}$ independently of one another each represent H; —C(=O)—$R^{36}$; —C(=O)—O—$R^{37}$; —C(=O)—$NH_2$; —C(=O)—NH—$R^{42}$; —C(=O)—$NR^{43}R^{44}$; —S(=O)—$R^{47}$; —S(=O)$_2$—$R^{48}$; unsubstituted or substituted alkyl, alkenyl or alkynyl; unsubstituted or substituted heteroalkyl, heteroalkenyl or heteroalkynyl; unsubstituted or substituted cycloalkyl or cycloalkenyl; unsubstituted or substituted heterocycloalkyl or heterocycloalkenyl; unsubstituted or substituted -(alkylene)-cycloalkyl, -(alkenylene)-cycloalkyl, -(alkynylene)-cycloalkyl, -(alkylene)-cycloalkenyl, -(alkenylene)-cycloalkenyl or -(alkynylene)-cycloalkenyl; unsubstituted or substituted -(heteroalkylene)-cycloalkyl, -(heteroalkenylene)-cycloalkyl, -(heteroalkylene)-cycloalkenyl or -(heteroalkenylene)-cycloalkenyl; unsubstituted or substituted -(alkylene)-heterocycloalkyl, -(alkenylene)-heterocycloalkyl, -(alkynylene)-heterocycloalkyl, -(alkylene)-heterocycloalkenyl, -(alkenylene)-heterocycloalkenyl or -(alkynylene)-heterocycloalkenyl; unsubstituted or substituted -(heteroalkylene)-heterocycloalkyl, -(heteroalkenylene)-heterocycloalkyl, -(heteroalkylene)-heterocycloalkenyl or -(heteroalkenylene)-heterocycloalkenyl; unsubstituted or substituted aryl; unsubstituted or substituted heteroaryl; unsubstituted or substituted -(alkylene)-aryl, -(alkenylene)-aryl, -(alkynylene)-aryl, -(heteroalkylene)-aryl or -(heteroalkenylene)-aryl; or unsubstituted or substituted -(alkylene)-heteroaryl, -(alkenylene)-heteroaryl, -(alkynylene)-heteroaryl, -(heteroalkylene)-heteroaryl or -(heteroalkenylene)-heteroaryl.

$R^4$, $R^5$, $R^6$, $R^7$, $R^8$, $R^9$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, $R^{26}$, $R^{27}$, $R^{28}$, $R^{29}$, $R^{30}$, $R^{31}$ and $R^{32}$ each independently of one another represent H; F; Cl; Br; I; —$NO_2$; —CN; —$NH_2$; —OH; —SH; —C(=O)—OH; —C(=O)—H; —NH—C(=O)—H; —NH—$R^{33}$; —$NR^{34}R^{35}$; —C(=O)—$R^{36}$; —C(=O)—O—$R^{37}$; —O—C(=O)—$R^{38}$; —NH—C(=O)—$R^{39}$; —$NR^{40}$—C(=O)—$R^{41}$; —C(=O)—$NH_2$; —C(=O)—NH—$R^{42}$; —C(=O)—$NR^{43}R^{44}$; —O—$R^{45}$; —S—$R^{46}$; —S(=O)—$R^{47}$; —S(=O)$_2$—$R^{48}$; —NH—C(=O)—NH—$R^{49}$; —NH—C(=S)—NH—$R^{50}$; —NH—S(=O)$_2$—$R^{51}$; —$NR^{52}$—S(=O)$_2$—$R^{53}$; unsubstituted or substituted alkyl, alkenyl or alkynyl; unsubstituted or substituted heteroalkyl, heteroalkenyl or heteroalkynyl; unsubstituted or substituted cycloalkyl or cycloalkenyl; unsubstituted or substituted heterocycloalkyl or heterocycloalkenyl; unsubstituted or substituted -(alkylene)-cycloalkyl, -(alkenylene)-cycloalkyl, -(alkynylene)-cycloalkyl, -(alkylene)-cycloalkenyl, -(alkenylene)-cycloalkenyl or -(alkynylene)-cycloalkenyl; unsubstituted or substituted -(heteroalkylene)-cycloalkyl, -(heteroalkenylene)-cycloalkyl, -(heteroalkylene)-cycloalkenyl or -(heteroalkenylene)-cycloalkenyl; unsubstituted or substituted -(alkylene)-heterocycloalkyl, -(alkenylene)-heterocycloalkyl, -(alkynylene)-heterocycloalkyl, -(alkylene)-heterocycloalkenyl, -(alkenylene)-heterocycloalkenyl or -(alkynylene)-heterocycloalkenyl; unsubstituted or substituted -(heteroalkylene)-heterocycloalkyl, -(heteroalkenylene)-heterocycloalkyl, -(heteroalkylene)-heterocycloalkenyl or -(heteroalkenylene)-heterocycloalkenyl; unsubstituted or substituted aryl; unsubstituted or substituted heteroaryl; unsubstituted or substituted -(alkylene)-aryl, -(alkenylene)-aryl, -(alkynylene)-aryl, -(heteroalkylene)-aryl or -(heteroalkenylene)-aryl; or unsubstituted or substituted -(alkylene)-heteroaryl, -(alkenylene)-heteroaryl, -(alkynylene)-heteroaryl, -(heteroalkylene)-heteroaryl or -(heteroalkenylene)-heteroaryl;

or $R^4$ and $R^5$ or $R^6$ and $R^7$ or $R^8$ and $R^9$ or $R^{12}$ and $R^{13}$ or $R^{14}$ and $R^{15}$ or $R^{16}$ and $R^{17}$ or $R^{18}$ and $R^{19}$ or $R^{20}$ and $R^{21}$ or $R^{22}$ and $R^{23}$ or $R^{24}$ and $R^{25}$ or $R^{26}$ and $R^{27}$ or $R^{28}$ and $R^{29}$ or $R^{31}$ and $R^{32}$, independently of one another represent, together in each case, a radical selected from the group consisting of an oxo group (=O) and a thioxo group (=S);

or $R^3$ and $R^4$ together with the —N—$CR^5$ group linking them form a radical of general formula A,

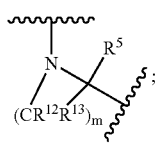

or $R^8$ and $R^{10}$ together with the —$CR^9$—N group linking them form a radical of general formula B,

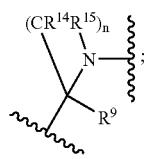

m and n each represent 2, 3, 4, 5 or 6;

or $R^3$ and $R^6$ together with the —N—$CR^4R^5$—$CR^7$ group linking them form a radical of general formula C,

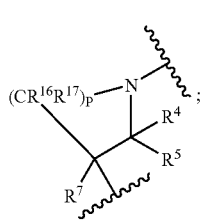

or $R^6$ and $R^{10}$ together with the —$CR^7$—$CR^8R^9$—N group linking them form a radical of general formula D,

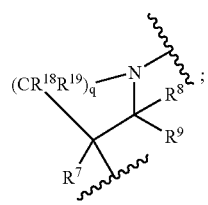

p and q each represent 1, 2, 3, 4 or 5;

or $R^3$ and $R^8$ together with the —N—$CR^4R^5$—$CR^6R^7$—$CR^9$ group linking them form a radical of general formula E,

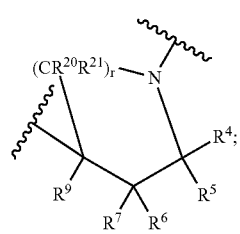

or $R^4$ and $R^{10}$ together with the —N—$CR^8R^9$—$CR^6R^7$—$CR^5$ group linking them form a radical of general formula F,

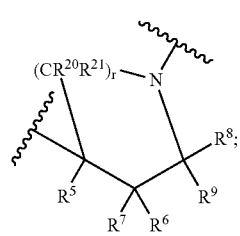

r and s each represent 2, 3 or 4;

or $R^4$ and $R^8$ together with the —$CR^5$—$CR^6R^7$—$CR^9$ group linking them form a radical of general formula G,

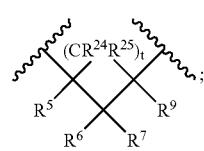

t represents 1, 2, 3, 4 or 5;

or $R^3$ and $R^{10}$ together with the —N—$CR^4R^5$—$CR^6R^7$—$CR^8R^9$—N group linking them form a radical of general formula H,

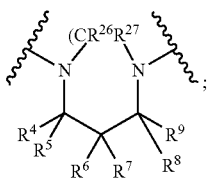

u represents 3 or 4;

or $R^3$ and $R^{10}$ together with the —N—$CR^4R^5$—$CR^6R^7$—$CR^8R^9$—N group linking them form a bicyclic radical of general formula K,

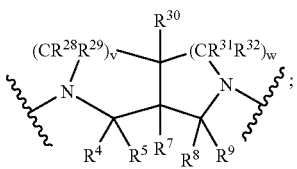

v and w independently of one another each represent 1, 2 or 3;

$R^{11}$ represents unsubstituted or substituted aryl or unsubstituted or substituted heteroaryl;

and $R^{33}$, $R^{34}$, $R^{35}$, $R^{36}$, $R^{37}$, $R^{38}$, $R^{39}$, $R^{40}$, $R^{41}$, $R^{42}$, $R^{43}$, $R^{44}$, $R^{45}$, $R^{46}$, $R^{47}$, $R^{48}$, $R^{49}$, $R^{50}$, $R^{51}$, $R^{52}$ and $R^{53}$ independently of one another each represent unsubstituted or substituted alkyl, alkenyl or alkynyl; unsubstituted or substituted heteroalkyl, heteroalkenyl or heteroalkynyl; unsubstituted or substituted cycloalkyl or cycloalkenyl; unsubstituted or substituted heterocycloalkyl or heterocycloalkenyl; unsubstituted or substituted (alkylene)-cycloalkyl, -(alkenylene)-cycloalkyl, -(alkynylene)-cycloalkyl, -(alkylene)-cycloalkenyl, -(alkenylene)-cycloalkenyl or -(alkynylene)-cycloalkenyl; unsubstituted or substituted -(heteroalkylene)-cycloalkyl, -(heteroalkenylene)-cycloalkyl, -(heteroalkylene)-cycloalkenyl or -(heteroalkenylene)-cycloalkenyl; unsubstituted or substituted -(alkylene)-heterocycloalkyl, -(alkenylene)-heterocycloalkyl, -(alkynylene)-heterocycloalkyl, -(alkylene)-heterocycloalkenyl, -(alkenylene)-heterocycloalkenyl or -(alkynylene)-heterocycloalkenyl; unsubstituted or substituted -(heteroalkylene)-heterocycloalkyl, -(heteroalkenylene)-heterocycloalkyl, -(heteroalkylene)-heterocycloalkenyl; or -(heteroalkenylene)-heterocycloalkenyl; unsubstituted or substituted aryl; unsubstituted or substituted heteroaryl; unsubstituted or substituted -(alkylene)-aryl, -(alkenylene)-aryl, -(alkynylene)-aryl, -(heteroalkylene)-aryl or -(heteroalkenylene)-aryl; or unsubstituted or substituted -(alkylene)-heteroaryl, -(alkenylene)-heteroaryl, -(alkynylene)-heteroaryl, -(heteroalkylene)-heteroaryl or -(heteroalkenylene)-heteroaryl;

each optionally in the form of one of one of the pure stereoisomers, in particular enantiomers or diastereomers thereof, or the racemates thereof, or in the form of a mixture of stereoisomers, in particular the enantiomers and/or diastereomers, mixed in any ratios, or each in the form of corresponding salts, or each in the form of corresponding solvates.

The term "alkyl" in the context of the present invention comprises acyclic saturated hydrocarbon radicals, which may be branched or linear and unsubstituted or substituted at least once with 1 to 12 (i.e. 1, 2, 3, 4, 5, 6, 7, 8, 9, 10, 11 or 12) C atoms as in the case of $C_{1-12}$ alkyl or with 1 to 6 (i.e. 1, 2, 3, 4, 5 or 6) C atoms as in the case of $C_{1-6}$ alkyl. If one or more of the substituents represent an alkyl radical or have an alkyl radical which is substituted one or more times, said radical may preferably be substituted with, as appropriate, 1, 2, 3, 4 or 5, particularly preferably with 1, 2 or 3 substituents selected independently of one another from the group consisting of F, Cl, Br, I, —$NO_2$, —CN, —OH, —SH, —$NH_2$, —$N(C_{1-5}$-alkyl$)_2$, —$N(C_{1-5}$-alkyl)(phenyl), —$N(C_{1-5}$-alkyl)($CH_2$-phenyl), —$N(C_{1-5}$-alkyl)($CH_2$—$CH_2$-phenyl), —C(=O)—H, —C(=O)—$C_{1-5}$-alkyl, —C(=O)-phenyl, —C(=S)—$C_{1-5}$-alkyl, —C(=S)-phenyl, —C(=O)—OH, —C(=O)—O—$C_{1-5}$-alkyl, —C(=O)—O-phenyl, —C(=O)—$NH_2$, —C(=O)—NH—$C_{1-5}$-alkyl, —C(=O)—N($C_{1-5}$-alkyl$)_2$, —S(=O)—$C_{1-5}$-alkyl, —S(=O)-phenyl, —S(=O)$_2$—$C_{1-5}$-alkyl, —S(=O)$_2$-phenyl, —S(=O)$_2$—$NH_2$ and —$SO_3$H, it being possible for each of the aforementioned $C_{1-5}$ alkyl radicals to be linear or branched and for the aforementioned phenyl radicals to be substituted preferably with 1, 2, 3, 4 or 5 substituents selected independently of one another from the group consisting of F, Cl, Br, I, —CN, —$CF_3$, —OH, —$NH_2$, —O—$CF_3$, —SH, —O—$CH_3$, —O—$C_2H_5$, —O—$C_3H_7$, methyl, ethyl, n-propyl, isopropyl, n-butyl, 2-butyl, isobutyl and tert-butyl. Particularly preferred substituents may be selected independently of one another from the group consisting of F, Cl, Br, I, —$NO_2$, —CN, —OH, —SH, —$NH_2$, —$N(CH_3)_2$, —$N(C_2H_5)_2$ and —$N(CH_3)(C_2H_5)$.

Suitable $C_{1-12}$ alkyl radicals, which may be unsubstituted or substituted one or more times, include for example methyl, ethyl, n-propyl, isopropyl, n-butyl, isobutyl, 2-butyl, tert-butyl, n-pentyl, 2-pentyl, 3-pentyl, isopentyl, neo-pentyl, n-hexyl, 2-hexyl, 3-hexyl, n-heptyl, n-octyl, —C(H)($C_2H_5)_2$, —C(H)(n-$C_3H_7)_2$ and —$CH_2$—$CH_2$—C(H)($CH_3$)—($CH_2)_3$—$CH_3$.

Suitable $C_{1-6}$ alkyl radicals include for example methyl, ethyl, n-propyl, isopropyl, n-butyl, isobutyl, 2-butyl, tert-butyl, n-pentyl, 2-pentyl, 3-pentyl, isopentyl, neo-pentyl, n-hexyl, 2-hexyl and 3-hexyl.

Multiply substituted alkyl radicals should be understood to mean those alkyl radicals which are substituted a plurality of times, preferably two or three times, either on the same or on different C atoms, for example three times on the same C atom as in the case of —$CF_3$ or in different positions as in the case of —(CHCl)—($CH_2$F). Multiple substitution can take place with the same substituent or with different substituents. Suitable substituted alkyl radicals include for example —$CF_3$, —$CF_2$H, —$CFH_2$, —($CH_2$)—OH, —($CH_2$)—$NH_2$, —($CH_2$)—CN, —($CH_2$)—($CF_3$), —($CH_2$)—($CHF_2$), —($CH_2$)—($CH_2$F), —($CH_2$)—($CH_2$)—OH, —($CH_2$)—($CH_2$)—$NH_2$, —($CH_2$)—($CH_2$)—CN, —($CF_2$)—($CF_3$), —($CH_2$)—($CH_2$)—($CF_3$) and —($CH_2$)—($CH_2$)—($CH_2$)—OH.

The term "alkenyl" in the context of the present invention comprises acyclic unsaturated hydrocarbon radicals, which may be branched or linear and unsubstituted or substituted at least once and have at least one double bond, preferably 1, 2 or 3 double bonds, with 2 to 12 (i.e. 2, 3, 4, 5, 6, 7, 8, 9, 10, 11 or 12) C atoms as in the case of $C_{2-12}$ alkenyl or with 2 to 6 (i.e. 2, 3, 4, 5 or 6) C atoms as in the case of $C_{2-6}$ alkenyl. If one or more of the substituents represent an alkenyl radical or have an alkenyl radical which is substituted one or more times, said radical may preferably be substituted with, as appropriate, 1, 2, 3, 4 or 5, particularly preferably with 1, 2 or 3 substituents selected independently of one another from the group consisting of F, Cl, Br, I, —$NO_2$, —CN, —OH, —SH, —$NH_2$, —$N(C_{1-5}$-alkyl$)_2$, —$N(C_{1-5}$-alkyl)(phenyl), —$N(C_{1-5}$-alkyl)

(CH$_2$-phenyl), —N(C$_{1-5}$-alkyl)(CH$_2$—CH$_2$-phenyl), —C(=O)—H, —C(=O)—C$_{1-5}$-alkyl, —C(=O)-phenyl, —C(=S)—C$_{1-5}$-alkyl, —C(=S)-phenyl, —C(=O)—OH, —C(=O)—O—C$_{1-5}$-alkyl, —C(=O)—O-phenyl, —C(=O)—NH$_2$, —C(=O)—NH—C$_{1-5}$-alkyl, —C(=O)—N(C$_{1-5}$-alkyl)$_2$, —S(=O)—C$_{1-5}$-alkyl, —S(=O)-phenyl, —S(=O)$_2$—C$_{1-5}$-alkyl, —S(=O)$_2$-phenyl, —S(=O)$_2$—NH$_2$ und —SO$_3$H, it being possible for each of the aforementioned C$_{1-5}$ alkyl radicals to be linear or branched and for the aforementioned phenyl radicals to be substituted preferably with 1, 2, 3, 4 or 5 substituents selected independently of one another from the group consisting of F, Cl, Br, I, —CN, —CF$_3$, —OH, —NH$_2$, —O—CF$_3$, —SH, —O—CH$_3$, —O—C$_2$H$_5$, —O—C$_3$H$_7$, methyl, ethyl, n-propyl, isopropyl, n-butyl, 2-butyl, isobutyl and tert-butyl. Particularly preferred substituents may be selected independently of one another from the group consisting of F, Cl, Br, I, —NO$_2$, —CN, —OH, —SH, —NH$_2$, —N(CH$_3$)$_2$, —N(C$_2$H$_5$)$_2$ and —N(CH$_3$)(C$_2$H$_5$).

Suitable C$_{2-12}$ alkenyl radicals include for example ethenyl, 1-propenyl, 2-propenyl, 1-butenyl, 2-butenyl, 3-butenyl, 1-pentenyl, 2-pentenyl, 3-pentenyl, 4-pentenyl, hexenyl, —CH=CH—CH=CH—CH$_3$ and —CH$_2$—CH$_2$—CH=CH$_2$ Multiply substituted alkenyl radicals should be understood to mean those alkenyl radicals which are substituted a plurality of times, preferably twice, either on the same or on different C atoms, for example twice on the same C atom as in the case of —CH=CCl$_2$ or in different positions as in the case of —CCl=CH—(CH$_2$)—NH$_2$. Multiple substitution can take place with the same substituent or with different substituents. Suitable substituted alkenyl radicals include for example —CH=CH—(CH$_2$)—OH, —CH=CH—(CH$_2$)—NH$_2$ and —CH=CH—CN.

The term "alkynyl" in the context of the present invention comprises acyclic unsaturated hydrocarbon radicals, which may be branched or linear and unsubstituted or substituted at least once and have at least one triple bond, preferably 1 or 2 triple bonds, with 2 to 12 (i.e. 2, 3, 4, 5, 6, 7, 8, 9, 10, 11 or 12) C atoms as in the case of C$_{2-12}$ alkynyl or with 2 to 6 (i.e. 2, 3, 4, 5 or 6) C atoms as in the case of C$_{2-6}$ aklynyl. If one or more of the substituents represent an alkynyl radical or have an alkynyl radical which is substituted one or more times, said radical may preferably be substituted with, as appropriate, 1, 2, 3, 4 or 5, particularly preferably with, as appropriate, 1 or 2 substituents, selected independently of one another from the group consisting of F, Cl, Br, I, —NO$_2$, —CN, —OH, —SH, —NH$_2$, —N(C$_{1-5}$-alkyl)$_2$, —N(C$_{1-5}$-alkyl)(phenyl), —N(C$_{1-5}$-alkyl)(CH$_2$-phenyl), —N(C$_{1-5}$-alkyl)(CH$_2$—CH$_2$-phenyl), —C(=O)—H, —C(=O)—C$_{1-5}$-alkyl, —C(=O)-phenyl, —C(=S)—C$_{1-5}$-alkyl, —C(=S)-phenyl, —C(=O)—OH, —C(=O)—O—C$_{1-5}$-alkyl, —C(=O)—O-phenyl, —C(=O)—NH$_2$, —C(=O)—NH—C$_{1-5}$-alkyl, —C(=O)—N(C$_{1-5}$-alkyl)$_2$, —S(=O)—C$_{1-5}$-alkyl, —S(=O)-phenyl, —S(=O)$_2$—C$_{1-5}$-alkyl, —S(=O)$_2$-phenyl, —S(=O)$_2$—NH$_2$ and —SO$_3$H, it being possible for each of the aforementioned C$_{1-5}$ alkyl radicals to be linear or branched and for the aforementioned phenyl radicals to be substituted preferably with 1, 2, 3, 4 or 5 substituents selected independently of one another from the group consisting of F, Cl, Br, I, —CN, —CF$_3$, —OH, —NH$_2$, —O—CF$_3$, —SH, —O—CH$_3$, —O—C$_2$H$_5$, —O—C$_3$H$_7$, methyl, ethyl, n-propyl, isopropyl, n-butyl, 2-butyl, isobutyl and tert-butyl. Particularly preferred substituents may be selected independently of one another from the group consisting of F, Cl, Br, I, —NO$_2$, —CN, —OH, —SH, —NH$_2$, —N(CH$_3$)$_2$, —N(C$_2$H$_5$)$_2$ and —N(CH$_3$)(C$_2$H$_5$).

Suitable C$_{2-12}$ alkynyl radicals include for example ethynyl, 1-propynyl, 2-propynyl, 1-butynyl, 2-butynyl, 3-butynyl, 1-pentynyl, 2-pentynyl, 3-pentynyl, 4-pentynyl and hexynyl.

Multiply substituted alkynyl radicals should be understood to mean those alkynyl radicals which are substituted a plurality of times on different C atoms, for example twice on different C atoms as in the case of —CHCl—C≡CCl. Suitable substituted alkynyl radicals include for example —C≡C—F, —C≡C—Cl and —C≡C—I.

The term "heteroalkyl" refers to an alkyl radical as described above, in which one or more C atoms have been replaced, each by a heteroatom selected independently of one another from the group consisting of oxygen, sulphur and nitrogen (NH). Heteroalkyl radicals may preferably have 1, 2 or 3 heteroatom(s), selected independently of one another from the group consisting of oxygen, sulphur and nitrogen (NH), as chain member(s). Heteroalkyl radicals may preferably have 2 to 12 members, particularly preferably 2 to 6 members.

Suitable heteroalkyl radicals, which may be unsubstituted or substituted one or more times, include for example —CH$_2$—O—CH$_3$, —CH$_2$—O—C$_2$H$_5$, —CH$_2$—O—CH(CH$_3$)$_2$, —CH$_2$—O—C(CH$_3$)$_3$, —CH$_2$—S—CH$_3$, —CH$_2$—S—C$_2$H$_5$, —CH$_2$—S—CH(CH$_3$)$_2$, —CH$_2$—S—C(CH$_3$)$_3$, —CH$_2$—NH—CH$_3$, —CH$_2$—NH—C$_2$H$_5$, —CH$_2$—NH—CH(CH$_3$)$_2$, —CH$_2$—NH—C(CH$_3$)$_3$, —CH$_2$—CH$_2$—O—CH$_3$, —CH$_2$—CH$_2$—O—C$_2$H$_5$, —CH$_2$—CH$_2$—O—CH(CH$_3$)$_2$, —CH$_2$—CH$_2$—O—C(CH$_3$)$_3$, —CH$_2$—CH$_2$—S—CH$_3$, —CH$_2$—CH$_2$—S—C$_2$H$_5$, —CH$_2$—CH$_2$—S—CH(CH$_3$)$_2$, —CH$_2$—CH$_2$—S—C(CH$_3$)$_3$, —CH$_2$—CH$_2$—NH—CH$_3$, —CH$_2$—CH$_2$—NH—C$_2$H$_5$, —CH$_2$—CH$_2$—NH—CH(CH$_3$)$_2$, —CH$_2$—CH$_2$—NH—C(CH$_3$)$_3$, —CH$_2$—S—CH$_2$—O—CH$_3$, —CH$_2$—O—CH$_2$—O—C$_2$H$_5$, —CH$_2$—O—CH$_2$—O—CH(CH$_3$)$_2$, —CH$_2$—S—CH$_2$—O—C(CH$_3$)$_3$, —CH$_2$—O—CH$_2$—S—CH$_3$, —CH$_2$—O—CH$_2$—S—C$_2$H$_5$, —CH$_2$—O—CH$_2$—S—CH(CH$_3$)$_2$, —CH$_2$—NH—CH$_2$—S—C(CH$_3$)$_3$, —CH$_2$—O—CH$_2$—NH—CH$_3$, —CH$_2$—O—CH$_2$—NH—C$_2$H$_5$, —CH$_2$—O—CH$_2$—NH—CH(CH$_3$)$_2$, —CH$_2$—S—CH$_2$—NH—C(CH$_3$)$_3$ and —CH$_2$—CH$_2$—C(H)(CH$_3$)—(CH$_2$)$_3$—CH$_3$.

Suitable substituted heteroalkyl radicals include for example —(CH$_2$)—O—(CF$_3$), —(CH$_2$)—O—(CHF$_2$), —(CH$_2$)—O—(CH$_2$F), —(CH$_2$)—S—(CF$_3$), —(CH$_2$)—S—(CHF$_2$), —(CH$_2$)—S—(CH$_2$F), —(CH$_2$)—(CH$_2$)—O—(CF$_3$), —(CF$_2$)—O—(CF$_3$), —(CH$_2$)—(CH$_2$)—S—(CF$_3$) and —(CH$_2$)—(CH$_2$)—(CH$_2$)—O—(CF$_3$).

The term "heteroalkenyl" refers to an alkenyl radical, as described above, in which one or more C atoms have been replaced, each by a heteroatom selected independently of one another from the group consisting of oxygen, sulphur and nitrogen (NH). Heteroalkenyl radicals may preferably have 1, 2 or 3 heteroatom(s), selected independently of one another from the group consisting of oxygen, sulphur and nitrogen (NH), as chain member(s). Heteroalkenyl radicals may preferably have 2 to 12 members, particularly preferably 2 to 6 members.

Suitable heteroalkenyl radicals include for example —CH$_2$—O—CH=CH$_2$, —CH=CH—O—CH=CH—CH$_3$, —CH$_2$—CH$_2$—O—CH=CH$_2$, —CH$_2$—S—CH=CH$_2$, —CH=CH—S—CH=CH—CH$_3$, —CH$_2$—CH$_2$—S—CH=CH$_2$, —CH$_2$—NH—CH=CH$_2$, —CH=CH—NH—CH=CH—CH$_3$ and —CH$_2$—CH$_2$—NH—CH=CH$_2$.

Suitable substituted heteroalkenyl radicals include for example —CH$_2$—O—CH=CH—(CH$_2$)—OH, —CH$_2$—S—CH=CH—(CH$_2$)—NH$_2$ and —CH$_2$—NH—CH=CH—CN.

The term "heteroalkynyl" refers to an alkynyl radical, as described above, in which one or more C atoms have been replaced, each by a heteroatom selected independently of one another from the group consisting of oxygen, sulphur and nitrogen (NH). Heteroalkynyl radicals may preferably have 1, 2 or 3 heteroatom(s), selected independently of one another from the group consisting of oxygen, sulphur and nitrogen (NH), as chain member(s). Heteroalkynyl radicals may preferably have 2 to 12 members, particularly preferably 2 to 6 members.

Suitable heteroalkynyl radicals include for example —$CH_2$—O—C≡CH, —$CH_2$—$CH_2$—O—C≡CH, —$CH_2$—O—C≡C—$CH_3$, —$CH_2$—$CH_2$—O—C≡C—$CH_3$, —$CH_2$—S—C≡CH, —$CH_2$—$CH_2$—S—C≡CH, —$CH_2$—S—C≡C—$CH_3$ and —$CH_2$—$CH_2$—S—C≡C—$CH_3$.

Suitable substituted heteroalkynyl radicals include for example —$CH_2$—O—C≡C—Cl, —$CH_2$—$CH_2$—O—C≡C—I, —CHF—O—C≡C—$CH_3$, —CHF—$CH_2$—O—C≡C—$CH_3$, —$CH_2$—S—C≡C—Cl, —$CH_2$—$CH_2$—S—C≡C—Cl, —CHF—S—C≡C—$CH_3$ and —CHF—$CH_2$—S—C≡C—$CH_3$.

The term "cycloalkyl" in the context of the present invention means a cyclic, saturated hydrocarbon radical with preferably 3, 4, 5, 6, 7, 8 or 9 C atoms, particularly preferably with 3, 4, 5, 6 or 7 C atoms, most preferably with 5 or 6 C atoms, it being possible for the radical to be unsubstituted or substituted one or more times in the same or different positions.

Suitable $C_{3-9}$ cycloalkyl radicals, which may be unsubstituted or substituted one or more times, include for example cyclopropyl, cyclobutyl, cyclopentyl, cyclohexyl, cycloheptyl, cyclooctyl and cyclononyl. Suitable $C_{3-7}$-cycloalkyl radicals include cyclopropyl, cyclobutyl, cyclopentyl, cyclohexyl and cycloheptyl.

The term "cycloalkenyl" in the context of the present invention means a cyclic, unsaturated hydrocarbon radical with preferably 3, 4, 5, 6, 7, 8 or 9 C atoms, particularly preferably with 3, 4, 5, 6 or 7 C atoms, most preferably with 5 or 6 C atoms, the radical having at least one double bond, preferably one double bond, and being able to be unsubstituted or substituted one or more times in the same or different positions.

Suitable $C_{3-9}$ cycloalkenyl radicals, which may be unsubstituted or substituted one or more times, include for example cyclobutenyl, cyclopentenyl, cyclohexenyl, cycloheptenyl, cyclononenyl and cyclooctenyl. Suitable $C_{5-6}$-cycloalkenyl radicals include cyclopentenyl and cyclohexenyl.

The term "heterocycloalkyl" in the context of the present invention means a cyclic, saturated hydrocarbon radical with preferably 3, 4, 5, 6, 7, 8 or 9 C atoms, particularly preferably with 3, 4, 5, 6 or 7 C atoms, most preferably with 5 or 6 C atoms, in which one or more C atoms have been replaced, each by a heteroatom selected independently of one another from the group consisting of oxygen, sulphur and nitrogen (NH). Heterocycloalkyl radicals may preferably have 1, 2 or 3 heteroatom(s), selected independently of one another from the group consisting of oxygen, sulphur and nitrogen (NH), as ring members. A heterocycloalkyl radical may be unsubstituted or substituted one or more times in the same or different positions. Heterocycloalkyl radicals may preferably have 3 to 9 members, particularly preferably 3 to 7 members, most preferably 5 to 7 members.

Suitable heterocycloalkyl radicals with 3 to 9 members, which radicals may be unsubstituted or substituted one or more times, include for example imidazolidinyl, tetrahydrofuranyl, tetrahydrothiophenyl, pyrrolidinyl, piperidinyl, morpholinyl, piperazinyl, thiomorpholinyl, tetrahydropyranyl, oxetanyl, azepanyl, azocanyl, diazepanyl, dithiolanyl, (1,3)-dioxolan-2-yl, isoxazolidinyl, isothioazolidinyl, pyrazolidinyl, oxazolidinyl, (1,2,4)-oxadiazolidinyl, (1,2,4)-thiadiazolidinyl, (1,2,4)-triazolidin-3-yl, (1,3,4)-thiadiazolidin-2-yl, (1,3,4)-triazolidin-1-yl, (1,3,4)-triazolidin-2-yl, tetrahydropyridazinyl, tetrahydropyrimidinyl, tetrahydropyrazinyl, (1,3,5)-tetrahydrotriazinyl, (1,2,4)-tetrahydrotriazin-1-yl, (1,3)-dithian-2-yl and (1,3)-thiazolidinyl. Suitable heterocycloalkyl radicals with 5 to 7 members include for example imidazolidinyl, tetrahydrofuranyl, tetrahydrothiophenyl, pyrrolidinyl, piperidinyl, morpholinyl, piperazinyl, thiomorpholinyl, tetrahydropyranyl, oxetanyl, azepanyl, diazepanyl und (1,3)-dioxolan-2-yl.

The term "heterocycloalkenyl" in the context of the present invention means a cyclic, unsaturated hydrocarbon radical with preferably 4, 5, 6, 7, 8 or 9 C atoms, particularly preferably with 4, 5, 6 or 7 C atoms, most preferably with 5 or 6 C atoms, which has at least one double bond, preferably one double bond, and in which one or more C atoms have been replaced, each by a heteroatom selected independently of one another from the group consisting of oxygen, sulphur and nitrogen (NH). Heterocycloalkenyl radicals may preferably have 1, 2 or 3 heteroatom(s), selected independently of one another from the group consisting of oxygen, sulphur and nitrogen (NH), as ring members. A heterocycloalkenyl radical may be unsubstituted or substituted one or more times in the same or different positions. Heterocycloalkenyl radicals may preferably have 4 to 9 members, particularly preferably 4 to 7 members, most preferably 5 to 7 members.

Suitable heterocycloalkenyl radicals or suitable heterocycloalkenyl radicals with 5 to 7 members, which radicals may be unsubstituted or substituted one or more times, include for example (2,3)-dihydrofuranyl, (2,5)-dihydrofuranyl, (2,3)-dihydrothienyl, (2,5)-dihydrothienyl, (2,3)-dihydropyrrolyl, (2,5)-dihydropyrrolyl, (2,3)-dihydroisoxazolyl, (4,5)-dihydroisoxazolyl, (2,5)-dihydroisothiazolyl, (2,3)-dihydropyrazolyl, (4,5)-dihydropyrazolyl, (2,5)-dihydropyrazolyl, (2,3)-dihydrooxazolyl, (4,5)-dihydrooxazolyl, (2,5)-dihydrooxazolyl, (2,3)-dihydrothiazolyl, (4,5)-dihydrothiazolyl, (2,5)-dihydrothiazolyl, (2,3)-dihydroimidazolyl, (4,5)-dihydroimidazolyl, (2,5)-dihydroimidazolyl, (3,4,5,6)-tetrahydropyridin-2-yl, (1,2,5,6)-tetrahydropyridin-1-yl, (1,2)-dihydropyridin-1-yl, (1,4)-dihydropyridin-1-yl, dihydropyranyl and (1,2,3,4)-tetrahydropyridin-1-yl.

The cycloalkyl radicals, heterocycloalkyl radicals, cycloalkenyl radicals or heterocycloalkenyl radicals may, within the context of the invention, be condensed (annellated) with a monocyclic or bicyclic ring system which is unsubstituted or substituted at least once. In the context of the present invention, a monocyclic or bicyclic ring system is understood to be a monocyclic or bicyclic hydrocarbon radical, which may be saturated, unsaturated or aromatic and may optionally have one or more heteroatoms as ring members. The rings of the aforementioned monocyclic or bicyclic ring systems preferably each have 4, 5 or 6 members and may each preferably have, as appropriate, 0, 1, 2, 3, 4 or 5 heteroatom(s), particularly preferably, as appropriate, 0, 1 or 2 heteroatom(s) as ring members, which are selected independently of one another from the group consisting of oxygen, nitrogen and sulphur. If a bicyclic ring system is involved, the various rings may independently of one another each have a different degree of saturation, i.e. be saturated, unsaturated or aromatic.

If one or more of the substituents have a monocyclic or bicyclic ring system which is substituted one or more times, said system may preferably be substituted with, as appropriate, 1, 2, 3, 4 or 5, particularly preferably with, as appropriate, 1, 2 or 3 substituents, selected independently of one another from the group consisting of F, Cl, Br, I, —CN, —NO$_2$, —OH, —SH, —NH$_2$, oxo (═O), thioxo (═S), —C(═O)—OH, C$_{1-5}$-alkyl, —C$_{2-5}$-alkenyl, —C$_{2-5}$-alkynyl, —C≡C—Si(CH$_3$)$_3$, —C≡C—Si(C$_2$H$_5$)$_3$, —(CH$_2$)—O—C$_{1-5}$-alkyl, —S—C$_{1-5}$-alkyl, —S-phenyl, —S—CH$_2$-phenyl, —O—C$_{1-5}$-alkyl, —O-phenyl, —O—CH$_2$-phenyl, —CF$_3$, —CHF$_2$, —CH$_2$F, —O—CF$_3$, —O—CHF$_2$, —O—CH$_2$F, —C(═O)—CF$_3$, —S—CF$_3$, —S—CHF$_2$, —S—CH$_2$F, —S(═O)$_2$-phenyl, —S(═O)$_2$—C$_{1-5}$-alkyl, —S(═O)—C$_{1-5}$-alkyl, —NH—C$_{1-5}$-alkyl, N(C$_{1-5}$alkyl)(C$_{1-5}$-alkyl), —C(═O)—O—C$_{1-5}$-alkyl, —C(═O)—H, —C(═O)—C$_{1-5}$-alkyl, —CH$_2$—O—C(═O)-phenyl, —O—C(═O)-phenyl, —NH—S(═O)$_2$—C$_{1-5}$-alkyl, —NH—C(═O)—C$_{1-5}$-alkyl, —C(═O)—NH$_2$, —C(═O)—NH—C$_{1-5}$-alkyl, —C(═O)—N(C$_{1-5}$-alkyl)$_2$, pyrazolyl, phenyl, furyl (furanyl), thiadiazolyl, thiophenyl (thienyl) and benzyl, the aforementioned C$_{1-5}$ alkyl radicals each being able to be linear or branched and the cyclic substituents and the cyclic radicals of these substituents each themselves being able to be substituted with, as appropriate, 1, 2, 3, 4 or 5, preferably with, as appropriate, 1, 2, 3 or 4 substituents, selected independently of one another from the group consisting of F, Cl, Br, I, —CN, —CF$_3$, —OH, —NH$_2$, —O—CF$_3$, —SH, —O—C$_{1-5}$-alkyl, —O-phenyl, —O—CH$_2$-phenyl, —(CH$_2$)—O—C$_{1-5}$-alkyl, —S—C$_{1-5}$-alkyl, —S-phenyl, —S—CH$_2$-phenyl, —C$_{1-5}$-alkyl, —C$_{2-5}$-alkenyl, —C$_{2-5}$-alkynyl, —C≡C—Si(CH$_3$)$_3$, —C≡C—Si(C$_2$H$_5$)$_3$, —C(═O)—O—C$_{1-5}$-alkyl and —C(═O)—CF$_3$.

Particularly preferably the substituents may each be selected independently of one another from the group consisting of F, Cl, Br, I, —CN, —NO$_2$, methyl, ethyl, n-propyl, isopropyl, n-butyl, isobutyl, 2-butyl, tert-butyl, n-pentyl, neopentyl, ethenyl, allyl, ethynyl, propynyl, —C≡C—Si(CH$_3$)$_3$, —C≡C—Si(C$_2$H$_5$)$_3$, —C≡C—Si(CH$_3$)$_3$, —C≡C—Si(C$_2$H$_5$)$_3$, —CH$_2$—O—CH$_3$, —CH$_2$—O—C$_2$H$_5$, —OH, —SH, —NH$_2$, OXO(═O), —C(═O)—OH, —S—CH$_3$, —S—C$_2$H$_5$, —S(═O)—CH$_3$, —S(═O)$_2$—CH$_3$, —S(═O)—C$_2$H$_5$, —S(═O)$_2$—C$_2$H$_5$, —O—CH$_3$, —O—C$_2$H$_5$, —O—C$_3$H$_7$, —O—C(CH$_3$)$_3$, —CF$_3$, —CHF$_2$, —CH$_2$F, —O—CF$_3$, —O—CHF$_2$, —O—CH$_2$F, —C(═O)—CF$_3$, —S—CF$_3$, —S—CHF$_2$, —S—CH$_2$F, —S(═O)$_2$-phenyl, pyrazolyl, phenyl, —N(CH$_3$)$_2$, —N(C$_2$H$_5$)$_2$, —NH—CH$_3$, —NH—C$_2$H$_5$, —CH$_2$—O—C(═O)-phenyl, —NH—S(═O)$_2$—CH$_3$, —C(═O)—O—CH$_3$, —C(═O)—O—C$_2$H$_5$, —C(═O)—O—C(CH$_3$)$_3$, —C(═O)—H, —C(═O)—CH$_3$, —C(═O)—C$_2$H$_5$, —NH—C(═O)—CH$_3$, —NH—C(═O)—C$_2$H$_5$, —NH—C(═O)—O—C(═O)-phenyl, —C(═O)—NH$_2$, —C(═O)—NH—CH$_3$, —C(═O)—N(CH$_3$)$_2$, phenyl, furyl (furanyl), thiadiazolyl, thiophenyl (thienyl) and benzyl, it being possible for the cyclic substituents and the cyclic radicals of these substituents to be substituted themselves with, as appropriate, 1, 2, 3, 4 or 5 substituents, preferably, as appropriate, 1, 2, 3 or 4 substituents, selected independently of one another from the group consisting of F, Cl, Br, I, —CN, —CF$_3$, —OH, —NH$_2$, —O—CF$_3$, —SH, —O—CH$_3$, —O—C$_2$H$_5$, —O—C$_3$H$_7$, methyl, ethyl, n-propyl, isopropyl, n-butyl, 2-butyl, isobutyl, tert-butyl, ethenyl, allyl, ethynyl, propynyl, —C≡C—Si(CH$_3$)$_3$, —C≡C—Si(C$_2$H$_5$)$_3$, —C(═O)—O—C$_{1-5}$-alkyl and —C(═O)—CF$_3$.

Suitable cycloalkyl radicals, heterocycloalkyl radicals, cycloalkenyl radicals or heterocycloalkenyl radicals, which may be unsubstituted or substituted one or more times and are condensed with a monocyclic or bicyclic ring system, include for example (1,2,3,4)-tetrahydroquinolinyl, (1,2,3,4)-tetrahydroisoquinolinyl, (2,3)-dihydro-1H-isoindolyl, (1,2,3,4)-tetrahydronaphthyl, (2,3)-dihydro-benzo[1.4]dioxinyl, benzo[1.3]dioxolyl, (3,4)-dihydro-2H-benzo[1.4]oxazinyl and octahydro-pyrrolo[3,4-c]pyrrolyl.

If one or more of the substituents represent a cycloalkyl radical, heterocycloalkyl radical, cycloalkenyl radical or heterocycloalkenyl radical or have a radical which is substituted one or more times, said substituent may preferably be substituted with, as appropriate, 1, 2, 3, 4 or 5, particularly preferably with, as appropriate, 1, 2 or 3 substituents, selected independently of one another from the group consisting of F, Cl, Br, I, —CN, —CF$_3$, —OH, —NH$_2$, —O—CF$_3$, —SH, —O—C$_{1-5}$-alkyl, —O-phenyl, —O—CH$_2$-phenyl, —(CH$_2$)—O—C$_{1-5}$-alkyl, —S—C$_{1-5}$-alkyl, —S-phenyl, —S—CH$_2$-phenyl, —C$_{1-5}$-alkyl, —C$_{2-5}$-alkenyl, —C$_{2-5}$-alkynyl, —C≡C—Si(CH$_3$)$_3$, —C≡C—Si(C$_2$H$_5$)$_3$, —C(═O)—O—C$_{1-5}$-alkyl, —C(═O)—CF$_3$, —S(═O)$_2$—C$_{1-5}$-alkyl, —S(═O)—C$_{1-5}$-alkyl, —S(═O)$_2$-phenyl, oxo (═O), thioxo (═S), —N(C$_{1-5}$-alkyl)$_2$, —N(H)(C$_{1-5}$-alkyl), —NO$_2$, —S—CF$_3$, —C(═O)—OH, —NH—S(═O)$_2$—C$_{1-5}$-alkyl, —NH—C(═O)—C$_{1-5}$-alkyl, —C(═O)—H, —C(═O)—C$_{1-5}$-alkyl, —C(═O)—NH$_2$, —C(═O)—N(C$_{1-5}$-alkyl)$_2$, —C(═O)—N(H)(C$_{1-5}$-alkyl) and phenyl, the aforementioned C$_{1-5}$ alkyl radicals each being able to be linear or branched and the phenyl radicals each being able to be unsubstituted or substituted with 1, 2, 3, 4 or 5, preferably with 1, 2, 3 or 4 substituents, selected independently of one another from the group consisting of F, Cl, Br, I, —CN, —CF$_3$, —OH, —NH$_2$, —O—CF$_3$, —SH, —O—C$_{1-5}$-alkyl, —O-phenyl, —O—CH$_2$-phenyl, —(CH$_2$)—O—C$_{1-5}$-alkyl, —S—C$_{1-5}$-alkyl, —S-phenyl, —S—CH$_2$-phenyl, —C$_{1-5}$-alkyl, —C$_{2-5}$-alkenyl, —C$_{2-5}$-alkynyl, —C≡C—Si(CH$_3$)$_3$, —C≡C—Si(C$_2$H$_5$)$_3$, —C(═O)—O—C$_{1-5}$-alkyl and —C(═O)—CF$_3$.

Particularly preferably the substituents may each be selected independently of one another from the group consisting of F, Cl, Br, I, —CN, methyl, ethyl, n-propyl, isopropyl, n-butyl, 2-butyl, isobutyl, tert-butyl, ethenyl, allyl, ethynyl, propynyl, —C≡C—Si(CH$_3$)$_3$, —C≡C—Si(C$_2$H$_5$)$_3$, —OH, oxo, thioxo, —O—CH$_3$, —O—C$_2$H$_5$, —O—C$_3$H$_7$, —(CH$_2$)—O—CH$_3$, —(CH$_2$)—O—C$_2$H$_5$, —NH$_2$, —N(CH$_3$)$_2$, —N(C$_2$H$_5$)$_2$, —NH—CH$_3$, —NH—C$_2$H$_5$, —NO$_2$, —CF$_3$, —O—CF$_3$, —S—CF$_3$, —SH, —S—CH$_3$, —S—C$_2$H$_5$, —S(═O)—CH$_3$, —S(═O)$_2$—CH$_3$, —S(═O)—C$_2$H$_5$, —S(═O)$_2$—C$_2$H$_5$, —NH—S(═O)$_2$—CH$_3$, —C(═O)—OH, —C(═O)—H; —C(═O)—CH$_3$, —C(═O)—C$_2$H$_5$, —C(═O)—N(CH$_3$)$_2$, —C(═O)—NH—CH$_3$, —C(═O)—NH$_2$, —NH—C(═O)—CH$_3$, —NH—C(═O)—C$_2$H$_5$, —C(═O)—O—CH$_3$, —C(═O)—O—C$_2$H$_5$, —C(═O)—O—C(CH$_3$)$_3$ and phenyl, it being possible for the phenyl radical to be substituted with 1, 2, 3, 4 or 5, preferably 1, 2 or 3 substituents, selected independently of one another from the group consisting of F, Cl, Br, I, —CN, —CF$_3$, —OH, —NH$_2$, —O—CF$_3$, —SH, —O—CH$_3$, —O—C$_2$H$_5$, —O—C$_3$H$_7$, methyl, ethyl, n-propyl, isopropyl, n-butyl, 2-butyl, isobutyl, tert-butyl, ethenyl, allyl, ethynyl, propynyl, —C≡C—Si(CH$_3$)$_3$, —C≡C—Si(C$_2$H$_5$)$_3$, —C(═O)—O—C$_{1-5}$-alkyl and —C(═O)—CF$_3$.

The term "phenylene" refers to a divalent aromatic hydrocarbon radical, with 6 members, of the following structure:

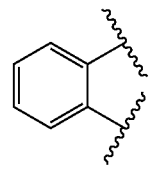

If $R^1$ and $R^2$ together with the carbon atom linking them form a phenylene radical which is unsubstituted or substituted at least once a benzothiazolyl radical, unsubstituted or substituted at least once, of the following structure is obtained along with the thiazolyl radical of general formula I:

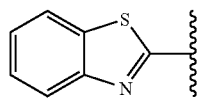

In the context of the present invention, the term "aryl" means a monocyclic or polycyclic, preferably monocyclic or bicyclic, aromatic hydrocarbon radical with preferably 6, 10 or 14 C atoms. An aryl radical may be unsubstituted or substituted one or more times in the same or different positions. Suitable aryl radicals include for example phenyl-, 1-naphthyl, 2-naphthyl and anthracenyl. It is particularly preferable for the aryl radical to be a phenyl radical.

The term "heteroaryl" in the context of the present invention means a monocyclic or polycyclic, preferably monocyclic, bicyclic or tricyclic, aromatic hydrocarbon radical with preferably 5, 6, 7, 8, 9, 10, 11, 12, 13 or 14 C atoms, particularly preferably with 5, 6, 9, 10, 13 or 14 C atoms, most preferably with 5 or 6 C atoms, in which one or more C atoms have been replaced, each by a heteroatom selected independently of one another from the group consisting of oxygen, sulphur and nitrogen (NH).

Heteroaryl radicals may preferably have 1, 2, 3, 4 or 5, particularly preferably 1, 2 or 3, heteroatom(s), selected independently of one another from the group consisting of oxygen, sulphur and nitrogen (NH), as ring members. A heteroaryl radical may be unsubstituted or substituted one or more times in the same or different positions.

Suitable heteroaryl radicals include for example thienyl, furyl, pyrrolyl, pyrazolyl, pyranyl, triazolyl, pyridinyl, imidazolyl, indolyl, isoindolyl, benzo[b]furanyl, benzo[b]thiophenyl, benzo[d]thiazolyl, benzodiazolyl, benzotriazolyl, benzoxazolyl, benzisoxazolyl, thiazolyl, thiadiazolyl, oxazolyl, oxadiazolyl, isoxazolyl, pyridazinyl, pyrazinyl, pyrimidinyl, indazolyl, quinoxalinyl, quinazolinyl, quinolinyl, naphthridinyl and isoquinolinyl.

Aryl or heteroaryl radicals may in the context of the present invention be condensed (annellated) with a monocyclic or bicyclic ring system.

Examples of aryl radicals which may be condensed with a monocyclic or bicyclic ring system include (1,2,3,4)-tetrahydroquinolinyl, (1,2,3,4)-tetrahydroisoquinolinyl, (2,3)-dihydro-1H-isoindolyl, (1,2,3,4)-tetrahydronaphthyl, (2,3)-dihydro-benzo[1.4]dioxinyl, benzo[1.3]dioxolyl und (3,4)-dihydro-2H-benzo[1.4]oxazinyl.

If one or more of the substituents represent a phenylene, aryl or heteroaryl radical or have an aryl or heteroaryl radical which is substituted one or more times, said substituent may preferably be substituted with, as appropriate, 1, 2, 3, 4 or 5, particularly preferably with, as appropriate, 1, 2 or 3 substituents, selected independently of one another from the group consisting of F, Cl, Br, I, —CN, —NO$_2$, —OH, —SH, —NH$_2$, —C(=O)—OH, —C$_{1-5}$-alkyl, —(CH$_2$)—O—C$_{1-5}$-alkyl, —C$_{2-5}$-alkenyl, —C$_{2-5}$-alkynyl, —C≡C—Si(CH$_3$)$_3$, —C≡C—Si(C$_2$H$_5$)$_3$, —S—C$_{1-5}$-alkyl, —S-phenyl, —S—CH$_2$-phenyl, —O—C$_{1-5}$-alkyl, —O-phenyl, —O—CH$_2$-phenyl, —CF$_3$, —CHF$_2$, —CH$_2$F, —O—CF$_3$, —O—CHF$_2$, —O—CH$_2$F, —C(=O)—CF$_3$, —S—CF$_3$, —S—CHF$_2$, —S—CH$_2$F, —S(=O)$_2$-phenyl, —S(=O)$_2$—C$_{1-5}$-alkyl, —S(=O)—C$_{1-5}$-alkyl, —NH—C$_{1-5}$-alkyl, —N(C$_{1-5}$Alkyl)$_2$, —C(=O)—O—C$_{1-5}$-alkyl, —C(=O)—H; —C(=O)—C$_{1-5}$-alkyl, —CH$_2$—O—C(=O)-phenyl, —O—C(=O)-phenyl, —NH—S(=O)$_2$—C$_{1-5}$-alkyl, —NH—C(=O)—C$_{1-5}$-alkyl, —C(=O)—NH$_2$, —C(=O)—NH—C$_{1-5}$-alkyl, —C(=O)—N(C$_{1-5}$-alkyl)$_2$, pyrazolyl, phenyl, furyl (furanyl), thiazolyl, thiadiazolyl, thiophenyl (thienyl), benzyl and phenethyl, the aforementioned C$_{1-5}$ alkyl radicals each being able to be linear or branched and the cyclic substituents and the cyclic radicals of these substituents themselves being able to be substituted with, as appropriate, 1, 2, 3, 4 or 5, preferably with, as appropriate, 1, 2, 3 or 4 substituents, selected independently of one another from the group consisting of F, Cl, Br, I, —CN, —NO$_2$, —OH, —SH, —NH$_2$, —C(=O)—OH, —C$_{1-5}$-alkyl, —(CH$_2$)—O—C$_{1-5}$-alkyl, —C$_{2-5}$-alkenyl, —C$_{2-5}$-alkynyl, —C≡C—Si(CH$_3$)$_3$, —C≡C—Si(C$_2$H$_5$)$_3$, —S—C$_{1-5}$-alkyl, —S-phenyl, —S—CH$_2$-phenyl, —O—C$_{1-5}$-alkyl, —O-phenyl, —O—CH$_2$-phenyl, —CF$_3$, —CHF$_2$, —CH$_2$F, —O—CF$_3$, —O—CHF$_2$, —O—CH$_2$F, —C(=O)—CF$_3$, —S—CF$_3$, —S—CHF$_2$ and —S—CH$_2$F.

Particularly preferably the substituents may each be selected independently of one another from the group consisting of F, Cl, Br, I, —CN, —NO$_2$, methyl, ethyl, n-propyl, isopropyl, n-butyl, isobutyl, 2-butyl, tert-butyl, n-pentyl, neo-pentyl, ethenyl, allyl, ethynyl, propynyl, —C≡C—Si(CH$_3$)$_3$, —C≡C—Si(C$_2$H$_5$)$_3$, —CH$_2$—O—CH$_3$, —CH$_2$—O—C$_2$H$_5$, —OH, —SH, —NH$_2$, —C(=O)—OH, —S—CH$_3$, —S—C$_2$H$_5$, —S(=O)—CH$_3$, —S(=O)$_2$—CH$_3$, —S(=O)—C$_2$H$_5$, —S(=O)$_2$—C$_2$H$_5$, —O—CH$_3$, —O—C$_2$H$_5$, —O—C$_3$H$_7$, —O—C(CH$_3$)$_3$, —CF$_3$, —CHF$_2$, —CH$_2$F, —O—CF$_3$, —O—CHF$_2$, —O—CH$_2$F, —C(=O)—CF$_3$, —S—CF$_3$, —S—CHF$_2$, —S—CH$_2$F, —S(=O)$_2$-phenyl, pyrazolyl, phenyl, —N(CH$_3$)$_2$, —N(C$_2$H$_5$)$_2$, —NH—CH$_3$, —NH—C$_2$H$_5$, —CH$_2$—O—C(=O)-phenyl, —NH—S(=O)$_2$—CH$_3$, —C(=O)—O—CH$_3$, —C(=O)—O—C$_2$H$_5$, —C(=O)—O—C(CH$_3$)$_3$, —C(=O)—H, —C(=O)—CH$_3$, —C(=O)—C$_2$H$_5$, —NH—C(=O)—CH$_3$, —NH—C(=O)—C$_2$H$_5$, —O—C(=O)-phenyl, —C(=O)—NH$_2$, —C(=O)—NH—CH$_3$, —C(=O)—N(CH$_3$)$_2$, phenyl, furyl (furanyl), thiadiazolyl, thiophenyl (thienyl) and benzyl, the cyclic substituents and the cyclic radicals of these substituents each being able themselves to be substituted with, as appropriate, 1, 2, 3, 4 or 5 substituents, preferably, as appropriate, 1, 2, 3 or 4 substituents, selected independently of one another from the group consisting of F, Cl, Br, I, —CN, —NO$_2$, —OH, —SH, —NH$_2$, —C(=O)—OH, methyl, ethyl, n-propyl, isopropyl, n-butyl, isobutyl, 2-butyl, tert-butyl, n-pentyl, neo-pentyl, ethenyl, allyl, ethynyl, propynyl, —C≡C—Si(CH$_3$)$_3$, —C≡C—Si(C$_2$H$_5$)$_3$, —CH$_2$—O—CH$_3$, —CH$_2$—O—C$_2$H$_5$, —S—CH$_3$, —S—C$_2$H$_5$, —S(=O)—CH$_3$, —S(=O)$_2$—CH$_3$, —S(=O)—C$_2$H$_5$, —S(=O)$_2$—C$_2$H$_5$, —O—CH$_3$, —O—C$_2$H$_5$, —O—C$_3$H$_7$, —O—C(CH$_3$)$_3$, —CF$_3$, —CHF$_2$, —CH$_2$F, —O—CF$_3$, —O—CHF$_2$, —O—CH$_2$F, —C(=O)—CF$_3$, —S—CF$_3$, —S—CHF$_2$ and —S—CH$_2$F.

It is particularly preferable for a substituted aryl radical to be selected from the group consisting of 2-methyl-phenyl, 3-methyl-phenyl, 4-methyl-phenyl, 2-fluoro-phenyl, 3-fluoro-phenyl, 4-fluoro-phenyl, 2-cyano-phenyl, 3-cyano-phenyl, 4-cyano-phenyl, 2-hydroxy-phenyl, 3-hydroxy-phenyl, 4-hydroxy-phenyl, 2-amino-phenyl, 3-amino-phenyl, 4-amino-phenyl, 2-dimethylamino-phenyl, 3-dimethylamino-phenyl, 4-dimethylamino-phenyl, 2-methylamino-phenyl, 3-methylamino-phenyl, 4-methylamino-phenyl, 2-acetyl-phenyl, 3-acetyl-phenyl, 4-acetyl-phenyl, 2-methyl-sulphinyl-phenyl, 3-methylsulphinyl-phenyl, 4-methylsulphinyl-phenyl, 2-methylsulphonyl-phenyl, 3-methylsulphonyl-phenyl, 4-methylsulphonyl-phenyl, 2-methoxy-phenyl, 3-methoxy-phenyl, 4-methoxy-phenyl, 2-chloro-phenyl, 3-chloro-phenyl, 4-chloro-phenyl, 2-ethoxy-phenyl, 3-ethoxy-phenyl, 4-ethoxy-phenyl, 2-trifluoromethyl-phenyl, 3-trifluoromethyl-phenyl, 4-trifluoromethyl-phenyl, 2-difluoromethyl-phenyl, 3-difluoromethyl-phenyl, 4-difluoromethyl-phenyl, 2-fluoromethyl-phenyl, 3-fluoromethyl-phenyl, 4-fluoromethyl-phenyl, 2-nitro-phenyl, 3-nitro-phenyl, 4-nitro-phenyl, 2-ethyl-phenyl, 3-ethyl-phenyl, 4-ethyl-phenyl, 2-propyl-phenyl, 3-propyl-phenyl, 4-propyl-phenyl, 2-isopropyl-phenyl, 3-isopropyl-phenyl, 4-isopropyl-phenyl, 2-tert-butyl-phenyl, 3-tert-butyl-phenyl, 4-tert-butyl-phenyl, 2-carboxy-phenyl, 3-carboxy-phenyl, 4-carboxy-phenyl, 2-ethenyl-phenyl, 3-ethenyl-phenyl, 4-ethenyl-phenyl, 2-ethynyl-phenyl, 3-ethynyl-phenyl, 4-ethynyl-phenyl, 2-allyl-phenyl, 3-allyl-phenyl, 4-allyl-phenyl, 2-trimethylsilanylethynyl-phenyl, 3-trimethylsilanylethynyl-phenyl, 4-trimethylsilanylethynyl-phenyl, 2-formyl-phenyl, 3-formyl-phenyl, 4-formyl-phenyl, 2-acetamino-phenyl, 3-acetamino-phenyl, 4-acetamino-phenyl, 2-dimethylaminocarbonyl-phenyl, 3-dimethylaminocarbonyl-phenyl, 4-dimethylaminocarbonyl-phenyl, 2-methoxymethyl-phenyl, 3-methoxymethyl-phenyl, 4-methoxymethyl-phenyl, 2-ethoxymethyl-phenyl, 3-ethoxymethyl-phenyl, 4-ethoxymethyl-phenyl, 2-aminocarbonyl-phenyl, 3-aminocarbonyl-phenyl, 4-aminocarbonyl-phenyl, 2-methylaminocarbonyl-phenyl, 3-methylaminocarbonyl-phenyl, 4-methylaminocarbonyl-phenyl, 2-carboxymethylester-phenyl, 3-carboxymethylester-phenyl, 4-carboxymethylester-phenyl, 2-carboxyethylester-phenyl, 3-carboxyethylester-phenyl, 4-carboxyethylester-phenyl, 2-carboxy-tert-butylester-phenyl, 3-carboxy-tert-butylester-phenyl, 4-carboxy-tert-butylester-phenyl, 2-methylmercapto-phenyl, 3-methylmercapto-phenyl, 4-methylmercapto-phenyl, 2-ethylmercapto-phenyl, 3-ethylmercapto-phenyl, 4-ethylmercaptophenyl, 2-biphenyl, 3-biphenyl, 4-biphenyl, 2-bromophenyl, 3-bromophenyl, 4-bromophenyl, 2-iodophenyl, 3-iodophenyl, 4-iodophenyl, 2-trifluoromethoxy-phenyl, 3-trifluoromethoxy-phenyl, 4-trifluoromethoxy-phenyl, 2-fluoro-3-trifluoromethylphenyl, 2-fluoro-4-methyl-phenyl, (2,3)-difluorophenyl, (2,3)-dimethylphenyl, (2,3)-dichlorophenyl, 3-fluoro-2-trifluoromethylphenyl, (2,4)-dichlorophenyl, (2,4)-difluorophenyl, 4-fluoro-2-trifluoromethyl-phenyl, (2,4)-dimethoxyphenyl, 2-chloro-4-fluoro-phenyl, 2-chloro-4-nitro-phenyl, 2-chloro-4-methyl-phenyl, 2-chloro-5-trifluoromethyl-phenyl, 2-chloro-5-methoxy-phenyl, 2-bromo-5-trifluoromethyl-phenyl, 2-bromo-5-methoxy-phenyl, (2,4)-dibromo-phenyl, (2,4)-dimethyl-phenyl, 2-fluoro-4-trifluoromethyl-phenyl, (2,5)-difluoro-phenyl, 2-fluoro-5-trifluoromethyl-phenyl, 5-fluoro-2-trifluoromethyl-phenyl, 5-chloro-2-trifluoromethyl-phenyl, 5-bromo-2-trifluoromethyl-phenyl, (2,5)-dimethoxy-phenyl, (2,5)-bis-trifluoromethyl-phenyl, (2,5)-dichloro-phenyl, (2,5)-dibromo-phenyl, 2-methoxy-5-nitro-phenyl, 2-fluoro-6-trifluoromethyl-phenyl, (2,6)-dimethoxy-phenyl, (2,6)-dimethyl-phenyl, (2,6)-dichloro-phenyl, 2-chloro-6-fluoro-phenyl, 2-bromo-6-chloro-phenyl, 2-bromo-6-fluoro-phenyl, (2,6)-difluoro-phenyl, (2,6)-difluoro-3-methyl-phenyl, (2,6)-dibromophenyl, (2,6)-dichlorophenyl, 3-chloro-2-fluoro-phenyl, 3-chloro-5-methyl-phenyl, (3,4)-dichlorophenyl, (3,4)-dimethyl-phenyl, 3-methyl-4-methoxy-phenyl, 4-chloro-3-nitro-phenyl, (3,4)-dimethoxy-phenyl, 4-fluoro-3-trifluoromethylphenyl, 3-fluoro-4-trifluormethyl-phenyl, (3,4)-difluoro-phenyl, 3-cyano-4-fluoro-phenyl, 3-cyano-4-methyl-phenyl, 3-cyano-4-methoxy-phenyl, 3-bromo-4-fluoro-phenyl, 3-bromo-4-methyl-phenyl, 3-bromo-4-methoxy-phenyl, 4-chloro-2-fluoro-phenyl, 4-chloro-3-trifluoromethyl, 4-bromo-3-methyl-phenyl, 4-bromo-5-methyl-phenyl, 3-chloro-4-fluoro-phenyl, 4-fluoro-3-nitro-phenyl, 4-bromo-3-nitro-phenyl, (3,4)-dibromo-phenyl, 4-chloro-3-methyl-phenyl, 4-bromo-3-methyl-phenyl, 4-fluoro-3-methyl-phenyl, 3-fluoro-4-methyl-phenyl, 3-fluoro-5-methyl-phenyl, 2-fluoro-3-methyl-phenyl, 4-methyl-3-nitro-phenyl, (3,5)-dimethoxy-phenyl, (3,5)-dimethyl-phenyl, (3,5)-bis-trifluoromethyl-phenyl, (3,5)-difluoro-phenyl, (3,5)-dinitro-phenyl, (3,5)-dichloro-phenyl, 3-fluoro-5-trifluoromethyl-phenyl, 5-fluoro-3-trifluoromethyl-phenyl, (3,5)-dibromo-phenyl, 5-chloro-4-fluoro-phenyl, 5-chloro-4-fluoro-phenyl, 5-bromo-4-methyl-phenyl, (2,3,4)-trifluorophenyl, (2,3,4)-trichlorophenyl, (2,3,6)-trifluorophenyl, 5-chloro-2-methoxy-phenyl, (2,3)-difluoro-4-methyl, (2,4,5)-trifluoro-phenyl, (2,4,5)-trichloro-phenyl, (2,4)-dichloro-5-fluoro-phenyl, (2,4,6)-trichloro-phenyl, (2,4,6)-trimethylphenyl, (2,4,6)-trifluoro-phenyl, (2,4,6)-trimethoxy-phenyl, (3,4,5)-trimethoxy-phenyl, (2,3,4,5)-tetrafluoro-phenyl, 4-methoxy-(2,3,6)-trimethyl-phenyl, 4-methoxy-(2,3,6)-trimethyl-phenyl, 4-chloro-2,5-dimethyl-phenyl, 2-chloro-6-fluoro-3-methyl-phenyl, 6-chloro-2-fluoro-3-methyl, (2,4,6)-trimethylphenyl and (2,3,4,5,6)-pentafluoro-phenyl.

It is particularly preferable for a substituted heteroaryl radical to be selected from the group consisting of 3-methyl-pyrid-2-yl, 4-methyl-pyrid-2-yl, 5-methyl-pyrid-2-yl, 6-methyl-pyrid-2-yl, 2-methyl-pyrid-3-yl, 4-methyl-pyrid-3-yl, 5-methyl-pyrid-3-yl, 6-methyl-pyrid-3-yl, 2-methyl-pyrid-4-yl, 3-methyl-pyrid-4-yl, 3-fluoro-pyrid-2-yl, 4-fluoro-pyrid-2-yl, 5-fluoro-pyrid-2-yl, 6-fluoro-pyrid-2-yl, 3-chloro-pyrid-2-yl, 4-chloro-pyrid-2-yl, 5-chloro-pyrid-2-yl, 6-chloro-pyrid-2-yl, 3-trifluoromethyl-pyrid-2-yl, 4-trifluoromethyl-pyrid-2-yl, 5-trifluoromethyl-pyrid-2-yl, 6-trifluoromethyl-pyrid-2-yl, 3-methoxy-pyrid-2-yl, 4-methoxy-pyrid-2-yl, 5-methoxy-pyrid-2-yl, 6-methoxy-pyrid-2-yl, 4-methyl-thiazol-2-yl, 5-methyl-thiazol-2-yl, 4-trifluoromethyl-thiazol-2-yl, 5-trifluoromethyl-thiazol-2-yl, 4-chloro-thiazol-2-yl, 5-chloro-thiazol-2-yl, 4-bromo-thiazol-2-yl, 5-bromo-thiazol-2-yl, 4-fluoro-thiazol-2-yl, 5-fluoro-thiazol-2-yl, 4-cyano-thiazol-2-yl, 5-cyano-thiazol-2-yl, 4-methoxy-thiazol-2-yl, 5-methoxy-thiazol-2-yl, 4-methyl-oxazol-2-yl, 5-methyl-oxazol-2-yl, 4-trifluoromethyl-oxazol-2-yl, 5-trifluoromethyl-oxazol-2-yl, 4-chloro-oxazol-2-yl, 5-chloro-oxazol-2-yl, 4-bromo-oxazol-2-yl, 5-bromo-oxazol-2-yl, 4-fluoro-oxazol-2-yl, 5-fluoro-oxazol-2-yl, 4-cyano-oxazol-2-yl, 5-cyano-oxazol-2-yl, 4-methoxy-oxazol-2-yl, 5-methoxy-oxazol-2-yl, 2-methyl-(1,2,4)-thiadiazol-5-yl, 2-trifluoromethyl-(1,2,4)-thiadiazol-5-yl, 2-chloro-(1,2,4)-thiadiazol-5-yl, 2-fluoro-(1,2,4)-thiadiazol-5-yl, 2-methoxy-(1,2,4)-thiadiazol-5-yl, 2-cyano-(1,2,4)-thiadiazol-5-yl, 2-methyl-(1,2,4)-oxadiazol-5-yl, 2-trifluoromethyl-(1,2,4)-oxadiazol-5-yl, 2-chloro-(1,2,4)-oxadiazol-5-yl, 2-fluoro-(1,2,4)-oxadiazol-5-yl, 2-methoxy-(1,2,4)-oxadiazol-5-yl and 2-cyano-(1,2,4)-oxadiazol-5-yl.

The term "alkylene" in the context of the present invention comprises acyclic, saturated hydrocarbon chains which link an aryl, heteroaryl, cycloalkyl, heterocycloalkyl, cycloalkenyl or heterocycloalkenyl radical to the substituted thiazole of general formula I or to another substituent. Alkylene chains may be branched or linear and unsubstituted or substituted at least once, with 1 to 12 (i.e. 1, 2, 3, 4, 5, 6, 7, 8, 9, 10, 11 or 12) C atoms as in the case of $C_{1-12}$ alkylene, with 1 to 6 (i.e. 1, 2, 3, 4, 5 or 6) C atoms as in the case of $C_{1-6}$ alkylene, or with 1 to 3 (i.e. 1, 2 or 3) C atoms as in the case of $C_{1-3}$ alkylene. Examples of $C_{1-6}$ alkylene groups include —$(CH_2)$—, —$(CH_2)_2$—, —$C(H)(CH_3)$—, —$(CH_2)_3$—, —$(CH_2)_4$—, —(CH$_2$)$_5$—, —C(CH$_3$)$_2$—, —C(H)(CH$_3$)—, —C(H)(C(H)(CH$_3$)$_2$)— and C(C$_2$H$_5$)(H)—. Suitable C$_{1-3}$ alkylene groups include for example —(CH$_2$)—, —(CH$_2$)$_2$— and —(CH$_2$)$_3$—.

The term "alkenylene" in the context of the present invention comprises acyclic, unsaturated hydrocarbon chains which link an aryl, heteroaryl, cycloalkyl, heterocycloalkyl, cycloalkenyl or heterocycloalkenyl radical to the substituted thiazole of general formula I or to another substituent. Alkenylene chains have at least one double bond, preferably 1, 2 or 3 double bonds, and may be branched or linear and unsubstituted or substituted at least once, with 2 to 12 (i.e. 2, 3, 4, 5, 6, 7, 8, 9, 10, 11 or 12) C atoms as in the case of C$_{2-12}$ alkylene, with 2 to 6 (i.e. 2, 3, 4, 5 or 6) C atoms as in the case of C$_{2-6}$ alkylene, or with 2 to 3 (i.e. 2 or 3) C atoms as in the case of C$_{2-3}$ alkylene. Examples of C$_{2-3}$ alkylene groups include —CH═CH— and —CH$_2$—CH═CH—.

The term "alkynylene" in the context of the present invention comprises acyclic, unsaturated hydrocarbon chains which link an aryl, heteroaryl, cycloalkyl, heterocycloalkyl, cycloalkenyl or heterocycloalkenyl radical to the substituted thiazole of general formula I or to another substituent. Alkynylene chains have at least one triple bond, preferably 1 or 2 triple bonds, and may be branched or linear and unsubstituted or substituted at least once, with 2 to 12 (i.e. 2, 3, 4, 5, 6, 7, 8, 9, 10, 11 or 12) C atoms as in the case of C$_{2-11}$ alkynylene, with 2 to 6 (i.e. 2, 3, 4, 5 or 6) C atoms as in the case of C$_{2-6}$ alkynylene, or with 2 to 3 (i.e. 2, or 3) C atoms as in the case of C$_{2-3}$ alkynylene. Examples of C$_{2-3}$ alkynylene groups include —C≡C— and —CH$_2$—C≡C—.

The term "heteroalkylene" refers to an alkylene chain, as described above, in which one or more C atoms have been replaced, each by a heteroatom selected independently of one another from the group consisting of oxygen, sulphur and nitrogen (NH). Heteroalkylene groups may preferably have 1, 2 or 3 heteroatom(s), particularly preferably one heteroatom, selected from the group consisting of oxygen, sulphur and nitrogen (NH), as chain member(s). Heteroalkylene groups may preferably have 2 to 12 members, particularly preferably 2 to 6 members, most preferably 2 to 3 members.

Examples of heteroalkylene radicals include —(CH$_2$)—O—, —(CH$_2$)$_2$—O—, —(CH$_2$)$_3$—O—, —(CH$_2$)$_4$—O—, —O—(CH$_2$)—, —O—(CH$_2$)$_2$—, —O—(CH$_2$)$_3$—, —O—(CH$_2$)$_4$—, —C(C$_2$H$_5$)(H)—O—, —O—C(C$_2$H$_5$)(H)—, —CH$_2$—O—CH$_2$—, —CH$_2$—S—CH$_2$—, —CH$_2$—NH—CH$_2$—, —CH$_2$—NH— and —CH$_2$—CH$_2$—NH—CH$_2$—CH$_2$.

The term "heteroalkenylene" refers to an alkenylene radical, as described above, in which one or more C atoms have been replaced, each by a heteroatom selected independently of one another from the group consisting of oxygen, sulphur and nitrogen (NH). Heteroalkenylene groups may preferably have 1, 2 or 3 heteroatom(s), particularly preferably one heteroatom, selected from the group consisting of oxygen, sulphur and nitrogen (NH), as chain member(s). Heteroalkenylene radicals may preferably have 2 to 12 members, particularly preferably 2 to 6 members, most preferably 2 to 3 members. Examples of heteroalkenylene radicals include —CH═CH—NH—, —CH═CH—O— and —CH═CH—S—.

If one or more of the substituents represent an alkylene, alkenylene, alkynylene, heteroalkylene or heteroalkenylene group, or have a group of one of these types, which is substituted one or more times, said group may preferably be substituted with, as appropriate, 1, 2, 3, 4 or 5, particularly preferably with, as appropriate, 1, 2 or 3 substituents, selected independently of one another from the group consisting of phenyl, F, Cl, Br, I, —NO$_2$, —CN, —OH, —O-phenyl, —O—CH$_2$-phenyl, —SH, —S-phenyl, —S—CH$_2$-phenyl, —NH$_2$, —N(C$_{1-5}$-alkyl)$_2$, —NH-phenyl, (phenyl)-N(C$_{1-5}$-alkyl)(phenyl), —N(C$_{1-5}$-alkyl)(CH$_2$-phenyl), —N(C$_{1-5}$-alkyl)(CH$_2$—CH$_2$-phenyl), —C(═O)—H, —C(═O)—C$_{1-5}$-alkyl, —C(═O)-phenyl, —C(═S)—C$_{1-5}$-alkyl, —C(═S)-phenyl, —C(═O)—OH, —C(═O)—O—C$_{1-5}$-alkyl, —C(═O)—O-phenyl, —C(═O)—NH$_2$, —C(═O)—NH—C$_{1-5}$-alkyl, —C(═O)—N(C$_{1-5}$-alkyl)$_2$, —S(═O)—C$_{1-5}$-alkyl, —S(═O)-phenyl, —S(═O)$_2$—C$_{1-5}$-alkyl, —S(═O)$_2$-phenyl, —S(═O)$_2$—NH$_2$ and —SO$_3$H, the aforementioned C$_{1-5}$ alkyl radicals each being able to be linear or branched and the aforementioned phenyl radicals each being able to be substituted with 1, 2, 3, 4 or 5, preferably with 1, 2, 3 or 4 substituents, selected independently of one another from the group consisting of F, Cl, Br, I, —CN, —NO$_2$, —OH, —SH, —NH$_2$, —C(═O)—OH, —C$_{1-5}$-alkyl, —(CH$_2$)—O—C$_{1-5}$-alkyl, —C$_{2-5}$-alkenyl, —C$_{2-5}$-alkynyl, —C≡C—Si(CH$_3$)$_3$, —C≡C—Si(C$_2$H$_5$)$_3$, —S—C$_{1-5}$-alkyl, —S-phenyl, —S—CH$_2$-phenyl, —O—C$_{1-5}$-alkyl, —O-phenyl, —O—CH$_2$-phenyl, —CF$_3$, —CHF$_2$, —CH$_2$F, —O—CF$_3$, —O—CHF$_2$, —O—CH$_2$F, —C(═O)—CF$_3$, —S—CF$_3$, —S—CHF$_2$ and —S—CH$_2$F.

Alkylene, alkenylene, alkynylene, heteroalkylene or heteroalkenylene groups may particularly preferably be substituted with 1, 2 or 3 substituents selected independently of one another from the group consisting of phenyl, F, Cl, Br, I, —NO$_2$, —CN, —OH, —O-phenyl, —SH, —S-phenyl, —NH$_2$, —N(CH$_3$)$_2$, —N(C$_2$H$_5$)$_2$ and —N(CH$_3$)(C$_2$H$_5$), the phenyl radical being able to be substituted with 1, 2, 3, 4 or 5 substituents selected independently of one another from the group consisting of F, Cl, Br, I, —OH, —SH, —NO$_2$, —CN, —O—CH$_3$, —O—CF$_3$ and —O—C$_2$H$_5$.

If compounds of general formula I have a plurality of substituents with the same designation selected from the group consisting of R$^{12}$, R$^{13}$, R$^{14}$, R$^{15}$, R$^{16}$, R$^{17}$, R$^{18}$, R$^{19}$, R$^{20}$, R$^{21}$, R$^{22}$, R$^{23}$, R$^{24}$, R$^{25}$, R$^{26}$, R$^{27}$, R$^{28}$, R$^{29}$, R$^{31}$ and R$^{32}$, each of these substituents may be selected independently of any other substituents with the same substituent designation.

For example, the following radical,

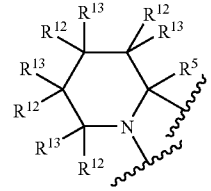

may according to the choice of the corresponding substituents represent this radical:

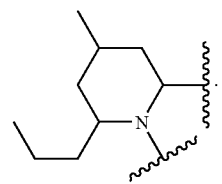

Substituted thiazoles are preferably of the foregoing general formula I, in which R$^1$ and R$^2$, independently of one another, represent H; F; Cl; Br; I; —NO$_2$; —CN; —NH$_2$; —OH; —SH; —C(═O)—OH; —C(═O)—H; —NH—C (=O)—H; —NH—R$^{33}$; —NR$^{34}$R$^{35}$; —C(=O)—R$^{36}$; —C(=O)—O—R$^{37}$; —O—C(=O)—R$^{38}$; —NH—C(=O)—R$^{39}$; —NR$^{40}$—C(=O)—R$^{41}$; —C(=O)—NH$_2$; —C(=O)—NH—R$^{42}$; —C(=O)—NR$^{43}$R$^{44}$; —O—R$^{45}$; —S—R$^{46}$; —S(=O)—R$^{47}$; —S(=O)$_2$—R$^{48}$; —NH—C(=O)—NH—R$^{49}$; —NH—C(=S)—NH—R$^{50}$; —NH—S(=O)$_2$—R$^{51}$; —NR$^{52}$—S(=O)$_2$—R$^{53}$; alkyl, alkenyl or alkynyl which is unsubstituted or substituted at least once; heteroalkyl, heteroalkenyl or heteroalkynyl which is unsubstituted or substituted at least once; cycloalkyl or cycloalkenyl which is unsubstituted or substituted at least once; heterocycloalkyl or heterocycloalkenyl which is unsubstituted or substituted at least once; -(alkylene)-cycloalkyl, -(alkenylene)-cycloalkyl, -(alkynylene)-cycloalkyl, -(alkylene)-cycloalkenyl, -(alkenylene)-cycloalkenyl or -(alkynylene)-cycloalkenyl which is unsubstituted or substituted at least once; -(heteroalkylene)-cycloalkyl, -(heteroalkenylene)-cycloalkyl, -(heteroalkylene)-cycloalkenyl or -(heteroalkenylene)-cycloalkenyl which is unsubstituted or substituted at least once; -(alkylene)-heterocycloalkyl, -(alkenylene)-heterocycloalkyl, -(alkynylene)-heterocycloalkyl, -(alkylene)-heterocycloalkenyl, -(alkenylene)-heterocycloalkenyl or -(alkynylene)-heterocycloalkenyl which is unsubstituted or substituted at least once; -(heteroalkylene)-heterocycloalkyl, -(heteroalkenylene)-heterocycloalkyl, -(heteroalkylene)-heterocycloalkenyl or -(heteroalkenylene)-heterocycloalkenyl which is unsubstituted or substituted at least once; aryl which is unsubstituted or substituted at least once; heteroaryl which is unsubstituted or substituted at least once; -(alkylene)-aryl, -(alkenylene)-aryl, -(alkynylene)-aryl, -(heteroalkylene)-aryl or -(heteroalkenylene)-aryl which is unsubstituted or substituted at least once; or -(alkylene)-heteroaryl, -(alkenylene)-heteroaryl, -(alkynylene)-heteroaryl, -(heteroalkylene)-heteroaryl or -(heteroalkenylene)-heteroaryl which is unsubstituted or substituted at least once;

or R$^1$ and R$^2$ together with the carbon atoms linking them form a phenylene radical which is unsubstituted or substituted at least once;

R$^3$ and R$^{10}$ independently of one another each represent H; —C(=O)—R$^{36}$; —C(=O)—O—R$^{37}$; —C(=O)—NH$_2$; —C(=O)—NH—R$^{42}$; —C(=O)—NR$^{43}$R$^{44}$; —S(=O)—R$^{47}$; —S(=O)$_2$—R$^{48}$; unsubstituted or substituted alkyl, alkenyl or alkynyl; unsubstituted or substituted heteroalkyl, heteroalkenyl or heteroalkynyl; unsubstituted or substituted cycloalkyl or cycloalkenyl; unsubstituted or substituted heterocycloalkyl or heterocycloalkenyl; unsubstituted or substituted -(alkylene)-cycloalkyl, -(alkenylene)-cycloalkyl, -(alkynylene)-cycloalkyl, -(alkylene)-cycloalkenyl, -(alkenylene)-cycloalkenyl or -(alkynylene)-cycloalkenyl; unsubstituted or substituted -(heteroalkylene)-cycloalkyl, -(heteroalkenylene)-cycloalkyl, -(heteroalkylene)-cycloalkenyl or -(heteroalkenylene)-cycloalkenyl; unsubstituted or substituted -(alkylene)-heterocycloalkyl, -(alkenylene)-heterocycloalkyl, -(alkynylene)-heterocycloalkyl, -(alkylene)-heterocycloalkenyl, -(alkenylene)-heterocycloalkenyl or -(alkynylene)-heterocycloalkenyl; unsubstituted or substituted -(heteroalkylene)-heterocycloalkyl, -(heteroalkenylene)-heterocycloalkyl, -(heteroalkylene)-heterocycloalkenyl or -(heteroalkenylene)-heterocycloalkenyl; unsubstituted or substituted aryl; unsubstituted or substituted heteroaryl; unsubstituted or substituted -(alkylene)-aryl, -(alkenylene)-aryl, -(alkynylene)-aryl, -(heteroalkylene)-aryl or -(heteroalkenylene)-aryl; or unsubstituted or substituted -(alkylene)-heteroaryl, -(alkenylene)-heteroaryl, -(alkynylene)-heteroaryl, -(heteroalkylene)-heteroaryl or -(heteroalkenylene)-heteroaryl.

R$^4$, R$^5$, R$^6$, R$^7$, R$^8$, R$^9$, R$^{12}$, R$^{13}$, R$^{14}$, R$^{15}$, R$^{16}$, R$^{17}$, R$^{18}$, R$^{19}$, R$^{20}$, R$^{21}$, R$^{22}$, R$^{23}$, R$^{24}$, R$^{25}$, R$^{26}$, R$^{27}$, R$^{28}$, R$^{29}$, R$^{30}$, R$^{31}$ and R$^{32}$, each independently of one another, represent H; F; Cl; Br; I; —NO$_2$; —CN; —NH$_2$; —OH; —SH; —C(=O)—OH; —C(=O)—H; —NH—C(=O)—H; —NH—R$^{33}$; —NR$^{34}$R$^{35}$; —C(=O)—R$^{36}$; —C(=O)—O—R$^{37}$; —O—C(=O)—R$^{38}$; —NH—C(=O)—R$^{39}$; —NR$^{40}$—C(=O)—R$^{41}$; —C(=O)—NH$_2$; —C(=O)—NH—R$^{42}$; —C(=O)—NR$^{43}$R$^{44}$; —O—R$^{45}$; —S—R$^{46}$; —S(=O)—R$^{47}$; —S(=O)$_2$—R$^{48}$; —NH—C(=O)—NH—R$^{49}$; —NH—C(=S)—NH—R$^{50}$; —NH—S(=O)$_2$—R$^{51}$; —NR$^{52}$—S(=O)$_2$—R$^{53}$; unsubstituted or substituted alkyl, alkenyl or alkynyl; unsubstituted or substituted heteroalkyl, heteroalkenyl or heteroalkynyl; unsubstituted or substituted cycloalkyl or cycloalkenyl; unsubstituted or substituted heterocycloalkyl or heterocycloalkenyl; unsubstituted or substituted -(alkylene)-cycloalkyl, -(alkenylene)-cycloalkyl, -(alkynylene)-cycloalkyl, -(alkylene)-cycloalkenyl, -(alkenylene)-cycloalkenyl or -(alkynylene)-cycloalkenyl; unsubstituted or substituted -(heteroalkylene)-cycloalkyl, -(heteroalkenylene)-cycloalkyl, -(heteroalkylene)-cycloalkenyl or -(heteroalkenylene)-cycloalkenyl; unsubstituted or substituted -(alkylene)-heterocycloalkyl, -(alkenylene)-heterocycloalkyl, -(alkynylene)-heterocycloalkyl, -(alkylene)-heterocycloalkenyl, -(alkenylene)-heterocycloalkenyl or -(alkynylene)-heterocycloalkenyl; unsubstituted or substituted -(heteroalkylene)-heterocycloalkyl, -(heteroalkenylene)-heterocycloalkyl, -(heteroalkylene)-heterocycloalkenyl or -(heteroalkenylene)-heterocycloalkenyl; unsubstituted or substituted aryl; unsubstituted or substituted heteroaryl; unsubstituted or substituted -(alkylene)-aryl, -(alkenylene)-aryl, -(alkynylene)-aryl, -(heteroalkylene)-aryl or -(heteroalkenylene)-aryl; or unsubstituted or substituted -(alkylene)-heteroaryl, -(alkenylene)-heteroaryl, -(alkynylene)-heteroaryl, -(heteroalkylene)-heteroaryl or -(heteroalkenylene)-heteroaryl;

or R$^4$ and R$^5$ or R$^6$ and R$^7$ or R$^8$ and R$^9$ or R$^{12}$ and R$^{13}$ or R$^{14}$ and R$^{15}$ or R$^{16}$ and R$^{17}$ or R$^{18}$ and R$^{19}$ or R$^{20}$ and R$^{21}$ or R$^{22}$ and R$^{23}$ or R$^{24}$ and R$^{25}$ or R$^{26}$ and R$^{27}$ or R$^{28}$ and R$^{29}$ or R$^{31}$ and R$^{32}$ independently of one another represent, together in each case, a radical selected from the group consisting of an oxo group (=O) and a thioxo group (=S);

or R$^3$ and R$^4$ together with the —N—CR$^5$ group linking them form a radical of general formula A,

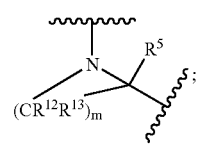

A or R$^3$ and R$^{10}$ together with the —CR$^9$—N group linking them form a radical of general formula B,

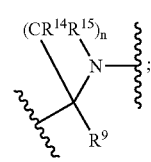

B m and n each represent 2, 3, 4, 5 or 6;

or $R^3$ and $R^6$ together with the —N—$CR^4R^5$—$CR^7$ group linking them form a radical of general formula C,

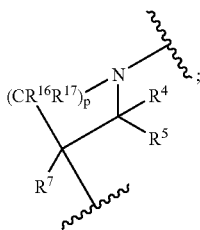

or $R^6$ and $R^{10}$ together with the —$CR^7$—$CR^8R^9$—N group linking them form a radical of general formula D,

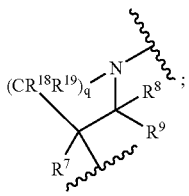

p and q each represent 1, 2, 3, 4 or 5;
or $R^3$ and $R^8$ together with the —N—$CR^4R^5$—$CR^6R^7$—$CR^9$ group linking them form a radical of general formula E,

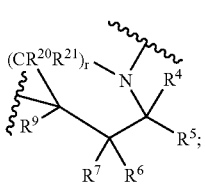

or $R^4$ and $R^{10}$ together with the —N—$CR^8R^9$—$CR^6R^7$—$CR^5$ group linking them form a radical of general formula F,

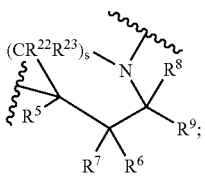

r and s each represent 2, 3 or 4;
or $R^4$ and $R^8$ together with the —$CR^5$—$CR^6R^7$—$CR^9$ group linking them form a radical of general formula G,

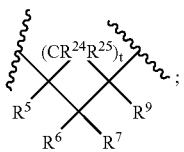

t represents 1, 2, 3, 4 or 5;

or $R^3$ and $R^{10}$ together with the —N—$CR^4R^5$—$CR^6R^7$—$CR^8R^9$—N group linking them form a radical of general formula H,

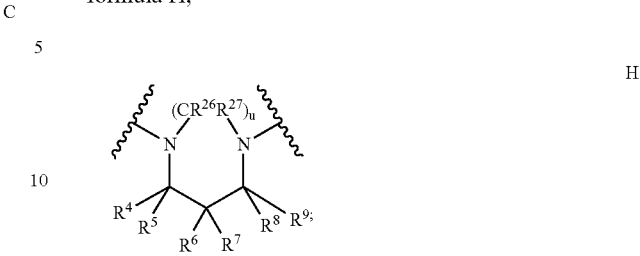

u represents 3 or 4;
or $R^3$ and $R^{10}$ together with the —N—$CR^4R^5$—$CR^6R^7$—$CR^8R^9$—N group linking them form a bicyclic radical of general formula K,

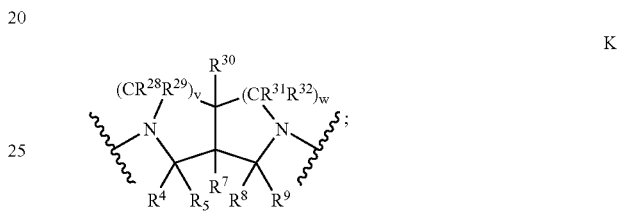

v and w independently of one another each represent 1, 2 or 3;
$R^{11}$ represents unsubstituted or substituted aryl or unsubstituted or substituted heteroaryl;
and $R^{33}$, $R^{34}$, $R^{35}$, $R^{36}$, $R^{37}$, $R^{38}$, $R^{39}$, $R^{40}$, $R^{41}$, $R^{42}$, $R^{43}$, $R^{44}$, $R^{45}$, $R^{46}$, $R^{47}$, $R^{48}$, $R^{49}$, $R^{50}$, $R^{51}$, $R^{52}$ and $R^{53}$ independently of one another each represent unsubstituted or substituted alkyl, alkenyl or alkynyl; unsubstituted or substituted heteroalkyl, heteroalkenyl or heteroalkynyl; unsubstituted or substituted cycloalkyl or cycloalkenyl; unsubstituted or substituted heterocycloalkyl or heterocycloalkenyl; unsubstituted or substituted (alkylene)-cycloalkyl, -(alkenylene)-cycloalkyl, -(alkynylene)-cycloalkyl, -(alkylene)-cycloalkenyl, -(alkenylene)-cycloalkenyl or -(alkynylene)-cycloalkenyl; unsubstituted or substituted -(heteroalkylene)-cycloalkyl, -(heteroalkenylene)-cycloalkyl, -(heteroalkylene)-cycloalkenyl or -(heteroalkenylene)-cycloalkenyl; unsubstituted or substituted -(alkylene)-heterocycloalkyl, -(alkenylene)-heterocycloalkyl, -(alkynylene)-heterocycloalkyl, -(alkylene)-heterocycloalkenyl, -(alkenylene)-heterocycloalkenyl or -(alkynylene)-heterocycloalkenyl; unsubstituted or substituted -(heteroalkylene)-heterocycloalkyl, -(heteroalkenylene)-heterocycloalkyl, -(heteroalkylene)-heterocycloalkenyl; or -(heteroalkenylene)-heterocycloalkenyl; unsubstituted or substituted aryl; unsubstituted or substituted heteroaryl; unsubstituted or substituted -(alkylene)-aryl, -(alkenylene)-aryl, -(alkynylene)-aryl, -(heteroalkylene)-aryl or -(heteroalkenylene)-aryl; or unsubstituted or substituted -(alkylene)-heteroaryl, -(alkenylene)-heteroaryl, -(alkynylene)-heteroaryl, -(heteroalkylene)-heteroaryl or -(heteroalkenylene)-heteroaryl; in which
the aforementioned alkyl radicals are each branched or linear and have 1, 2, 3, 4, 5, 6, 7, 8, 9, 10, 11 or 12 carbon atoms as members of the chain;
the aforementioned alkenyl radicals are each branched or linear and have 2, 3, 4, 5, 6, 7, 8, 9, 10, 11 or 12 carbon atoms as members of the chain;

the aforementioned alkynyl radicals are each branched or linear and have 2, 3, 4, 5, 6, 7, 8, 9, 10, 11 or 12 carbon atoms as members of the chain;

the aforementioned heteroalkyl radicals, heteroalkenyl radicals and heteroalkynyl radicals each have 2, 3, 4, 5, 6, 7, 8, 9, 10, 11 or 12 members; the aforementioned heteroalkyl radicals, heteroalkenyl radicals and heteroalkynyl radicals each optionally have 1, 2 or 3 heteroatom(s), selected independently of one another from the group consisting of oxygen, sulphur and nitrogen, as chain member(s);

the aforementioned alkyl radicals, alkenyl radicals, alkynyl radicals, heteroalkyl radicals, heteroalkenyl radicals and heteroalkynyl radicals may each be substituted with, as appropriate, 1, 2, 3, 4 or 5 substituents selected independently of one another from the group consisting of F, Cl, Br, I, —NO$_2$, —CN, —OH, —SH, —NH$_2$, —N(C$_{1-5}$-alkyl)$_2$, —N(C$_{1-5}$-alkyl)(phenyl), —N(C$_{1-5}$-alkyl)(CH$_2$-phenyl), —N(C$_{1-5}$-alkyl)(CH$_2$—CH$_2$-phenyl), —C(=O)—H, —C(=O)—C$_{1-5}$-alkyl, —C(=O)-phenyl, —C(=S)—C$_{1-5}$-alkyl, —C(=S)-phenyl, —C(=O)—OH, —C(=O)—O—C$_{1-5}$-alkyl, —C(=O)—O-phenyl, —C(=O)—NH$_2$, —C(=O)—NH—C$_{1-5}$-alkyl, —C(=O)—N(C$_{1-5}$-alkyl)$_2$, —S(=O)—C$_{1-5}$-alkyl, —S(=O)-phenyl, —S(=O)$_2$—C$_{1-5}$-alkyl, S(=O)$_2$-phenyl, —S(=O)$_2$—NH$_2$ and —SO$_3$H, it being possible for the phenyl radicals to be substituted with 1, 2, 3, 4 or 5 substituents selected independently of one another from the group comprising F, Cl, Br, I, —CN, —CF$_3$, —OH, —NH$_2$, —O—CF$_3$, —SH, —O—CH$_3$, —O—C$_2$H$_5$, —O—C$_3$H$_7$, methyl, ethyl, n-propyl, isopropyl, n-butyl, 2-butyl, isobutyl and tert-butyl;

the aforementioned cycloalkyl radicals each have 3, 4, 5, 6, 7, 8 or 9 carbon atoms as ring members;

the aforementioned cycloalkenyl radicals each have 3, 4, 5, 6, 7, 8 or 9 carbon atoms as ring members;

the aforementioned heterocycloalkyl radicals each have 3, 4, 5, 6, 7, 8 or 9 members;

the aforementioned heterocycloalkenyl radicals each have 4, 5, 6, 7, 8 or 9 members;

the aforementioned heterocycloalkyl radicals and heterocycloalkenyl radicals each optionally have 1, 2 or 3 heteroatom(s), selected independently of one another from the group consisting of oxygen, sulphur and nitrogen (NH), as chain member(s);

the aforementioned cycloalkyl radicals, heterocycloalkyl radicals, cycloalkenyl radicals or heterocycloalkenyl radicals may each be substituted with, as appropriate, 1, 2, 3, 4 or 5 substituents selected from the groups consisting of F, Cl, Br, I, —CN, —CF$_3$, —OH, —NH$_2$, —O—CF$_3$, —SH, —O—C$_{1-5}$-alkyl, —O-phenyl, —O—CH$_2$-phenyl, —(CH$_2$)—O—C$_{1-5}$-alkyl, —S—C$_{1-5}$-alkyl, —S-phenyl, —S—CH$_2$-phenyl, —C$_{1-5}$-alkyl, —C$_{2-5}$-alkenyl, —C$_{2-5}$-alkynyl, —C≡C—Si(CH$_3$)$_3$, —C≡C—Si(C$_2$H$_5$)$_3$, —C(=O)—O—C$_{1-5}$-alkyl, —C(=O)—CF$_3$, —S(=O)$_2$—C$_{1-5}$-alkyl, —S(=O)—C$_{1-5}$-alkyl, —S(=O)$_2$-phenyl, oxo (=O), thioxo (=S), —N(C$_{1-5}$-alkyl)$_2$, —N(H)(C$_{1-5}$-alkyl), —NO$_2$, —S—CF$_3$, —C(=O)—OH, —NH—S(=O)$_2$—C$_{1-5}$-alkyl, —NH—C(=O)—C$_{1-5}$-alkyl, —C(=O)—H, —C(=O)—C$_{1-5}$-alkyl, —C(=O)—NH$_2$, —C(=O)—N(C$_{1-5}$-alkyl)$_2$, —C(=O)—N(H)(C$_{1-5}$-alkyl) and phenyl, the phenyl radicals each being unsubstituted or substituted with 1, 2, 3, 4 or 5 substituents selected independently of one another from the group consisting of F, Cl, Br, I, —CN, —CF$_3$, —OH, —NH$_2$, —O—CF$_3$, —SH, —O—C$_{1-5}$-alkyl, —O-phenyl, —O—CH$_2$-phenyl, —(CH$_2$)—O—C$_{1-5}$-alkyl, —S—C$_{1-5}$-alkyl, —S-phenyl, —S—CH$_2$-phenyl, —C$_{1-5}$-alkyl, —C$_{2-5}$-alkenyl, —C$_{2-5}$-alkynyl, —C≡C—Si(CH$_3$)$_3$, —C≡C—Si(C$_2$H$_5$)$_3$, —C(=O)—O—C$_{1-5}$-alkyl and —C(=O)—CF$_3$, the aforementioned phenyl radicals preferably being able to be substituted with 1, 2, 3, 4 or 5 substituents selected independently of one another from the group consisting of F, Cl, Br, I, —CN, —CF$_3$, —OH, —NH$_2$, —O—CF$_3$, —SH, —O—CH$_3$, —O—C$_2$H$_5$, —O—C$_3$H$_7$, methyl, ethyl, n-propyl, isopropyl, n-butyl, 2-butyl, isobutyl und tert-butyl; the aforementioned alkylene radicals are each branched or linear and have 1, 2, 3, 4, 5, 6, 7, 8, 9, 10, 11 or 12 carbon atoms as members of the chain;

the aforementioned alkenylene radicals are each branched or linear and have 2, 3, 4, 5, 6, 7, 8, 9, 10, 11 or 12 carbon atoms as members of the chain;

the aforementioned alkynylene radicals are each branched or linear and have 2, 3, 4, 5, 6, 7, 8, 9, 10, 11 or 12 carbon atoms as members of the chain;

the aforementioned heteroalkylene radicals, heteroalkenylene radicals and heteroalkynylene radicals each have 2, 3, 4, 5, 6, 7, 8, 9, 10, 11 or 12 members;

the aforementioned heteroalkylene, heteroalkenylene and heteroalkynylene groups each optionally have 1, 2 or 3 heteroatom(s), selected independently of one another from the group consisting of oxygen, sulphur and nitrogen (NH), as chain member(s);

the aforementioned alkylene, alkenylene, alkynylene, heteroalkylene, heteroalkenylene and heteroalkynylene groups may each be unsubstituted or substituted with, as appropriate, 1, 2, 3, 4 or 5 substituents selected independently of one another from the group consisting of Phenyl, F, Cl, Br, I, —NO$_2$, —CN, —OH, —O-phenyl, —O—CH$_2$-phenyl, —SH, —S-phenyl, —S—CH$_2$-phenyl, NH$_2$, —N(C$_{1-5}$-alkyl)$_2$, —NH-phenyl, —N(C$_{1-5}$-alkyl)(phenyl), —N(C$_{1-5}$-alkyl)(CH$_2$-phenyl), —N(C$_{1-5}$-alkyl)(CH$_2$—CH$_2$-phenyl), —C(=O)—H, —C(=O)—C$_{1-5}$-alkyl, —C(=O)-phenyl, —C(=S)—C$_{1-5}$-alkyl, —C(=S)-phenyl, —C(=O)—OH, —C(=O)—O—C$_{1-5}$-alkyl, —C(=O)—O-phenyl, —C(=O)—NH$_2$, —C(=O)—NH—C$_{1-5}$-alkyl, —C(=O)—N(C$_{1-5}$-alkyl)$_2$, —S(=O)—C$_{1-5}$-alkyl, —S(=O)-phenyl, —S(=O)$_2$—C$_{1-5}$-alkyl, —S(=O)$_2$-phenyl, —S(=O)$_2$—NH$_2$ and —SO$_3$H, the phenyl radicals each being substituted with 1, 2, 3, 4 or 5 substituents selected independently of one another from the group consisting of F, Cl, Br, I, —CN, —NO$_2$, —OH, —SH, —NH$_2$, —C(=O)—OH, —C$_{1-5}$-alkyl, —(CH$_2$)—O—C$_{1-5}$-alkyl, —C$_{2-5}$-alkenyl, —C$_{2-5}$-alkynyl, —C≡C—Si(CH$_3$)$_3$, —C≡C—Si(C$_2$H$_5$)$_3$, —S—C$_{1-5}$-alkyl, —S-phenyl, —S—CH$_2$-phenyl, —O—C$_{1-5}$-alkyl, —O-phenyl, —O—CH$_2$-phenyl, —CF$_3$, —CHF$_2$, —CH$_2$F, —O—CF$_3$, —O—CHF$_2$, —O—CH$_2$F, —C(=O)—CF$_3$, —S—CF$_3$, —S—CHF$_2$ and —S—CH$_2$F;

the aforementioned aryl radicals are monocyclic or bicyclic and have 6, 10 or 14 carbon atoms;

the aforementioned heteroaryl radicals are monocyclic, bicyclic or tricyclic and have 5, 6, 7, 8, 9, 10, 11, 12, 13 or 14 members;

the aforementioned heteroaryl radicals with 5 to 14 members optionally have 1, 2, 3, 4 or 5 heteroatom(s), selected independently of one another from the group consisting of oxygen, sulphur and nitrogen (NH), as chain member(s);

and the aforementioned phenylene radicals, aryl radicals and heteroaryl radicals may each be substituted with, as appropriate, 1, 2, 3, 4 or 5 substituents selected independently of one another from the group consisting of F, Cl, Br, I, —CN, —NO$_2$, —OH, —SH, —NH$_2$, —C(=O)—OH, —C$_{1-5}$- alkyl, —(CH$_2$)—O—C$_{1-5}$-alkyl, —C$_{2-5}$-alkenyl, —C$_{2-5}$-alkynyl, —C≡C—Si(CH$_3$)$_3$, —C≡C—Si(C$_2$H$_5$)$_3$, —S—C$_{1-5}$-alkyl, —S-phenyl, —S—CH$_2$-phenyl, —O—C$_{1-5}$-alkyl, —O-phenyl, —O—CH$_2$-phenyl, —CF$_3$, —CHF$_2$, —CH$_2$F, —O—CF$_3$, —O—CHF$_2$, —O—CH$_2$F, —C(=O)—CF$_3$, —S—CF$_3$, —S—CHF$_2$, —S—CH$_2$F, —S(=O)$_2$-phenyl, —S(=O)$_2$—C$_{1-5}$-alkyl, —S(=O)—C$_{1-5}$-alkyl, —NH—C$_{1-5}$-alkyl, N(C$_{1-5}$alkyl)$_2$, —C(=O)—O—C$_{1-5}$-alkyl, —C(=O)—H, —C(=O)—C$_{1-5}$-alkyl, —CH$_2$—O—C(=O)-phenyl, —O—C(=O)-phenyl, —NH—S(=O)$_2$—C$_{1-5}$-alkyl, —NH—C(=O)—C$_{1-5}$-alkyl, —C(=O)—NH$_2$, —C(=O)—NH—C$_{1-5}$-alkyl, —C(=O)—N(C$_{1-5}$-alkyl)$_2$, pyrazolyl, phenyl, furyl (furanyl), thiazolyl, thiadiazolyl, thiophenyl (thienyl), benzyl and Phenethyl, the cyclic substituents and the cyclic radicals of these substituents themselves being able to be substituted with, as appropriate, 1, 2, 3, 4 or 5 substituents selected independently of one another from the group consisting of F, Cl, Br, I, —CN, —NO$_2$, —OH, —SH, —NH$_2$, —C(=O)—OH, —C$_{1-5}$-alkyl, —(CH$_2$)—O—C$_{1-5}$-alkyl, —C$_{2-5}$-alkenyl, —C$_{2-5}$-alkynyl, —C≡C—Si(CH$_3$)$_3$, —C≡C—Si(C$_2$H$_5$)$_3$, —S—C$_{1-5}$-alkyl, —S-phenyl, —S—CH$_2$-phenyl, —O—C$_{1-5}$-alkyl, —O-phenyl, —O—CH$_2$-phenyl, —CF$_3$, —CHF$_2$, —CH$_2$F, —O—CF$_3$, —O—CHF$_2$, —O—CH$_2$F, —C(=O)—CF$_3$, —S—CF$_3$, —S—CHF$_2$ and —S—CH$_2$F;

each optionally in the form of one of the pure stereoisomers, in particular enantiomers or diastereomers thereof, or the racemates thereof, or in the form of a mixture of stereoisomers, in particular the enantiomers and/or diastereomers, mixed in any ratios, or each in the form of corresponding salts, or each in the form of corresponding solvates.

Also preferred are substituted thiazoles of the foregoing general formula I, in which $R^1$ represents H; F; Cl; Br; I; —NO$_2$; —CN; —NH$_2$; —OH; —SH; —C(=O)—OH; —C(=O)—H; —NH—C(=O)—H; —NH—R$^{33}$; —NR$^{34}$R$^{35}$; —C(=O)—R$^{36}$; —C(=O)—O—R$^{37}$; —O—C(=O)—R$^{38}$; —NH—C(=O)—R$^{39}$; —NR$^{40}$—C(=O)—R$^{41}$; —C(=O)—NH$_2$; —C(=O)—NH—R$^{42}$; —C(=O)—NR$^{43}$R$^{44}$; —O—R$^{45}$; —S—R$^{46}$; —S(=O)—R$^{47}$; —S(=O)$_2$—R$^{48}$; —NH—C(=O)—NH—R$^{49}$; —NH—C(=S)—NH—R$^{50}$; —NH—S(=O)$_2$—R$^{51}$; —NR$^{52}$—S(=O)$_2$—R$^{53}$; C$_{1-6}$-alkyl, which is unsubstituted or substituted with, as appropriate, 1, 2, 3, 4 or 5 substituents selected independently of one another from the group consisting of F, Cl, Br, I, —NO$_2$, —CN, —OH, —SH and —NH$_2$; C$_{3-7}$ cycloalkyl, C$_{5-6}$ cycloalkenyl, heterocycloalkyl with 5 to 7 members and heterocycloalkenyl with 5 to 7 members, each of which may be linked by a C$_{1-3}$ alkylene, C$_{2-3}$ alkenylene or C$_{2-3}$ alkynylene group and/or is unsubstituted or substituted with, as appropriate, 1, 2, 3, 4 or 5 substituents selected independently of one another from the group consisting of F, Cl, Br, I, —CN, methyl, ethyl, n-propyl, isopropyl, n-butyl, 2-butyl, isobutyl, tert-butyl, —OH, oxo, thioxo, —O—CH$_3$, —O—C$_2$H$_5$, —O—C$_3$H$_7$, —NH$_2$, —N(CH$_3$)$_2$, —N(C$_2$H$_5$)$_2$, —NH—CH$_3$, —NH—C$_2$H$_5$, —NO$_2$, —CF$_3$, —O—CF$_3$, —S—CF$_3$, —SH, —S—CH$_3$ and —S—C$_2$H$_5$; or represents a radical selected from the group consisting of phenyl, naphthyl, anthracenyl, thienyl, furyl, pyridinyl, thiazolyl, thiadiazolyl, oxazolyl, oxadiazolyl and isoxazolyl, each of which may be linked by a C$_{1-3}$ alkylene, C$_{2-3}$ alkenylene or C$_{2-3}$ alkynylene group and/or is unsubstituted or substituted with, as appropriate, 1, 2, 3, 4 or 5 substituents selected independently of one another from the group consisting of F, Cl, Br, I, —CN, methyl, ethyl, n-propyl, isopropyl, n-butyl, isobutyl, 2-butyl, tert-butyl, —OH, oxo, thioxo, —O—CH$_3$, —O—C$_2$H$_5$, —O—C$_3$H$_7$, —NH$_2$, —N(CH$_3$)$_2$, —N(C$_2$H$_5$)$_2$, —NH—CH$_3$, —NH—C$_2$H$_5$, —NO$_2$, —CF$_3$, —O—CF$_3$, —S—CF$_3$, —SH, —S—CH$_3$, —S—C$_2$H$_5$, —S(=O)—CH$_3$, —S(=O)$_2$—CH$_3$, —S(=O)—C$_2$H$_5$, —S(=O)$_2$—C$_2$H$_5$, —O—CH$_3$, —O—C$_2$H$_5$, —O—C$_3$H$_7$, —CF$_3$, —CHF$_2$, —CH$_2$F and —O—CF$_3$;

and the remaining radicals each have the meaning given above, each optionally in the form of one of the pure stereoisomers, in particular enantiomers or diastereomers thereof, or the racemates thereof, or in the form of a mixture of stereoisomers, in particular the enantiomers and/or diastereomers, mixed in any ratios, or each in the form of corresponding salts, or each in the form of corresponding solvates.

Also preferred are substituted thiazoles of the foregoing general formula I, in which $R^2$ represents H; F; Cl; Br; I; —NO$_2$; —CN; —NH$_2$; —OH; —SH; —C(=O)—OH; —NH—R$^{33}$; —NR$^{34}$R$^{35}$; —C(=O)—R$^{36}$; —C(=O)—O—R$^{37}$; —C(=O)—NH$_2$; —C(=O)—NH—R$^{42}$; —C(=O)—NR$^{43}$R$^{44}$; O—R$^{45}$; —S—R$^{46}$; —S(=O)—R$^{47}$; —S(=O)$_2$—R$^{48}$; —NH—C(=O)—NH—R$^{49}$; —NH—C(=O)—NH—R$^{50}$; —NH—S(=O)$_2$—R$^{51}$; —NR$^{52}$—S(=O)$_2$—R$^{53}$; C$_{1-6}$-alkyl, which is unsubstituted or substituted with, as appropriate, 1, 2, 3, 4 or 5 substituents selected independently of one another from the group consisting of F, Cl, Br, I, —NO$_2$, —CN, —OH, —SH and —NH$_2$; C$_{3-7}$ cycloalkyl, C$_{5-6}$ cycloalkenyl, heterocycloalkyl with 5 to 7 members and heterocycloalkenyl with 5 to 7 members, each of which may be linked by a C$_{1-3}$ alkylene, C$_{2-3}$ alkenylene or C$_{2-3}$ alkynylene group and/or is unsubstituted or substituted with, as appropriate, 1, 2, 3, 4 or 5 substituents selected independently of one another from the group consisting of F, Cl, Br, I, —CN, methyl, ethyl, n-propyl, isopropyl, n-butyl, 2-butyl, isobutyl, tert-butyl, —OH, oxo, thioxo, —O—CH$_3$, —O—C$_2$H$_5$, —O—C$_3$H$_7$, —NH$_2$, —N(CH$_3$)$_2$, —N(C$_2$H$_5$)$_2$, —NH—CH$_3$, —NH—C$_2$H$_5$, —NO$_2$, —CF$_3$, —O—CF$_3$, —S—CF$_3$, —SH, —S—CH$_3$ and —S—C$_2$H$_5$; or represents a radical selected from the group consisting of phenyl, naphthyl, anthracenyl, thienyl, furyl, pyridinyl, thiazolyl, thiadiazolyl, oxazolyl, oxadiazolyl and isoxazolyl, each of which may be linked by a C$_{1-3}$ alkylene, C$_{2-3}$ alkenylene or C$_{2-3}$ alkynylene group and/or is unsubstituted or substituted with, as appropriate, 1, 2, 3, 4 or 5 substituents selected independently of one another from the group consisting of F, Cl, Br, I, —CN, methyl, ethyl, n-propyl, isopropyl, n-butyl, isobutyl, 2-butyl, tert-butyl, —OH, —SH, —NH$_2$, —C(=O)—OH, —S—CH$_3$, —S—C$_2$H$_5$, —S(=O)—CH$_3$, —S(=O)$_2$—CH$_3$, —S(=O)—C$_2$H$_5$, —S(=O)$_2$—C$_2$H$_5$, —O—CH$_3$, —O—C$_2$H$_5$, —O—C$_3$H$_7$, —CF$_3$, —CHF$_2$, —CH$_2$F and —O—CF$_3$;

Further preferred are substituted thiazoles of the foregoing general formula I, in which $R^1$ and $R^2$ together with the carbon atoms linking them form a phenylene radical, which is unsubstituted or substituted with 1, 2, 3 or 4 substituents selected independently of one another from the group consisting of F, Cl, Br, I, —CN, methyl, ethyl, n-propyl, isopropyl, n-butyl, isobutyl, 2-butyl, tert-butyl, —OH, —SH, —NH$_2$, —C(=O)—OH, —S—CH$_3$, —S—C$_2$H$_5$, —S(=O)—CH$_3$, —S(=O)$_2$—CH$_3$, —S(=O)—C$_2$H$_5$, —S(=O)$_2$—C$_2$H$_5$, —O—CH$_3$, —O—C$_2$H$_5$, —O—C$_3$H$_7$, —CF$_3$, —CHF$_2$, —CH$_2$F and —O—CF$_3$;

and the remaining radicals each have the meaning given above, each optionally in the form of one of the pure stereoisomers, in particular enantiomers or diastereomers thereof, or the racemates thereof, or in the form of a mixture of stereoisomers, in particular the enantiomers and/or diastereomers, mixed in any ratios, or each in the form of corresponding salts, or each in the form of corresponding solvates.

Also preferred are substituted thiazoles of the foregoing general formula I, in which $R^3$ and $R^{10}$, independently of one another, represent H; —C(=O)—$R^{36}$; —C(=O)—O—$R^{37}$; —C(=O)—$NH_2$; —C(=O)—NH—$R^{42}$; —C(=O)—$NR^{43}R^{44}$; —S(=O)—$R^{47}$; —S(=O)$_2$—$R^{48}$; $C_{1-6}$-alkyl, which is unsubstituted or substituted with, as appropriate, 1, 2, 3, 4 or 5 substituents selected independently of one another from the group consisting of F, Cl, Br, I, —$NO_2$, —CN, —OH, —SH and —$NH_2$; $C_{3-8}$-cycloalkyl, which is unsubstituted or substituted with, as appropriate, 1, 2, 3, 4 or 5 substituents selected independently of one another from the group consisting of F, Cl, Br, I, —$NO_2$, —CN, —OH, —SH and —$NH_2$; or represent a phenyl radical, which in each case may be linked by a $C_{1-3}$ alkylene, $C_{2-3}$ alkenylene or $C_{2-3}$ alkynylene group and/or is unsubstituted or substituted with 1, 2, 3, 4 or 5 substituents selected independently of one another from the group consisting of F, Cl, Br, I, —CN, methyl, ethyl, n-propyl, isopropyl, n-butyl, 2-butyl, isobutyl, tert-butyl, —OH, —O—$CH_3$, —O—$C_2H_5$ and —O—$C_3H_7$; and the remaining radicals each have the meaning given above, each optionally in the form of one of the pure stereoisomers, in particular enantiomers or diastereomers thereof, or the racemates thereof, or in the form of a mixture of stereoisomers, in particular the enantiomers and/or diastereomers, mixed in any ratios, or each in the form of corresponding salts, or each in the form of corresponding solvates.

Further preferred are substituted thiazoles of the foregoing general formula I, in which $R^4$, $R^5$, $R^6$, $R^7$, $R^8$, $R^9$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, $R^{26}$, $R^{27}$, $R^{28}$, $R^{29}$, $R^{30}$, $R^{31}$ and $R^{32}$, independently of one another, each represent H; F; Cl; Br; I; —$NO_2$; —CN; —$NH_2$; —OH; —SH; —C(=O)—OH; —NH—$R^{33}$; —$NR^{34}R^{35}$; —C(=O)—$R^{36}$; —C(=O)—O—$R^{37}$; —O—$R^{45}$; —S—$R^{46}$; $C_{1-6}$ alkyl, which is unsubstituted or substituted with, as appropriate, 1, 2, 3, 4 or 5 substituents selected independently of one another from the group consisting of F, Cl, Br, I, —$NO_2$, —CN, —OH, —SH and —$NH_2$; $C_{3-7}$ cycloalkyl, $C_{5-6}$ cycloalkenyl, heterocycloalkyl with 5 to 7 members and heterocycloalkenyl with 5 to 7 members, each of which may be linked by a $C_{1-3}$ alkylene, $C_{2-3}$ alkenylene or $C_{2-3}$ alkynylene group and/or is unsubstituted or substituted with, as appropriate, 1, 2, 3, 4 or 5 substituents selected independently of one another from the group consisting of F, Cl, Br, I, —CN, methyl, ethyl, n-propyl, isopropyl, n-butyl, 2-butyl, isobutyl, tert-butyl, —OH, oxo, thioxo, —O—$CH_3$, —O—$C_2H_5$, —O—$C_3H_7$, —$NH_2$, —N($CH_3$)$_2$, —N($C_2H_5$)$_2$, —NH—$CH_3$, —NH—$C_2H_5$, —$NO_2$, —$CF_3$, —O—$CF_3$, —S—$CF_3$, —SH, —S—$CH_3$ and —S—$C_2H_5$; or a radical selected from the group consisting of phenyl, naphthyl, anthracenyl, pyrrolyl, indolyl, furanyl, benzo[b]furanyl, thiophenyl, benzo[b]thiophenyl, benzo[d]thiazolyl, pyrazolyl, imidazolyl, thiazolyl, thiadiazolyl, triazolyl, oxazolyl, oxadiazolyl, isoxazolyl, pyridinyl, pyridazinyl, pyrimidinyl, pyrazinyl, pyranyl, indazolyl, quinolinyl, isoquinolinyl and quinazolinyl, each of which may be linked by a $C_{1-3}$ alkylene, $C_{2-3}$ alkenylene or $C_{2-3}$ alkynylene group and/or is unsubstituted or substituted with, as appropriate, 1, 2, 3, 4 or 5 substituents selected independently of one another from the group consisting of F, Cl, Br, I, —CN, methyl, ethyl, n-propyl, isopropyl, n-butyl, 2-butyl, isobutyl, tert-butyl, —OH, —O—$CH_3$, —O—$C_2H_5$ and —O—$C_3H_7$;

or $R^4$ and $R^5$ or $R^6$ and $R^7$ or $R^8$ and $R^9$ or $R^{12}$ and $R^{13}$ or $R^{14}$ and $R^{15}$ or $R^{16}$ and $R^{17}$ or $R^{18}$ and $R^{19}$ or $R^{20}$ or $R^{21}$ or $R^{22}$ and $R^{23}$ or $R^{24}$ and $R^{25}$ or $R^{26}$ and $R^{27}$ or $R^{28}$ and $R^{29}$ or $R^{31}$ and $R^{32}$ independently of one another represent, together in each case, a radical selected from the group consisting of an oxo group (=O) and a thioxo group (=S);

and the remaining radicals each have the meaning given above, each optionally in the form of one of the pure stereoisomers, in particular enantiomers or diastereomers thereof, or the racemates thereof, or in the form of a mixture of stereoisomers, in particular the enantiomers and/or diastereomers, mixed in any ratios, or each in the form of corresponding salts, or each in the form of corresponding solvates.

Also preferred are substituted thiazoles of the foregoing general formula I, in which $R^3$ and $R^4$ together with the —N—$CR^5$ group linking them form a radical selected from the group consisting of

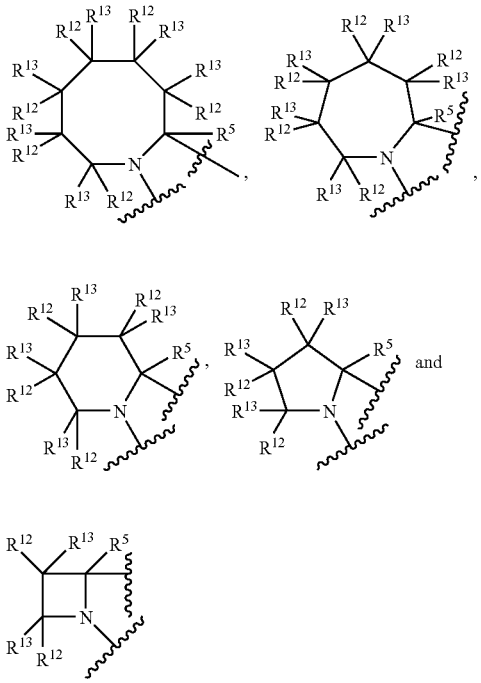

and the remaining radicals each have the meaning given above, each optionally in the form of one of the pure stereoisomers, in particular enantiomers or diastereomers thereof, or the racemates thereof, or in the form of a mixture of stereoisomers, in particular the enantiomers and/or diastereomers, mixed in any ratios, or each in the form of corresponding salts, or each in the form of corresponding solvates.

Further preferred are substituted thiazoles of the foregoing general formula I, in which $R^8$ and $R^{10}$ together with the —N—$CR^9$ group linking them form a radical selected from the group consisting of

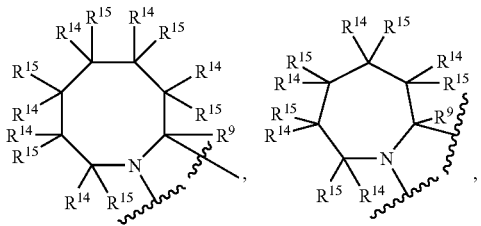

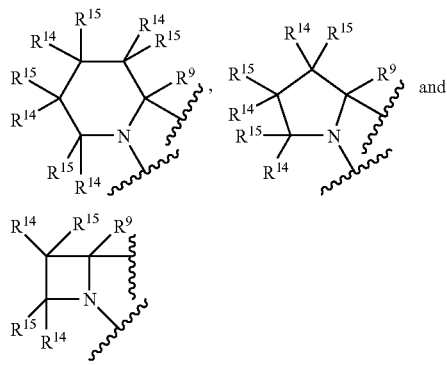

and the remaining radicals each have the meaning given above, each optionally in the form of one of the pure stereoisomers, in particular enantiomers or diastereomers thereof, or the racemates thereof, or in the form of a mixture of stereoisomers, in particular the enantiomers and/or diastereomers, mixed in any ratios, or each in the form of corresponding salts, or each in the form of corresponding solvates.

Also preferred are substituted thiazoles of the foregoing general formula I, in which $R^3$ and $R^6$ together with the —N—$CR^4R^5$—$CR^7$ group linking them form a radical selected from the group consisting of:

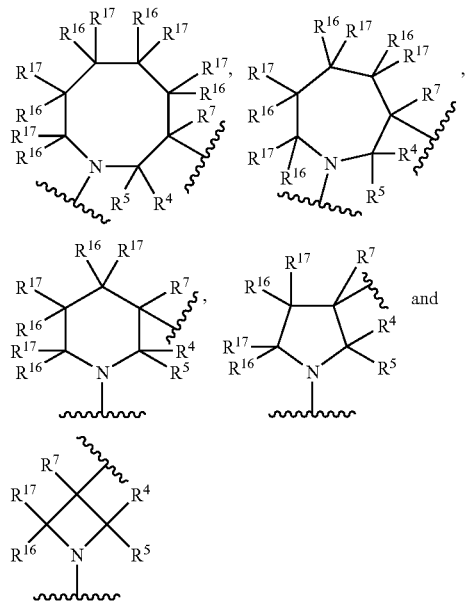

and the remaining radicals each have the meaning given above, each optionally in the form of one of the pure stereoisomers, in particular enantiomers or diastereomers thereof, or the racemates thereof, or in the form of a mixture of stereoisomers, in particular the enantiomers and/or diastereomers, mixed in any ratios, or each in the form of corresponding salts, or each in the form of corresponding solvates.

Further preferred are substituted thiazoles of the foregoing general formula I, in which $R^6$ and $R^{10}$ together with the —$CR^7$—$CR^8CR^9$—N group linking them form a radical selected from the group consisting of

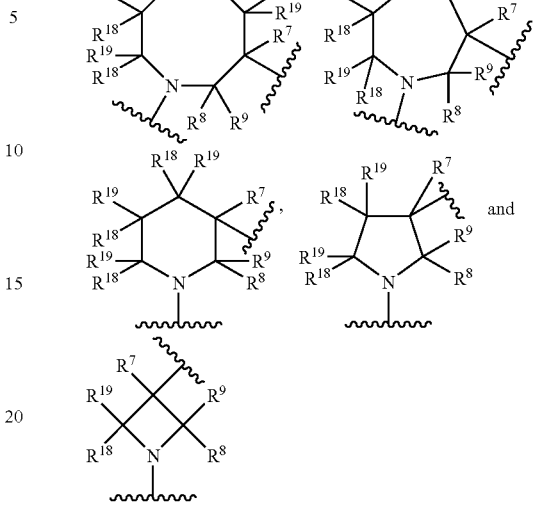

and the remaining radicals each have the meaning given above, each optionally in the form of one of the pure stereoisomers, in particular enantiomers or diastereomers thereof, or the racemates thereof, or in the form of a mixture of stereoisomers, in particular the enantiomers and/or diastereomers, mixed in any ratios, or each in the form of corresponding salts, or each in the form of corresponding solvates.

Also preferred are substituted thiazoles of the foregoing general formula I, in which $R^3$ and $R^8$ together with the —N—$CR^4R^5$—$CR^6R^7$—$CR^9$ group linking them form a radical selected from the group consisting of:

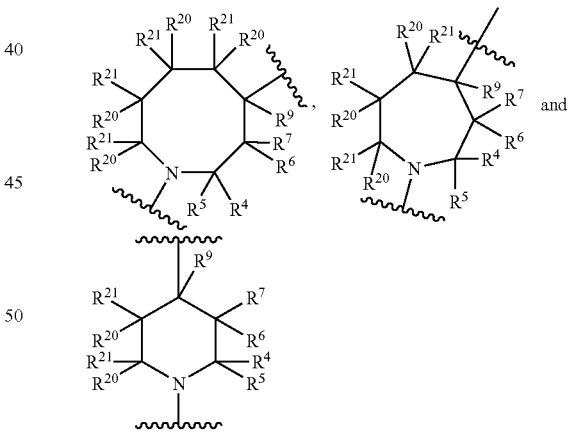

and the remaining radicals each have the meaning given above, each optionally in the form of one of the pure stereoisomers, in particular enantiomers or diastereomers thereof, or the racemates thereof, or in the form of a mixture of stereoisomers, in particular the enantiomers and/or diastereomers, mixed in any ratios, or each in the form of corresponding salts, or each in the form of corresponding solvates.

Further preferred are substituted thiazoles of the foregoing general formula I, in which $R^4$ and $R^{10}$ together with the —N—$CR^8R^9$—$CR^6R^7$—$CR^5$ group linking them form a radical selected from the group consisting of:

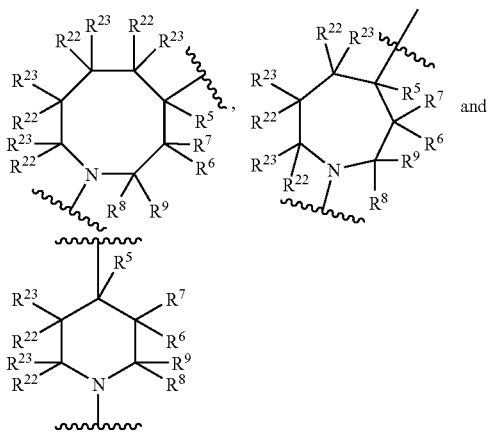

and the remaining radicals each have the meaning given above, each optionally in the form of one of the pure stereoisomers, in particular enantiomers or diastereomers thereof, or the racemates thereof, or in the form of a mixture of stereoisomers, in particular the enantiomers and/or diastereomers, mixed in any ratios, or each in the form of corresponding salts, or each in the form of corresponding solvates.

Also preferred are substituted thiazoles of the foregoing general formula I, in which $R^4$ and $R^8$ together with the —$CR^5$—$CR^6R^7$—$CR^9$ group linking them form a radical selected from the group consisting of:

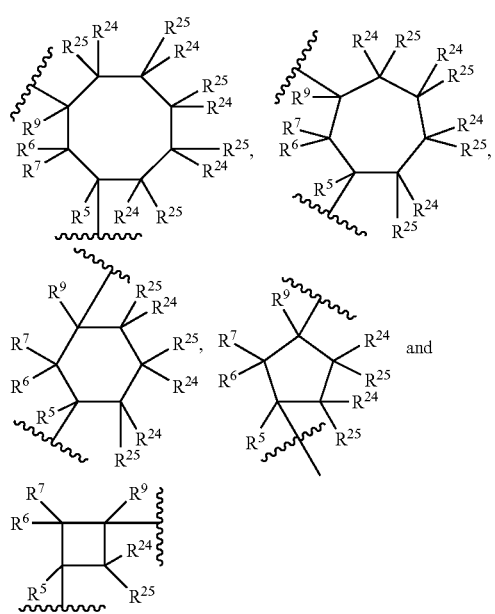

and the remaining radicals each have the meaning given above, each optionally in the form of one of the pure stereoisomers, in particular enantiomers or diastereomers thereof, or the racemates thereof, or in the form of a mixture of stereoisomers, in particular the enantiomers and/or diastereomers, mixed in any ratios, or each in the form of corresponding salts, or each in the form of corresponding solvates.

Further preferred are substituted thiazoles of the foregoing general formula I, in which $R^3$ and $R^{10}$ together with the —N—$CR^4R^5$—$CR^6R^7$—$CR^8R^9$—N group linking them form a radical selected from the group consisting of:

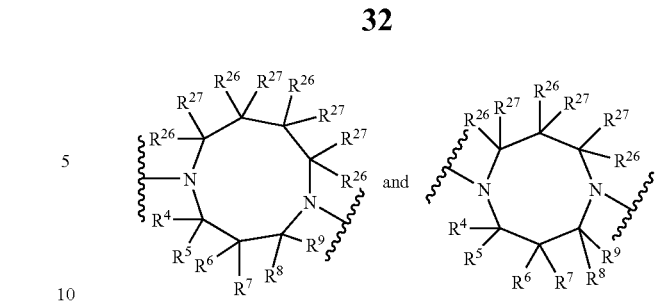

and the remaining radicals each have the meaning given above, each optionally in the form of one of the pure stereoisomers, in particular enantiomers or diastereomers thereof, or the racemates thereof, or in the form of a mixture of stereoisomers, in particular the enantiomers and/or diastereomers, mixed in any ratios, or each in the form of corresponding salts, or each in the form of corresponding solvates.

Further preferred are substituted thiazoles of the foregoing general formula I, in which $R^3$ and $R^{10}$ together with the —N—$CR^4R^5$—$CR^6R^7$—$CR^8R^9$—N group linking them form a bicyclic radical selected from the group consisting of:

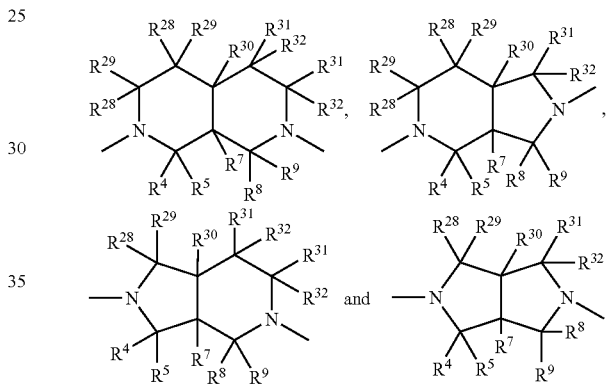

and the remaining radicals each have the meaning given above, each optionally in the form of one of the pure stereoisomers, in particular enantiomers or diastereomers thereof, or the racemates thereof, or in the form of a mixture of stereoisomers, in particular the enantiomers and/or diastereomers, mixed in any ratios, or each in the form of corresponding salts, or each in the form of corresponding solvates.

Also preferred are substituted thiazoles of the foregoing general formula I, in which $R^{11}$ represents a radical selected from the group consisting of phenyl, naphthyl, anthracenyl, furyl, thienyl, pyrazolyl, pyrazinyl, pyridazinyl, pyrimidinyl, pyridinyl, pyrrolyl, oxazolyl, isoxazolyl, thiazolyl, thiadiazolyl, oxadiazolyl, triazolyl, imidazolyl, indolyl, benzo[b]thiophenyl, benzo[d]thiazolyl, benzo[b]furanyl, quinolinyl, isoquinolinyl and quinazolinyl, each of which is unsubstituted or substituted with, as appropriate, 1, 2, 3, 4 or 5 substituents selected independently of one another from the group consisting of F, Cl, Br, I, —CN, methyl, ethyl, n-propyl, isopropyl, n-butyl, 2-butyl, isobutyl, tert-butyl, ethenyl, allyl, ethynyl, propynyl, —C≡C—Si(CH$_3$)$_3$, —C≡C—Si(C$_2$H$_5$)$_3$, —CH$_2$—O—CH$_3$, —CH$_2$—O—C$_2$H$_5$, —OH, —O—CH$_3$, —O—C$_2$H$_5$, —O—C$_3$H$_7$, —S—CH$_3$, —S—C$_2$H$_5$, —S(═O)—CH$_3$, —S(═O)$_2$—CH$_3$, —S(═O)—C$_2$H$_5$, —S(═O)$_2$—C$_2$H$_5$, —NH$_2$, —N(CH$_3$)$_2$, —N(C$_2$H$_5$)$_2$, —NH—CH$_3$, —NH—C$_2$H$_5$, —NO$_2$, —CF$_3$, —CH$_2$F, —CHF$_2$, —O—CF$_3$, —S—CF$_3$, —SH, —NH—S(═O)$_2$—CH$_3$, —C(═O)—OH, —C(═O)—H;

—C(=O)—CH₃, —C(=O)—C₂H₅, —C(=O)—NH₂, —C(=O)—N(CH₃)₂, —C(=O)—NH—CH₃, —NH—C(=O)—CH₃, —NH—C(=O)—C₂H₅, —C(=O)—O—CH₃, —C(=O)—O—C₂H₅, —C(=O)—O—C(CH₃)₃ and phenyl;

and the remaining radicals each have the meaning given above, each optionally in the form of one of the pure stereoisomers, in particular enantiomers or diastereomers thereof, or the racemates thereof, or in the form of a mixture of stereoisomers, in particular the enantiomers and/or diastereomers, mixed in any ratios, or each in the form of corresponding salts, or each in the form of corresponding solvates.

Also preferred are substituted thiazoles of the foregoing general formula I, in which $R^{33}$, $R^{34}$, $R^{35}$, $R^{36}$, $R^{37}$, $R^{38}$, $R^{39}$, $R^{40}$, $R^{41}$, $R^{42}$, $R^{43}$, $R^{44}$, $R^{45}$, $R^{46}$, $R^{47}$, $R^{48}$, $R^{49}$, $R^{50}$, $R^{51}$, $R^{52}$ and $R^{53}$ independently of one another each represent $C_{1-6}$-alkyl, which is unsubstituted or substituted with, as appropriate, 1, 2, 3, 4 or 5 substituents selected independently of one another from the group consisting of F, Cl, Br, I, —NO₂, —CN, —OH, —SH and —NH₂; $C_{3-7}$ cycloalkyl, $C_{5-6}$ cycloalkenyl, heterocycloalkyl with 5 to 7 members and heterocycloalkenyl with 5 to 7 members, each of which may be linked by a $C_{1-3}$ alkylene, $C_{2-3}$ alkenylene or $C_{2-3}$ alkynylene group and/or is unsubstituted or substituted with, as appropriate, 1, 2, 3, 4 or 5 substituents selected independently of one another from the group consisting of F, Cl, Br, I, —CN, methyl, ethyl, n-propyl, isopropyl, n-butyl, 2-butyl, isobutyl, tert-butyl, —OH, oxo, thioxo, —O—CH₃, —O—C₂H₅, —O—C₃H₇, —NH₂, —N(CH₃)₂, —N(C₂H₅)₂, —NH—CH₃, —NH—C₂H₅, —NO₂, —CF₃, —O—CF₃, —S—CF₃, —SH, —S—CH₃ and —S—C₂H₅; or a radical selected from the group consisting of phenyl, naphthyl, anthracenyl, pyrrolyl, indolyl, furanyl, benzo[b]furanyl, thiophenyl, benzo[b]thiophenyl, benzo[d]thiazolyl, pyrazolyl, imidazolyl, thiazolyl, thiadiazolyl, triazolyl, oxazolyl, oxadiazolyl, isoxazolyl, pyridinyl, pyridazinyl, pyrimidinyl, pyrazinyl, pyranyl, indazolyl, quinolinyl, isoquinolinyl and quinazolinyl, each of which may be linked by a $C_{1-3}$ alkylene, $C_{2-3}$ alkenylene or $C_{2-3}$ alkynylene group and/or is unsubstituted or substituted with, as appropriate, 1, 2, 3, 4 or 5 substituents selected independently of one another from the group consisting of F, Cl, Br, I, —CN, methyl, ethyl, n-propyl, isopropyl, n-butyl, 2-butyl, isobutyl, tert-butyl, —OH, —O—CH₃, —O—C₂H₅, —O—C₃H₇, —NH₂, —N(CH₃)₂, —N(C₂H₅)₂, —NH—CH₃, —NH—C₂H₅, —NO₂, —CF₃, —O—CF₃, —S—CF₃, —SH, —NH—S(=O)₂—CH₃, —C(=O)—OH, —C(=O)—CH₃, —C(=O)—C₂H₅, —C(=O)—N(CH₃)₂, —C(=O)—NH—CH₃, —NH—C(=O)—CH₃, —NH—C(=O)—C₂H₅, —C(=O)—O—CH₃ and —C(=O)—O—C₂H₅;

and the remaining radicals each have the meaning given above, each optionally in the form of one of the pure stereoisomers, in particular enantiomers or diastereomers thereof, or the racemates thereof, or in the form of a mixture of stereoisomers, in particular the enantiomers and/or diastereomers, mixed in any ratios, or each in the form of corresponding salts, or each in the form of corresponding solvates.

Further preferred are substituted thiazoles of the foregoing general formula I, in which $R^1$ represents H; F; Cl; Br; I; —CF₃; —NO₂; —CN; —NH₂; —OH; —SH; —C(=O)—OH; —C(=O)—H; —NH—C(=O)—H; —NH—$R^{33}$; —N$R^{34}R^{35}$; —C(=O)—$R^{36}$; —C(=O)—O—$R^{37}$; —C(=O)—NH₂; —C(=O)—NH—$R^{42}$; —C(=O)—N$R^{43}R^{44}$; —O—$R^{45}$; —S—$R^{46}$; —S(=O)—$R^{47}$; —S(=O)₂—$R^{48}$; unsubstituted $C_{1-6}$ alkyl; or a radical selected from the group consisting of (1,3)-dioxolan-2-yl, phenyl, benzyl, phenethyl, oxadiazolyl, 2-pyridyl, 3-pyridyl, 4-pyridyl, 2-thienyl, 3-thienyl, 2-furyl and 3-furyl, each of which is unsubstituted or substituted with, as appropriate, 1, 2, 3, 4 or 5 substituents selected independently of one another from the group consisting of F, Cl, Br, I, —CN, methyl, ethyl, n-propyl, isopropyl, n-butyl, 2-butyl, isobutyl, tert-butyl, —OH, —O—CH₃, —O—C₂H₅ and —O—C₃H₇;

$R^2$ represents H; F; Cl; Br; I; —CF₃; —NO₂; —CN; —NH₂; —OH; —SH; —C(=O)—OH; —C(=O)—H; —NH—C(=O)—H; —NH—$R^{33}$; —N$R^{34}R^{35}$; —C(=O)—$R^{36}$; —C(=O)—O—$R^{37}$; —C(=O)—NH₂; —C(=O)—NH—$R^{42}$; —C(=O)—N$R^{43}R^{44}$; —O—$R^{45}$; —S—$R^{46}$; —S(=O)—$R^{47}$; —S(=O)₂—$R^{48}$; unsubstituted $C_{1-6}$-alkyl or a radical selected from the group consisting of (1,3)-dioxolan-2-yl, phenyl, benzyl, phenethyl, oxadiazolyl, 2-pyridyl, 3-pyridyl, 4-pyridyl, 2-thienyl, 3-thienyl, 2-furyl and 3-furyl, each of which is unsubstituted or substituted with, as appropriate, 1, 2, 3, 4 or 5 substituents selected independently of one another from the group consisting of F, Cl, Br, I, —CN, methyl, ethyl, n-propyl, isopropyl, n-butyl, 2-butyl, isobutyl, tert-butyl, —OH, —O—CH₃, —O—C₂H₅ and —O—C₃H₇;

or $R^1$ and $R^2$ together with the carbon atoms linking them form a phenylene radical, which is unsubstituted or substituted with 1, 2, 3 or 4 substituents selected independently of one another from the group consisting of F, Cl, Br, I, —CN, methyl, ethyl, n-propyl, isopropyl, n-butyl, isobutyl, 2-butyl, tert-butyl, —OH, —SH, —NH₂, —C(=O)—OH, —S—CH₃, —S—C₂H₅, —S(=O)—CH₃, —S(=O)₂—CH₃, —S(=O)—C₂H₅, —S(=O)₂—C₂H₅, —O—CH₃, —O—C₂H₅, —O—C₃H₇, —CF₃, —CHF₂, —CH₂F and —O—CF₃;

$R^3$ and $R^{10}$ independently of one another each represent H; —C(=O)—$R^{36}$; —C(=O)—O—$R^{37}$; —C(=O)—NH₂; —C(=O)—NH—$R^{42}$; —C(=O)—N$R^{43}R^{44}$; —S(=O)—$R^{47}$; —S(=O)₂—$R^{48}$; $C_{1-6}$ alkyl, which is unsubstituted or substituted with, as appropriate, 1, 2, 3, 4 or 5 substituents selected independently of one another from the group consisting of F, Cl, Br, I, —NO₂, —CN, —OH, —SH and —NH₂; $C_{3-6}$-cycloalkyl, which is unsubstituted or substituted with, as appropriate, 1, 2, 3, 4 or 5 substituents selected independently of one another from the group consisting of F, Cl, Br, I, —NO₂, —CN, —OH, —SH and —NH₂; or a phenyl radical, each of which may be linked by a $C_{1-3}$ alkylene, $C_{2-3}$ alkenylene or $C_{2-3}$ alkynylene group and/or is unsubstituted or substituted with, as appropriate, 1, 2, 3, 4 or 5 substituents selected independently of one another from the group consisting of F, Cl, Br, I, —CN, methyl, ethyl, n-propyl, isopropyl, n-butyl, 2-butyl, isobutyl, tert-butyl, —OH, —O—CH₃, —O—C₂H₅ and —O—C₃H₇;

$R^4$, $R^5$, $R^6$, $R^7$, $R^8$, $R^9$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, $R^{26}$, $R^{27}$, $R^{28}$, $R^{29}$, $R^{30}$, $R^{31}$ and $R^{32}$ each independently of one another represent H; F; Cl; Br; I; —NO₂; —CN; —NH₂; —OH; —SH; —C(=O)—OH; —NH—$R^{33}$; —N$R^{34}R^{35}$; —C(=O)—$R^{36}$; —C(=O)—O—$R^{37}$; —O—$R^{45}$; —S—$R^{46}$; unsubstituted $C_{1-6}$-alkyl; or a radical selected from the group consisting of phenyl, benzyl and phenethyl, which is unsubstituted or substituted with, as appropriate, 1, 2, 3, 4 or 5 substituents selected independently of one another from the group consisting of F, Cl, Br, I, —CN, methyl, ethyl, n-propyl, isopropyl, n-butyl, 2-butyl, isobutyl, tert-butyl, —OH, —O—CH₃, —O—C₂H₅ and —O—C₃H₇;

or $R^4$ and $R^5$ or $R^6$ and $R^7$ or $R^8$ and $R^9$ or $R^{12}$ and $R^{13}$ or $R^{14}$ and $R^{15}$ or $R^{16}$ and $R^{17}$ or $R^{18}$ and $R^{19}$ or $R^{20}$ and $R^{21}$ or $R^{22}$ and $R^{23}$ or $R^{24}$ and $R^{25}$ or $R^{26}$ and $R^{27}$ or $R^{28}$ and $R^{29}$ or $R^{31}$ and $R^{32}$ independently of one another represent, together in each case, a radical selected from the group consisting of an oxo group (=O) and a thioxo group (=S);

or $R^3$ and $R^4$ together with the —N—$CR^5$ group linking them form a radical selected from the group consisting of:

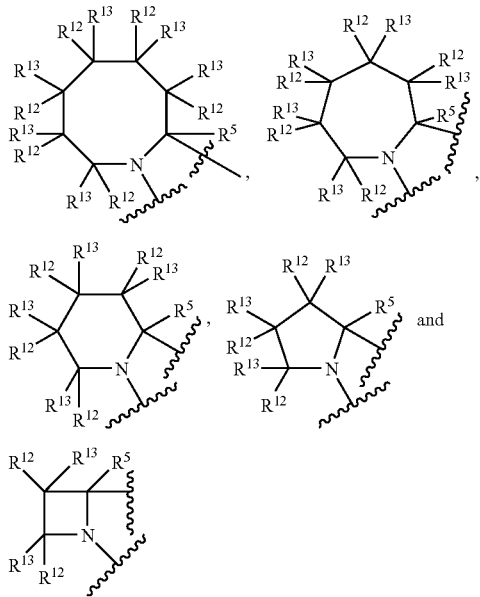

or $R^8$ and $R^{10}$ together with the —N—$CR^9$ group linking them form a radical selected from the group consisting of:

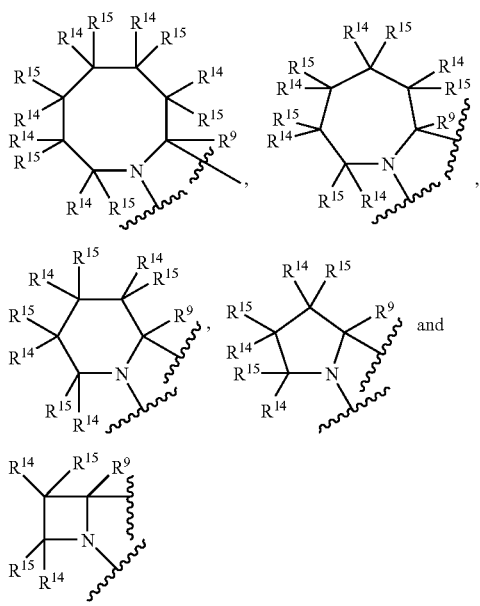

or $R^3$ and $R^6$ together with the —N—$CR^4R^5$—$CR^7$ group linking them form a radical selected from the group consisting of:

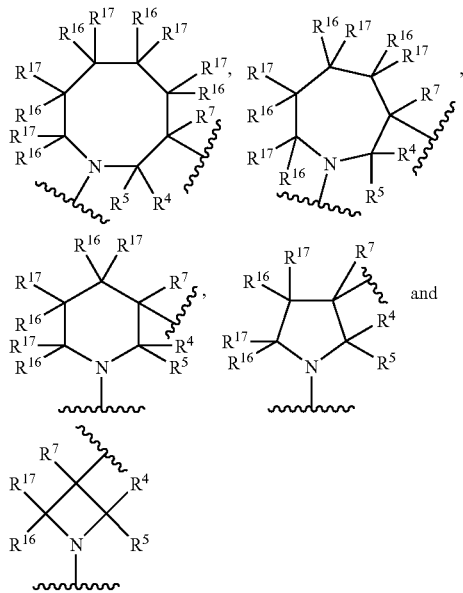

or $R^6$ and $R^{10}$ together with the —$CR^7$—$CR^8CR^9$—N group linking them form a radical selected from the group consisting of:

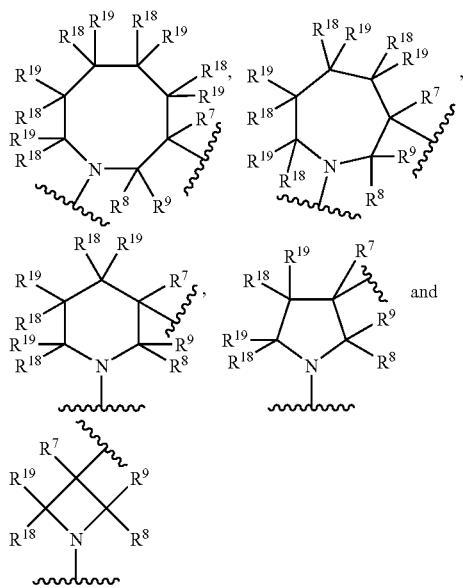

or $R^3$ and $R^8$ together with the —N—$CR^4R^5$—$CR^6R^7$—$CR^9$ group linking them form a radical selected from the group consisting of:

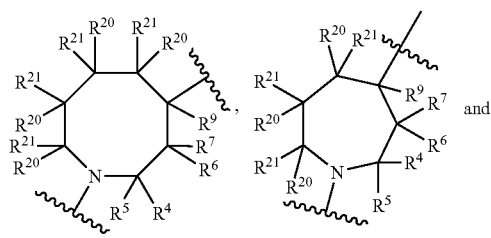

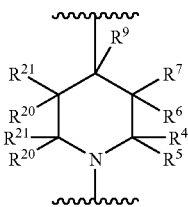

or R⁴ and R¹⁰ together with the —N—CR⁸R⁹—CR⁶R⁷—CR⁵ group linking them form a radical selected from the group consisting of:

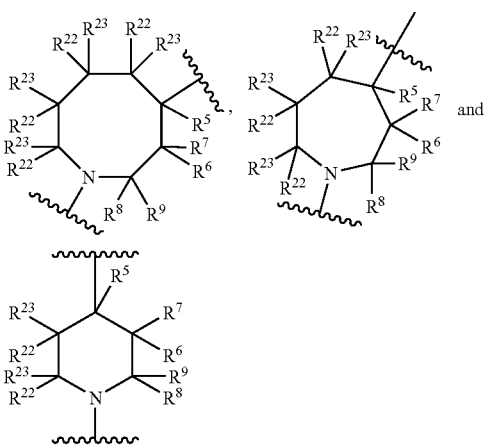

or R⁴ and R⁸ together with the —CR⁵—CR⁶R⁷—CR⁹ group linking them form a radical selected from the group consisting of:

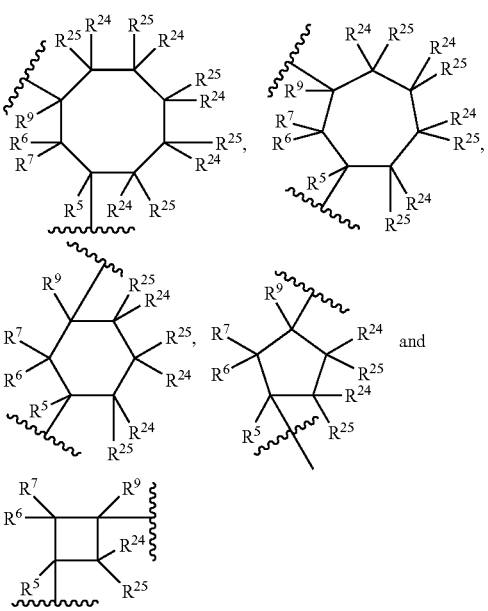

or R³ and R¹⁰ together with the —N—CR⁴R⁵—CR⁶R⁷—CR⁸R⁹—N group linking them form a radical selected from the group consisting of

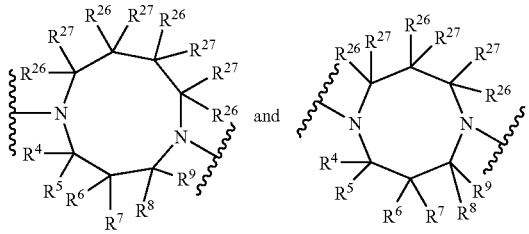

or R³ and R¹⁰ together with the —N—CR⁴R⁵—CR⁶R⁷—CR⁸R⁹—N group linking them form a bicyclic radical selected from the group consisting of:

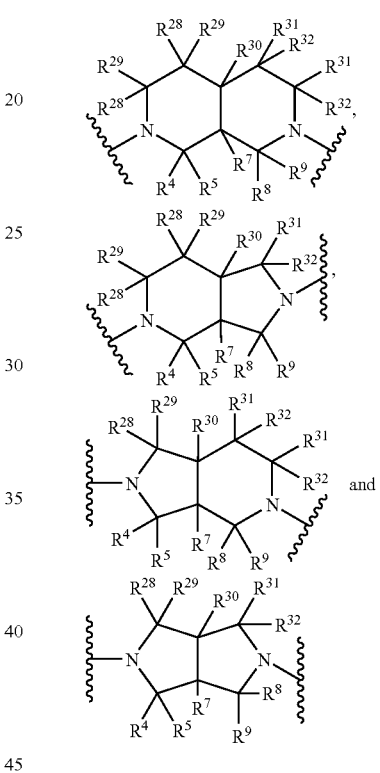

R¹¹ represents a radical selected from the group consisting of phenyl, naphthyl, anthracenyl, furyl, thienyl, pyrazolyl, pyridazinyl, pyrazinyl, pyrimidinyl, pyridinyl, pyrrolyl, oxazolyl, isoxazolyl, thiazolyl, thiadiazolyl, oxadiazolyl, triazolyl, imidazolyl, indolyl, benzo[b]thiophenyl, benzo[d]thiazolyl, benzo[b]furanyl, quinolinyl, isoquinolinyl and quinazolinyl, each of which is unsubstituted or substituted with, as appropriate, 1, 2, 3, 4 or 5 substituents selected independently of one another from the group consisting of F, Cl, Br, I, —CN, methyl, ethyl, n-propyl, isopropyl, n-butyl, 2-butyl, isobutyl, tert-butyl, ethenyl, allyl, ethynyl, propynyl, —C≡C—Si(CH₃)₃, —C≡C—Si(C₂H₅)₃, —CH₂—O—CH₃, —CH₂—O—C₂H₅, —OH, —O—CH₃, —O—C₂H₅, —O—C₃H₇, —S—CH₃, —S—C₂H₅, —S(=O)—CH₃, —S(=O)₂—CH₃, —S(=O)—C₂H₅, —S(=O)₂—C₂H₅, —NH₂, —N(CH₃)₂, —N(C₂H₅)₂, —NH—CH₃, —NH—C₂H₅, —NO₂, —CF₃, —CH₂F, —CHF₂, —O—CF₃, —S—CF₃, —SH, —NH—S(=O)₂—CH₃, —C(=O)—OH, —C(=O)—H; —C(=O)—CH₃, —C(=O)—C₂H₅, —C(=O)—NH₂, —C(=O)—N(CH₃)₂, —C(=O)—

NH—CH$_3$, —NH—C(=O)—CH$_3$, —NH—C(=O)—C$_2$H$_5$, —C(=O)—O—CH$_3$, —C(=O)—O—C$_2$H$_5$, —C(=O)—O—C(CH$_3$)$_3$ and phenyl;

and R$^{33}$, R$^{34}$, R$^{35}$, R$^{36}$, R$^{37}$, R$^{42}$, R$^{43}$, R$^{44}$, R$^{45}$, R$^{46}$, R$^{47}$ and R$^{43}$ independently of one another each represent unsubstituted C$_{1-6}$-alkyl; unsubstituted C$_{3-7}$-cycloalkyl; unsubstituted C$_{5-6}$-cycloalkenyl; unsubstituted heterocycloalkyl with 5 to 7 members and unsubstituted heterocycloalkenyl with 5 to 7 members; or a radical selected from the group consisting of phenyl, benzyl, naphthyl, anthracenyl, pyrrolyl, indolyl, furanyl, benzo[b]furanyl, thiophenyl, benzo[b]thiophenyl, benzo[d]thiazolyl, pyrazolyl, imidazolyl, thiazolyl, thiadiazolyl, triazolyl, oxazolyl, oxadiazolyl, isoxazolyl, pyridinyl, pyridazinyl, pyrimidinyl, pyrazinyl, pyranyl, indazolyl, quinolinyl, isoquinolinyl and quinazolinyl, each of which is unsubstituted or substituted with, as appropriate, 1, 2, 3, 4 or 5 substituents selected independently of one another from the group consisting of F, Cl, Br, I, —CN, methyl, ethyl, n-propyl, isopropyl, n-butyl, 2-butyl, isobutyl, tert-butyl, —OH, —O—CH$_3$, —O—C$_2$H$_5$, —O—C$_3$H$_7$, —NH$_2$, —N(CH$_3$)$_2$, —N(C$_2$H$_5$)$_2$, —NH—CH$_3$, —NH—C$_2$H$_5$, —NO$_2$, —CF$_3$, —O—CF$_3$, —S—CF$_3$, —SH, —NH—S(=O)$_2$—CH$_3$, —C(=O)—OH, —C(=O)—CH$_3$, —C(=O)—C$_2$H$_5$, —C(=O)—N(CH$_3$)$_2$, —C(=O)—NH—CH$_3$, —NH—C(=O)—CH$_3$, —NH—C(=O)—C$_2$H$_5$, —C(=O)—O—CH$_3$ and —C(=O)—O—C$_2$H$_5$;

each optionally in the form of one of the pure stereoisomers, in particular enantiomers or diastereomers thereof, or the racemates thereof, or in the form of a mixture of stereoisomers, in particular the enantiomers and/or diastereomers, mixed in any ratios, or each in the form of corresponding salts, or each in the form of corresponding solvates.

Further preferred are substituted thiazoles of the foregoing general formula I, in which R$^1$ represents H; F; Cl; Br; I; —CF$_3$; —NO$_2$; —CN; —C(=O)—OH; —C(=O)—O—R$^{37}$; —C(=O)—NH$_2$; —C(=O)—NH—R$^{42}$; —C(=O)—NR$^{43}$R$^{44}$; —O—R$^{45}$; —S—R$^{46}$; —S(=O)—R$^{47}$; —S(=O)$_2$—R$^{48}$; an alkyl radical selected from the group consisting of methyl, ethyl, n-propyl, isopropyl, n-butyl, 2-butyl, isobutyl and tert-butyl; or a radical selected from the group consisting of (1,3)-dioxolan-2-yl, phenyl, benzyl, phenethyl, oxadiazolyl, 2-pyridyl, 3-pyridyl, 4-pyridyl, 2-thienyl, 3-thienyl, 2-furyl and 3-furyl, each of which is unsubstituted or substituted with, as appropriate, 1, 2, 3, 4 or 5 substituents selected independently of one another from the group consisting of F, Cl, Br, methyl, ethyl, n-propyl, isopropyl, n-butyl, 2-butyl, isobutyl, tert-butyl, —OH, —O—CH$_3$, —O—C$_2$H$_5$ and —O—C$_3$H$_7$;

R$^2$ represents H; F; Cl; Br; I; —CF$_3$; —NO$_2$; —CN; —C(=O)—OH; —C(=O)—O—R$^{37}$; —C(=O)—NH$_2$; —C(=O)—NH—R$^{42}$; —C(=O)—NR$^{43}$R$^{44}$; —O—R$^{45}$; —S—R$^{46}$; —S(=O)—R$^{47}$; —S(=O)$_2$—R$^{48}$; an alkyl radical selected from the group consisting of methyl, ethyl, n-propyl, isopropyl, n-butyl, 2-butyl, isobutyl and tert-butyl; or a radical selected from the group consisting of (1,3)-dioxolan-2-yl, phenyl, benzyl, phenethyl, oxadiazolyl, 2-pyridyl, 3-pyridyl, 4-pyridyl, 2-thienyl, 3-thienyl, 2-furyl and 3-furyl, each of which is unsubstituted or substituted with, as appropriate, 1, 2, 3, 4 or 5 substituents selected independently of one another from the group consisting of F, Cl, Br, methyl, ethyl, n-propyl, isopropyl, n-butyl, 2-butyl, isobutyl, tert-butyl, —OH, —O—CH$_3$, —O—C$_2$H$_5$ and —O—C$_3$H$_7$;

or R$^1$ and R$^2$ together with the carbon atoms linking them form a phenylene radical, which is unsubstituted or substituted with 1, 2, 3 or 4 substituents selected independently of one another from the group consisting of F, Cl, Br, I, —CN, methyl, ethyl, n-propyl, isopropyl, n-butyl, isobutyl, 2-butyl, tert-butyl, —O—CH$_3$, —O—C$_2$H$_5$, —O—C$_3$H$_7$, —CF$_3$, —CHF$_2$, —CH$_2$F and —O—CF$_3$;

R$^3$ and R$^{10}$ independently of one another each represent H; —C(=O)—R$^{36}$; —C(=O)—O—R$^{37}$; —S(=O)—R$^{47}$; —S(=O)$_2$—R$^{48}$; an alkyl radical selected from the group consisting of methyl, ethyl, n-propyl, isopropyl, n-butyl, 2-butyl, isobutyl, tert-butyl, n-pentyl and n-hexyl; a cycloalkyl radical selected from the group consisting of cyclopropyl, cyclobutyl, cyclopentyl and cyclohexyl; or a benzyl or phenethyl radical which is unsubstituted or substituted with 1, 2, 3, 4 or 5 substituents selected independently of one another from the group consisting of F, Cl, Br, methyl, ethyl, n-propyl, isopropyl, n-butyl, 2-butyl, isobutyl, tert-butyl, —OH, —O—CH$_3$, —O—C$_2$H$_5$ and —O—C$_3$H$_7$;

R$^4$, R$^5$, R$^6$, R$^7$, R$^8$, R$^9$, R$^{12}$, R$^{13}$, R$^{14}$, R$^{15}$, R$^{16}$, R$^{17}$, R$^{18}$, R$^{19}$, R$^{20}$, R$^{21}$, R$^{22}$, R$^{23}$, R$^{24}$, R$^{25}$, R$^{26}$, R$^{27}$, R$^{28}$, R$^{29}$, R$^{30}$, R$^{31}$ and R$^{32}$ independently of one another each represent H; F; Cl; Br; I; —NO$_2$; —CN; —NH$_2$; —OH; —SH; —NH—R$^{33}$; —NR$^{34}$R$^{35}$; —O—R$^{45}$; —S—R$^{46}$; —CF$_3$; —C$_2$F$_5$; an alkyl radical selected from the group consisting of methyl, ethyl, n-propyl, isopropyl, n-butyl, 2-butyl, isobutyl, tert-butyl, n-pentyl and n-hexyl;

or R$^4$ and R$^5$ or R$^6$ and R$^7$ or R$^8$ and R$^9$ or R$^{12}$ and R$^{13}$ or R$^{14}$ and R$^{15}$ or R$^{16}$ and R$^{17}$ or R$^{18}$ and R$^{19}$ or R$^{20}$ and R$^{21}$ or R$^{22}$ and R$^{23}$ or R$^{24}$ and R$^{25}$ or R$^{26}$ and R$^{27}$ and R$^{28}$ and R$^{29}$ or R$^{31}$ and R$^{32}$ independently of one another represent, together in each case, a radical selected from the group consisting of an oxo group (=O) and a thioxo group (=S);

or R$^3$ and R$^4$ together with the —N—CR$^5$ group linking them form a radical selected from the group consisting of:

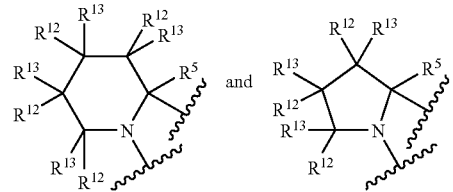

or R$^3$ and R$^{10}$ together with the —N—CR$^9$ group linking them form a radical selected from the group consisting of:

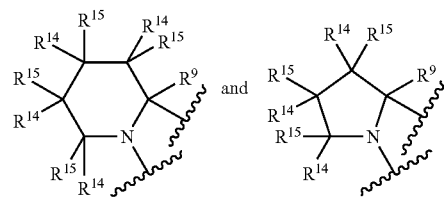

or R$^3$ and R$^6$ together with the —N—CR$^4$R$^5$—CR$^7$ group linking them form a radical selected from the group consisting of:

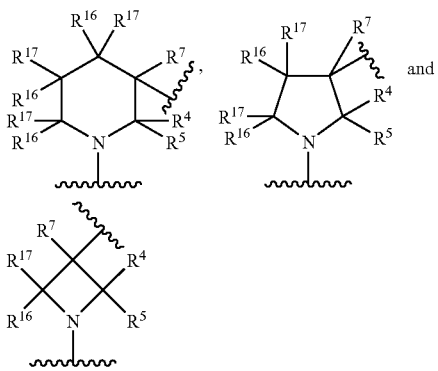

or R⁶ and R¹⁰ together with the —CR⁷—CR⁸CR⁹—N group linking them form a radical selected from the group consisting of:

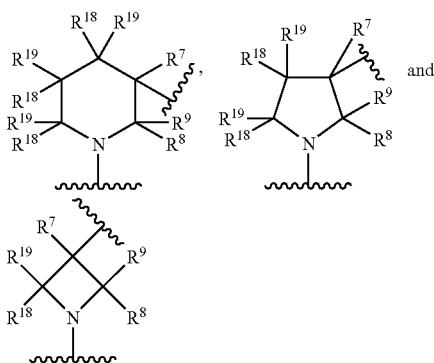

or R³ and R⁸ together with the —N—CR⁴R⁵—CR⁶R⁷—CR⁹ group linking them form the following radical:

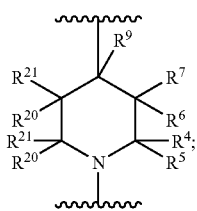

or R⁴ and R¹⁰ together with the —N—CR⁸R⁹—CR⁶R⁷—CR⁵ group linking them form the following radical:

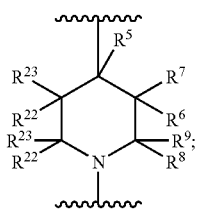

or R⁴ and R⁸ together with the —CR⁵—CR⁶R⁷—CR⁹ group linking them form a radical selected from the group consisting of:

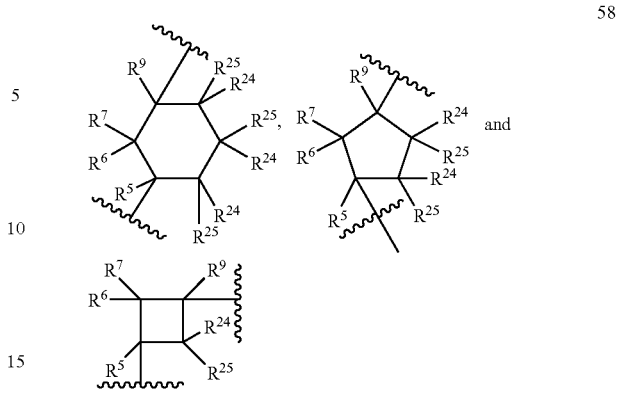

or R³ and R¹⁰ together with the —N—CR⁴R⁵—CR⁶R⁷—CR⁸R⁹—N group linking them form the following radical:

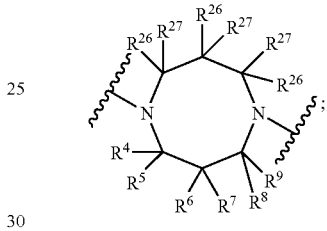

or R³ and R¹⁰ together with the —N—CR⁴R⁵—CR⁶R⁷—CR⁸R⁹—N group linking them form a bicyclic radical selected from the group consisting of

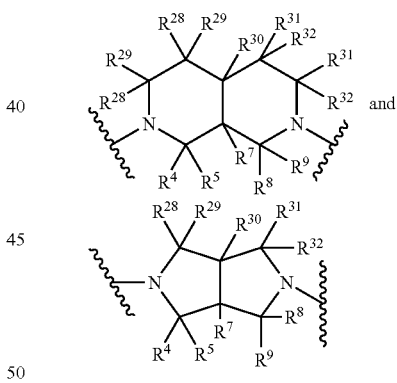

R¹¹ represents a radical selected from the group consisting of phenyl, naphthyl, anthracenyl, furyl, thienyl, pyrazolyl, pyridazinyl, pyrazinyl, pyrimidinyl, pyridinyl, pyrrolyl, oxazolyl, isoxazolyl, thiazolyl, thiadiazolyl, oxadiazolyl, triazolyl, imidazolyl, indolyl, benzo[b]thiophenyl, benzo[d]thiazolyl, benzo[b]furanyl, quinolinyl, isoquinolinyl and quinazolinyl. each of which is unsubstituted or substituted with, as appropriate, 1, 2, 3, 4 or 5 substituents selected independently of one another from the group consisting of F, Cl, Br, I, —CN, methyl, ethyl, n-propyl, isopropyl, n-butyl, 2-butyl, isobutyl, tert-butyl, ethenyl, allyl, ethynyl, propynyl, —C≡C—Si(CH₃)₃, —C≡C—Si(C₂H₅)₃, —CH₂—O—CH₃, —CH₂—O—C₂H₅, —OH, —O—CH₃, —O—C₂H₅, —O—C₃H₇, —S—CH₃, —S—C₂H₅, —S(=O)—CH₃, —S(=O)₂—CH₃, —S(=O)—C₂H₅, —S(=O)₂—C₂H₅, —NH₂, —N(CH$_3$)$_2$, —N(C$_2$H$_5$)$_2$, —NH—CH$_3$, —NH—C$_2$H$_5$, —NO$_2$, —CF$_3$, —CH$_2$F, —CHF$_2$, —O—CF$_3$, —S—CF$_3$, —SH, —NH—S(=O)$_2$—CH$_3$, —C(=O)—OH, —C(=O)—CH$_3$, —C(=O)—CH$_3$, —C(=O)—C$_2$H$_5$, —C(=O)—H; —C(=O)—CH$_3$, —C(=O)—C$_2$H$_5$, —C(=O)—NH$_2$, —C(=O)—N(CH$_3$)$_2$, —C(=O)—NH—CH$_3$, —NH—C(=O)—CH$_3$, —NH—C(=O)—C$_2$H$_5$, —C(=O)—O—CH$_3$, —C(=O)—O—C$_2$H$_5$, —C(=O)—O—C(CH$_3$)$_3$ and phenyl;

and $R^{33}$, $R^{34}$, $R^{35}$, $R^{36}$, $R^{37}$, $R^{42}$, $R^{43}$, $R^{44}$, $R^{45}$, $R^{46}$, $R^{47}$ and $R^{48}$ independently of one another each represent an alkyl radical selected from the group consisting of methyl, ethyl, n-propyl, isopropyl, n-butyl, 2-butyl, isobutyl, tert-butyl, n-pentyl and n-hexyl; or a phenyl, benzyl or phenethyl radical which is unsubstituted or substituted with 1, 2, 3, 4 or 5 substituents selected independently of one another from the group consisting of F, Cl, Br, methyl, ethyl, n-propyl, isopropyl, n-butyl, 2-butyl, isobutyl, tert-butyl, OH, —O—CH$_3$, —O—C$_2$H$_5$ and —O—C$_3$H$_7$;

each optionally in the form of one of the pure stereoisomers, in particular enantiomers or diastereomers thereof, or the racemates thereof, or in the form of a mixture of stereoisomers, in particular the enantiomers and/or diastereomers, mixed in any ratios, or each in the form of corresponding salts, or each in the form of corresponding solvates.

Most preferred are substituted thiazoles of the foregoing general formula I, in which $R^1$ represents H; F; Cl; Br; I; —CF$_3$; —NO$_2$; —CN; —C(=O)—OH; —C(=O)—O—R$^{37}$; —C(=O)—NH$_2$; —C(=O)—NH—R$^{42}$; —C(=O)—NR$^{43}$R$^{44}$; —O—R$^{45}$; —S—R$^{46}$; —S(=O)—R$^{47}$; —S(=O)$_2$—R$^{48}$; an alkyl radical selected from the group consisting of methyl, ethyl, n-propyl, isopropyl, n-butyl, 2-butyl, isobutyl and tert-butyl; or a radical selected from the group consisting of (1,3)-dioxolan-2-yl, phenyl, benzyl, phenethyl, oxadiazolyl, 2-pyridyl, 3-pyridyl, 4-pyridyl, 2-thienyl, 3-thienyl, 2-furyl and 3-furyl, each of which is unsubstituted or substituted with, as appropriate, 1, 2, 3, 4 or 5 substituents selected independently of one another from the group consisting of F, Cl, Br, methyl, ethyl, n-propyl, isopropyl, n-butyl, 2-butyl, isobutyl, tert-butyl, —OH, —O—CH$_3$, —O—C$_2$H$_5$ and —O—C$_3$H$_7$;

$R^2$ represents H; F; Cl; Br; I; —CF$_3$; —NO$_2$; —CN; —C(=O)—OH; —C(=O)—O—R$^{37}$; —C(=O)—NH$_2$; —C(=O)—NH—R$^{42}$; —C(=O)—NR$^{43}$R$^{44}$; —O—R$^{45}$; —S—R$^{46}$; —S(=O)—R$^{47}$; —S(=O)$_2$—R$^{48}$; an alkyl radical selected from the group consisting of methyl, ethyl, n-propyl, isopropyl, n-butyl, 2-butyl, isobutyl and tert-butyl; or a radical selected from the group consisting of (1,3)-dioxolan-2-yl, phenyl, benzyl, phenethyl, oxadiazolyl, 2-pyridyl, 3-pyridyl, 4-pyridyl, 2-thienyl, 3-thienyl, 2-furyl and 3-furyl, each of which is unsubstituted or substituted with, as appropriate, 1, 2, 3, 4 or 5 substituents selected independently of one another from the group consisting of F, Cl, Br, methyl, ethyl, n-propyl, isopropyl, n-butyl, 2-butyl, isobutyl, tert-butyl, —OH, —O—CH$_3$, —O—C$_2$H$_5$ and —O—C$_3$H$_7$;

or $R^1$ and $R^2$ together with the carbon atoms linking them form a phenylene radical, which is unsubstituted or substituted with 1, 2, 3 or 4 substituents selected independently of one another from the group consisting of F, Cl, Br, I, —CN, methyl, ethyl, n-propyl, isopropyl, n-butyl, isobutyl, 2-butyl, tert-butyl, —O—CH$_3$, —O—C$_2$H$_5$, —O—C$_3$H$_7$, —CF$_3$, —CHF$_2$, —CH$_2$F and —O—CF$_3$;

$R^3$ and $R^{10}$ independently of one another each represent H; —C(=O)—R$^{36}$; —C(=O)—O—R$^{37}$; —S(=O)—R$^{47}$; —S(=O)$_2$—R$^{48}$; an alkyl radical selected from the group consisting of methyl, ethyl, n-propyl, isopropyl, n-butyl, 2-butyl, isobutyl, tert-butyl, n-pentyl and n-hexyl; a cycloalkyl radical selected from the group consisting of cyclopropyl, cyclobutyl, cyclopentyl and cyclohexyl; or a benzyl or phenethyl radical which is unsubstituted or substituted with 1, 2, 3, 4 or 5 substituents selected independently of one another from the group consisting of F, Cl, Br, methyl, ethyl, n-propyl, isopropyl, n-butyl, 2-butyl, isobutyl, tert-butyl, —OH, —O—CH$_3$, —O—C$_2$H$_5$ and —O—C$_3$H$_7$;

$R^4$, $R^5$, $R^6$, $R^7$, $R^8$, $R^9$, $R^{20}$, $R^{21}$, $R^{22}$, $R^{23}$, $R^{26}$, $R^{27}$, $R^{28}$, $R^{29}$, $R^{30}$, $R^{31}$ and $R^{32}$ independently of one another each represent H; F; Cl; Br; I; —NO$_2$; —CN; —NH$_2$; —OH; —SH; —NH—R$^{33}$; —NR$^{34}$R$^{35}$; —O—R$^{45}$; —S—R$^{46}$; —CF$_3$; —C$_2$F$_5$; or an alkyl radical selected from the group consisting of methyl, ethyl, n-propyl, isopropyl, n-butyl, 2-butyl, isobutyl, tert-butyl, n-pentyl and n-hexyl;

or $R^4$ and $R^5$ or $R^6$ and $R^7$ or $R^8$ and $R^9$ or $R^{20}$ and $R^{21}$ or $R^{22}$ and $R^{23}$ or $R^{26}$ and $R^{27}$ or $R^{28}$ and $R^{29}$ or $R^{31}$ and $R^{32}$ independently of one another represent, together in each case, a radical selected from the group consisting of an oxo group (=O) and a thioxo group (=S);

or $R^3$ and $R^8$ together with the —N—CR$^4$R$^5$—CR$^6$R$^7$—CR$^9$ group linking them form the following radical:

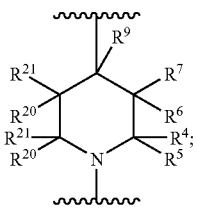

or $R^4$ and $R^{10}$ together with the —N—CR$^8$R$^9$—CR$^6$R$^7$—CR$^5$ group linking them form the following radical:

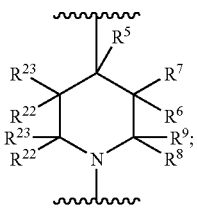

or $R^3$ and $R^{10}$ together with the —N—CR$^4$R$^5$—CR$^6$R$^7$—CR$^8$R$^9$—N group linking them form the following radical:

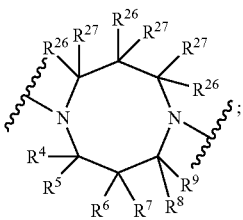

or $R^3$ and $R^{10}$ together with the —N—CR$^4$R$^5$—CR$^6$R$^7$—CR$^8$R$^9$—N group linking them form the following bicyclic radical:

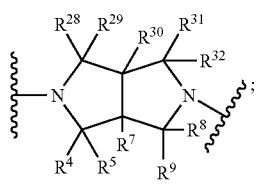

R$^{11}$ represents a radical selected from the group consisting of phenyl, naphthyl, furyl, thienyl, pyrazolyl, pyrazinyl, pyridazinyl, pyrimidinyl, pyridinyl, pyrrolyl, oxazolyl, isoxazolyl, thiazolyl, thiadiazolyl, oxadiazolyl, triazolyl, imidazolyl, indolyl, benzo[b]thiophenyl, benzo[d]thiazolyl, benzo[b]furanyl, quinolinyl, isoquinolinyl and quinazolinyl, each of which is unsubstituted or substituted with, as appropriate, 1, 2, 3, 4 or 5 substituents selected independently of one another from the group consisting of F, Cl, Br, I, —CN, methyl, ethyl, n-propyl, isopropyl, n-butyl, 2-butyl, isobutyl, tert-butyl, ethenyl, allyl, ethynyl, propynyl, —O—CH$_3$, —O—C$_2$H$_5$, —NO$_2$, —CF$_3$, —CH$_2$F, —CHF$_2$, —O—CF$_3$ and —S—CF$_3$ substituiet ist;

and R$^{33}$, R$^{34}$, R$^{35}$, R$^{36}$, R$^{37}$, R$^{42}$, R$^{43}$, R$^{44}$, R$^{45}$, R$^{46}$, R$^{47}$ and R$^{48}$ independently of one another each represent an alkyl radical selected from the group consisting of methyl, ethyl, n-propyl, isopropyl, n-butyl, 2-butyl, isobutyl, tert-butyl, n-pentyl and n-hexyl; or a phenyl, benzyl or phenethyl radical which is unsubstituted or substituted with 1, 2, 3, 4 or 5 substituents selected independently of one another from the group consisting of F, Cl, Br, methyl, ethyl, n-propyl, isopropyl, n-butyl, 2-butyl, isobutyl, tert-butyl, OH, —O—CH$_3$, —O—C$_2$H$_5$ and —O—C$_3$H$_7$;

each optionally in the form of one of the pure stereoisomers, in particular enantiomers or diastereomers thereof, or the racemates thereof, or in the form of a mixture of stereoisomers, in particular the enantiomers and/or diastereomers, mixed in any ratios, or each in the form of corresponding salts, or each in the form of corresponding solvates.

Further preferred are substituted thiazoles of the foregoing general formula I, in which R$^1$ represents H; F; Cl; Br; I; —CF$_3$; —NO$_2$; —C(=O)—O—R$^{37}$; an alkyl radical selected from the group consisting of methyl, ethyl, n-propyl, isopropyl, n-butyl, 2-butyl, isobutyl and tert-butyl; or a radical selected from the group consisting of (1,3)-dioxolan-2-yl, phenyl, benzyl, phenethyl, oxadiazolyl, 2-pyridyl, 3-pyridyl, 4-pyridyl, 2-thienyl, 3-thienyl, 2-furyl and 3-furyl;

R$^2$ represents H; F; Cl; Br; I; —CF$_3$; —NO$_2$; —C(=O)—O—R$^{37}$; an alkyl radical selected from the group consisting of methyl, ethyl, n-propyl, isopropyl, n-butyl, 2-butyl, isobutyl and tert-butyl; or a radical selected from the group consisting of (1,3)-dioxolan-2-yl, phenyl, benzyl, phenethyl, oxadiazolyl, 2-pyridyl, 3-pyridyl, 4-pyridyl, 2-thienyl, 3-thienyl, 2-furyl and 3-furyl;

or R$^1$ and R$^2$ together with the carbon atoms linking them form a phenylene radical;

R$^3$ and R$^{10}$ independently of one another each represent H; —C(=O)—R$^{36}$; —C(=O)—O—R$^{37}$; an alkyl radical selected from the group consisting of methyl, ethyl, n-propyl, isopropyl, n-butyl, 2-butyl, isobutyl, tert-butyl, n-pentyl and n-hexyl; a cycloalkyl radical selected from the group consisting of cyclopropyl, cyclobutyl, cyclopentyl and cyclohexyl; or a benzyl or phenethyl radical which is unsubstituted or substituted with 1, 2, 3, 4 or 5 substituents selected independently of one another from the group consisting of F, Cl, Br, methyl, ethyl, n-propyl, isopropyl, n-butyl, 2-butyl, isobutyl, tert-butyl, —OH, —O—CH$_3$, —O—C$_2$H$_5$ and —O—C$_3$H$_7$;

R$^4$, R$^5$, R$^6$, R$^7$, R$^8$, R$^9$, R$^{20}$, R$^{21}$, R$^{22}$, R$^{23}$, R$^{26}$, R$^{27}$, R$^{28}$, R$^{29}$, R$^{30}$, R$^{31}$ and R$^{32}$ independently of one another each represent H; F; Cl; Br; I; —OH; —SH; —NH—R$^{33}$; —NR$^{34}$R$^{35}$; —O—R$^{45}$; —S—R$^{46}$; —CF$_3$; —C$_2$F$_5$; or an alkyl radical selected from the group consisting of methyl, ethyl, n-propyl, isopropyl, n-butyl, 2-butyl, isobutyl, tert-butyl, n-pentyl and n-hexyl;

or R$^3$ and R$^8$ together with the —N—CR$^4$R$^5$—CR$^6$R$^7$—CR$^9$ group linking them form the following radical:

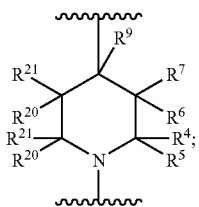

or R$^4$ and R$^{10}$ together with the —N—CR$^8$R$^9$—CR$^6$R$^7$—CR$^5$ group linking them form the following radical:

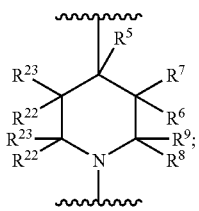

or R$^3$ and R$^{10}$ together with the —N—CR$^4$R$^5$—CR$^6$R$^7$—CR$^8$R$^9$—N group linking them form the following radical:

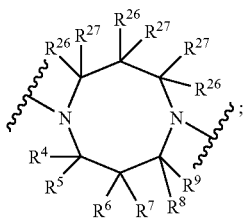

or R$^3$ and R$^{10}$ together with the —N—CR$^4$R$^5$—CR$^6$R$^7$—CR$^8$R$^9$—N group linking them form the following bicyclic radical:

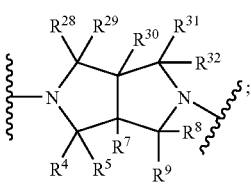

R$^{11}$ represents a radical selected from the group consisting of phenyl, furyl, thienyl, pyrazolyl, pyrazinyl, pyrimidinyl, pyridazinyl, pyridinyl, pyrrolyl, oxazolyl, isoxazolyl, thiazolyl, thiadiazolyl, oxadiazolyl, triazolyl and imidazolyl each of which is unsubstituted or substituted with, as appropriate, 1, 2, 3, 4 or 5 substituents selected independently of one another from the group consisting of F, Cl, Br, I, —CN, methyl, ethyl, n-propyl, isopropyl, n-butyl, 2-butyl, isobutyl, tert-butyl, ethenyl, allyl, ethynyl, propynyl, —O—CH$_3$, —O—C$_2$H$_5$, —NO$_2$, —CF$_3$, —CH$_2$F, —CHF$_2$, —O—CF$_3$ and —S—CF$_3$;

and R$^{33}$, R$^{34}$, R$^{35}$, R$^{36}$, R$^{37}$, R$^{45}$ and R$^{46}$ independently of one another each represent an alkyl radical selected from the group consisting of methyl, ethyl, n-propyl, isopropyl, n-butyl, 2-butyl, isobutyl, tert-butyl, n-pentyl and n-hexyl;

each optionally in the form of one of the pure stereoisomers, in particular enantiomers or diastereomers thereof, or the racemates thereof, or in the form of a mixture of stereoisomers, in particular the enantiomers and/or diastereomers, mixed in any ratios, or each in the form of corresponding salts, or each in the form of corresponding solvates.

Further preferred are substituted thiazoles of the foregoing general formula I, in which R$^1$ represents H, methyl, ethyl, n-propyl, —C(═O)—O—CH$_3$, —C(═O)—O—C$_2$H$_5$ or —C(═O)—O—C(CH$_3$)$_3$;

R$^2$ represents H, methyl, ethyl, n-propyl, —C(═O)—O—CH$_3$, —C(═O)—O—C$_2$H$_5$ or —C(═O)—O—C(CH$_3$)$_3$;

or R$^1$ and R$^2$ together with the carbon atoms linking them form a phenylene radical;

R$^3$ and R$^{10}$ independently of one another each represent H; an alkyl radical selected from the group consisting of methyl, ethyl, n-propyl, isopropyl, n-butyl, 2-butyl, isobutyl and tert-butyl; or cyclopropyl;

R$^4$, R$^5$, R$^6$, R$^7$, R$^8$ and R$^9$ each represent H;

or R$^3$ and R$^8$ together with the —N—CH$_2$—CH$_2$—CH group linking them form the following radical:

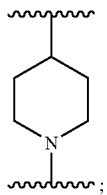

or R$^4$ and R$^{10}$ together with the —N—CH$_2$—CH$_2$—CH group linking them form the following radical:

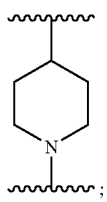

or R$^3$ and R$^{10}$ together with the —N—CH$_2$—CH$_2$—CH$_2$—N group linking them form the following radical:

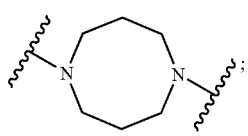

or R$^3$ and R$^{10}$ together with the group linking them form the following bicyclic radical:

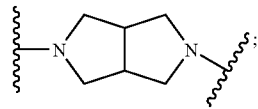

and R$^{11}$ represents a radical selected from the group consisting of 3,4-dimethyl-phenyl, 3-methoxy-phenyl, 2-methoxy-phenyl, 4-methoxy-phenyl, 4-fluoro-phenyl, 2-methyl-phenyl, 4-methyl-phenyl, 2-fluoro-phenyl, 2,4-difluoro-phenyl, 4-trifluoromethyl-phenyl, 2-trifluoromethyl-phenyl, 3-fluoro-4-methyl-phenyl, pyrid-2-yl, pyrid-3-yl, pyrid-4-yl, phenyl, 3-methyl-phenyl, 3-fluoro-phenyl, 3-cyano-phenyl, 3-chloro-phenyl, 3-trifluoromethyl-phenyl, 3-difluoromethyl-phenyl, 3-fluoromethyl-phenyl, 3-nitro-phenyl, 3-ethenyl-phenyl, 3-ethynyl-phenyl, 3-allyl-phenyl, 3-bromophenyl und 3-trifluoromethoxy-phenyl;

each optionally in the form of one of the pure stereoisomers, in particular enantiomers or diastereomers thereof, or the racemates thereof, or in the form of a mixture of stereoisomers, in particular the enantiomers and/or diastereomers, mixed in any ratios, or each in the form of corresponding salts, or each in the form of corresponding solvates.

Even more strongly preferred are substituted thiazoles of general formulae Ia1 and Ia2,

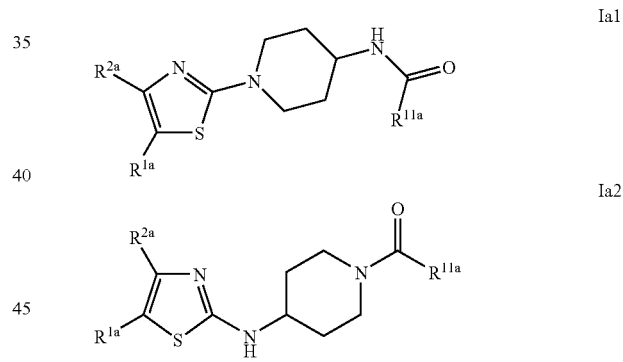

in which

R$^{1a}$ represents H, methyl, ethyl, n-propyl, —C(═O)—O—CH$_3$, —C(═O)—O—C$_2$H$_5$ or —C(═O)—O—C(CH$_3$)$_3$;

R$^{2a}$ represents H, methyl, ethyl, n-propyl, —C(═O)—O—CH$_3$, —C(═O)—O—C$_2$H$_5$ or —C(═O)—O—C(CH$_3$)$_3$;

or R$^{1a}$ and R$^{2a}$ together with the carbon atoms linking them form a phenylene radical;

and R$^{11a}$ represents a radical selected from the group consisting of 2-trifluoromethyl-phenyl, 3,4-dimethyl-phenyl, 3-methoxy-phenyl, 2-methoxy-phenyl, 4-methoxy-phenyl, 4-fluoro-phenyl, 2-methyl-phenyl, 4-methyl-phenyl, 2-fluoro-phenyl, 2,4-difluoro-phenyl, 4-trifluoromethyl-phenyl, 3-fluoro-4-methyl-phenyl, pyrid-2-yl, pyrid-3-yl, pyrid-4-yl, phenyl, 3-methyl-phenyl, 3-fluoro-phenyl, 3-cyano-phenyl, 3-chloro-phenyl, 3-trifluoromethyl-phenyl, 3-difluoromethyl-phenyl, 3-fluoromethyl-phenyl, 3-nitro-phenyl, 3-ethenyl-phenyl, 3-ethynyl-phenyl, 3-allyl-phenyl, 3-bromophenyl and 3-trifluoromethoxy-phenyl;

each optionally in the form of corresponding salts or in the form of corresponding solvates.

Even further preferred are substituted thiazoles of the foregoing general formula I, selected from the group consisting of

[1] N-(3-((thiazol-2-yl)amino)propyl)-3-phenylpropiolamide,
[2] 4-(thiazol-2-yl-amino)-1-(3-phenyl-propiolyl)piperidine,
[3] 3-(thiazol-2-yl)-7-(3-phenyl-propiolyl-3,7-diaza-bicyclo[3.3.0]octane,
[4] 4-(methyl-thiazol-2-yl-amino)-1-(3-phenyl-propiolyl)piperidine,
[5] 3-phenyl-N-(1-(thiazol-2-yl)piperidin-4-yl)propiolamide,
[6] N-methyl-3-phenyl-N-(1-(thiazol-2-yl)piperidin-4-yl)propiolamide,
[7] 4-(benzothiazol-2-yl-amino)-1-(3-(3-trifluormethyl-phenyl)-propiolyl)piperidine,
[8] 1-((3,4-dimethyl-phenyl)-propiolyl)-4-(thiazol-2-yl-amino)-piperidine,
[9] 4-(benzothiazol-2-yl-amino)-1-(3,4-dimethyl-phenyl)-propiolyl)piperidine,
[10] N-(1-(4-methyl-thiazol-2-yl)piperidin-4-yl)-3-phenyl-propiolamide,
[11] N-(1-(4-methyl-thiazol-2-yl)piperidin-4-yl)-3-(3-methoxyphenyl)-propiolamide,
[12] N-(1-(4-methyl-thiazol-2-yl)piperidin-4-yl)-3-(2-methoxyphenyl)-propiolamide,
[13] N-(1-(4-Methyl-thiazol-2-yl)piperidin-4-yl)-3-(4-methoxyphenyl)-propiolamide,
[14] 3-(4-fluoro-phenyl)-N-(1-(4-methyl-thiazol-2-yl)piperidin-4-yl)-propiolamide,
[15] N-(1-(4-methyl-thiazol-2-yl)piperidin-4-yl)-3-(4-tolyl)-propiolamide,
[16] 3-(2-fluoro-phenyl)-N-(1-(4-methyl-thiazol-2-yl)piperidin-4-yl)-propiolamide,
[17] 3-(2,4-difluoro-phenyl)-N-(1-(4-methyl-thiazol-2-yl)piperidin-4-yl)-propiolamide,
[18] N-(1-(4-methyl-thiazol-2-yl)piperidin-4-yl)-3-(4-trifluoromethyl-phenyl)-propiolamide,
[19] 3-(3-fluoro-phenyl)-N-(1-(4-methyl-thiazol-2-yl)piperidin-4-yl)-propiolamide,
[20] 3-(3-fluoro-4-methyl-phenyl)-N-(1-(4-methyl-thiazol-2-yl)piperidin-4-yl)-propiolamide,
[21] N-(1-(4-methyl-thiazol-2-yl)piperidin-4-yl)-3-(3-trifluoromethyl-phenyl)-propiolamide,
[22] N-(1-(4-methyl-thiazol-2-yl)piperidin-4-yl)-3-(3-tolyl)-propiolamide and
[23] N-(1-(4-methyl-thiazol-2-yl)piperidin-4-yl)-3-(2-tolyl)-propiolamide;

each optionally in the form of corresponding salts or each in the form of corresponding solvates.

Also particularly preferred are substituted thiazoles of the foregoing general formula I, which after 60 minutes of incubation in 450 µg protein from pig brain homogenate, at a temperature between 20° C. and 25° C., at a concentration less than 2000 nM, preferably less then 1000 nM, particularly preferably less than 700 nm, more particularly preferably less than 100 nM, even more preferably less than 30 nM, cause a 50 percent displacement of [$^3$H]-2-methyl-6-(3-methoxyphenyl)-ethynylpyridine which is present in a concentration of 5 nM.

The determination of the displacement of [$^3$H]-2-methyl-6-(3-methoxyphenyl)-ethynylpyridine thus takes place as described in the section Pharmacological Methods, I. Method for determining the inhibition of the [$^3$H]-MPEP binding in the mGluR5 receptor binding assay.

The present invention further relates to a method for the production of compounds of the foregoing general formula I, according to which at least one compound of general formula II,

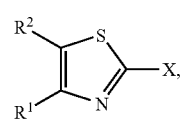

in which the radicals $R^1$ and $R^2$ have the meaning given above and X represents a leaving group, preferably a halogen radical or a sulphonic acid ester, particularly preferably a chlorine or bromine radical, together with at least one compound of general formula III,

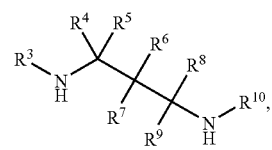

in which $R^3$, $R^4$, $R^5$, $R^6$, $R^7$, $R^8$, $R^9$ and $R^{10}$ have the meaning given above, optionally in a reaction medium, optionally in the presence of at least one base and/or at least one organometallic compound and/or at least one metal hydride reagent or in the presence of at least one copper salt and optionally in the presence of at least one metal, preferably at a temperature of −70° C. to 300° C., particularly preferably −70° C. to 150° C., is converted into at least one corresponding compound of general formula IV, optionally in the form of a corresponding salt,

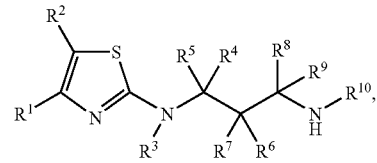

in which $R^1$, $R^2$, $R^3$, $R^4$, $R^5$, $R^6$, $R^7$, $R^8$, $R^9$ und $R^{10}$ have the meaning given above, and this is optionally purified and/or isolated;

or at least one compound of general formula II, together with at least one compound of general formula V,

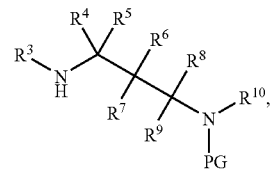

in which $R^3$, $R^4$, $R^5$, $R^6$, $R^7$, $R^8$, $R^9$ and $R^{10}$ have the meaning given above and PG represents a protecting group, preferably a protecting group selected from the group consisting of tert-butyloxy-carbonyl, benzyl, benzyloxycarbonyl and 9-fluorenylmethyloxycarbonyl, optionally in a reaction medium, optionally in the presence of at least one base and/or at least one organometallic compound and/or at least one metal hydride reagent, preferably at a temperature of −70° C. to 300° C., is converted into at least one corresponding compound of general formula VI,

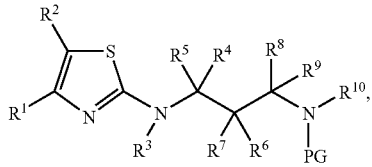

VI in which $R^1$, $R^2$, $R^3$, $R^4$, $R^5$, $R^6$, $R^7$, $R^8$, $R^9$, $R^{10}$ and PG have the meaning given above, and this is optionally purified and/or isolated;

or at least one compound of general formula XI II,

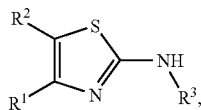

XIII in which $R^1$, $R^2$ and $R^3$ have the meaning given above, together with at least one compound of general formula XIV,

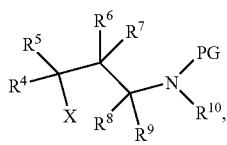

XIV in which $R^4$, $R^5$, $R^6$, $R^7$, $R^8$, $R^9$ and $R^{10}$ have the meaning given above and X represents a leaving group, preferably a halogen radical or a sulphonic acid ester, particularly preferably a chlorine or bromine radical, optionally in a reaction medium, optionally in the presence of at least one base, preferably in the presence of at least one base selected from the group consisting of potassium tert-butylate, sodium hydroxide, potassium hydroxide, dimethylamine and trimethylamine, particularly preferably in the presence of diethylamine, or optionally in the presence of at least one organometallic compound, preferably in the presence of at least one organometallic compound selected from the group consisting of methyl lithium and butyl lithium, or optionally in the presence of at least one metal hydride compound, particularly preferably in the presence of sodium hydride, preferably at a temperature of −70° C. to 300° C., particularly preferably −70° C. to 150° C., is converted into at least one corresponding compound of general formula VI and this is optionally purified and/or isolated;

or at least one compound of general formula VII,

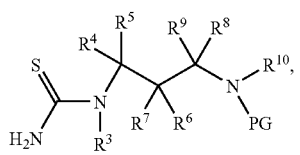

VII in which $R^3$, $R^4$, $R^5$, $R^6$, $R^7$, $R^8$, $R^9$ and $R^{10}$ have the meaning given above and PG represents a protecting group, preferably a protecting group selected from the group consisting of tert-butyloxy-carbonyl, benzyl, benzyloxycarbonyl and 9-fluorenylmethyloxycarbonyl, by reaction with at least one compound of general formula $R^1$—C(=O)—$CH_2$—X or $(C_{1-5}$-alkyl-0$)_2$—CH—$CH_2$—X, in which $R^1$ has the meaning given above and X represents a leaving group, preferably a halogen radical, particularly preferably a bromine atom, in a reaction medium, optionally in the presence of at least one organic base or in the presence of at least one acid, preferably in the presence of at least one base selected from the group consisting of triethylamine, diisopropylethylamine, N-methylmorpholine, dimethylaminopyridine and pyridine or in the presence of at least one acid selected from the group consisting of acetic acid, trifluoroacetic acid and hydrochloric acid, preferably at a temperature between −70° C. and 300° C., is converted into at least one corresponding compound of general formula VI, optionally in the form of a corresponding salt, and this is optionally purified and/or isolated;

and at least one compound of general formula VI, when PG represents a tert-butoxycarbonyl or 9-fluorenylmethyloxycarbonyl group, in a reaction medium in the presence of at least one acid, preferably in the presence of at least one acid selected from the group consisting of hydrochloric acid and trifluoroacetic acid, preferably at a temperature between −70° C. and 100° C., or when PG represents a benzyl or benzyloxycarbonyl group, in a reaction medium in the presence of hydrogen and in the presence of at least one catalyst, preferably in the presence of palladium on carbon, preferably at a temperature between −70° C. and 100° C., is converted into at least one corresponding compound of general formula IV, optionally in the form of a corresponding salt, and this is optionally purified and/or isolated;

and at least one compound of general formula IV, by reaction with at least one compound of general formula $R^{11}$—C≡C—C(=O)—OH, in which $R^{11}$ has the meaning given above, in a reaction medium, optionally in the presence of at least one suitable coupling agent, optionally in the presence of at least one base, preferably at a temperature of −70° C. to 100° C., or by reaction with at least one compound of general formula $R^{11}$—C≡C—C(=O)—X, in which $R^{11}$ has the meaning given above and X represents a leaving group, preferably a halogen radical, particularly preferably a chlorine or bromine radical, in a reaction medium, optionally in the presence of at least one base, preferably at a temperature of −70° C. to 100° C., is converted into at least one corresponding compound of general formula I, optionally in the form of a corresponding salt,

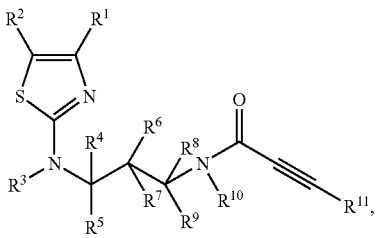

I in which $R^1$, $R^2$, $R^3$, $R^4$, $R^5$, $R^6$, $R^7$, $R^8$, $R^9$, $R^{10}$ and $R^{11}$ have the meaning given above, and this is optionally purified and/or isolated;

or at least one compound of general formula IV, by reaction with propiolic acid [HC≡C—C(=O)—OH] in a reaction medium, optionally in the presence of at least one suitable coupling agent, optionally in the presence of at least one base, preferably at a temperature of −70° C. to 100° C., or by reaction with at least one compound of general formula HC≡C—C(=O)—X, in which X represents a leaving group, preferably a halogen radical, particularly preferably a chlorine or bromine radical, in a reaction medium, optionally in the presence of at least one base, preferably at a temperature of −70° C. to 100° C., is converted into at least one corresponding compound of general formula VIII, optionally in the form of a corresponding salt,

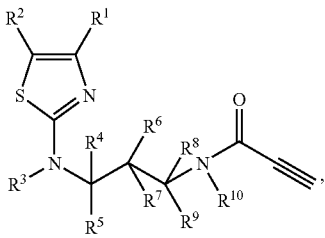

VIII in which $R^1$, $R^2$, $R^3$, $R^4$, $R^5$, $R^6$, $R^7$, $R^8$, $R^9$ and $R^{10}$ have the meaning given above, and this is optionally purified and/or isolated, and at least one compound of general formula VIII, by reaction with at least one compound of general formula $R^{11}$—X, in which $R^{11}$ has the meaning given above and X represents a leaving group, preferably a halogen radical or a sulphonic acid ester, particularly preferably iodine, bromine or triflate, in a reaction medium, optionally in the presence of at least one catalyst, preferably in the presence of at least one palladium catalyst selected from the group consisting of palladium chloride [PdCl$_2$], palladium acetate [Pd(OAc)$_2$], tetrakis(triphenylphosphine) palladium [Pd(PPh$_3$)$_4$], bis(triphenylphosphine) palladium dichloride [Pd(PPh$_3$)$_2$Cl$_2$] and bis(triphenylphosphine) palladium acetate [Pd(PPh$_3$)$_2$(OAc)$_2$], optionally in the presence of at least one ligand, preferably in the presence of at least one ligand selected from the group consisting of triphenyl phosphine, triphenyl arsine and tri(2-furyl)phosphine, optionally in the presence of at least one inorganic salt, preferably in the presence of at least one inorganic salt selected from the group consisting of lithium chloride and zinc chloride, optionally in the presence of at least one copper salt, preferably in the presence of copper iodide, optionally in the presence of at least one organic or inorganic base, preferably in the presence of at least one base selected from the group consisting of triethyl amine, [1,4]-diazabicyclo-[2.2.2]-octane, diisopropylamine, diisopropylethylamine, potassium carbonate and sodium hydrogencarbonate, preferably at a temperature between −70° C. and 300° C., is converted into at least one corresponding compound of general formula I, optionally in the form of a corresponding salt, and this is optionally purified and/or isolated.

The present invention further relates to a method for the production of compounds of general formula I, according to which at least one compound of general formula XVI,

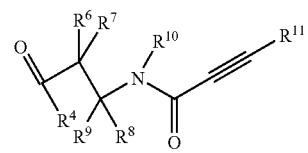

XVI in which $R^4$, $R^6$, $R^7$, $R^8$, $R^9$, $R^{10}$ and $R^{11}$ have the meaning given above, by reaction with at least one compound of general formula XIII

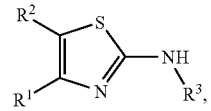

XIII in which $R^1$, $R^2$ and $R^3$ have the meaning given above, in a reaction medium, preferably selected from the group consisting of diethyl ether, tetrahydrofuran, methanol, ethanol, dichloromethane and toluene, with the addition of at least one reducing agent, preferably with the addition of at least one reducing agent selected from the group consisting of sodium borohydride, sodium acetoxy borohydride, sodium acetoxy borohydride bound to resin, and sodium cyanoborohydride, at temperatures of −80° C. to 150° C., preferably of −78° C. to 100° C., is converted to compounds of general formula I, optionally in the form of a corresponding salt, and this is optionally purified and/or isolated.

The present invention further relates to a method for the production of compounds of general formula I, according to which at least one compound of general formula III,

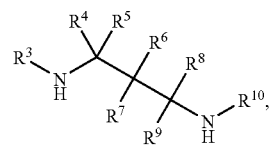

III in which $R^3$, $R^4$, $R^5$, $R^6$, $R^7$, $R^8$, $R^9$ and $R^{10}$ have the meaning given above, by reaction with at least one compound of general formula $R^{11}$—C≡C—C(=O)—OH, in which $R^{11}$ has the meaning given above, in a reaction medium, optionally in the presence of at least one suitable coupling agent, optionally in the presence of at least one base, preferably at a temperature of −70° C. to 100° C., or by reaction with at least one compound of general formula $R^{11}$—C≡C—C(=O)—X, in which $R^{11}$ has the meaning given above and X represents a leaving group, preferably a halogen radical, particularly preferably a chlorine or bromine radical, in a reaction medium, optionally in the presence of at least one base, preferably at a temperature of −70° C. to 100° C., is converted into at least one corresponding compound of general formula IX, optionally in the form of a corresponding salt,

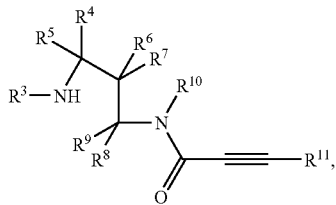

in which $R^3$, $R^4$, $R^5$, $R^6$, $R^7$, $R^8$, $R^9$, $R^{10}$ and $R^{11}$ have the meaning given above, and this is optionally purified and/or isolated;

or at least one compound of general formula V,

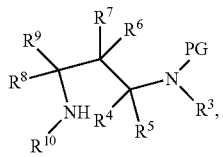

in which $R^3$, $R^4$, $R^5$, $R^6$, $R^7$, $R^8$, $R^9$ and $R^{10}$ have the meaning given above and PG represents a protecting group, preferably a protecting group selected from the group consisting of tert-butyloxy-carbonyl, benzyl, benzyloxycarbonyl and 9-fluorenylmethyloxycarbonyl, by reaction with at least one compound of general formula $R^{11}$—C≡C—C(=O)—OH, in which $R^{11}$ has the meaning given above, in a reaction medium, optionally in the presence of at least one suitable coupling agent, optionally in the presence of at least one base, preferably at a temperature of −70° C. to 100° C., or by reaction with at least one compound of general formula $R^{11}$—C≡C—C(=O)—X, in which $R^{11}$ has the meaning given above and X represents a leaving group, preferably a halogen radical, particularly preferably a chlorine or bromine radical, in a reaction medium, optionally in the presence of at least one base, preferably at a temperature of −70° C. to 100° C., is converted into at least one corresponding compound of general formula XI, optionally in the form of a corresponding salt,

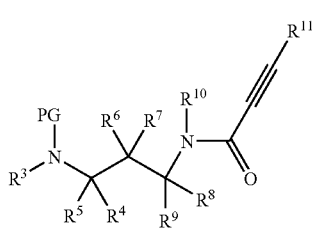

in which $R^3$, $R^4$, $R^5$, $R^6$, $R^7$, $R^8$, $R^9$, $R^{10}$, $R^{11}$ and PG have the meaning given above, and this is optionally purified and/or isolated; and at least one compound of general formula XI, when PG represents a tert-butoxycarbonyl or 9-fluorenylmethyloxycarbonyl group, in a reaction medium in the presence of at least one acid, preferably in the presence of at least one acid selected from the group consisting of hydrochloric acid and trifluoroacetic acid, preferably at a temperature between −70° C. and 100° C., or when PG represents a benzyl or benzyloxycarbonyl group, in a reaction medium in the presence of hydrogen and in the presence of at least one catalyst, preferably in the presence of palladium on carbon, preferably at a temperature between −70° C. and 100° C., is converted into at least one corresponding compound of general formula IX, optionally in the form of a corresponding salt, and this is optionally purified and/or isolated;

and at least one compound of general formula IX, by reaction with at least one compound of general formula II,

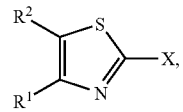

in which the radicals $R^1$ and $R^2$ have the meaning given above and X represents a leaving group, preferably a halogen radical or a sulphonic acid ester, particularly preferably a chlorine or bromine radical, in a reaction medium, optionally in the presence of at least one base and/or at least one organometallic compound and/or at least one metal hydride reagent, preferably at a temperature of −70° C. to 300° C., is converted into at least one corresponding compound of general formula I, optionally in the form of a corresponding salt, in which $R^1$, $R^2$, $R^3$, $R^4$, $R^5$, $R^6$, $R^7$, $R^8$, $R^9$, $R^{10}$ and $R^{11}$ have the meaning given above, and this is optionally purified and/or isolated;

or optionally at least one compound of general formula IX, by reaction with potassium thiocyanate and ethyl chloroformate or ammonium thiocyanate or trimethylsilylisothiocyanate or thiophosgene and ammoniac or bromocyan and hydrogen sulphide, in a reaction medium, optionally in the presence of at least one acid, preferably in the presence of at least one acid selected from the group consisting of hydrochloric acid, sulphuric acid, acetic acid and trifluoroacetic acid, particularly preferably in the presence of hydrochloric acid, or optionally in the presence of at least one base, preferably in the presence of at least one base selected from the group consisting of potassium-tert-butylate, sodium hydroxide, potassium hydroxide, dimethylamine and triethylamine, particularly preferably in the presence of diethylamine, or optionally in the presence of at least one organometallic compound, preferably in the presence of at least one organometallic compound selected from the group consisting of methyl lithium and butyl lithium, or optionally in the presence of at least one metal hydride compound, particularly preferably in the presence of sodium hydride, preferably at a temperature of −70° C. to 250° C., is converted into at least one corresponding compound of general formula XII, optionally in the form of a corresponding salt,

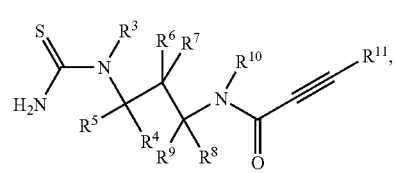

in which $R^3$, $R^4$, $R^5$, $R^6$, $R^7$, $R^8$, $R^9$, $R^{10}$ and $R^{11}$ have the meaning given above, and this is optionally purified and/or isolated;

and at least one compound of general formula XII by reaction with at least one compound of general formula $R^1$—C(=O)—CH$_2$—X or $(C_{1-5}$-alkyl-O)$_2$—CH—CH$_2$—X, in which $R^1$ has the meaning given above and X represents a leaving group, preferably a halogen radical, particularly preferably a bromine atom, in a reaction medium, optionally in the presence of at least one organic base or in the presence of at least one acid, preferably in the presence of at least one base selected from the group consisting of triethylamine, diisopropylethylamine, N-methylmorpholine, dimethylaminopyridine and pyridine or in the presence of at least one acid selected from the group consisting of acetic acid, trifluoroacetic acid and hydrochloric acid, preferably at a temperature between −70° C. and 300° C., is converted into at least one corresponding compound of general formula I, optionally in the form of a corresponding salt, and this is optionally purified and/or isolated.

A method according to the invention for the production of substituted thiazoles of the foregoing general formula I is also given in Diagram 1 below.

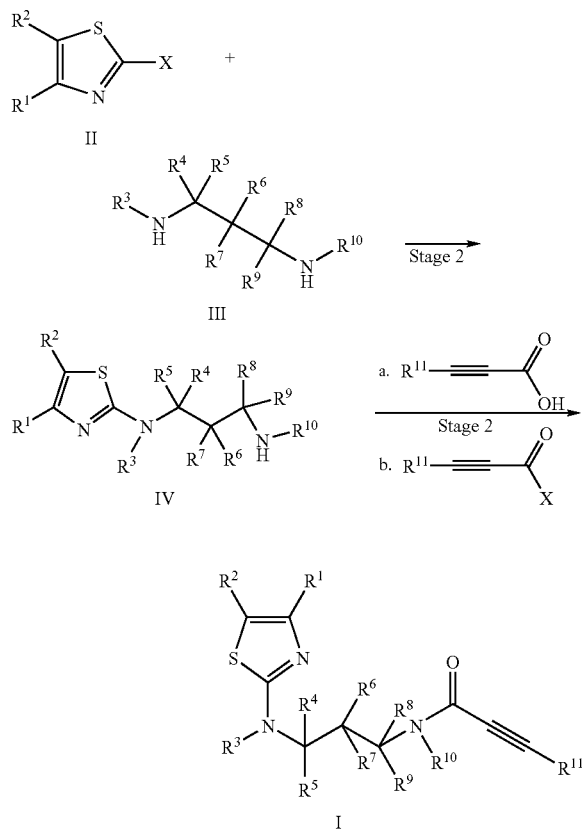

Diagram 1

In Stage 1, thiazoles of the foregoing general formula II, in which X represents a leaving group, preferably a halogen radical or a sulphonic acid ester selected from the group consisting of mesylate, triflate and tosylate, particularly preferably a chlorine or bromine atom, together with compounds of the foregoing general formula III, optionally in a reaction medium, preferably selected from the group consisting of methanol, ethanol, isopropanol, n-butanol, diethyl ether, tetrahydrofuran, dichloromethane, chloroform, dimethylformamide, acetonitrile, pyridine, dioxan, ethylacetate, dimethylsulphoxide, toluene and corresponding mixtures, particularly preferably in a reaction medium selected from the group consisting of methanol, ethanol and n-butanol, optionally in the presence of an organic or inorganic base, preferably selected from the group consisting of triethylamine, sodium hydrogencarbonate, dimethylaminopyridine, potassium carbonate and sodium hydroxide, and/or optionally in the presence of at least one metal salt, preferably a copper salt, particularly preferably copper(I) iodide and/or copper(I) chloride, and/or optionally in the presence of at least one metal, preferably copper, and/or optionally in the presence of an organometallic compound or a metal hydride reagent, preferably selected from the group consisting of n-butyl lithium, phenyl lithium, sodium hydride, potassium hydride and sodium amide, preferably at temperature of −70° C. to 300° C., particularly preferably at temperatures of −70° C. to 150° C., are reacted to form compounds of the general formula IV.

In Stage 2, compounds of the foregoing general formula IV, together with carboxylic acids of the foregoing general formula $R^{11}$—C≡C—(C=O)—OH, in a reaction medium, preferably selected from the group consisting of diethyl ether, tetrahydrofuran, acetonitrile, methanol, ethanol, (1,2)-dichloroethane, dimethylformamide, dichloromethane and corresponding mixtures thereof, optionally in the presence of at least one coupling reagent, preferably selected from the group consisting of 1-benzotriazolyloxy-tris-(dimethylamino)-phosphonium hexafluorophosphate (BOP), dicyclohexylcarbodiimide (DCC), N'-(3-dimethylaminopropyl)-N-ethylcarbodiimide (EDCI), diisoproylcarbodiimide, 1,1'-carbonyl-diimidazole (CDI), N—[(dimethyamino)-1H-1,2,3-triazolo[4,5-b]pyridino-1-ylmethylene]-N-methylmethanaminium hexafluorophosphate N-oxide (HATU), O-(benzotriazol-1-yl)-N,N,N',N'-tetramethyluronium hexafluorophosphate (HBTU), O-(benzotriazol-1-yl)-N,N,N',N'-tetramethyluronium-tetrafluoroborate (TBTU) and 1-hydroxy-7-azabenzotriazole (HOAt), preferably in the presence of TBTU as a coupling reagent, optionally in the presence of at least one organic base, preferably selected from the group consisting of triethylamine, pyridine, dimethylaminopyridine, N-methylmorpholine and diisopropylethylamine, preferably in the presence of diisopropylethylamine, preferably at temperatures of −70° C. to 100° C., are reacted to form compounds of general formula I.

Alternatively, compounds of the foregoing general formula IV, together with carboxylic acid derivatives of the foregoing general formula $R^{11}$—C≡C—(C=O)—X, in which X represents a leaving group, preferably a halogen radical, particularly preferably chlorine or bromine, in a reaction medium, preferably selected from the group consisting of diethyl ether, tetrahydrofuran, acetonitrile, methanol, ethanol, dimethylformamide, dichloromethane and corresponding mixtures, optionally in the presence of at least one organic or inorganic base, preferably selected from the group consisting of triethylamine, dimethylaminopyridine, pyridine and diisopropylamine, at temperatures of −70° C. to 100° C. are reacted to form compounds of general formula I.

A further method according to the invention for the production of substituted thiazoles of the foregoing general formula I is also given in Diagram 2 below.

Diagram 2

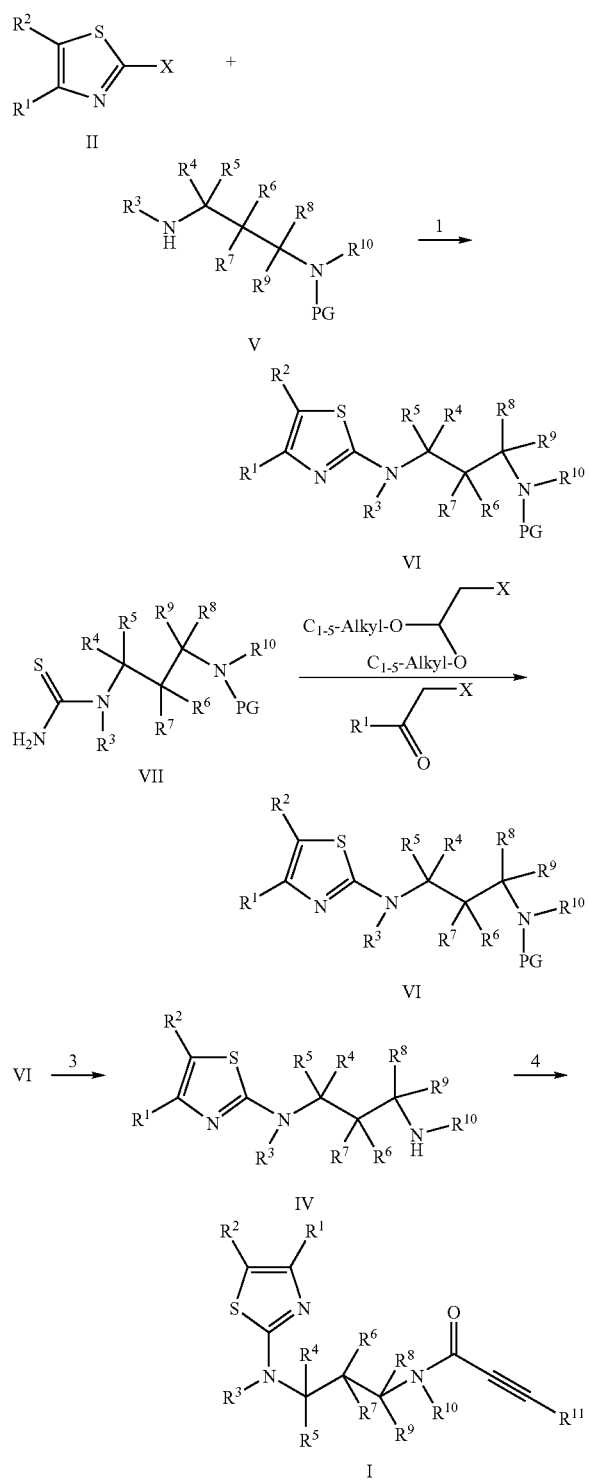

In Stage 1, thiazoles of the foregoing general formula II, in which X represents a leaving group, preferably a halogen radical or a sulphonic acid ester selected from the group consisting of mesylate, triflate and tosylate, particularly preferably a chlorine or bromine atom, together with compounds of the foregoing general formula V, in which PG represents a protecting group, preferably a protecting group selected from the group consisting of tert-butyloxy-carbonyl, benzyloxy-carbonyl, benzyl and 9-fluorenylmethyloxycarbonyl, are reacted to form compounds of general formula VI.

Precise conditions may also be taken from the Journal of Medicinal Chemistry 1972, 15(3), pages 295 to 301. The corresponding parts of said publication are hereby incorporated as a part of this disclosure.

In Stage 2, compounds of the foregoing general formula VII, in which PG represents a protecting group, preferably a protecting group selected from the group consisting of tert-butyloxy-carbonyl, benzyl, benzyloxycarbonyl and 9-fluorenylmethyloxycarbonyl, together with at least one compound of general formula $R^1$—C(=O)—$CH_2$—X or ($C_{1-5}$-Alkyl-O)$_2$—CH—$CH_2$—X, preferably with at least one compound of general formula $R^1$—C(=O)—$CH_2$—X or ($C_2H_5$—O)$_2$—CH—$CH_2$—X, in which X represents a leaving group, preferably a halogen radical, particularly preferably a bromine atom, in a reaction medium, preferably in a reaction medium selected from the group consisting of methanol, ethyl acetate, ethanol, isopropanol, n-butanol, diethyl ether, dioxane, tetrahydrofuran, chloroform, dichloromethane, dimethylformamide, acetonitrile, pyridine, dimethyl sulphoxide, toluene and corresponding mixtures, particularly preferably in ethanol and/or dioxane, optionally in the presence of at least one organic base or in the presence of at least one acid, preferably in the presence of at least one base selected from the group consisting of triethylamine, diisopropylethylamine, N-methylmorpholine, dimethylaminopyridine and pyridine or in the presence of at least one acid selected from the group consisting of acetic acid, trifluoroacetic acid and hydrochloric acid, preferably at a temperature of −70° C. to 300° C., are reacted to form a corresponding compound of general formula VI.

Precise conditions may also be taken from the Journal of Medicinal Chemistry 1998, 41(25), pages 5027 to 5054. The corresponding parts of said publication are hereby incorporated as a part of this disclosure.

In Stage 3, compounds of general compound VI, when PG represents a tert-butoxycarbonyl or 9-fluorenylmethyloxycarbonyl group, in a reaction medium, preferably in a reaction medium selected from the group consisting of methanol, ethyl acetate, ethanol, isopropanol, n-butanol, diethyl ether, dioxane, tetrahydrofuran, chloroform, dichloromethane, dimethylformamide, acetonitrile, pyridine, dimethyl sulphoxide, toluene and corresponding mixtures, in the presence of at least one acid, preferably in the presence of at least one acid selected from the group consisting of hydrochloric acid and trifluoroacetic acid, preferably at a temperature of −70° C. to 100° C., or when PG represents a benzyl group or benzyloxycarbonyl group, in a reaction medium, preferably in a reaction medium selected from the group consisting of methanol, ethyl acetate, ethanol, isopropanol, n-butanol, diethyl ether, dioxane, tetrahydrofuran, chloroform, dichloromethane, dimethylformamide, acetonitrile, pyridine, dimethyl sulphoxide, toluene and corresponding mixtures, in the presence of hydrogen and in the presence of at least one catalyst, preferably in the presence of palladium on carbon, preferably at a temperature of −70° C. to 100° C., are converted into a corresponding compound of general formula IV.

Suitable methods for the removal of the aforementioned protecting groups may be taken from the monographs Protective Groups in Organic Synthesis, T. W. Greene et al., 3$^{rd}$ edition, 1999, Wiley, New York and Protecting Groups, P. J. Kocienski, 3$^{rd}$ edition, 2004, published by Georg Thieme, Stuttgart 2004. The corresponding parts of said literature references are hereby incorporated as a part of this disclosure.

In Stage 4, compounds of the foregoing general formula IV, together with carboxylic acids of the foregoing general formula $R^{11}$—C≡C—(C═O)—OH, or with carboxylic acid derivates of the foregoing general formula $R^{11}$—C≡C—(C═O)—X, are reacted as described in Diagram 1, stage 2 to produce compounds of general formula I.

A further method according to the invention for the production of substituted thiazoles of the foregoing general formula I is also given in Diagram 3 below.

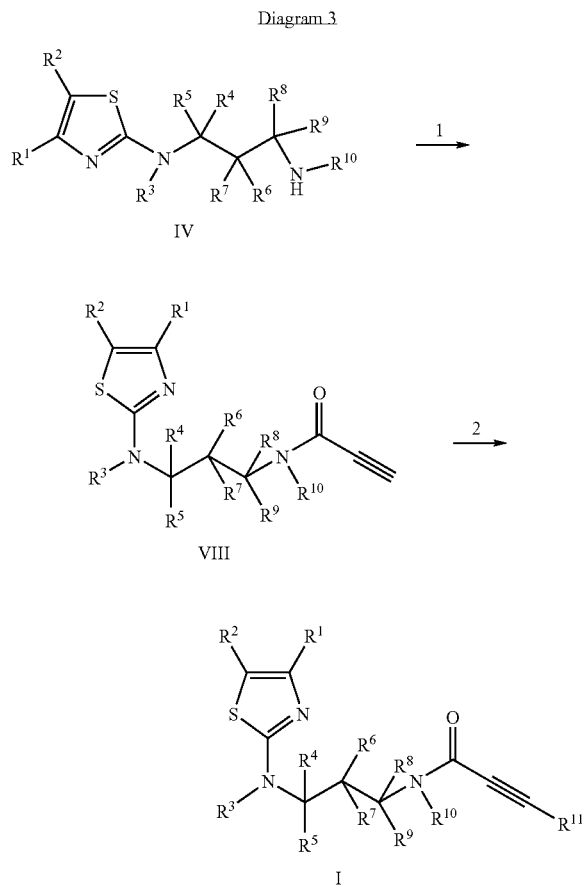

In Stage 1, compounds of the foregoing general formula IV, together with propiolic acid H—C≡C—(C═O)—OH or with carboxylic acid derivatives of the general formula H—C≡C—(C═O)—X, in which X represents a leaving group, preferably a halogen radical, particularly preferably chlorine or bromine, as described in Diagram 1, Stage 2, are reacted to form compounds of general formula VIII.

In Stage 2, compounds of the foregoing general formula VIII, together with compounds of the general formula $R^{11}$—X, in which $R^{11}$ has the meaning given above and X represents a leaving group, preferably a halogen radical or a sulphonic acid ester, particularly preferably iodine, bromine or triflate, in a reaction medium, preferably in a reaction medium selected from the group consisting of methanol, ethyl acetate, ethanol, isopropanol, n-butanol, diethyl ether, dioxane, tetrahydrofuran, chloroform, dichloromethane, dimethylformamide, acetonitrile, pyridine, dimethyl sulphoxide, water, toluene and corresponding mixtures, preferably in dimethylformamide, water, ethyl acetate, tetrahydrofuran and corresponding mixtures, optionally in the presence of at least one catalyst, preferably in the presence of at least one palladium catalyst selected from the group consisting of palladium chloride [$PdCl_2$], palladium acetate [$Pd(OAc)_2$], tetrakis(triphenylphosphine) palladium [$Pd(PPh_3)_4$], bis(triphenylphosphine) palladium dichloride [$Pd(PPh_3)_2Cl_2$] and bis(triphenylphosphine) palladium acetate [$Pd(PPh_3)_2(OAc)_2$], preferably in the presence of $Pd(PPh_3)_4$, $Pd(PPh_3)_2Cl_2$ and $Pd(PPh_3)_2(OAc)_2$, optionally in the presence of at least one ligand, preferably in the presence of at least one ligand selected from the group consisting of triphenylphosphine, triphenylarsine und tri-2-furyl-phosphine, preferably in the presence of triphenylphosphine, optionally in the presence of at least one inorganic salt, preferably in the presence of at least one inorganic salt selected from the group consisting of lithium chloride and zinc chloride, optionally in the presence of at least one copper salt, preferably in the presence of copper iodide, optionally in the presence of at least one organic or inorganic base, preferably in the presence of at least one base selected from the group consisting of triethylamine, [1,4]-diazabicyclo-[2.2.2]-octane, diisopropylamine, diisopropylethylamine, potassium carbonate and sodium hydrogen carbonate, preferably at a temperature of −70° C. to 300° C. are reacted to form a compound of general formula I. Particularly preferably, compounds of general formula $R^{11}$—I or $R^{11}$—Br are reacted with compounds of general formula VIII, in dimethylformamide in the presence of $Pd(PPh_3)_2Cl_2$, copper(I) iodide and diisopropylamine or triethylamine.

A further method according to the invention for the production of substituted thiazoles of the foregoing general formula I is also given in Diagram 4 below.

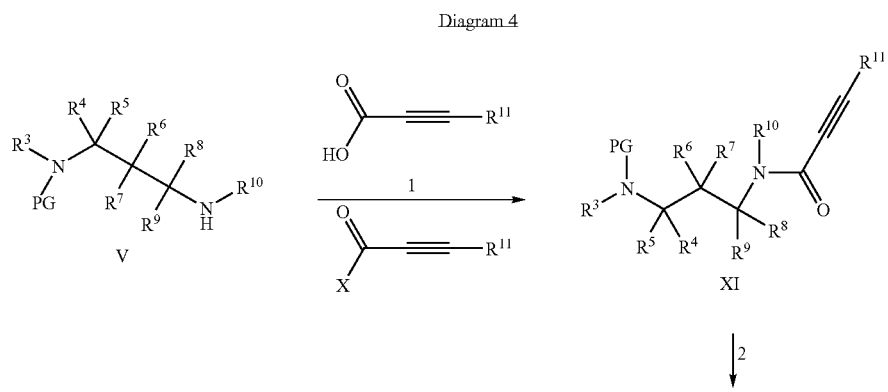

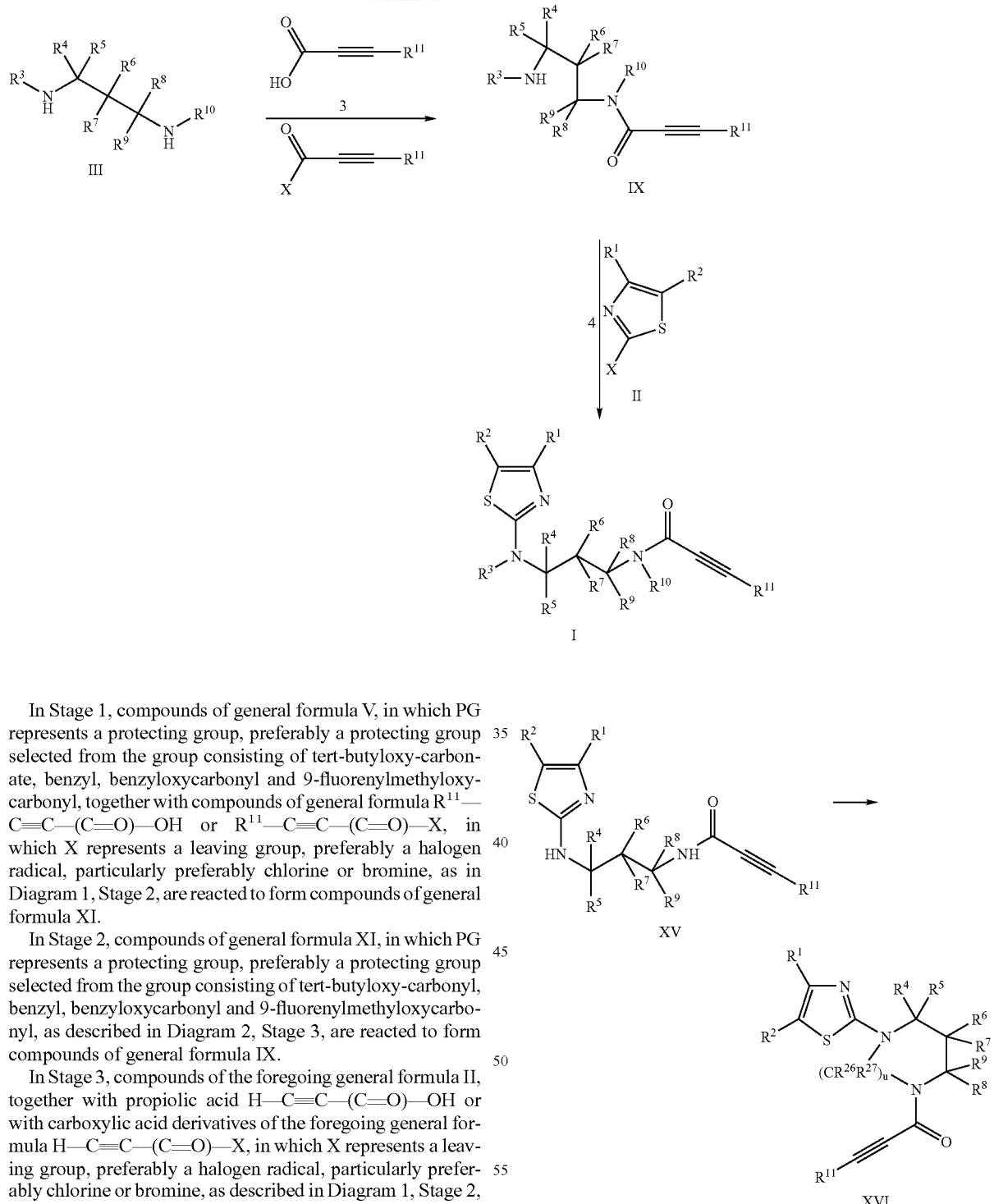

In Stage 1, compounds of general formula V, in which PG represents a protecting group, preferably a protecting group selected from the group consisting of tert-butyloxy-carbonate, benzyl, benzyloxycarbonyl and 9-fluorenylmethyloxycarbonyl, together with compounds of general formula $R^{11}$—C≡C—(C═O)—OH or $R^{11}$—C≡C—(C═O)—X, in which X represents a leaving group, preferably a halogen radical, particularly preferably chlorine or bromine, as in Diagram 1, Stage 2, are reacted to form compounds of general formula XI.

In Stage 2, compounds of general formula XI, in which PG represents a protecting group, preferably a protecting group selected from the group consisting of tert-butyloxy-carbonyl, benzyl, benzyloxycarbonyl and 9-fluorenylmethyloxycarbonyl, as described in Diagram 2, Stage 3, are reacted to form compounds of general formula IX.

In Stage 3, compounds of the foregoing general formula II, together with propiolic acid H—C≡C—(C═O)—OH or with carboxylic acid derivatives of the foregoing general formula H—C≡C—(C═O)—X, in which X represents a leaving group, preferably a halogen radical, particularly preferably chlorine or bromine, as described in Diagram 1, Stage 2, are reacted to form compounds of general formula IX.

In Stage 4, compounds of general formula IX, together with compounds of general formula II, as in Diagram 1, Stage 1, are reacted to form compounds of general formula I.

Compounds of general formula I, in which $R^3$ and $R^{10}$ each represent a hydrogen radical, designated in the following as compounds of general formula XV, are converted into compounds of general formula I, in which $R^3$ and $R^{10}$ along with the —N—$CR^4R^5$—$CR^6R^7$—$CR^8R^9$—N group linking them form a cyclic radical, designated in the following as compounds of general formula XVI.

Compounds of general formula XV, together with compounds of general formula Y—($CR^{26}R^{27}$)—W, in which $R^{26}$, $R^{27}$ and u have the meaning given above and Y and W independently of one another each represent a leaving group, preferably a halogen radical or a sulphonic acid ester selected from the group consisting of mesylate, triflate and tosylate, particularly preferably a chlorine or bromine atom, optionally in a reaction medium, preferably selected from the group consisting of methanol, ethanol, isopropanol, n-butanol, diethyl ether, tetrahydrofuran, dichloromethane, chloroform, dimethylformamide, acetonitrile, pyridine, dioxan, ethylacetate, dimethylsulphoxide, toluene and corresponding mixtures, particularly preferably in a reaction medium selected from the group consisting of acetonitrile, dichloroethane, chloroform, dimethylformamide, tetrahydrofuran and diethyl ether, optionally in the presence of at least one organic or inorganic base, preferably selected from the group consisting of triethylamine, sodium hydrogen carbonate, dimethylaminopyridine, potassium carbonate and sodium hydroxide, and/or optionally in the presence of at least one organometallic compound or a metal hydride reagent, preferably selected from the group consisting of n-butyllithium, phenyllithium, sodium hydride, potassium-tert-butanolate, potassium hydride and sodium amide, preferably at temperatures of $-70°$ C. to $300°$ C., particularly preferably at temperatures of $-70°$ C. to $150°$ C., are reacted to form compounds of general formula XVI.

Compounds of general formula XV are converted into compounds of general formula I, in which at least one of the radicals $R^3$ and $R^{10}$ does not represent a hydrogen radical.

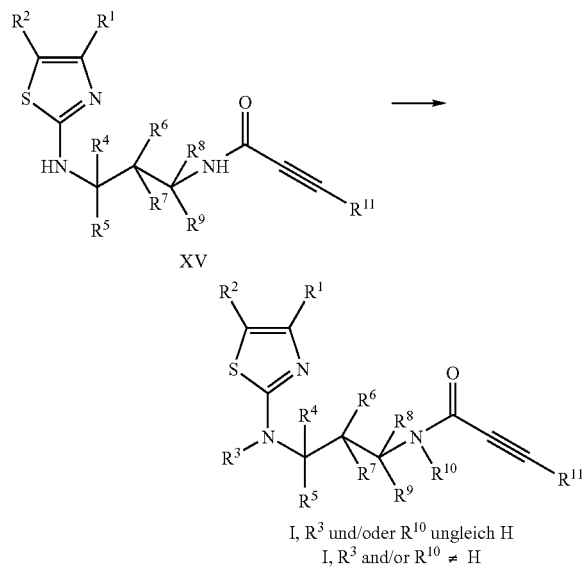

I, $R^3$ und/oder $R^{10}$ ungleich H
I, $R^3$ and/or $R^{10} \neq$ H

Compounds of general formula XV, together with compounds of general formula $R^3$—X or $R^{10}$—X, in which $R^3$ and $R^{10}$ have the meaning given above and X represents a leaving group, preferably a halogen radical or a sulphonic acid ester selected from the group consisting of mesylate, triflate and tosylate, particularly preferably a chlorine or bromine atom, optionally in a reaction medium, preferably selected from the group consisting of methanol, ethanol, isopropanol, n-butanol, diethyl ether, tetrahydrofuran, dichloromethane, chloroform, dimethylformamide, acetonitrile, pyridine, dioxan, ethylacetate, dimethylsulphoxide, toluene and corresponding mixtures, particularly preferably in a reaction medium selected from the group consisting of acetonitrile, dichloroethane, chloroform, dimethylformamide, tetrahydrofuran and diethyl ether, optionally in the presence of at least one organic or inorganic base, preferably selected from the group consisting of triethylamine, sodium hydrogen carbonate, dimethylaminopyridine, potassium carbonate and sodium hydroxide, and/or optionally in the presence of at least one organometallic compound or a metal hydride reagent, preferably selected from the group consisting of n-butyllithium, phenyllithium, sodium hydride, potassium-tert-butanolate, potassium hydride and sodium amide, preferably at temperatures of $-70°$ C. to $300°$ C., particularly preferably at temperatures of $-70°$ C. to $150°$ C., are reacted to form compounds of general formula I, in which at least one of the radicals $R^3$ and $R^{10}$ does not represent a hydrogen radical.

Compounds of the formulae II, III, V, VII, XIII, XIV given above, and of the general formulae $R^{11}$—X, Y—$(CR^{26}R^{27})_u$—W, $R^3$—X, $R^{10}$—X, $R^{11}$—C≡C—(C═O)—OH, $R^{11}$—C≡C—(C═O)—X and H—C≡C—C(═O)—X are in each case commercially available on the market and/or can be produced according to the conventional methods known to the person skilled in the art.

The reactions disclosed above may in each case be carried out under conventional conditions which are familiar to the person skilled in the art, for example in terms of pressure or the sequence in which the components are added. Optionally, the optimal manner of proceeding, in terms of the conditions in each case, can be determined by the person skilled in the art by way of simple preliminary experiments.

The by-products and final products obtained from the reactions disclosed above may in each case, if desired and/or required, be purified and/or isolated by conventional methods known to the person skilled in the art. Suitable purification processes include, for example, extraction methods and chromatographic methods such as column chromatography or preparative chromatography All of the method steps disclosed above and the purification and/or isolation of by-products or final products in each case may be carried out partially or completely in an inert gas atmosphere, preferably in a nitrogen atmosphere.

If the substituted thiazoles according to the invention, represented by the foregoing general formula I, are obtained after their production in the form of a mixture of the stereoisomers thereof, preferably in the form of the racemates thereof or other mixtures of the various enantiomers and/or diastereomers thereof, these may be separated and optionally isolated according to conventional methods known to the person skilled in the art. For example, chromatographic separation methods, in particular liquid chromatography methods at standard pressure or increased pressure, preferably MPLC and HPLC methods, and fractional crystallisation methods are included. Thus, individual enantiomers in particular can be separated from the diastereomeric salts that are formed, for example by means of chiral phase HPLC or crystallisation with chiral acids, such as (+)-tartaric acid, (−)-tartaric acid or (+)-10-camphorsulphonic acid.

The substituted thiazoles according to the invention, of the foregoing general formula I, and optionally respectively corresponding stereoisomers can be obtained in the from of corresponding salts, in particular in the form of corresponding physiologically acceptable salts, by conventional methods known to the person skilled in the art, it being possible for the drugs according to the invention to comprise one or more salts of one or more of these compounds.

The respective salts of the substituted thiazoles according to the invention, of the foregoing general formula I, and of corresponding stereoisomers can be obtained for example by a reaction with one or more inorganic acids and/or one or more organic acids. Suitable acids may preferably be selected from the group consisting of perchloric acid, hydrochloric acid, hydrobromic acid, sulphuric acid, methanesulphonic acid, formic acid, acetic acid, oxalic acid, succinic acid, tartaric acid, mandelic acid, fumaric acid, lactic acid, citric acid, glutamic acid, saccharic acid, cyclohexanesulphamic acid, aspartame, monomethylsebacic acid, 5-oxo-proline, hexane- 1-sulphonic acid, niacin, 2-aminobenzoic acid, 3-aminobenzoic acid or 4-aminobenzoic acid, 2,4,6-trimethylbenzoic acid, α-lipoic acid, acetyl glycine, hippuric acid, phosphoric acid, maleic acid, malonic acid and aspartic acid.

The substituted thiazoles according to the invention, of the foregoing general formula I, and optionally corresponding stereoisomers and respectively corresponding salts thereof can also be obtained in the form of the solvates thereof, in particular in the form of the hydrates thereof, by conventional methods known to the person skilled in the art.

It has now surprisingly been found that the substituted thiazoles according to the invention, of the foregoing general formula I, are suitable for mGluR5 receptor regulation and thus can be used in particular as active pharmaceutical ingredients in drugs for the prophylaxis and/or treatment of disorders or diseases connected with these receptors and/or processes.

The substituted thiazoles according to the invention, of the foregoing general formula I, and optionally corresponding stereoisomers and respective physiologically acceptable salts and solvates appear to be toxicologically harmless and are thus suitable as active pharmaceutical ingredients in drugs.

The present invention further relates to a drug containing at least one substituted thiazole according to the invention, of the foregoing general formula I, in each case optionally in the form of one of the pure stereoisomers, in particular enantiomers or diastereomers thereof, the racemates thereof or in the form of a mixture of stereoisomers, in particular the enantiomers and/or diastereomers, in any ratio desired, or in each case in the form of a corresponding salt, or in each case in the form of a corresponding solvate, as well as optionally one or more pharmaceutically acceptable excipients.

The drug according to the invention is suitable for mGluR5 receptor regulation, in particular for mGluR5 receptor inhibition.

Preferably, the drug according to the invention is suitable for the prophylaxis and/or treatment of disorders and/or diseases which are mediated at least in part by mGluR5 receptors.

Particularly preferably, the drug according to the invention is thus suitable for the treatment and/or prophylaxis of pain, preferably of pain selected from the group consisting of acute pain, chronic pain, neuropathic pain and visceral pain; migraines; depression; neurodegenerative diseases, preferably selected from the group consisting of multiple sclerosis, Alzheimer's disease, Parkinson's disease and Huntington's disease; cognitive impairments, preferably cognitive deficiencies, particularly preferably attention deficit disorder (ADD); anxiety states; panic attacks; epilepsy; coughs; urinary incontinence; diarrhœa; pruritus; schizophrenia; cerebral ischæmia; muscle spasms; cramps; lung diseases, preferably selected from the group consisting of asthma and pseudo-croup; regurgitation (vomiting); apoplexy; dyskinesia; retinopathy; lethargy; laryngitis; dietary disorders, preferably selected from the group consisting of bulimia, cachexia, anorexia and adiposis; alcohol dependency; medication dependency; drug dependency, especially nicotine and/or cocaine dependency; alcohol abuse; medication abuse; drug abuse; preferably nicotine and/or cocaine abuse; withdrawal symptoms from alcohol, medication and/or drug (in particular nicotine and/or cocaine) dependency; development of tolerance to medications, preferably to natural or synthetic opioids; gastrocesophageal reflux syndrome; gastrocesophageal reflux disease; irritable bowel syndrome; for diuresis; for antinatriuresis; for influencing the cardiovascular system; for increasing alertness; for increasing libido; for the modulation of locomotor activity and for local anaesthesia.

More particularly preferably, the drug according to the invention is suitable for the prophylaxis of pain, preferably of pain selected from the group consisting of acute pain, chronic pain, neuropathic pain and visceral pain; anxiety states; panic attacks; alcohol dependency; medication dependency; dietary disorders, preferably selected from the group consisting of bulimia, cachexia, anorexia and adiposis; drug dependency, especially nicotine and/or cocaine dependency; alcohol abuse; medication abuse; drug abuse; preferably nicotine and/or cocaine abuse; withdrawal symptoms from alcohol, medication and/or drug (in particular nicotine and/or cocaine) dependency; development of tolerance to medications and/or drugs, in particular to natural or synthetic opioids; gastrocesophageal reflux syndrome, gastrocesophageal reflux disease and irritable bowel syndrome.

Even more preferably, the drug according to the invention is suitable for the prophylaxis and/or treatment of pain, preferably of pain selected from the group consisting of acute pain, chronic pain, neuropathic pain and visceral pain, anxiety states and panic attacks.

Most preferably of all, the drug according to the invention is suitable for the prophylaxis and/or treatment of pain, preferably of acute pain, chronic pain, neuropathic pain or visceral pain.

The invention further relates to the use of at least one substituted thiazole according to the invention, of the foregoing general formula I, in each case optionally in the form of one of the pure stereoisomers, in particular enantiomers or diastereomers thereof, the racemates thereof or in the form of a mixture of stereoisomers, in particular the enantiomers and/or diastereomers, in any ratio desired, or in each case in the form of a corresponding salt, or in each case in the form of a corresponding solvate, as well as optionally one or more pharmaceutically acceptable excipients, for producing a drug for mGluR5 receptor regulation, in particular for mGluR5 receptor inhibition.

Preferably, the use of at least one substituted thiazole according to the invention, of the foregoing general formula I, in each case optionally in the form of one of the pure stereoisomers, in particular enantiomers or diastereomers thereof, the racemates thereof or in the form of a mixture of stereoisomers, in particular the enantiomers and/or diastereomers, in any ratio desired, or in each case in the form of a corresponding salt, or in each case in the form of a corresponding solvate, as well as optionally one or more pharmaceutically acceptable excipients, is for the production of a drug for the prophylaxis and/or treatment of disorders and/or diseases which are mediated at least partially by mGluR5 receptors.

Particularly preferably, the use of a substituted thiazole according to the invention, of the foregoing general formula I, in each case optionally in the form of one of the pure stereoisomers, in particular enantiomers or diastereomers thereof, the racemates thereof or in the form of a mixture of stereoisomers, in particular the enantiomers and/or diastereomers, in any ratio desired, or in each case in the form of a corresponding salt, or in each case in the form of a corresponding solvate, as well as optionally one or more pharmaceutically acceptable excipients, is for the production of a drug for the prophylaxis and/or treatment of pain, preferably of pain selected from the group consisting of acute pain, chronic pain, neuropathic pain and visceral pain; migraines; depression; neurodegenerative diseases, preferably selected from the group consisting of multiple sclerosis, Alzheimer's disease, Parkinson's disease and Huntington's disease; cognitive impairments, preferably cognitive deficiencies, particularly preferably attention deficit disorder (ADD); anxiety states; panic attacks; epilepsy; coughs; urinary incontinence; diarrhœa;

pruritus; schizophrenia; cerebral ischæmia; muscle spasms; cramps; lung diseases, preferably selected from the group consisting of asthma and pseudo-croup; regurgitation (vomiting); apoplexy; dyskinesia; retinopathy; lethargy; laryngitis; dietary disorders, preferably selected from the group consisting of bulimia, cachexia, anorexia and adiposis; alcohol dependency; medication dependency; drug dependency, preferably nicotine and/or cocaine dependency; alcohol abuse; medication abuse; drug abuse; preferably nicotine and/or cocaine abuse; withdrawal symptoms from alcohol, medication and/or drug (in particular nicotine and/or cocaine) dependency; development of tolerance to medications, in particular to natural or synthetic opioids; gastrocesophageal reflux syndrome; gastrocesophageal reflux disease; irritable bowel syndrome; for diuresis; for antinatriuresis; for influencing the cardiovascular system; for increasing alertness; for increasing libido; for the modulation of locomotor activity and for local anaesthesia.

More particularly preferably, the use of a substituted thiazole according to the invention, of the foregoing general formula I, in each case optionally in the form of one of the pure stereoisomers, in particular enantiomers or diastereomers thereof, the racemates thereof or in the form of a mixture of stereoisomers, in particular the enantiomers and/or diastereomers, in any ratio desired, or in each case in the form of a corresponding salt, or in each case in the form of a corresponding solvate, as well as optionally one or more pharmaceutically acceptable excipients, is for the production of a drug for the prophylaxis and/or treatment of pain, preferably of pain selected from the group consisting of acute pain, chronic pain, neuropathic pain and visceral pain; anxiety states; panic attacks; alcohol dependency; medication dependency; dietary disorders, preferably selected from the group consisting of bulimia, cachexia, anorexia and adiposis; drug dependency, especially nicotine and/or cocaine dependency; alcohol abuse; medication abuse; drug abuse; preferably nicotine and/or cocaine abuse; withdrawal symptoms from alcohol, medication and/or drug (in particular nicotine and/or cocaine) dependency; development of tolerance to medications and/or drugs, in particular to natural or synthetic opioids; gastrocesophageal reflux syndrome, gastrocesophageal reflux disease and irritable bowel syndrome.

Even more preferably, the use of at least one substituted thiazole according to the invention, of the foregoing general formula I, in each case optionally in the form of one of the pure stereoisomers, in particular enantiomers or diastereomers thereof, the racemates thereof or in the form of a mixture of stereoisomers, in particular the enantiomers and/or diastereomers, in any ratio desired, or in each case in the form of a corresponding salt, or in each case in the form of a corresponding solvate, as well as optionally one or more pharmaceutically acceptable excipients, is for the production of a drug for the prophylaxis and/or treatment of pain, preferably of pain selected from the group consisting of acute pain, chronic pain, neuropathic pain and visceral pain, anxiety states and panic attacks.

The drug according to the invention is suitable for administration to adults and children including young children and babies.

The drug according to the invention may be present in a liquid, semi-solid or solid form, for example in the form of injection solutions, drops, juices, syrups, sprays, suspensions, tablets, patches, capsules, plasters, suppositories, ointments, creams, lotions, gels, emulsions, aerosols or in multi-particulate form, for example in the form of pellets or granules, optional pressed into tablets, filled into capsules or suspended in a liquid, and may likewise be administered in these forms.

As well as at least one substituted thiazole according to the invention, of the foregoing general formula I, in each case optionally in the form of one of the pure stereoisomers, in particular enantiomers or diastereomers thereof, the racemates thereof or in the form of a mixture of stereoisomers, in particular the enantiomers and/or diastereomers, in any ratio desired, or in each case in the form of a corresponding salt, or optionally in the form of a corresponding solvate, the drug according to the invention usually contains other physiologically acceptable pharmaceutical excipients, which may preferably be selected from the group consisting of carriers, fillers, solvents, diluents, surface active agents, dyes, preservatives, disintegrants, slip agents, lubricants, flavourings and binders.

The selection of physiologically acceptable excipients and the amounts thereof to be used depends on whether the drug is to be administered orally, subcutaneously, parenterally, intravenously, intraperitoneally, intradermally, intramuscularly, intranasally, buccally, rectally or topically, for example to infections of the skin, the mucous membranes or the eyes. Preparations in the form of tablets, dragées, capsules, granules, pellets, drops, juices and syrups are suitable for oral administration; solutions, suspensions, easily reconstitutable dry preparations and sprays are suitable for parenteral, topical and inhalative administration.

The substituted thiazoles of the foregoing general formula I, which are used in the drugs according to the invention are suitable percutaneous application preparations when in a deposit, in dissolved form or in a plaster, optionally with the addition of agents to promote skin penetration.

Orally and percutaneously administrable forms of the preparation may also release the respective substituted thiazoles of the foregoing general formula I, in a delay.

The production of the drugs according to the invention takes place by conventional means, devices, methods and processes known from the state of the art, as described for example in "Remington's Pharmaceutical Sciences", A. R. Gennaro (ed.), 17th Edition, Mack Publishing Company, Easton, Pa., 1985, in particular in part 8, chapters 76 to 93. The corresponding description is hereby introduced as a reference and is deemed to be part of the disclosure.

The amount of the respective substituted thiazole, of the foregoing general formula I, to be administered to the patient may vary and is dependent, for example, on the weight or age of the patient and on the method of administration, the indication and the severity of the disease. Conventionally, based on the body weight of the patient, 0.05 to 100 mg/kg, in particular 0.05 to 10 mg/kg of at least one such compound should be administered.

Pharmacological Methods:

I. Method for Determining the Inhibition of the [$^3$H]-MPEP Binding in the mGluR5 Receptor Binding Assay Pig brain homogenate is produced by the homogenisation (Polytron PT 3000, Kinematica AG, 10,000 rpm for 90 seconds) of pig brain halves without medulla, cerebellum and pons, in a buffer with pH 8.0 (30 mM Hepes, Sigma, order no. H3375+1 "Complete Tablet" to 100 ml, Roche Diagnostics, order no. 1836145) in the ratio 1:20 (brain weight/volume) and differential centrifuging at 900×g and 40,000×g. 450 µg of protein from brain homogenate are incubated in 250 µl incubation preparation in 96-well microtiter plates, for 60 minutes at room temperature in a buffer (as above), along with 5 nM $^3$[H]-MPEP (Tocris, order no. R1212) (MPEP=2-methyl-6-(3-methoxyphenyl)-ethynylpyridine) and the compounds to be analysed (10 µM in the test).

Subsequently, the preparations are filtered on unifilter plates with fibreglass filter mats (Perkin Elmer, order no. 6005177) using a Brandel Cell Harvester (Brandel, TYP Robotic 9600) and subsequently washed with buffer (as above) 3 times with 250 µl per sample in each case. The filter plates are subsequently dried for 60 min at 55° C. Subsequently 30 µl Ultima Gold™ scintillator (Packard Bioscience, order no. 6013159) are added to each well, and after 3 hours the samples are measured with the β-counter (Mikrobeta, Perkin Elmer). The non-specific binding is determined by adding 10 μM MPEP (Tocris, order no. 1212).

II. Method for Determining the $Ca^{2+}$ Influx in the mGluR5 Receptor Assay

An agonistic and/or antagonistic effect of substances can be determined at the mGluR5 receptor of the rat species with the following assay. According to this assay, the intracellular $Ca^{2+}$ release is quantified after activation of the mGluR5-receptor by means of a $Ca^{2+}$ sensitive dye (Fluo-4 type, Molecular Probes Europe BV, Leiden, the Netherlands) in the FlexStation (Molecular Devices, Sunnyvale, USA).

Preparation of Cortical Neurones:

Cortical neurones are prepared from postnatal rats (P2-6) under sterile conditions. For this purpose, the cortex is removed and transferred directly into collagenase solution (PAA Laboratories GmbH, Colbe, Germany) and incubated for 45 minutes in the hot shaker (37° C., 300 rpm). Subsequently, the collagenase solution is removed and culture medium is added to the tissue.

Culture Medium (100 ml):

Neurobasal medium (Gibco Invitrogen GmbH, Karlsruhe, Germany)
2 mM L-Glutamin (Sigma, Taufkirchen, Germany)
1% by volume antibiotic/antimycotic solution (PAA Laboratories GmbH, Colbe, Germany)
15 ng/ml NGF (Gibco Invitrogen GmbH, Karlsruhe, Germany)
1 ml B27 Supplement (Gibco Invitrogen GmbH, Karlsruhe, Germany)
1 ml ITS Supplement (Sigma, Taufkirchen, Germany)

The cells are isolated by resuspension and centrifuged after the addition of 15 ml neurobasal medium by a 70 μm filter element (BD Biosciences, Heidelberg, Germany). The resulting cell pellet is absorbed in culture medium. Subsequently, the cells are plated onto poly-D-lysine-coated, black, 96-hole plates with clear bases (BD Biosciences, Heidelberg, Germany), which have previously additionally been coated with laminine (2 μg/cm², Gibco Invitrogen GmbH, Karlsruhe, Germany). The cell density is about 15,000 cells/hole. The cells are incubated at 37° C. and 5% $CO_2$, and the medium is changed on the 2nd or 3rd day after preparation. Depending on the cell growth, the functional analysis can be carried out on the 3rd to 7th day after preparation.

Description of the Functional $Ca^{2+}$ Influx Assay 20,000 CHO-mGluR5 cells/well (Euroscreen, Gosselies, Belgium) are pipetted into 96-well plates (BD Biosciences, Heidelberg, Germany, Ref. 356640, clear bottom, 96 well, poly-D-lysine) and incubated overnight in HBSS buffer (Gibco no. 14025-050) with the following additives: 10% FCS (GIBCO, 10270-106) and Doxycyclin (BD Biosciences Clontech 631311 600 ng/ml).

For the functional analysis, the cells were loaded with 2 μM Fluo-4 and 0.01% by volume Pluronic F127 (Molecular Probes Europe BV, Leiden Netherlands) in HBSS buffer (Hank's buffered saline solution, Gibco Invitrogen GmbH, Karlsruhe, Deutschland) with Probenicid (Sigma P8761, 0.69 mg/ml) for 30 minutes at 37° C.

The cells are then washed 3 times with wash buffer (HBSS buffer, Gibco no. 14025-050, with Probenicid (Sigma P8761, 0.69 mg/ml)) and subsequently taken up to 100 μl with the same buffer. After 15 minutes, the plates are transferred into a fluorometric imaging plate reader (FLIPR, Molecular Devices, Sunnyvale, Calif.), in the presence of DHPG ((S)-3,5-dihydroxyphenylglycine, Tocris Biotrend Chemikalien GmbH, Cologne, Germany, final DHPG concentration: 10 μM) and in the presence or absence of test substances, for the determination of $Ca^{2+}$ measurements.

The $Ca^{2+}$ dependent fluorescence is in this case measured before and after the addition of test substances. The quantification takes place by measuring the highest fluorescence intensity over time.

Once a fluorescence baseline has been obtained for 10 seconds, 50 μl of test substance solution (various test substance concentrations in HBSS buffer with 1% DMSO and 0.02% Tween 20, Sigma) are added and the fluorescence signal is measured for 6 minutes. Subsequently, 50 μl DHPG solution ((S)-3,5-dihydroxyphenylglycine, Tocris Biotrend Chemikalien GmbH, Cologne, Germany, final DHPG concentration: 10 μM) is added and the influx of $Ca^{2+}$ is simultaneously measured for 60 seconds. The final DMSO concentration is 0.25% and the final Tween 20 content is 0.005%. The data were analysed using Microsoft Excel and GraphPad Prism. The dose effect graphs were calculated with non-linear regression and $IC_{50}$ values were determined. Each data point was determined 3 times and $IC_{50}$ values were obtained from at least 2 independent measurements.

Ki values are calculated according to the following formula: $Ki=IC_{50}/(1+(AG_{conc.}/EC50))$.

$AG_{conc.}=10$ μM; EC50 corresponds to the DHPG concentration necessary for half of the maximum influx of $Ca^{2+}$.

III. Formalin Test on the Rat:

The formalin test (Dubuisson, D. and Dennis, S. G., 1977, Pain, 4, 161 to 174) is a model for acute and chronic pain. By means of a single formalin injection into the dorsal side of a hind paw of test animals that were able to move freely, a biphasic nociceptive reaction, which was detected by the observation of three clearly distinguishable behavioural patterns, was induced. The reaction is in two phases: Phase 1=immediate reaction (duration up to 10 min.; paw shaking, licking), Phase 2=later reaction (after a calm phase; likewise, paw shaking, licking; duration up to 60 min.). The 1st phase reflects a direct stimulation of the peripheral nocisensors with high spinal nociceptive input and glutamate release (acute pain phase); the 2nd phase reflects a spinal and peripheral hypersensitivity (chronic pain phase). In the analyses presented here, the chronic pain component (phase 2) was evaluated.

Formalin was administered subcutaneously into the dorsal side of the right hind paw of each animal in a volume of 50 μl and a concentration of 5%. The substances to be tested are applied orally (p.o.), intravenously (i.v.) or intraperitoneally (i.p.) 30 minutes before the formalin injection. The specific behavioural changes, such as raising and shaking of the paw, weight loss in the animal and biting and licking reactions, were continuously observed and recorded for 21 to 27 min after the formalin injection. The collation of the various types of behaviour results in what is known as the pain rate (PR) which, based on the sub-intervals of 3 min., represents the calculation of an average nociception reaction. The PR is calculated on the basis of a numerical weighting (=each factor 1, 2, 3) of the observed behaviours (corresponding behaviour scores 1, 2, 3) and is calculated with the following formula:

$$PR=[(T_0\times0)+(T_1\times1)+(T_2\times2)+(T_3\times3)]/180$$

in which $T_0$, $T_1$, $T_2$, and $T_3$ respectively correspond to the time in seconds for which the animal exhibits the behaviour 0, 1, 2 or 3. The group contained 10 animals (n=10).

The following examples serve to describe the invention in more detail, but do not limit the general idea of the invention.

EXAMPLES

The yields of the compounds produced were not optimised.
All temperatures are uncorrected.
The term "equivalent" denotes equivalent substance quantities, "RT" room temperature, "conc." concentrated, "d" days", "min." minutes, "h" hours, "M" is a concentration indication in mol/l, "aq." aqueous, "sat." saturated, "soln" solution, "CC" column chromatography Further Abbreviations Brine saturated aqueous NaCl solution
BOC tert-butoxy-carbonyl
CDI 1,1'-carbonyl-diimidazole DCC dicyclohexylcarbodiimide
DCE dichloroethane
DCM dichloromethane
DIC N,N'-diisopropylcarbodiimide
DMF N,N-dimethylformamide
DIPE diisopropylether
DIPEA diisopropylethylamine
EDCI N-Ethyl-N'-(3-dimethylaminopropyl)-carbodiimide hydrochloride
EE ethyl acetate
EtOH ethanol
$H_2O$ water
HOBt 1-hydroxy-benzotriazole
Soln solution
MeCN acetonitrile
MeOH methanol
TBTU O-(benzotriazol-1-yl)-N,N,N',N'-tetramethyluronium-tetrafluoroborate
TMSCl trimethylchlorosilane
THF tetrahydrofuran The chemicals and solvents used were acquired commercially from conventional suppliers (Acros, Avocado, Aldrich, Bachem, Fluka, Lancaster, Maybridge, Merck, Sigma, TCI etc.) or synthesised using the conventional methods known to the person skilled in the art.

Silica gel 60 (0.040-0.063 mm) from E. Merck, Darmstadt was used as the stationary phase for column chromatography.

Thin-layer chromatography was performed with precoated silica gel 60 F 254 HPTLC plates from E. Merck, Darmstadt.

The mixing ratios of solvents, eluants or for chromatographic analyses are always given by volume/volume.

Analysis was carried out by mass spectroscopy and/or NMR.

Example Compound 1

N-(3-((thiazol-2-yl)amino)propyl)-3-phenylpropiolamide

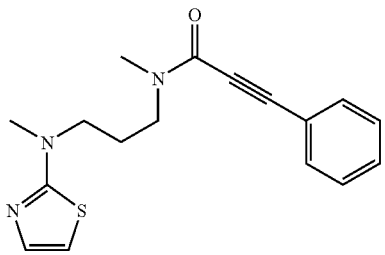

a) Synthesis of $N^1,N^3$-dimethyl-$N^1$-(thiazol-2-yl)propane-1,3-diamine 2.45 g (24.0 mmol) N,$N^3$-dimethylpropane-1,3-diamine was added to 0.36 ml (4.0 mmol) 2-bromothiazole and heated to 120° C. for 1 h. After cooling to RT, dilution with water and chloroform took place. The phases were separated and the aqueous phase was extracted with chloroform. The combined organic phases were dried over $MgSO_4$, filtered, and concentrated in vacuo. Column chromatography (SiO$_2$, DCE/MeOH/25% aq. NH$_3$-soln 4:4:1) was carried out on the residue, yielding 440 mg (2.4 mmol, 59%) $N^1,N^3$-dimethyl-$N^1$-(thiazol-2-yl)propane-1,3-diamine.

b) Synthesis of N-(3-((thiazol-2-yl)amino)propyl)-3-phenylpropiolamide 440 mg (2.37 mmol) $N^1,N^3$-dimethyl-$N^1$-(thiazol-2-yl)propane-1,3-diamine was dissolved, together with 347 mg (2.37 mmol) 3-phenyl propiolic acid, 412 µl (2.37 mmol) DIPEA and 761 mg (2.37 mmol) TBTU, in THF (30 ml), and stirred for 2 h at RT. The reaction solution was concentrated in vacuo and the residue was taken up by chloroform, washed with water and brine, dried over $MgSO_4$ and concentrated in vacuo. CC (DCE/EtOH 10:1) was carried out on the residue, yielding 314 mg (1.00 mmol, 42%) N-(3-((thiazol-2-yl)amino)propyl)-3-phenylpropiolamide. MS [MH+] 314.1

Example Compound 2

4-(thiazol-2-yl-amino)-1-(3-phenyl-propiolyl)piperidine

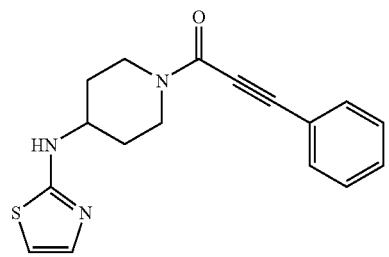

a) Synthesis of tert-butyl-4-(thiazol-2-ylamino)piperidine-1-carboxylate

A mixture of 5.0 g (50 mmol) 2-aminothiazole, 10.0 g (50 mmol) tert-butyl 4-aminopiperidine-1-carboxylate, 21.2 g (100 mmol) sodium triacetoxyborohydride and 5.7 ml (100 mmol) acetic acid in THF (100 ml) was stirred for 24 h at RT. Subsequently, a further 10.6 g (50 mmol) sodium triacetoxyborohydride and 2.85 ml (50 mmol) acetic acid were added and stirring took place for a further 2 d at RT. The solvent was removed in vacuo and the residue was taken up by chloroform and washed a plurality of times with 10% aq. NaOH soln and water. The organic phase was dried over $MgSO_4$, filtered, and concentrated in vacuo. Column chromatography (SiO$_2$, Chloroform/EtOH 20:1) was carried out on the residue, yielding 712 mg (2.5 mmol, 25%) tert-butyl-4-(thiazol-2-ylamino)piperidine-1-carboxylate.

b) Synthesis of N-(piperidin-4-yl)thiazole-2-amine 810 mg (2.85 mmol) tert-butyl-4-(thiazol-2-ylamino)piperidine-1-carboxylate was dissolved in DCE (10 ml) and an ethereal HCl soln (10 ml) was added. After 3 h of stirring at RT, the solvent was removed in vacuo. The residue was taken up by water and adjusted to a pH of 11 with a 10% aq. NaOH soln. Extraction then took place with chloroform. The organic phase was washed with water and sat. aq. NaCl soln, dried over $MgSO_4$ and filtered, and the solvent was removed in vacuo. 483 mg (2.64 mmol, 93%) N-(piperidin-4-yl)thiazol-2-amine was thus obtained.

c) Synthesis of 4-(thiazol-2-yl-amino)-1-(3-phenyl-propiolyl)piperidine 3.93 g (corresponding to 5.12 mmol) PS-carbodiimide resin (polystyrene-carbodiimide resin) were added to a solution of 470 mg (2.56 mmol) N-(piperidin-4-yl)thiazole-2-amine and 374 mg (2.56 mmol) phenylpropiolic acid in DCM (15 ml). The reaction solution was shaken for 16 h at RT. Subsequently, filtering and washing with DCM and ethanol took place. The combined filtrates were washed with a 5% aq. potassium carbonate soln, water and sat. aq. NaCl soln, dried over MgSO$_4$, filtered and concentrated in vacuo. Column chromatography (SiO$_2$, DCE/EtOH 10:1) was carried out on the residue. 245 mg (0.79 mmol, 21%) 4-(thiazol-2-yl-amino)-1-(3-phenyl-propiolyl)piperidine was thus obtained. MS [MH+] 312.1

Example Compound 3

3-(thiazol-2-yl)-7-(3-phenyl)-propiolyl-3,7-diaza-bicyclo[3.3.0]octane

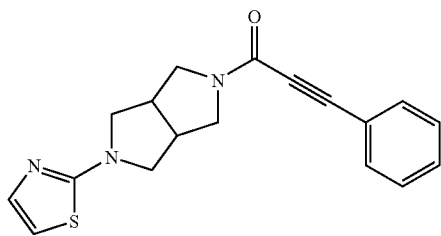

a) Synthesis of 5-thiazol-2-yl-hexahydro-pyrrolo[3,4-c]pyrrol-2-carboxylic acid tert-butyl-ester A solution of 541 µl (6.0 mmol) 2-bromothiazole and 1.27 g (6.0 mmol) hexahydro-pyrrolo[3,4-c]pyrrol-2-carboxylic acid tert-butyl-ester in n-butanol (10 ml) was heated for 2 h under reflux. Subsequently, the solvent was removed in vacuo and the residue taken up by chloroform. This solution was washed with water and brine in turn, dried over MgSO$_4$, filtered and concentrated in vacuo. Column chromatography was carried out on the residue (SiO$_2$, DCM/EtOH 10:1), yielding 450 mg (1.53 mmol, 25%) 5-thiazol-2-yl-hexahydro-pyrrolo[3,4-c]pyrrol-2-carboxylic acid tert-butyl-ester.

b) Synthesis of 2-thiazol-2-yl-octahydro-pyrrolo[3,4-c]pyrrole hydrochloride 400 mg (1.36 mmol) 5-thiazol-2-yl-hexahydro-pyrrolo[3,4-c]pyrrole-2-carboxylic acid tert-butyl-ester was dissolved in an ethereal HCl soln. After stirring for 1 h at RT, the resulting precipitate was filtered off and subsequently washed with ether. 130 mg (0.56 mmol, 41%) 2-thiazol-2-yl-octahydro-pyrrolo[3,4-c]pyrrole hydrochloride was thus obtained.

c) Synthesis of 3-(thiazol-2-yl)-7-(3-phenyl)-propiolyl-3,7-diaza-bicyclo[3.3.0]octane 130 mg (0.56 mmol) 2-thiazol-2-yl-octahydro-pyrrolo[3,4-c]pyrrole hydrochloride was dissolved, together with 97 mg (0.66 mmol) 3-phenylpropiolic acid, 64 µl (0.66 mmol) DIPEA and 224 mg (0.7 mmol), in MeCN (15 ml), and stirred for 3 h at RT. The reaction solution was concentrated in vacuo and the residue was taken up by chloroform, washed with water and brine, dried over MgSO$_4$ and concentrated in vacuo. CC (DCM/EtOH 40:1) was carried out on the residue, yielding 32 mg (0.10 mmol, 18%) 3-(thiazol-2-yl)-7-(3-phenyl)-propiolyl-3,7-diaza-bicyclo[3.3.0]octane. MS [MH+] 324.1

Example Compound 4

4-(methyl-thiazol-2-yl-amino)-1-(3-phenyl-propiolyl)piperidine

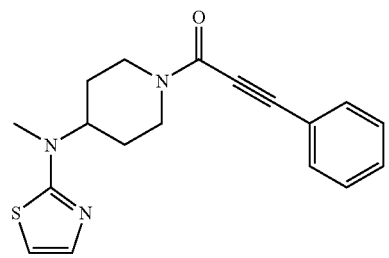

20 mg (0.50 mmol, 60% in mineral oil) sodium hydride was added to a suspension of 132 mg (0.42 mmol) 4-(thiazol-2-yl-amino)-1-(3-phenyl-propiolyl)piperidine (example compound 2) in MeCN (4 ml) and stirred for 10 min. at RT. Subsequently, 53 µl (0.84 mmol) iodomethane were added, and stirring took place for a further 2 h at RT. The solution was concentrated in vacuo, taken up by DCM and washed with water and sat. aq. NaCl soln. After drying over MgSO$_4$, filtering and removal of the solvent in vacuo, column chromatography (SiO$_2$, chloroform) was carried out on the residue, yielding 110 mg (0.34 mmol, 80%) 4-(methyl-thiazol-2-yl-amino)-1-(3-phenyl-propiolyl)piperidine. MS [MH+] 326.1

Example Compound 5

3-phenyl-N-(1-(thiazol-2-yl)piperidin-4-yl)propiolamide

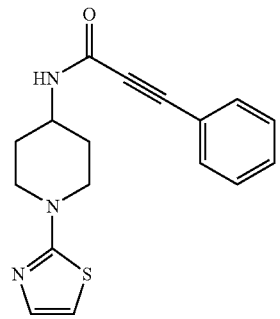

a) Synthesis of (1-thiazol-2-yl-piperidin-4-yl)-carbamic acid-tert-butyl ester 6.91 g (75.0 mmol) potassium carbonate was added to a solution of 1.35 ml (15.0 mmol) 2-bromothiazole and 3.00 g (15.0 mmol) piperidin-4-yl-carbamic acid-tert-butyl ester in DMF (50 ml) and heated to 120° C. for 8 h. Subsequently, the solvent was removed in vacuo and the residue taken up by chloroform. This solution was washed with water and brine in turn, dried over MgSO₄, filtered and concentrated in vacuo. Column chromatography (SiO₂, chloroform) was carried out on the residue, yielding 1.14 g (4.0 mmol, 27%) (1-thiazol-2-yl-piperidin-4-yl)-carbamic acid-tert-butyl ester.

b) Synthesis of 1-(thiazol-2-yl)piperidine-4-amine trifluoroacetate

Trifluoroacetic acid (10 ml) was added to a solution of 1.14 g (4.00 mmol) (1-thiazol-2-yl-piperidin-4-yl)-carbamic acid-tert-butyl ester in DCM (10 ml). The reaction solution was stirred for 1 h at RT and subsequently concentrated in vacuo. 1.02 g (0.34 mmol, 86%) 1-(thiazol-2-yl)piperidin-4-amine trifluoroacetate were obtained by crystallisation of the residue from an ethanol/EE-mixture.

c) Synthesis of 3-phenyl-N-(1-(thiazol-2-yl)piperidin-4-yl)propiolamide

A solution of 500 mg (1.68 mmol) 1-(thiazol-2-yl)piperidin-4-amine trifluoroacetate, 332 mg (2.02 mmol) 3-phenyl-propiolic acid and 1.17 ml DIPEA in DCE (20 ml) was stirred for 5 h at RT. Subsequently, the reaction solution was washed with water and a sat. aqueous Na₂CO₃ soln and dried over MgSO₄. After filtering and concentration in vacuo, column chromatography (SiO₂, chloroform) was performed on the residue, yielding 267 mg (0.86 mmol, 51%) 3-phenyl-N-(1-(thiazol-2-yl)piperidin-4-yl)propiolamide. MS [MH+] 312.1

Example Compound 6

N-methyl-3-phenyl-N-(1-(thiazol-2-yl)piperidin-4-yl)propiolamide

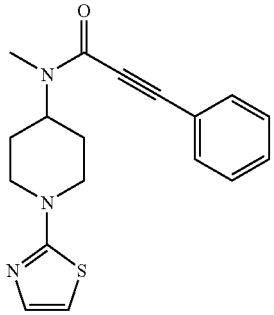

a) Synthesis of N-methyl-1-(thiazol-2-yl)piperidine-4-amine 384 mg (8.0 mmol, 60% in mineral oil) sodium hydride and 500 μl (8.0 mmol) iodomethane were added in turn to a solution of 1.13 g (4.0 mmol) (1-thiazol-2-yl-piperidin-4-yl)-carbamic acid-tert-butyl ester (see example 5a) for synthesis) in MeCN (40 ml). The reaction solution was stirred for 1 h at RT. Subsequently, a further 192 mg (4.0 mmol, 60% in mineral oil) sodium hydride and 250 μl (4.0 mmol) iodomethane were added and stirring took place for a further hour. Subsequently, 25% aq. ammoniac solution (2 ml) were added and concentration took place in vacuo. The residue was extracted with chloroform. The organic solution was washed with water and brine in turn, dried over MgSO₄, filtered, and concentrated in vacuo. This residue was dissolved in EtOH (10 ml) and a sat. ethereal HCl soln (20 ml) was added. After 1 h stirring at RT, concentration took place in vacuo. The residue was taken up by ether (20 ml) and water (30 ml) was added. After separation of the organic phase, the aqueous phase was made basic (pH>11) with a 20% NaOH soln. Extraction subsequently took place with chloroform. The organic phase was dried over MgSO₄, filtered, and concentrated in vacuo. 786 mg (3.99 mmol, 99%) N-methyl-1-(thiazol-2-yl)piperidine-4-amine were thus obtained.

b) Synthesis of N-methyl-3-phenyl-N-(1-(thiazol-2-yl)piperidin-4-yl)propiolamide 685 μl (4.38 mmol) DIC was added to a solution of 785 mg (4.00 mmol) N-methyl-1-(thiazol-2-yl)piperidin-4-amine and 640 mg (4.38 mmol) 3-phenyl-propiolic acid in MeCN (40 ml) and the reaction solution was stirred for 3 h at RT. Subsequently, concentration took place in vacuo and the residue was taken up by chloroform, washed with water and brine, dried over MgSO₄, filtered and concentrated in vacuo. 421 mg (1.30 mmol, 32%) (N-methyl-3-phenyl-N-(1-(thiazol-2-yl)piperidin-4-yl)propiolamide was obtained by CC (SiO₂, 1.DCE 2.Chloroform). MS [MH+] 326.1

Example Compound 7

4-(benzothiazol-2-yl-amino)-1-(3-(3-trifluoromethyl-phenyl)-propiolyl)piperidine

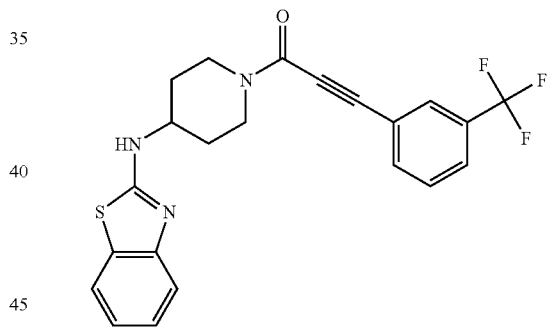

A solution of 15.0 mg (0.1 mmol) 2-amino-benzothiazole in THF (1 ml) was added to a solution of 29.5 mg (0.1 mmol) 1-(3-(3-(trifluoromethyl)phenyl)-propiolyl)piperidin-4-one in THF (1 ml) and heated for 6 h under reflux. After cooling to RT, 0.5 g (corresponding to 0.4 mmol) sodium acetoxyborohydride resin (load 1.8-2.4 mmol/g) were added and shaking took place for 24 h at RT. Subsequently, the resin was filtered off and the filtrate evaporated in vacuo. The residue was purified by preparative HPLC. 13.7 mg (0.032 mmol, 32%) 4-(benzothiazol-2-yl-amino)-1-(3-(3-trifluoromethyl-phenyl)-propiolyl)piperidinide were thus obtained. MS [MH+] 430.1

Example compounds 8 1-((3,4-dimethyl-phenyl)-propiolyl)-4-(thiazol-2-yl-amino)-piperidine (MS [MH+] 340.1) and 9 4-(benzothiazol-2-yl-amino)-1-(3,4-dimethyl-phenyl)-propiolyl)piperidine (MS [MH+] 390.2) were produced according to the method disclosed for example compound 7 above.

Example compounds 10 N-(1-(4-methyl-thiazol-2-yl)piperidin-4-yl)-3-phenyl-propiolamide (MS [MH+] 326.1), 11

N-(1-(4-methyl-thiazol-2-yl)piperidin-4-yl)-3-(3-methoxyphenyl)-propiolamide (MS [MH+] 356.1), 12 N-(1-(4-methyl-thiazol-2-yl)piperidin-4-yl)-3-(2-methoxyphenyl)-propiolamide (MS [MH+] 356.1), 13 N-(1-(4-methyl-thiazol-2-yl)piperidin-4-yl)-3-(4-methoxyphenyl)-propiolamide (MS [MH+] 356.1), 14 3-(4-fluoro-phenyl)-N-(1-(4-methyl-thiazol-2-yl)piperidin-4-yl)-propiolamide (MS [MH+] 344.1), 15 N-(1-(4-methyl-thiazol-2-yl)piperidin-4-yl)-3-(4-tolyl)-propiolamide (MS [MH+] 340.1), 16 3-(2-fluoro-phenyl)-N-(1-(4-methyl-thiazol-2-yl)piperidin-4-yl)-propiolamide (MS [MH+] 344.1), 17 3-(2,4-difluoro-phenyl)-N-(1-(4-methyl-thiazol-2-yl)piperidin-4-yl)-propiolamide (MS [MH+] 362.1), 18 N-(1-(4-methyl-thiazol-2-yl)piperidin-4-yl)-3-(4-trifluormethyl-phenyl)-propiolamide (MS [MH+] 394.1), 19 3-(3-fluoro-phenyl)-N-(1-(4-methyl-thiazol-2-yl)piperidin-4-yl)-propiolamide (MS [MH+] 344.1), 20 3-(3-fluoro-4-methyl-phenyl)-N-(1-(4-methyl-thiazol-2-yl)piperidin-4-yl)-propiolamide (MS [MH+] 358.1), 21 N-(1-(4-methyl-thiazol-2-yl)piperidin-4-yl)-3-(3-trifluoromethyl-phenyl)-propiolamide (MS [MH+] 394.1), 22 N-(1-(4-methyl-thiazol-2-yl)piperidin-4-yl)-3-(3-tolyl)-propiolamide (MS [MH+] 340.1) and 23 N-(1-(4-methyl-thiazol-2-yl)piperidin-4-yl)-3-(2-tolyl)-propiolamide (MS [MH+] 340.1) were produced according to the method disclosed above for example compound 5, section c).

Pharmacological Data:

1. The affinity of the substituted thiazoles of general formula I according to the invention for the mGluR5 receptor was determined as disclosed above.

The substituted thiazoles according to the invention have an excellent affinity for the mGluR5 receptor.

In Table I below, the pharmacological data for some substituted thiazoles are reproduced:

TABLE I

| Ex. | % inhibition of mGluR5 receptor (pig) [$^3$H]-MPEP bonding at 1 μM | $IC_{50}$ mGluR5 receptor (pig) [$^3$H]-MPEP bonding [μM] |
|---|---|---|
| 1 | | 0.99 |
| 2 | | 3.04 |
| 3 | | 4.46 |
| 4 | | 4.22 |
| 5 | | 7.41 |
| 6 | | 1.00 |
| 10 | 36 | |
| 11 | 26 | |
| 16 | 22 | |
| 20 | 39 | |
| 21 | 32 | |
| 22 | 79 | |

The invention claimed is:

1. A substituted thiazoles of formula I,

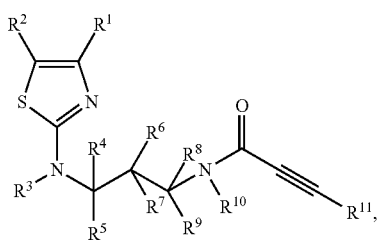

in which
$R^1$ and $R^2$ independently of one another each represent H; F; Cl; Br; I; $-NO_2$; $-CN$; $-NH_2$; $-OH$; $-SH$; $-C(=O)-OH$; $-C(=O)-H$; $-NH-C(=O)-H$; $-NH-R^{33}$; $-NR^{34}R^{35}$; $-C(=O)-R^{36}$; $-C(=O)-O-R^{37}$; $-O-C(=O)-R^{38}$; $-NH-C(=O)-R^{39}$; $-NR^{40}-C(=O)-R^{41}$; $-C(=O)-NH_2$; $-C(=O)-NH-R^{42}$; $-C(=O)-NR^{43}R^{44}$; $-O-R^{45}$; $-S-R^{46}$; $-S(=O)-R^{47}$; $-S(=O)_2-R^{48}$; $-NH-C(=O)-NH-R^{49}$; $-NH-C(=S)-NH-R^{50}$; $-NH-S(=O)_2-R^{51}$; $-NR^{52}-S(=O)_2-R^{53}$; alkyl, alkenyl or alkynyl which is unsubstituted or substituted at least once; heteroalkyl, heteroalkenyl or heteroalkynyl which is unsubstituted or substituted at least once; cycloalkyl or cycloalkenyl which is unsubstituted or substituted at least once; heterocycloalkyl or heterocycloalkenyl which is unsubstituted or substituted at least once; -(alkylene)-cycloalkyl, -(alkenylene)-cycloalkyl, -(alkynylene)-cycloalkyl, -(alkylene)-cycloalkenyl, -(alkenylene)-cycloalkenyl or -(alkynylene)-cycloalkenyl which is unsubstituted or substituted at least once; -(heteroalkylene)-cycloalkyl, -(heteroalkenylene)-cycloalkyl, -(heteroalkylene)-cycloalkenyl or -(heteroalkenylene)-cycloalkenyl which is unsubstituted or substituted at least once; -(alkylene)-heterocycloalkyl, -(alkenylene)-heterocycloalkyl, -(alkynylene)-heterocycloalkyl, -(alkylene)-heterocycloalkenyl, -(alkenylene)-heterocycloalkenyl or -(alkynylene)-heterocycloalkenyl which is unsubstituted or substituted at least once; -(heteroalkylene)-heterocycloalkyl, -(heteroalkenylene)-heterocycloalkyl, -(heteroalkylene)-heterocycloalkenyl or -(heteroalkenylene)-heterocycloalkenyl which is unsubstituted or substituted at least once; aryl which is unsubstituted or substituted at least once; heteroaryl which is unsubstituted or substituted at least once; -(alkylene)-aryl, -(alkenylene)-aryl, -(alkynylene)-aryl, -(heteroalkylene)-aryl or -(heteroalkenylene)-aryl which is unsubstituted or substituted at least once; or -(alkylene)-heteroaryl, -(alkenylene)-heteroaryl, -(alkynylene)-heteroaryl, -(heteroalkylene)-heteroaryl or -(heteroalkenylene)-heteroaryl which is unsubstituted or substituted at least once;

or $R^1$ and $R^2$ together with the carbon atoms linking them form a phenylene radical which is unsubstituted or substituted at least once;

$R^3$ and $R^{10}$ independently of one another each represent H; $-C(=O)-R^{36}$; $-C(=O)-O-R^{37}$; $-C(=O)-NH_2$; $-C(=O)-NH-R^{42}$; $-C(=O)-NR^{43}R^{44}$; $-S(=O)-R^{47}$; $-S(=O)_2-R^{48}$; unsubstituted or substituted alkyl, alkenyl or alkynyl; unsubstituted or substituted heteroalkyl, heteroalkenyl or heteroalkynyl; unsubstituted or substituted cycloalkyl or cycloalkenyl; unsubstituted or substituted heterocycloalkyl or heterocycloalkenyl; unsubstituted or substituted (alkylene)-cycloalkyl, -(alkenylene)-cycloalkyl, -(alkynylene)-cycloalkyl, -(alkylene)-cycloalkenyl, -(alkenylene)-cycloalkenyl or -(alkynylene)-cycloalkenyl; unsubstituted or substituted -(heteroalkylene)-cycloalkyl, -(heteroalkenylene)-cycloalkyl, -(heteroalkylene)-cycloalkenyl or -(heteroalkenylene)-cycloalkenyl; unsubstituted or substituted -(alkylene)-heterocycloalkyl, -(alkenylene)-heterocycloalkyl, -(alkynylene)-heterocycloalkyl, -(alkylene)-heterocycloalkenyl, -(alkenylene)-heterocycloalkenyl or -(alkynylene)-heterocycloalkenyl; unsubstituted or substituted -(heteroalkylene)-heterocycloalkyl, -(heteroalkenylene)-heterocycloalkyl, -(heteroalkylene)-heterocycloalkenyl or -(heteroalkenylene)-heterocycloalkenyl; unsubstituted or substituted aryl; unsubstituted or substituted heteroaryl; unsubstituted or substituted -(alkylene)-aryl, -(alkenylene)-aryl, -(alkynylene)-aryl, -(heteroalkylene)-aryl or -(heteroalkenylene)-aryl; or unsubstituted or substituted -(alkylene)-heteroaryl, -(alkenylene)-heteroaryl, -(alkynylene)-heteroaryl, -(heteroalkylene)-heteroaryl or -(heteroalkenylene)-heteroaryl;

$R^4$, $R^5$, $R^6$, $R^7$, $R^8$, $R^9$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, $R^{26}$, $R^{27}$, $R^{28}$, $R^{29}$, $R^{30}$, $R^{31}$ and $R^{32}$ independently of one another each represent H; F; Cl; Br; I; —$NO_2$; —CN; —$NH_2$; —OH; —SH; —C(=O)—OH; —C(=O)—H; —NH—C(=O)—H; —NH—$R^{33}$; —$NR^{34}R^{35}$; —C(=O)—$R^{36}$; —C(=O)—O—$R^{37}$; —O—C(=O)—$R^{38}$; —NH—C(=O)—$R^{39}$; —$NR^{40}$—C(=O)—$R^{41}$; —C(=O)—$NH_2$; —C(=O)—NH—$R^{42}$; —C(=O)—$NR^{43}R^{44}$; —O—$R^{45}$; —S—$R^{46}$; —S(=O)—$R^{47}$; —S(=O)$_2$—$R^{48}$; —NH—C(=O)—NH—$R^{49}$; —NH—C(=S)—NH—$R^{50}$; —NH—S(=O)$_2$—$R^{51}$; —$NR^{52}$—S(=O)$_2$—$R^{53}$; unsubstituted or substituted alkyl, alkenyl or alkynyl; unsubstituted or substituted heteroalkyl, heteroalkenyl or heteroalkynyl; unsubstituted or substituted cycloalkyl or cycloalkenyl; unsubstituted or substituted heterocycloalkyl or heterocycloalkenyl; unsubstituted or substituted -(alkylene)-cycloalkyl, -(alkenylene)-cycloalkyl, -(alkynylene)-cycloalkyl, -(alkylene)-cycloalkenyl, -(alkenylene)-cycloalkenyl or -(alkynylene)-cycloalkenyl; unsubstituted or substituted -(heteroalkylene)-cycloalkyl, -(heteroalkenylene)-cycloalkyl, -(heteroalkylene)-cycloalkenyl or -(heteroalkenylene)-cycloalkenyl; unsubstituted or substituted -(alkylene)-heterocycloalkyl, -(alkenylene)-heterocycloalkyl, -(alkynylene)-heterocycloalkyl, -(alkylene)-heterocycloalkenyl, -(alkenylene)-heterocycloalkenyl or -(alkynylene)-heterocycloalkenyl; unsubstituted or substituted -(heteroalkylene)-heterocycloalkyl, -(heteroalkenylene)-heterocycloalkyl, -(heteroalkylene)-heterocycloalkenyl or -(heteroalkenylene)-heterocycloalkenyl; unsubstituted or substituted aryl; unsubstituted or substituted heteroaryl; unsubstituted or substituted -(alkylene)-aryl, -(alkenylene)-aryl, -(alkynylene)-aryl, -(heteroalkylene)-aryl or -(heteroalkenylene)-aryl; or unsubstituted or substituted -(alkylene)-heteroaryl, -(alkenylene)-heteroaryl, -(alkynylene)-heteroaryl, -(heteroalkylene)-heteroaryl or -(heteroalkenylene)-heteroaryl;

or $R^4$ and $R^5$ or $R^6$ and $R^7$ or $R^8$ and $R^9$ or $R^{12}$ and $R^{13}$ or $R^{14}$ and $R^{15}$ or $R^{16}$ and $R^{17}$ or $R^{18}$ and $R^{19}$ or $R^{20}$ and $R^{21}$ or $R^{22}$ and $R^{23}$ or $R^{24}$ and $R^{25}$ or $R^{26}$ and $R^{27}$ or $R^{28}$ and $R^{29}$ or $R^{31}$ and $R^{32}$ independently of one another represent, together in each case, a radical selected from the group consisting of an oxo group (=O) and a thioxo group (=S);

or $R^3$ and $R^4$ together with the —N—$CR^5$ group linking them form a radical of formula A,

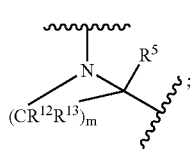

or $R^8$ and $R^{10}$ together with the —$CR^9$—N group linking them form a radical of formula B,

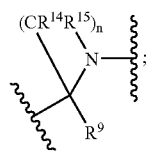

m and n each represent 2, 3, 4, 5 or 6;

or $R^3$ and $R^6$ together with the —N—$CR^4R^5$—$CR^7$ group linking them form a radical of formula C,

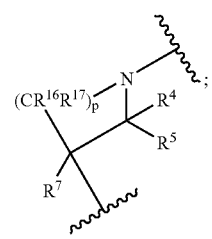

or $R^6$ and $R^{10}$ together with the —$CR^7$—$CR^8R^9$—N group linking them form a radical of formula D,

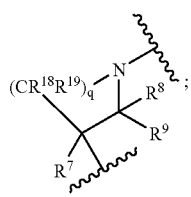

p and q each represent 1, 2, 3, 4 or 5;

or $R^3$ and $R^8$ together with the —N—$CR^4R^5$—$CR^6R^7$—$CR^9$ group linking them form a radical of formula E,

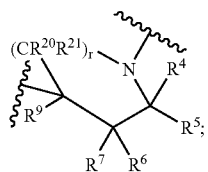

or $R^4$ and $R^{10}$ together with the —N—$CR^8R^9$—$CR^6R^7$—$CR^5$ group linking them form a radical of formula F,

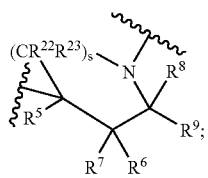

r and s each represent 2, 3 or 4;

or $R^4$ and $R^8$ together with the —$CR^5$—$CR^6R^7$—$CR^9$ group linking them form a radical of formula G,

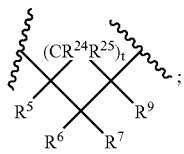

t represents 1, 2, 3, 4 or 5;
or $R^3$ and $R^{10}$ together with the —N—$CR^4R^5$—$CR^6R^7$—$CR^8R^9$—N group linking them form a radical of formula H,

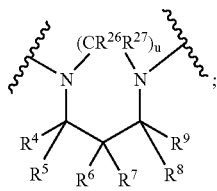

u represents 3 or 4;
or $R^3$ and $R^{10}$ together with the —N—$CR^4R^5$—$CR^6R^7$—$CR^8R^9$—N group linking them form a bicyclic radical of formula K,

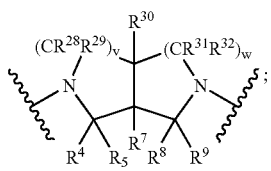

v and w independently of one another each represent 1, 2 or 3;

$R^{11}$ represents unsubstituted or substituted aryl or unsubstituted or substituted heteroaryl;

and $R^{33}$, $R^{34}$, $R^{35}$, $R^{36}$, $R^{37}$, $R^{38}$, $R^{39}$, $R^{40}$, $R^{41}$, $R^{42}$, $R^{43}$, $R^{44}$, $R^{45}$, $R^{46}$, $R^{47}$, $R^{48}$, $R^{49}$, $R^{50}$, $R^{51}$, $R^{52}$ and $R^{53}$ independently of one another each represent unsubstituted or substituted alkyl, alkenyl or alkynyl; unsubstituted or substituted heteroalkyl, heteroalkenyl or heteroalkynyl; unsubstituted or substituted cycloalkyl or cycloalkenyl; unsubstituted or substituted heterocycloalkyl or heterocycloalkenyl; unsubstituted or substituted (alkylene)-cycloalkyl, -(alkenylene)-cycloalkyl, -(alkynylene)-cycloalkyl, -(alkylene)-cycloalkenyl, -(alkenylene)-cycloalkenyl or -(alkynylene)-cycloalkenyl; unsubstituted or substituted -(heteroalkylene)-cycloalkyl, -(heteroalkenylene)-cycloalkyl, -(heteroalkylene)-cycloalkenyl or -(heteroalkenylene)-cycloalkenyl; unsubstituted or substituted -(alkylene)-heterocycloalkyl, -(alkenylene)-heterocycloalkyl, -(alkynylene)-heterocycloalkyl, -(alkylene)-heterocycloalkenyl, -(alkenylene)-heterocycloalkenyl or -(alkynylene)-heterocycloalkenyl; unsubstituted or substituted -(heteroalkylene)-heterocycloalkyl, -(heteroalkenylene)-heterocycloalkyl, -(heteroalkylene)-heterocycloalkenyl or -(heteroalkenylene)-heterocycloalkenyl; unsubstituted or substituted aryl; unsubstituted or substituted heteroaryl; unsubstituted or substituted -(alkylene)-aryl, -(alkenylene)-aryl, -(alkynylene)-aryl, -(heteroalkylene)-aryl or -(heteroalkenylene)-aryl; or unsubstituted or substituted -(alkylene)-heteroaryl, -(alkenylene)-heteroaryl, -(alkynylene)-heteroaryl, -(heteroalkylene)-heteroaryl or -(heteroalkenylene)-heteroaryl; in which the aforementioned alkyl radicals are each branched or linear and have 1, 2, 3, 4, 5, 6, 7, 8, 9, 10, 11 or 12 carbon atoms as members of the chain;

the aforementioned alkenyl radicals are each branched or linear and have 2, 3, 4, 5, 6, 7, 8, 9, 10, 11 or 12 carbon atoms as members of the chain;

the aforementioned alkynyl radicals are each branched or linear and have 2, 3, 4, 5, 6, 7, 8, 9, 10, 11 or 12 carbon atoms as members of the chain;

the aforementioned heteroalkyl radicals, heteroalkenyl radicals and heteroalkynyl radicals each have 2, 3, 4, 5, 6, 7, 8, 9, 10, 11 or 12 members;

the aforementioned heteroalkyl radicals, heteroalkenyl radicals and heteroalkynyl radicals each optionally have 1, 2 or 3 heteroatom(s), selected independently of one another from the group consisting of oxygen, sulphur and nitrogen, as chain member(s);

the aforementioned alkyl radicals, alkenyl radicals, alkynyl radicals, heteroalkyl radicals, heteroalkenyl radicals and heteroalkynyl radicals may each be substituted with, as appropriate, 1, 2, 3, 4 or 5 substituents selected from the group consisting of F, Cl, Br, I, —$NO_2$, —CN, —OH, —SH, —$NH_2$, —$N(C_{1-5}$-alkyl$)_2$, —$N(C_{1-5}$-alkyl)(phenyl), —$N(C_{1-5}$alkyl)($CH_2$-phenyl), —$N(C_{1-5}$-alkyl)($CH_2$—$CH_2$-phenyl), —C(=O)—H, —C(=O)—$C_{1-5}$-alkyl, —C(=O)-phenyl, —C(=S)—$C_{1-5}$-alkyl, —C(=S)-phenyl, —C(=O)—OH, —C(=O)—O—$C_{1-5}$-alkyl, —C(=O)—O-phenyl, —C(=O)—$NH_2$, —C(=O)—NH—$C_{1-5}$-alkyl, —C(=O)—N($C_{1-5}$-alkyl$)_2$, —S(=O)—$C_{1-5}$-alkyl, —S(=O)-phenyl, —S(=O$)_2$—$C_{1-5}$-alkyl, —S(=O$)_2$-phenyl, —S(=O$)_2$—$NH_2$ and —$SO_3H$, it being possible for the phenyl radicals to be substituted with 1, 2, 3, 4 or 5 substituents selected independently of one another from the group consisting of F, Cl, Br, I, —CN, —$CF_3$, —OH, —$NH_2$, —O—$CF_3$, —SH, —O—$CH_3$, —O—$C_2H_5$, —O—$C_3H_7$, methyl, ethyl, n-propyl, isopropyl, n-butyl, 2-butyl, isobutyl and tert-butyl;

the aforementioned cycloalkyl radicals each have 3, 4, 5, 6, 7, 8 or 9 carbon atoms as ring members;

the aforementioned cycloalkenyl radicals each have 3, 4, 5, 6, 7, 8 or 9 carbon atoms as ring members;

the aforementioned heterocycloalkyl radicals each have 3, 4, 5, 6, 7, 8 or 9 members;

the aforementioned heterocycloalkenyl radicals each have 4, 5, 6, 7, 8 or 9 members;

the aforementioned heterocycloalkyl radicals and heterocycloalkenyl radicals each optionally have 1, 2 or 3 heteroatom(s), selected independently of one another from the group consisting of oxygen, sulphur and nitrogen (NH), as chain member(s);

the aforementioned cycloalkyl radicals, heterocycloalkyl radicals, cycloalkenyl radicals or heterocycloalkenyl radicals may each be substituted with, as appropriate, 1, 2, 3, 4 or 5 substituents selected independently of one another from the groups consisting of F, Cl, Br, I, —CN, —$CF_3$, —OH, —$NH_2$, —O—$CF_3$, —SH, —O—$C_{1-5}$-alkyl, —O-phenyl, —O—$CH_2$-phenyl, —($CH_2$)—O—

$C_{1-5}$-alkyl, —S—$C_{1-5}$-alkyl, —S-phenyl, —S—$CH_2$-phenyl, —$C_{1-5}$-alkyl, —$C_{2-5}$-alkenyl, —$C_{2-5}$-alkynyl, —C≡C—Si($CH_3$)$_3$, —C≡C—Si($C_2H_5$)$_3$, —C(=O)—O—$C_{1-5}$-alkyl, —C(=O)—$CF_3$, —S(=O)$_2$—$C_{1-5}$-alkyl, —S(=O)—$C_{1-5}$-alkyl, —S(=O)$_2$-phenyl, oxo (=O), thioxo (=S), —N($C_{1-5}$-alkyl)$_2$, —N(H)($C_{1-5}$-alkyl), —NO$_2$, —S—$CF_3$, —C(=O)—OH, —NH—S(=O)$_2$—$C_{1-5}$-alkyl, —NH—C(=O)—$C_{1-5}$-alkyl, —C(=O)—H, —C(=O)—$C_{1-5}$-alkyl, —C(=O)—$NH_2$, —C(=O)—N($C_{1-5}$-alkyl)$_2$, —C(=O)—N(H)($C_{1-5}$-alkyl) and phenyl, it being possible for the phenyl radicals to be unsubstituted or substituted with 1, 2, 3, 4 or 5 substituents selected independently of one another from the group consisting of F, Cl, Br, I, —CN, —$CF_3$, —OH, —$NH_2$, —O—$CF_3$, —SH, —O—$C_{1-5}$-alkyl, —O-phenyl, —O—$CH_2$-phenyl, —($CH_2$)—O—$C_{1-5}$-alkyl, —S—$C_{1-5}$-alkyl, —S-phenyl, —S—$CH_2$-phenyl, —$C_{1-5}$-alkyl, —$C_{2-5}$-alkenyl, —$C_{2-5}$-alkynyl, —C≡C—Si($CH_3$)$_3$, —C≡C—Si($C_2H_5$)$_3$, —C(=O)—O—$C_{1-5}$-alkyl and —C(=O)—$CF_3$, it being possible for the aforementioned phenyl radicals to be substituted with 1, 2, 3, 4 or 5 substituents selected independently of one another from the group consisting of F, Cl, Br, I, —CN, —$CF_3$, —OH, —$NH_2$, —O—$CF_3$, —SH, —O—$CH_3$, —O—$C_2H_5$, —O—$C_3H_7$, methyl, ethyl, n-propyl, isopropyl, n-butyl, 2-butyl, isobutyl and tert-butyl;

the aforementioned alkylene radicals are each branched or linear and have 1, 2, 3, 4, 5, 6, 7, 8, 9, 10, 11 or 12 carbon atoms as members of the chain;

the aforementioned alkenylene radicals are each branched or linear and have 2, 3, 4, 5, 6, 7, 8, 9, 10, 11 or 12 carbon atoms as members of the chain;

the aforementioned alkynylene radicals are each branched or linear and have 2, 3, 4, 5, 6, 7, 8, 9, 10, 11 or 12 carbon atoms as members of the chain;

the aforementioned heteroalkylene radicals, heteroalkenylene radicals and heteroalkynylene radicals each have 2, 3, 4, 5, 6, 7, 8, 9, 10, 11 or 12 members;

the aforementioned heteroalkylene, heteroalkenylene and heteroalkynylene groups each optionally have 1, 2 or 3 heteroatom(s), selected independently of one another from the group consisting of oxygen, sulphur and nitrogen (NH), as chain member(s);

the aforementioned alkylene, alkenylene, alkynylene, heteroalkylene, heteroalkenylene or heteroalkynylene groups may each be unsubstituted or substituted with, as appropriate, 1, 2, 3, 4 or 5 substituents selected independently of one another from the group consisting of phenyl, F, Cl, Br, I, —NO$_2$, —CN, —OH, —O-phenyl, —O—$CH_2$-phenyl, —SH, —S-phenyl, —S—$CH_2$-phenyl, $NH_2$, —N($C_{1-5}$-alkyl)$_2$, —NH-phenyl, —N($C_{1-5}$-alkyl)(phenyl), —N($C_{1-5}$-alkyl)($CH_2$-phenyl), —N($C_{1-5}$-alkyl)($CH_2$—$CH_2$-phenyl), —C(=O)—H, —C(=O)—$C_{1-5}$-alkyl, —C(=O)-phenyl, —C(=S)—$C_{1-5}$-alkyl, —C(=S)-phenyl, —C(=O)—OH, —C(=O)—O—$C_{1-5}$-alkyl, —C(=O)—O-phenyl, —C(=O)—$NH_2$, —C(=O)—NH—$C_{1-5}$-alkyl, —C(=O)—N($C_{1-5}$-alkyl)$_2$, —S(=O)—$C_{1-5}$-alkyl, —S(=O)-phenyl, —S(=O)$_2$—$C_{1-5}$-alkyl, —S(=O)$_2$-phenyl, —S(=O)$_2$—$NH_2$ and —$SO_3H$, it being possible for the phenyl radicals to be substituted with 1, 2, 3, 4 or 5 substituents selected independently of one another from the group consisting of F, Cl, Br, I, —CN, —NO$_2$, —OH, —SH, —$NH_2$, —C(=O)—OH, —$C_{1-5}$-alkyl, —($CH_2$)—O—$C_{1-5}$-alkyl, —$C_{2-5}$-alkenyl, —$C_{2-5}$-alkynyl, —C≡C—Si($CH_3$)$_3$, —C≡C—Si($C_2H_5$)$_3$, —S—$C_{1-5}$-alkyl, —S-phenyl, —S—$CH_2$-phenyl, —O—$C_{1-5}$-alkyl, —O-phenyl, —O—$CH_2$-phenyl, —$CF_3$, —$CHF_2$, —$CH_2F$, —O—$CF_3$, —O—$CHF_2$, —O—$CH_2F$, —C(=O)—$CF_3$, —S—$CF_3$, —S—$CHF_2$ and —S—$CH_2F$;

the aforementioned aryl radicals are monocyclic or bicyclic and have 6, 10 or 14 carbon atoms;

the aforementioned heteroaryl radicals are monocyclic, bicyclic or tricyclic and have 5, 6, 7, 8, 9, 10, 11, 12, 13 or 14 members;

the aforementioned heteroaryl radicals with 5 to 14 members optionally have 1, 2, 3, 4 or 5 heteroatom(s), selected independently of one another from the group consisting of oxygen, sulphur and nitrogen (NH), as chain member(s);

and the aforementioned phenylene radicals, aryl radicals and heteroaryl radicals may each be substituted with, as appropriate, 1, 2, 3, 4 or 5 substituents selected independently of one another from the group consisting of F, Cl, Br, I, —CN, —NO$_2$, —OH, —SH, —$NH_2$, —C(=O)—OH, —$C_{1-5}$-alkyl, —($CH_2$)—O—$C_{1-5}$-alkyl, —$C_{2-5}$-alkenyl, —$C_{2-5}$-alkynyl, —C≡C—Si($CH_3$)$_3$, —C≡C—Si($C_2H_5$)$_3$, —S—$C_{1-5}$-alkyl, —S-phenyl, —S—$CH_2$-phenyl, —O—$C_{1-5}$-alkyl, —O-phenyl, —O—$CH_2$-phenyl, —$CF_3$, —$CHF_2$, —$CH_2F$, —O—$CF_3$, —O—$CHF_2$, —O—$CH_2F$, —C(=O)—$CF_3$, —S—$CF_3$, —S—$CHF_2$, —S—$CH_2F$, —S(=O)$_2$-phenyl, —S(=O)$_2$—$C_{1-5}$-alkyl, —S(=O)—$C_{1-5}$-alkyl, —NH—$C_{1-5}$-alkyl, N($C_{1-5}$alkyl)$_2$, —C(=O)—O—$C_{1-5}$-alkyl, —C(=O)—H, —C(=O)—$C_{1-5}$-alkyl, —$CH_2$—O—C(=O)-phenyl, —O—C(=O)-phenyl, —NH—S(=O)$_2$—$C_{1-5}$-alkyl, —NH—C(=O)—$C_{1-5}$-alkyl, —C(=O)—$NH_2$, —C(=O)—NH—$C_{1-5}$-alkyl, —C(=O)—N($C_{1-5}$-alkyl)$_2$, Pyrazolyl, phenyl, furyl (furanyl), thiazolyl, thiadiazolyl, thiophenyl (thienyl), benzyl and phenethyl, it being possible for the cyclic substituents or the cyclic radicals of these substituents themselves to be substituted with, as appropriate, 1, 2, 3, 4 or 5 substituents selected independently of one another from the group consisting of F, Cl, Br, I, —CN, —NO$_2$, —OH, —SH, —$NH_2$, —C(=O)—OH, —$C_{1-5}$-alkyl, —($CH_2$)—O—$C_{1-5}$-alkyl, —$C_{2-5}$-alkenyl, —$C_{2-5}$-alkynyl, —C≡C—Si($CH_3$)$_3$, —C≡C—Si($C_2H_5$)$_3$, —S—$C_{1-5}$-alkyl, —S-phenyl, —S—$CH_2$-phenyl, —O—$C_{1-5}$-alkyl, —O-phenyl, —O—$CH_2$-phenyl, —$CF_3$, —$CHF_2$, —$CH_2F$, —O—$CF_3$, —O—$CHF_2$, —O—$CH_2F$, —C(=O)—$CF_3$, —S—$CF_3$, —S—$CHF_2$ and —S—$CH_2F$;

each optionally in the form of one of the pure stereoisomers, or the racemate thereof, or in the form of a mixture of stereoisomers mixed in any ratios, or each in the form of a corresponding salt.

2. The compound according to claim 1, wherein
$R^1$ and $R^2$ independently of one another each represent H; F; Cl; Br; I; —NO$_2$; —CN; —$NH_2$; —OH; —SH; —C(=O)—OH; —C(=O)—H; —NH—C(=O)—H; —NH—$R^{33}$; —$NR^{34}R^{35}$; —C(=O)—$R^{36}$; —C(=O)—O—$R^{37}$; —O—C(=O)—$R^{38}$; —NH—C(=O)—$R^{39}$; —$NR^{40}$—C(=O)—$R^{41}$; —C(=O)—$NH_2$; —C(=O)—NH—$R^{42}$; —C(=O)—$NR^{43}R^{44}$; —O—$R^{45}$; —S—$R^{46}$; —S(=O)—$R^{47}$; —S(=O)$_2$—$R^{48}$; —NH—C(=O)—NH—$R^{49}$; —NH—C(=S)—NH—$R^{50}$; —NH—S(=O)$_2$—$R^{51}$; —$NR^{52}$—S(=O)$_2$—$R^{53}$; alkyl, alkenyl or alkynyl which is unsubstituted or substituted at least once; heteroalkyl, heteroalkenyl or heteroalkynyl which is unsubstituted or substituted at least once; cycloalkyl or cycloalkenyl which is unsubstituted or substituted at least once; heterocycloalkyl or heterocycloalkenyl which is unsubstituted or substituted at least once; -(alkylene)-cycloalkyl, -(alkenylene)-cycloalkyl, -(alkynylene)-cycloalkyl, -(alkylene)-cycloalkenyl, -(alkenylene)-cycloalkenyl or -(alkynylene)-cycloalkenyl which is unsubstituted or substituted at least once; -(heteroalkylene)-cycloalkyl, -(heteroalkenylene)-cycloalkyl, -(heteroalkylene)-cycloalkenyl or -(heteroalkenylene)-cycloalkenyl which is unsubstituted or substituted at least once; -(alkylene)-heterocycloalkyl, -(alkenylene)-heterocycloalkyl, -(alkynylene)-heterocycloalkyl, -(alkylene)-heterocycloalkenyl, -(alkenylene)-heterocycloalkenyl or -(alkynylene)-heterocycloalkenyl which is unsubstituted or substituted at least once; -(heteroalkylene)-heterocycloalkyl, -(heteroalkenylene)-heterocycloalkyl, -(heteroalkylene)-heterocycloalkenyl or -(heteroalkenylene)-heterocycloalkenyl which is unsubstituted or substituted at least once; aryl which is unsubstituted or substituted at least once; heteroaryl which is unsubstituted or substituted at least once; -(alkylene)-aryl, -(alkenylene)-aryl, -(alkynylene)-aryl, -(heteroalkylene)-aryl or -(heteroalkenylene)-aryl which is unsubstituted or substituted at least once; or -(alkylene)-heteroaryl, -(alkenylene)-heteroaryl, -(alkynylene)-heteroaryl, -(heteroalkylene)-heteroaryl or -(heteroalkenylene)-heteroaryl which is unsubstituted or substituted at least once;

or $R^1$ and $R^2$ together with the carbon atoms linking them form a phenylene radical which is unsubstituted or substituted at least once;

$R^3$ and $R^{10}$ independently of one another each represent H; —C(=O)—$R^{36}$; —C(=O)—O—$R^{37}$; —C(=O)—NH$_2$; —C(=O)—NH—$R^{42}$; —C(=O)—NR$^{43}$R$^{44}$; —S(=O)—$R^{47}$; —S(=O)$_2$—$R^{48}$; unsubstituted or substituted alkyl, alkenyl or alkynyl; unsubstituted or substituted heteroalkyl, heteroalkenyl or heteroalkynyl; unsubstituted or substituted cycloalkyl or cycloalkenyl; unsubstituted or substituted heterocycloalkyl or heterocycloalkenyl; unsubstituted or substituted -(alkylene)-cycloalkyl, -(alkenylene)-cycloalkyl, -(alkynylene)-cycloalkyl, -(alkylene)-cycloalkenyl, -(alkenylene)-cycloalkenyl or -(alkynylene)-cycloalkenyl; unsubstituted or substituted -(heteroalkylene)-cycloalkyl, -(heteroalkenylene)-cycloalkyl, -(heteroalkylene)-cycloalkenyl or -(heteroalkenylene)-cycloalkenyl; unsubstituted or substituted -(alkylene)-heterocycloalliyl, -(alkenylene)-heterocycloalkyl, -(alkynylene)-heterocycloalkyl, -(alkylene)-heterocycloalkenyl, -(alkenylene)-heterocycloalkenyl or -(alkynylene)-heterocycloalkenyl; unsubstituted or substituted -(heteroalkylene)-heterocycloalkyl, -(heteroalkenylene)-heterocycloalkyl, -(heteroalkylene)-heterocycloalkenyl or -(heteroalkenylene)-heterocycloalkenyl; unsubstituted or substituted aryl; unsubstituted or substituted heteroaryl; unsubstituted or substituted -(alkylene)-aryl, -(alkenylene)-aryl, -(alkynylene)-aryl, -(heteroalkylene)-aryl or -(heteroalkenylene)-aryl; or unsubstituted or substituted -(alkylene)-heteroaryl, -(alkenylene)-heteroaryl, -(alkynylene)-heteroaryl, -(heteroalkylene)-heteroaryl or -(heteroalkenylene)-heteroaryl;

$R^4$, $R^5$, $R^6$, $R^7$, $R^8$, $R^9$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, $R^{26}$, $R^{27}$, $R^{28}$, $R^{29}$, $R^{30}$, $R^{31}$ and $R^{32}$ independently of one another each represent H; F; Cl; Br; I; —NO$_2$; —CN; —NH$_2$; —OH; —SH; —C(=O)—OH; —C(=O)—H; —NH—C(=O)—H; —NH—$R^{33}$; —NR$^{34}$R$^{35}$; —C(=O)—$R^{36}$; —C(=O)—O—$R^{37}$; —O—C(=O)—$R^{38}$; —NH—C(=O)—$R^{39}$; —NR$^{40}$—C(=O)—$R^{41}$; —C(=O)—NH$_2$; —C(=O)—NH—$R^{42}$; —C(=O)—NR$^{43}$R$^{44}$; —O—$R^{45}$; —S—$R^{46}$; —S(=O)—$R^{47}$; —S(=O)$_2$—$R^{48}$; —NH—C(=O)—NH—$R^{49}$; —NH—C(=S)—NH—$R^{50}$; —NH—S(=O)$_2$—$R^{51}$; —NR$^{52}$—S(=O)$_2$—$R^{53}$; unsubstituted or substituted alkyl, alkenyl or alkynyl; unsubstituted or substituted heteroalkyl, heteroalkenyl or heteroalkynyl; unsubstituted or substituted cycloalkyl or cycloalkenyl; unsubstituted or substituted heterocycloalkyl or heterocycloalkenyl; unsubstituted or substituted -(alkylene)-cycloalkyl, -(alkenylene)-cycloalkyl, -(alkynylene)-cycloalkyl, -(alkylene)-cycloalkenyl, -(alkenylene)-cycloalkenyl or -(alkynylene)-cycloalkenyl; unsubstituted or substituted -(heteroalkylene)-cycloalkyl, -(heteroalkenylene)-cycloalkyl, -(heteroalkylene)-cycloalkenyl or -(heteroalkenylene)-cycloalkenyl; unsubstituted or substituted -(alkylene)-heterocycloalkyl, -(alkenylene)-heterocycloalkyl, -(alkynylene)-heterocycloalkyl, -(alkylene)-heterocycloalkenyl, -(alkenylene)-heterocycloalkenyl or -(alkynylene)-heterocycloalkenyl; unsubstituted or substituted -(heteroalkylene)-heterocycloalkyl, -(heteroalkenylene)-heterocycloalkyl, -(heteroalkylene)-heterocycloalkenyl or -(heteroalkenylene)-heterocycloalkenyl; unsubstituted or substituted aryl; unsubstituted or substituted heteroaryl; unsubstituted or substituted -(alkylene)-aryl, -(alkenylene)-aryl, -(alkynylene)-aryl, -(heteroalkylene)-aryl or -(heteroalkenylene)-aryl; or unsubstituted or substituted -(alkylene)-heteroaryl, -(alkenylene)-heteroaryl, -(alkynylene)-heteroaryl, -(heteroalkylene)-heteroaryl or -(heteroalkenylene)-heteroaryl;

or $R^4$ and $R^5$ or $R^6$ and $R^7$ or $R^8$ and $R^9$ or $R^{12}$ and $R^{13}$ or $R^{14}$ and $R^{15}$ or $R^{16}$ and $R^{17}$ or $R^{18}$ and $R^{19}$ or $R^{20}$ and $R^{21}$ or $R^{22}$ and $R^{23}$ or $R^{24}$ and $R^{25}$ or $R^{26}$ and $R^{27}$ or $R^{28}$ and $R^{29}$ or $R^{31}$ and $R^{32}$ independently of one another represent, together in each case, a radical selected from the group consisting of an oxo group (=O) and a thioxo group (=S);

or $R^3$ and $R^4$ together with the —N—CR$^5$ group linking them form a radical of formula A,

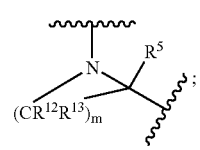

A or $R^8$ and $R^{10}$ together with the —CR$^9$—N group linking them form a radical of formula B,

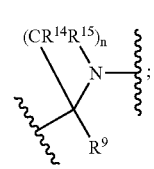

B m and n each represent 2, 3, 4, 5 or 6;

or $R^3$ and $R^6$ together with the —N—$CR^4R^5$—$CR^7$ group linking them form a radical of formula C,

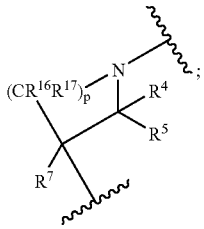

or $R^6$ and $R^{10}$ together with the —$CR^7$—$CR^8R^9$—N group linking them form a radical of formula D,

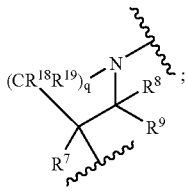

p and q each represent 1, 2, 3, 4 or 5;
or $R^3$ and $R^8$ together with the —N—$CR^4R^5$—$CR^6R^7$—$CR^9$ group linking them form a radical of formula E,

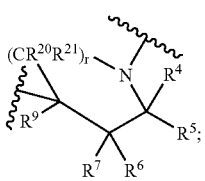

or $R^4$ and $R^{10}$ together with the —N—$CR^8R^9$—$CR^6R^7$—$CR^5$ group linking them form a radical of formula F,

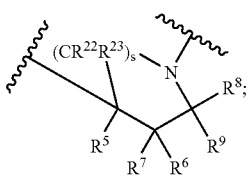

r and s each represent 2, 3 or 4;
or $R^4$ and $R^8$ together with the —$CR^5$—$CR^6R^7$—$CR^9$ group linking them form a radical of formula G,

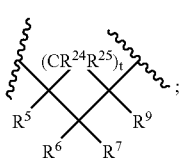

t represents 1, 2, 3, 4 or 5;

or $R^3$ and $R^{10}$ together with the —N—$CR^4R^5$—$CR^6R^7$—$CR^8R^9$—N group linking them form a radical of formula H,

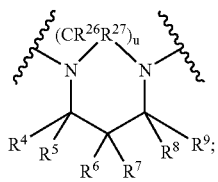

u represents 3 or 4;
or $R^3$ and $R^{10}$ together with the —N—$CR^4R^5$—$CR^6R^7$—$CR^8R^9$—N group linking them form a bicyclic radical of formula K,

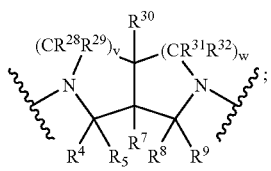

v and w independently of one another each represent 1, 2 or 3;
$R^{11}$ represents unsubstituted or substituted aryl or unsubstituted or substituted heteroaryl;
and $R^{33}$, $R^{34}$, $R^{35}$, $R^{36}$, $R^{37}$, $R^{38}$, $R^{39}$, $R^{40}$, $R^{41}$, $R^{42}$, $R^{43}$, $R^{44}$, $R^{45}$, $R^{46}$, $R^{47}$, $R^{48}$, $R^{49}$, $R^{50}$, $R^{51}$, $R^{52}$ and $R^{53}$ independently of one another each represent unsubstituted or substituted alkyl, alkenyl or alkynyl; unsubstituted or substituted heteroalkyl, heteroalkenyl or heteroalkynyl; unsubstituted or substituted cycloalkyl or cycloalkenyl; unsubstituted or substituted heterocycloalkyl or heterocycloalkenyl; unsubstituted or substituted -(alkylene)-cycloalkyl, -(alkenylene)-cycloalkyl, -(alkynylene)-cycloalkyl, -(alkylene)-cycloalkenyl, -(alkenylene)-cycloalkenyl or -(alkynylene)-cycloalkenyl; unsubstituted or substituted -(heteroalkylene)-cycloalkyl, -(heteroalkenylene)-cycloalkyl, -(heteroalkylene)-cycloalkenyl or -(heteroalkenylene)-cycloalkenyl; unsubstituted or substituted -(alkylene)-heterocycloalkyl, -(alkenylene)-heterocycloalkyl, -(alkynylene)-heterocycloallyl, -(alkylene)-heterocycloalkenyl, -(alkenylene)-heterocycloalkenyl or -(alkynylene)-heterocycloalkenyl; unsubstituted or substituted -(heteroalkylene)-heterocycloalkyl, -(heteroalkenylene)-heterocycloalkyl, -(heteroalkylene)-heterocycloalkenyl or -(heteroalkenylene)-heterocycloalkenyl; unsubstituted or substituted aryl; unsubstituted or substituted heteroaryl; unsubstituted or substituted -(alkylene)-aryl, -(alkenylene)-aryl, -(alkynylene)-aryl, -(heteroalkylene)-aryl or -(heteroalkenylene)-aryl; or unsubstituted or substituted -(alkylene)-heteroaryl, -(alkenylene)-heteroaryl, -(alkynylene)-heteroaryl, -(heteroalkylene)-heteroaryl or -(heteroalkenylene)-heteroaryl;
in which
the aforementioned alkyl radicals are each branched or linear and have 1, 2, 3, 4, 5, 6, 7, 8, 9, 10, 11 or 12 carbon atoms as members of the chain;

the aforementioned alkenyl radicals are each branched or linear and have 2, 3, 4, 5, 6, 7, 8, 9, 10, 11 or 12 carbon atoms as members of the chain;

the aforementioned alkynyl radicals are each branched or linear and have 2, 3, 4, 5, 6, 7, 8, 9, 10, 11 or 12 carbon atoms as members of the chain;

the aforementioned heteroalkyl radicals, heteroalkenyl radicals and heteroalkynyl radicals each have 2, 3, 4, 5, 6, 7, 8, 9, 10, 11 or 12 members;

the aforementioned heteroalkyl radicals, heteroalkenyl radicals and heteroalkynyl radicals each optionally have 1, 2 or 3 heteroatom(s), selected independently of one another from the group consisting of oxygen, sulphur and nitrogen, as chain member(s);

the aforementioned alkyl radicals, alkenyl radicals, alkynyl radicals, heteroalkyl radicals, heteroalkenyl radicals and heteroalkynyl radicals may each be substituted with, as appropriate, 1, 2, 3, 4 or 5 substituents selected from the group consisting of F, Cl, Br, I, —NO$_2$, —CN, —OH, —SH, —NH$_2$, —N(C$_{1-5}$-alkyl)$_2$, —N(C$_{1-5}$-alkyl)(phenyl), —N(C$_{1-5}$-alkyl)(CH$_2$-phenyl), —N(C$_{1-5}$-alkyl)(CH$_2$—CH$_2$-phenyl), —C(=O)—H, —C(=O)—C$_{1-5}$-alkyl, —C(=O)-phenyl, —C(=S)—C$_{1-5}$-alkyl, —C(=S)-phenyl, —C(=O)—OH, —C(=O)—O—C$_{1-5}$-alkyl, —C(=O)—O-phenyl, —C(=O)—NH$_2$, —C(=O)—NH—C$_{1-5}$-alkyl, —C(=O)—N(C$_{1-5}$-alkyl)$_2$, —S(=O)—C$_{1-5}$-alkyl, —S(=O)-phenyl, —S(=O)$_2$—C$_{1-5}$-alkyl, —S(=O)$_2$-phenyl, —S(=O)$_2$—NH$_2$ and —SO$_3$H, it being possible for the phenyl radicals to be substituted with 1, 2, 3, 4 or 5 substituents selected independently of one another from the group consisting of F, Cl, Br, I, —CN, —CF$_3$, —OH, —NH$_2$, —O—CF$_3$, —SH, —O—CH$_3$, —O—C$_2$H$_5$, —O—C$_3$H$_7$, methyl, ethyl, n-propyl, isopropyl, n-butyl, 2-butyl, isobutyl and tert-butyl;

the aforementioned cycloalkyl radicals each have 3, 4, 5, 6, 7, 8 or 9 carbon atoms as ring members;

the aforementioned cycloalkenyl radicals each have 3, 4, 5, 6, 7, 8 or 9 carbon atoms as ring members;

the aforementioned heterocycloalkyl radicals each have 3, 4, 5, 6, 7, 8 or 9 members;

the aforementioned heterocycloalkenyl radicals each have 4, 5, 6, 7, 8 or 9 members;

the aforementioned heterocycloalkyl radicals and heterocycloalkenyl radicals each optionally have 1, 2 or 3 heteroatom(s), selected independently of one another from the group consisting of oxygen, sulphur and nitrogen (NH), as chain member(s);

the aforementioned cycloalkyl radicals, heterocycloalkyl radicals, cycloalkenyl radicals or heterocycloalkyl radicals may each be substituted with, as appropriate, 1, 2, 3, 4 or 5 substituents selected independently of one another from the groups consisting of F, Cl, Br, I, —CN, —CF$_3$, —OH, —NH$_2$, —O—CF$_3$, —SH, —O—C$_{1-5}$-alkyl, —O-phenyl, —O—CH$_2$-phenyl, —(CH$_2$)—O—C$_{1-5}$-alkyl, —S—C$_{1-5}$-alkyl, —S-phenyl, —S—CH$_2$-phenyl, —C$_{1-5}$-alkyl, —C$_{2-5}$-alkenyl, —C$_{2-5}$-alkynyl, —C≡C—Si(CH$_3$)$_3$, —C≡C—Si(C$_2$H$_5$)$_3$, —C(=O)—O—C$_{1-5}$-alkyl, —C(=O)—CF$_3$, —S(=O)$_2$—C$_{1-5}$-alkyl, —S(=O)—C$_{1-5}$-alkyl, —S(=O)$_2$-phenyl, oxo (=O), thioxo (=S), —N(C$_{1-5}$-alkyl)$_2$, —N(H)(C$_{1-5}$-alkyl), —NO$_2$, —S—CF$_3$, —C(=O)—OH, —NH—S(=O)$_2$—C$_{1-5}$-alkyl, —NH—C(=O)—C$_{1-5}$-alkyl, —C(=O)—H, —C(=O)—C$_{1-5}$-alkyl, —C(=O)—NH$_2$, —C(=O)—N(C$_{1-5}$-alkyl)$_2$, —C(=O)—N(H)(C$_{1-5}$-alkyl) and phenyl, it being possible for the phenyl radicals to be unsubstituted or substituted with 1, 2, 3, 4 or 5 substituents selected independently of one another from the group consisting of F, Cl, Br, I, —CN, —CF$_3$, —OH, —NH$_2$, —O—CF$_3$, —SH, —O—C$_{1-5}$-alkyl, —O-phenyl, —O—CH$_2$-phenyl, —(CH$_2$)—O—C$_{1-5}$-alkyl, —S—C$_{1-5}$-alkyl, —S-phenyl, —S—CH$_2$-phenyl, —C$_{1-5}$-alkyl, —C$_{2-5}$-alkenyl, —C$_{2-5}$-alkynyl, —C≡C—Si(CH$_3$)$_3$, —C≡C—Si(C$_2$H$_5$)$_3$, —C(=O)—O—C$_{1-5}$-alkyl and —C(=O)—CF$_3$, it being possible for the aforementioned phenyl radicals to be substituted with 1, 2, 3, 4 or 5 substituents selected independently of one another from the group consisting of F, Cl, Br, I, —CN, —CF$_3$, —OH, —NH$_2$, —O—CF$_3$, —SH, —O—CH$_3$, —O—C$_2$H$_5$, —O—C$_3$H$_7$, methyl, ethyl, n-propyl, isopropyl, n-butyl, 2-butyl, isobutyl and tert-butyl;

the aforementioned alkylene radicals are each branched or linear and have 1, 2, 3, 4, 5, 6, 7, 8, 9, 10, 11 or 12 carbon atoms as members of the chain;

the aforementioned alkenylene radicals are each branched or linear and have 2, 3, 4, 5, 6, 7, 8, 9, 10, 11 or 12 carbon atoms as members of the chain;

the aforementioned alkynylene radicals are each branched or linear and have 2, 3, 4, 5, 6, 7, 8, 9, 10, 11 or 12 carbon atoms as members of the chain;

the aforementioned heteroalkylene radicals, heteroalkenylene radicals and heteroalkynylene radicals each have 2, 3, 4, 5, 6, 7, 8, 9, 10, 11 or 12 members;

the aforementioned heteroalkylene, heteroalkenylene and heteroalkynylene groups each optionally have 1, 2 or 3 heteroatom(s), selected independently of one another from the group consisting of oxygen, sulphur and nitrogen (NH), as chain member(s);

the aforementioned alkylene, alkenylene, alkynylene, heteroalkylene, heteroalkenylene or heteroalkynylene groups may each be unsubstituted or substituted with, as appropriate, 1, 2, 3, 4 or 5 substituents selected independently of one another from the group consisting of phenyl, F, Cl, Br, I, —NO$_2$, —CN, —OH, —O-phenyl, —O—CH$_2$-phenyl, —SH, —S-phenyl, —S—CH$_2$-phenyl, NH$_2$, —N(C$_{1-5}$-alkyl)$_2$, —NH-phenyl, —N(C$_{1-5}$-alkyl)(phenyl), —N(C$_{1-5}$-alkyl)(CH$_2$-phenyl), —N(C$_{1-5}$-alkyl)(CH$_2$—CH$_2$-phenyl), —C(=O)—H, —C(=O)—C$_{1-5}$-alkyl, —C(=O)-phenyl, —C(=S)—C$_{1-5}$-alkyl, —C(=S)-phenyl, —C(=O)—OH, —C(=O)—O—C$_{1-5}$-alkyl, —C(=O)—O-phenyl, —C(=O)—NH$_2$, —C(=O)—NH—C$_{1-5}$-alkyl, —C(=O)—N(C$_{1-5}$-alkyl)$_2$, —S(=O)—C$_{1-5}$-alkyl, —S(=O)-phenyl, —S(=O)$_2$—C$_{1-5}$-alkyl, —S(=O)$_2$-phenyl, —S(=O)$_2$—NH$_2$ and —SO$_3$H, it being possible for the phenyl radicals to be substituted with 1, 2, 3, 4 or 5 substituents selected independently of one another from the group consisting of F, Cl, Br, I, —CN, —NO$_2$, —OH, —SH, —NH$_2$, —C(=O)—OH, —C$_{1-5}$-alkyl, —(CH$_2$)—O—C$_{1-5}$-alkyl, —C$_{2-5}$-alkenyl, —C$_{2-5}$-alkynyl, —C≡C—Si(CH$_3$)$_3$, —C≡C—Si(C$_2$H$_5$)$_3$, —S—C$_{1-5}$-alkyl, —S-phenyl, —S—CH$_2$-phenyl, —O—C$_{1-5}$-alkyl, —O-phenyl, —O—CH$_2$-phenyl, —CF$_3$, —CHF$_2$, —CH$_2$F, —O—CF$_3$, —O—CHF$_2$, —O—CH$_2$F, —C(=O)—CF$_3$, —S—CF$_3$, —S—CHF$_2$ and —S—CH$_2$F;

the aforementioned aryl radicals are monocyclic or bicyclic and have 6, 10 or 14 carbon atoms;

the aforementioned heteroaryl radicals are monocyclic, bicyclic or tricyclic and have 5, 6, 7, 8, 9, 10, 11, 12, 13 or 14 members;

the aforementioned heteroaryl radicals with 5 to 14 members optionally have 1, 2, 3, 4 or 5 heteroatom(s), selected independently of one another from the group consisting of oxygen, sulphur and nitrogen (NH), as chain member(s);

and the aforementioned phenylene radicals, aryl radicals and heteroaryl radicals may each be substituted with, as appropriate, 1, 2, 3, 4 or 5 substituents selected independently of one another from the group consisting of F, Cl, Br, I, —CN, —NO$_2$, —OH, —SH, —NH$_2$, —C(=O)—OH, —C$_{1-5}$-alkyl, —(CH$_2$)—O—C$_{1-5}$-alkyl, —C$_{2-5}$-alkenyl, —C$_{2-5}$-alkynyl, —C≡C—Si(CH$_3$)$_3$, —C≡C—Si(C$_2$H$_5$)$_3$, —S—C$_{1-5}$-alkyl, —S-phenyl, —S—CH$_2$-phenyl, —O—C$_{1-5}$-alkyl, —O-phenyl, —O—CH$_2$-phenyl, —CF$_3$, —CHF$_2$, —CH$_2$F, —O—CF$_3$, —O—CHF$_2$, —O—CH$_2$F, —C(=O)—CF$_3$, —S—CF$_3$, —S—CHF$_2$, —S—CH$_2$F, —S(=O)$_2$-phenyl, —S(=O)$_2$—C$_{1-5}$-alkyl, —S(=O)—C$_{1-5}$-alkyl, —NH—C$_{1-5}$-alkyl, N(C$_{1-5}$alkyl)$_2$, —C(=O)—O—C$_{1-5}$-alkyl, —C(=O)—H, —C(=O)—C$_{1-5}$-alkyl, —CH$_2$—O—C(=O)-phenyl, —O—C(=O)-phenyl, —NH—S(=O)$_2$—C$_{1-5}$-alkyl, —NH—C(=O)—C$_{1-5}$-alkyl, —C(=O)—NH$_2$, —C(=O)—NH—C$_{1-5}$-alkyl, —C(=O)—N(C$_{1-5}$-alkyl)$_2$, pyrazolyl, phenyl, furyl (furanyl), thiazolyl, thiadiazolyl, thiophenyl (thienyl), benzyl and phenethyl, it being possible for the cyclic substituents or the cyclic radicals of these substituents themselves to be substituted with, as appropriate, 1, 2, 3, 4 or 5 substituents selected independently of one another from the group consisting of F, Cl, Br, I, —CN, —NO$_2$, —OH, —SH, —NH$_2$, —C(=O)—OH, —C$_{1-5}$-alkyl, —(CH$_2$)—O—C$_{1-5}$-alkyl, —C$_{2-5}$-alkenyl, —C$_{2-5}$-alkynyl, —C≡C—Si(CH$_3$)$_3$, —C≡C—Si(C$_2$H$_5$)$_3$, —S—C$_{1-5}$-alkyl, —S-phenyl, —S—CH$_2$-phenyl, —O—C$_{1-5}$-alkyl, —O-phenyl, —O—CH$_2$-phenyl, —CF$_3$, —CHF$_2$, —CH$_2$F, —O—CF$_3$, —O—CHF$_2$, —O—CH$_2$F, —C(=O)—CF$_3$, —S—CF$_3$, —S—CHF$_2$ and —S—CH$_2$F;

each optionally in the form of one of the pure stereoisomers, or the racemates thereof, or in the form of a mixture of stereoisomers mixed in any ratios, or each in the form of a corresponding salts.

3. The compound according to claim 1, wherein
$R^1$ represents H; F; Cl; Br; I; —NO$_2$; —CN; —NH$_2$; —OH; —SH; —C(=O)—OH; —C(=O)—H; —NH—C(=O)—H; —NH—R$^{33}$; —NR$^{34}$R$^{35}$; —C(=O)—R$^{36}$; —C(=O)—O—R$^{37}$; —O—C(=O)—R$^{38}$; —NH—C(=O)—R$^{39}$; —NR$^{40}$—C(=O)—R$^{41}$; —C(=O)—NH$_2$; —C(=O)—NH—R$^{42}$; —C(=O)—NR$^{43}$R$^{44}$; —O—R$^{45}$; —S—R$^{46}$; —S(=O)—R$^{47}$; —S(=O)$_2$—R$^{48}$; —NH—C(=O)—NH—R$^{49}$; —NH—C(=S)—NH—R$^{50}$; —NH—S(=O)$_2$—R$^{51}$; —NR$^{52}$—S(=O)$_2$—R$^{53}$; C$_{1-6}$-alkyl, which is unsubstituted or substituted with, as appropriate, 1, 2, 3, 4 or 5 substituents selected independently of one another from the group consisting of F, Cl, Br, I, —NO$_2$, —CN, —OH, —SH and —NH$_2$;

C$_{3-7}$-cycloalkyl, C$_{5-6}$-cycloalkenyl, heterocycloalkyl with 5 to 7 members and heterocycloalkenyl with 5 to 7 members, which in each case may be connected by a C$_{1-3}$-alkylene, C$_{2-3}$-alkenylene or C$_{2-3}$-alkynylene group or is unsubstituted or substituted with, as appropriate, 1, 2, 3, 4 or 5 substituents selected independently of one another from the group consisting of F, Cl, Br, I, —CN, methyl, ethyl, n-propyl, isopropyl, n-butyl, 2-butyl, isobutyl, tert-butyl, —OH, oxo, thioxo, —O—CH$_3$, —O—C$_2$H$_5$, —O—C$_3$H$_7$, —NH$_2$, —N(CH$_3$)$_2$, —N(C$_2$H$_5$)$_2$, —NH—CH$_3$, —NH—C$_2$H$_5$, —NO$_2$, —CF$_3$, —O—CF$_3$, —S—CF$_3$, —SH, —S—CH$_3$ and —S—C$_2$H$_5$; or represents a radical selected from the group consisting of phenyl, naphthyl, anthracenyl, thienyl, furyl, pyridinyl, thiazolyl, thiadiazolyl, ozazolyl, oxadiazolyl and isoxazolyl, which in each case is connected by a C$_{1-3}$-alkylene, C$_{2-3}$-alkenylene or C$_{2-3}$-alkynylene group and/or is unsubstituted or substituted with, as appropriate, 1, 2, 3, 4 or 5 substituents selected independently of one another from the group consisting of F, Cl, Br, I, —CN, methyl, ethyl, n-propyl, isopropyl, n-butyl, isobutyl, 2-butyl, tert-butyl, —OH, —SH, —NH$_2$, —C(=O)—OH, —S—CH$_3$, —S—C$_2$H$_5$, —S(=O)—CH$_3$, —S(=O)$_2$—CH$_3$, —S(=O)—C$_2$H$_5$, —S(=O)$_2$—C$_2$H$_5$, —O—CH$_3$, —O—C$_2$H$_5$, —O—C$_3$H$_7$, —CF$_3$, —CHF$_2$, —CH$_2$F and —O—CF$_3$.

4. The compound according to claim 1, wherein
$R^2$ represents H; F; Cl; Br; I; —NO$_2$; —CN; —NH$_2$; —OH; —SH; —C(=O)—OH; —NH—R$^{33}$; —NR$^{34}$R$^{35}$; —C(=O)—R$^{36}$; —C(=O)—O—R$^{37}$; —C(=O)—NH$_2$; —C(=O)—NH—R$^{42}$; —C(=O)—NR$^{43}$R$^{44}$; —O—R$^{45}$; —S—R$^{46}$; —S(=O)—R$^{47}$; —S(=O)$_2$—R$^{48}$; —NH—C(=O)—NH—R$^{49}$; —NH—C(=O)—NH—R$^{50}$; —NH—S(=O)$_2$—R$^{51}$; —NR$^{52}$—S(=O)$_2$—R$^{53}$; C$_{1-6}$-alkyl, which is unsubstituted or substituted with, as appropriate, 1, 2, 3, 4 or 5 substituents selected independently of one another from the group consisting of F, Cl, Br, I, —NO$_2$, —CN, —OH, —SH and —NH$_2$; C$_{3-7}$-cycloalkyl, C$_{5-6}$-cycloalkenyl, heterocycloalkyl with 5 to 7 members or heterocycloalkenyl with 5 to 7 members, which in each case may be connected by a C$_{1-3}$-alkylene, C$_{2-3}$-alkenylene or C$_{2-3}$-alkynylene group or is unsubstituted or substituted with, as appropriate, 1, 2, 3, 4 or 5 substituents selected independently of one another from the group consisting of F, Cl, Br, I, —CN, methyl, ethyl, n-propyl, isopropyl, n-butyl, 2-butyl, isobutyl, tert-butyl, —OH, oxo, thioxo, —O—CH$_3$, —O—C$_2$H$_5$, —O—C$_3$H$_7$, —NH$_2$, —N(CH$_3$)$_2$, —N(C$_2$H$_5$)$_2$, —NH—CH$_3$, —NH—C$_2$H$_5$, —NO$_2$, —CF$_3$, —O—CF$_3$, —S—CF$_3$, —SH, —S—CH$_3$ and —S—C$_2$H$_5$; or represents a radical selected from the group consisting of phenyl, naphthyl, anthracenyl, thienyl, furyl, pyridinyl, thiazolyl, thiadiazolyl, ozazolyl, oxadiazolyl and isoxazolyl, which in each case is connected by a C$_{1-3}$-alkylene, C$_{2-3}$-alkenylene or C$_{2-3}$-alkynylene group or is unsubstituted or substituted with, as appropriate, 1, 2, 3, 4 or 5 substituents selected independently of one another from the group consisting of F, Cl, Br, I, —CN, methyl, ethyl, n-propyl, isopropyl, n-butyl, isobutyl, 2-butyl, tert-butyl, —OH, —SH, —NH$_2$, —C(=O)—OH, —S—CH$_3$, —S—C$_2$H$_5$, —S(=O)—CH$_3$, —S(=O)$_2$—CH$_3$, —S(=O)—C$_2$H$_5$, —S(=O)$_2$—C$_2$H$_5$, —O—CH$_3$, —O—C$_2$H$_5$, —O—C$_3$H$_7$, —CF$_3$, —CHF$_2$, —CH$_2$F and —O—CF$_3$.

5. The compound according to claim 1, wherein
$R^1$ and $R^2$ together with the carbon atoms linking them form a phenyl radical, which is unsubstituted or substituted with 1, 2, 3 or 4 substituents selected independently of one another from the group consisting of F, Cl, Br, I, —CN, methyl, ethyl, n-propyl, isopropyl, n-butyl, isobutyl, 2-butyl, tert-butyl, —OH, —SH, —NH$_2$, —C(=O)—OH, —S—CH$_3$, —S—C$_2$H$_5$, —S(=O)—CH$_3$, —S(=O)$_2$—CH$_3$, —S(=O)—C$_2$H$_5$, —S(=O)$_2$—C$_2$H$_5$, —O—CH$_3$, —O—C$_2$H$_5$, —O—C$_3$H$_7$, —CF$_3$, —CHF$_2$, —CH$_2$F and —O—CF$_3$.

6. The compound according to claim 1, wherein
$R^3$ and $R^{10}$ independently of one another each represent H; —C(=O)—$R^{36}$; —C(=O)—O—$R^{37}$; —C(=O)—$NH_2$; —C(=O)—NH—$R^{42}$; —C(=O)—$NR^{43}R^{44}$; —S(=O)—$R^{47}$; —S(=O)$_2$—$R^{48}$; $C_{1-6}$alkyl, which is unsubstituted or substituted with, as appropriate, 1, 2, 3, 4 or 5 substituents selected independently of one another from the group consisting of F, Cl, Br, I, —$NO_2$, —CN, —OH, —SH and —$NH_2$;
$C_{3-8}$-cycloalkyl, which is unsubstituted or substituted with, as appropriate, 1, 2, 3, 4 or 5 substituents selected independently of one another from the group consisting of F, Cl, Br, I, —$NO_2$, —CN, —OH, —SH and —$NH_2$;
or represent a phenyl radical, which in each case may be connected by a $C_{1-3}$-alkylene, $C_{2-3}$-alkenylene or $C_{2-3}$-alkynylene group or is unsubstituted or substituted with 1, 2, 3, 4 or 5 substituents selected independently of one another from the group consisting of F, Cl, Br, I, —CN, methyl, ethyl, n-propyl, isopropyl, n-butyl, 2-butyl, isobutyl, tert-butyl, —OH, —O—$CH_3$, —O—$C_2H_5$ and —O—$C_3H_7$.

7. The compound according to one or more of claim 1, wherein
$R^4$, $R^5$, $R^6$, $R^7$, $R^8$, $R^9$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, $R^{26}$, $R^{27}$, $R^{28}$, $R^{29}$, $R^{30}$, $R^{31}$ and $R^{32}$ independently of one another each represent H; F; Cl; Br; I; —$NO_2$; —CN; —$NH_2$; —OH; —SH; —C(=O)—OH; —NH—$R^{33}$; —$NR^{34}R^{35}$; —C(=O)—$R^{36}$; —C(=O)—O—$R^{37}$; —O—$R^{45}$; —S—$R^{46}$; $C_{1-6}$-alkyl, which is unsubstituted or substituted with, as appropriate, 1, 2, 3, 4 or 5 substituents selected independently of one another from the group consisting of F, Cl, Br, I, —$NO_2$, —CN, —OH, —SH and —$NH_2$; $C_{3-7}$-cycloalkyl, $C_{5-6}$-cycloalkenyl, heterocycloalkyl with 5 to 7 members or heterocycloalkenyl with 5 to 7 members, which in each case may be connected by a $C_{1-3}$-alkylene, $C_{2-3}$-alkenylene or $C_{2-3}$-alkynylene group or is unsubstituted or substituted with, as appropriate, 1, 2, 3, 4 or 5 substituents selected independently of one another from the group consisting of F, Cl, Br, I, —CN, methyl, ethyl, n-propyl, isopropyl, n-butyl, 2-butyl, isobutyl, tert-butyl, —OH, oxo, thioxo, —O—$CH_3$, —O—$C_2H_5$, —O—$C_3H_7$, —$NH_2$, —N($CH_3$)$_2$, —N($C_2H_5$)$_2$, —NH—$CH_3$, —NH—$C_2H_5$, —$NO_2$, —$CF_3$, —O—$CF_3$, —SH, —S—$CH_3$ and —S—$C_2H_5$; or represent a radical selected from the group consisting of phenyl, naphthyl, anthracenyl, pyrrolyl, indolyl, furanyl, benzo[b]furanyl, thiophenyl, benzo[b]thiophenyl, benzo[d]thiazolyl, pyrazolyl, imidazolyl, thiazolyl, thiadiazolyl, triazolyl, oxazolyl, oxadiazolyl, isoxazolyl, pyridinyl, pyridazinyl, pyrimidinyl, pyrazinyl, pyranyl, indazolyl, quinolinyl, isoquinolinyl and quinazolinyl, each of which may be connected by a $C_{1-3}$-alkylene, $C_{2-3}$-alkenylene or $C_{2-3}$-alkynylene group or is unsubstituted or substituted with, as appropriate, 1, 2, 3, 4 or 5 substituents selected independently of one another from the group consisting of F, Cl, Br, I, —CN, methyl, ethyl, n-propyl, isopropyl, n-butyl, 2-butyl, isobutyl, tert-butyl, —OH, —O—$CH_3$, —O—$C_2H_5$ and —O—$C_3H_7$;
or $R^4$ and $R^5$ or $R^6$ and $R^7$ or $R^8$ and $R^9$ or $R^{12}$ and $R^{13}$ or $R^{14}$ and $R^{15}$ or $R^{16}$ and $R^{17}$ or $R^{18}$ and $R^{19}$ or $R^{20}$ and $R^{21}$ or $R^{22}$ and $R^{23}$ or $R^{24}$ and $R^{25}$ or $R^{26}$ and $R^{27}$ or $R^{28}$ and $R^{29}$ or $R^{31}$ and $R^{32}$ independently of one another represent, together in each case, a radical selected from the group consisting of an oxo group (=O) and a thioxo group (=S).

8. The compound according to claim 1, wherein
$R^3$ and $R^4$ together with the —N—$CR^5$ group linking them form a radical selected from the group consisting of:

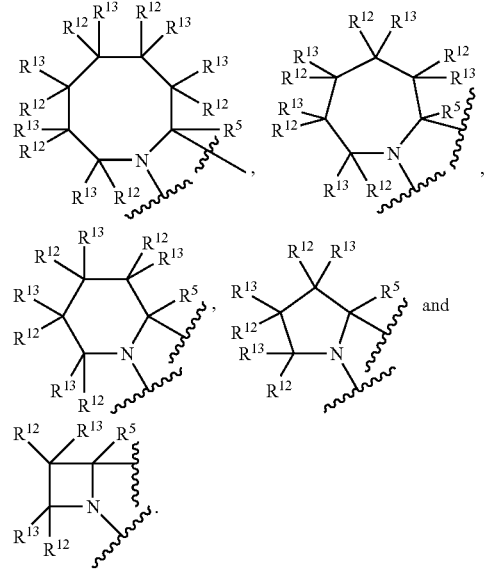

9. The compound according to claim 1, wherein
$R^8$ and $R^{10}$ together with the —N—$CR^9$ group linking them form a radical selected from the group consisting of:

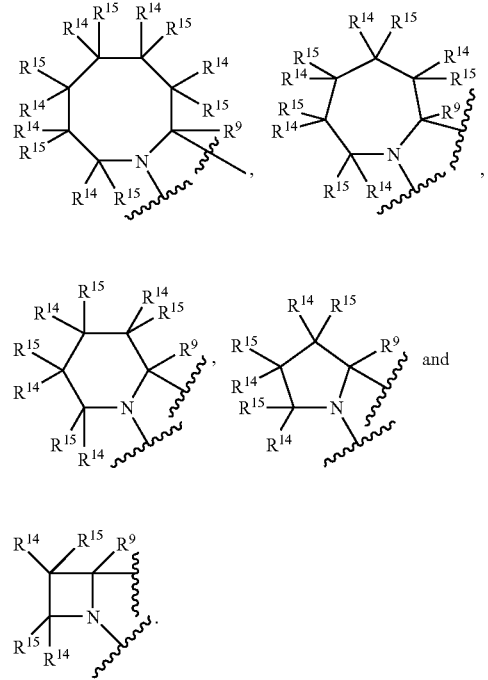

10. The compound according to claim 1, wherein
$R^3$ and $R^6$ together with the —N—$CR^4R^5$—$CR^7$ group linking them form a radical selected from the group consisting of:

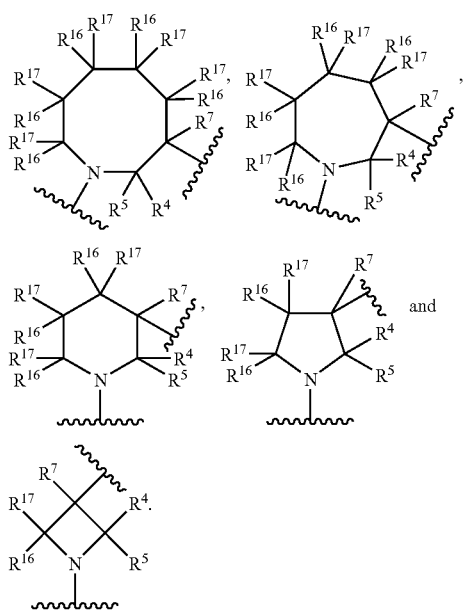

11. The compound according to claim 1, wherein

R$^6$ and R$^{10}$ together with the —CR$^7$—CR$^8$CR$^9$—N group linking them form a radical selected from the group consisting of

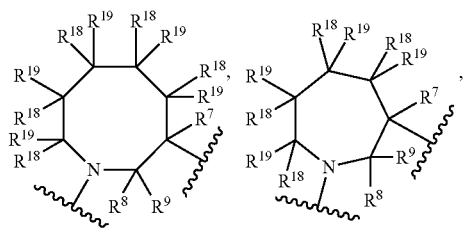

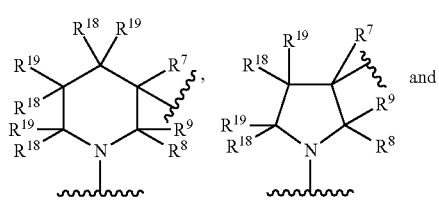

12. The compound according to claim 1, wherein

R$^3$ and R$^8$ together with the —N—CR$^4$R$^5$—CR$^6$R$^7$—CR$^9$ group linking them form a radical selected from the group consisting of:

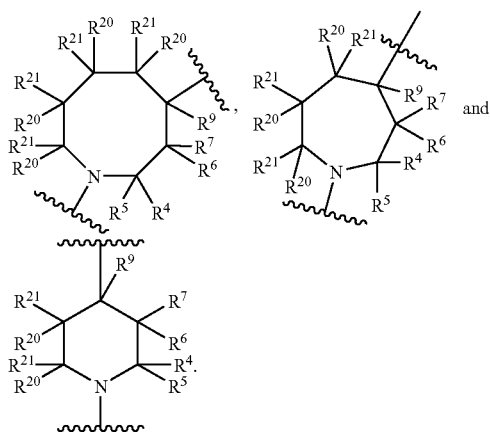

13. The compound according to claim 1, wherein

R$^4$ and R$^{10}$ together with the —N—CR$^8$R$^9$—CR$^6$R$^7$—CR$^5$ group linking them form a radical selected from the group consisting of:

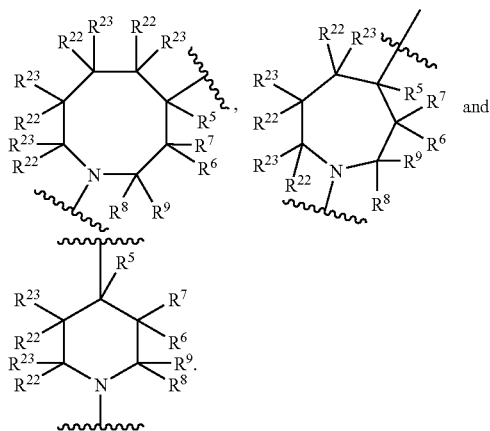

14. The compound according to claim 1, wherein

R$^4$ and R$^8$ together with the —CR$^5$—CR$^6$R$^7$—CR$^9$ group linking them form a radical selected from the group consisting of:

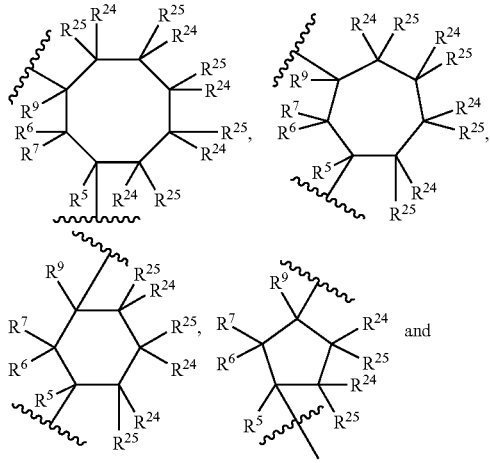

-continued

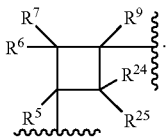

15. The compound according to claim 1, wherein R³ and R¹⁰ together with the —N—CR⁴R⁵—CR⁶R⁷—CR⁸R⁹—N group linking them form a radical selected from the group consisting of:

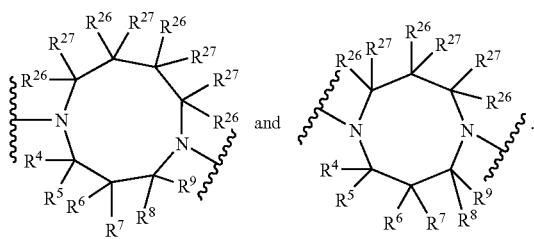

16. The compound according to claim 1, wherein R³ and R¹⁰ together with the —N—CR⁴R⁵—CR⁶R⁷—CR⁸R⁹—N group linking them form a bicyclic radical selected from the group consisting of:

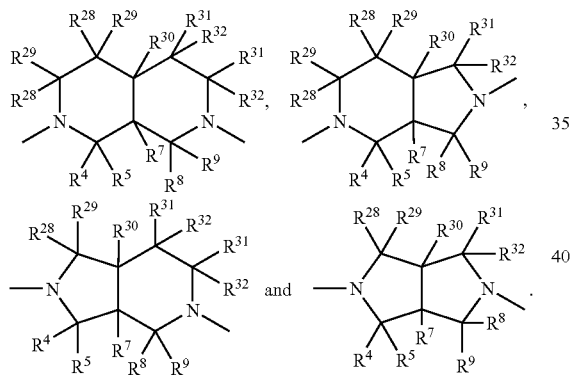

17. The compound according to claim 1, wherein R¹¹ represents a radical selected from the group consisting of phenyl, naphthyl, anthracenyl, furyl, thienyl, pyrazolyl, pyridazinyl, pyrazinyl, pyrimidinyl, pyridinyl, pyrrolyl, oxazolyl, isoxazolyl, thiazolyl, thiadiazolyl, oxadiazolyl, triazolyl, imidazolyl, indolyl, benzo[b]thiophenyl, benzo[d]thiazolyl, benzo[b]furanyl, quinolinyl, isoquinolinyl and quinazolinyl, each of which is unsubstituted or substituted with, as appropriate, 1, 2, 3, 4 or 5 substituents selected independently of one another from the group consisting of F, Cl, Br, I, —CN, methyl, ethyl, n-propyl, isopropyl, n-butyl, 2-butyl, isobutyl, tert-butyl, ethenyl, allyl, ethynyl, propynyl, —C≡C—Si(CH₃)₃, —C≡C—Si(C₂H₅)₃, —CH₂—O—CH₃, —CH₂—O—C₂H₅, —OH, —O—CH₃, —O—C₂H₅, —O—C₃H₇, —S—CH₃, —S—C₂H₅, —S(=O)—CH₃, —S(=O)₂—CH₃, —S(=O)—C₂H₅, —S(=O)₂—C₂H₅, —NH₂, —N(CH₃)₂, —N(C₂H₅)₂, —NH—CH₃, —NH—C₂H₅, —NO₂, —CF₃, —O—CF₃, —S—CF₃, —CH₂F, —CHF₂, —O—CF₃, —S—CF₃, —SH, —NH—S(=O)₂—CH₃, —C(=O)—OH, —C(=O)—H, —C(=O)—CH₃, —C(=O)—C₂H₅, —C(=O)—NH₂, —C(=O)—N(CH₃)₂, —C(=O)—NH—CH₃, —NH—C(=O)—CH₃, —NH—C(=O)—C₂H₅, —C(=O)—O—CH₃, —C(=O)—O—C₂H₅, —C(=O)—O—C(CH₃)₃ and phenyl.

18. The compound according to claim 1, wherein R³³, R³⁴, R³⁵, R³⁶, R³⁷, R³⁸, R³⁹, R⁴⁰, R⁴¹, R⁴², R⁴³, R⁴⁴, R⁴⁵, R⁴⁶, R⁴⁷, R⁴⁸, R⁴⁹, R⁵⁰, R⁵¹, R⁵² and R⁵³ independently of one another each represent $C_{1-6}$-alkyl, which is unsubstituted or substituted with, as appropriate, 1, 2, 3, 4 or 5 substituents selected independently of one another from the group consisting of F, Cl, Br, I, —NO₂, —CN, —OH, —SH and —NH₂; $C_{3-7}$-cycloalkyl, $C_{5-6}$-cycloalkenyl, heterocycloalkyl with 5 to 7 members or heterocycloalkenyl with 5 to 7 members, which in each case may be connected by a $C_{1-3}$-alkylene, $C_{2-3}$-alkenylene or $C_{2-3}$-alkynylene group or is unsubstituted or substituted with, as appropriate, 1, 2, 3, 4 or 5 substituents selected independently of one another from the group consisting of F, Cl, Br, I, —CN, methyl, ethyl, n-propyl, isopropyl, n-butyl, 2-butyl, isobutyl, tert-butyl, —OH, Oxo, Thioxo, —O—CH₃, —O—C₂H₅, —O—C₃H₇, —NH₂, —N(CH₃)₂, —N(C₂H₅)₂, —NH—CH₃, —NH—C₂H₅, —NO₂, —CF₃, —O—CF₃, —S—CF₃, —SH, —S—CH₃ and —S—C₂H₅; or represent a radical selected from the group consisting of phenyl, naphthyl, anthracenyl, pyrrolyl, indolyl, furanyl, benzo[b]furanyl, thiophenyl, benzo[b]thiophenyl, benzo[d]thiazolyl, pyrazolyl, imidazolyl, thiazolyl, thiadiazolyl, triazolyl, oxazolyl, oxadiazolyl, isoxazolyl, pyridinyl, pyridazinyl, pyrimidinyl, pyrazinyl, pyranyl, indazolyl, quinolinyl, isoquinolinyl and quinazolinyl, each of which may be connected by a $C_{1-3}$-alkylene, $C_{2-3}$-alkenylene or $C_{2-3}$-alkynylene group or is unsubstituted or substituted with, as appropriate, 1, 2, 3, 4 or 5 substituents selected independently of one another from the group consisting of F, Cl, Br, I, —CN, methyl, ethyl, n-propyl, isopropyl, n-butyl, 2-butyl, isobutyl, tert-butyl, —OH, —O—CH₃, —O—C₂H₅, —O—C₃H₇, —NH₂, —N(CH₃)₂, —N(C₂H₅)₂, —NH—CH₃, —NH—C₂H₅, —NO₂, —CF₃, —O—CF₃, —S—CF₃, —SH, —NH—S(=O)₂—CH₃, —C(=O)—OH, —C(=O)—CH₃, —C(=O)—C₂H₅, —C(=O)—N(CH₃)₂, —C(=O)—NH—CH₃, —NH—C(=O)—CH₃, —NH—C(=O)—C₂H₅, —C(=O)—O—CH₃ and —C(=O)—O—C₂H₅.

19. The compound according to claim 1, wherein R¹ represents H; F; Cl; Br; I; —CF₃; —NO₂; —CN; —NH₂; —OH; —SH; —C(=O)—OH; —C(=O)—H; —NH—C(=O)—H; —NH—R³³; —NR³⁴R³⁵; —C(=O)—R³⁶; —C(=O)—O—R³⁷; —C(=O)—NH₂; —C(=O)—NH—R⁴²; —C(=O)—NR⁴³R⁴⁴; —O—R⁴⁵; —S—R⁴⁶; —S(=O)—R⁴⁷; —S(=O)₂—R⁴⁸;

unsubstituted $C_{1-6}$-alkyl or a radical selected from the group consisting of (1,3)-dioxolan-2-yl, phenyl, benzyl, phenethyl, oxadiazolyl, 2-pyridyl, 3-pyridyl, 4-pyridyl, 2-thienyl, 3-thienyl, 2-furyl and 3-furyl, each of which is unsubstituted or substituted with, as appropriate, 1, 2, 3, 4 or 5 substituents selected independently of one another from the group consisting of F, Cl, Br, I, —CN, methyl, ethyl, n-propyl, isopropyl, n-butyl, 2-butyl, isobutyl, tert-butyl, —OH, —O—CH₃, —O—C₂H₅ and —O—C₃H₇;

R² represents H; F; Cl; Br; I; —CF₃; —NO₂; —CN; —NH₂; —OH; —SH; —C(=O)—OH; —C(=O)—H;

—NH—C(=O)—H; —NH—R$^{33}$; —NR$^{34}$R$^{35}$; —C(=O)—R$^{36}$; —C(=O)—O—R$^{37}$; —C(=O)—NH$_2$; —C(=O)—NH—R$^{42}$; —C(=O)—NR$^{43}$R$^{44}$; —O—R$^{45}$; —S—R$^{46}$; —S(=O)—R$^{47}$; —S(=O)$_2$—R$^{48}$; unsubstituted C$_{1-6}$-alkyl or a radical selected from the group consisting of (1,3)-dioxolan-2-yl, phenyl, benzyl, phenethyl, oxadiazolyl, 2-pyridyl, 3-pyridyl, 4-pyridyl, 2-thienyl, 3-thienyl, 2-furyl and 3-furyl, each of which is unsubstituted or substituted with, as appropriate, 1, 2, 3, 4 or 5 substituents selected independently of one another from the group consisting of F, Cl, Br, I, —CN, methyl, ethyl, n-propyl, isopropyl, n-butyl, 2-butyl, isobutyl, tert-butyl, —OH, —O—CH$_3$, —O—C$_2$H$_5$ and —O—C$_3$H$_7$;

or R$^1$ and R$^2$ together with the carbon atoms linking them form a phenylene radical, which is unsubstituted or substituted with 1, 2, 3 or 4 substituents selected independently of one another from the group consisting of F, Cl, Br, I, —CN, methyl, ethyl, n-propyl, isopropyl, n-butyl, isobutyl, 2-butyl, tert-butyl, —OH, —SH, —NH$_2$, —C(=O)—OH, —S—CH$_3$, —S—C$_2$H$_5$, —S(=O)—CH$_3$, —S(=O)$_2$—CH$_3$, —S(=O)—C$_2$H$_5$, —S(=O)$_2$—C$_2$H$_5$, —O—CH$_3$, —O—C$_2$H$_5$, —O—C$_3$H$_7$, —CF$_3$, —CHF$_2$, —CH$_2$F and —O—CF$_3$;

R$^3$ and R$^{10}$ independently of one another each represent H; —C(=O)—R$^{36}$; —C(=O)—O—R$^{37}$; —C(=O)—NH$_2$; —C(=O)—NH—R$^{42}$; —C(=O)—NR$^{43}$R$^{44}$; —S(=O)—R$^{47}$; —S(=O)$_2$—R$^{48}$; C$_{1-6}$-alkyl, which is unsubstituted or substituted with, as appropriate, 1, 2, 3, 4 or 5 substituents selected independently of one another from the group consisting of F, Cl, Br, I, —NO$_2$, —CN, —OH, —SH and —NH$_2$;

C$_{3-6}$-cycloalkyl, which is unsubstituted or substituted with, as appropriate, 1, 2, 3, 4 or 5 substituents selected independently of one another from the group consisting of F, Cl, Br, I, —NO$_2$, —CN, —OH, —SH and —NH$_2$;

or represent a phenyl radical, which in each case may be connected by a C$_{1-3}$-alkylene, C$_{2-3}$-alkenylene or C$_{2-3}$-alkynylene group or is unsubstituted or substituted with 1, 2, 3, 4 or 5 substituents selected independently of one another from the group consisting of F, Cl, Br, I, —CN, methyl, ethyl, n-propyl, isopropyl, n-butyl, 2-butyl, isobutyl, tert-butyl, —OH, —O—CH$_3$, —O—C$_2$H$_5$ and —O—C$_3$H$_7$;

R$^4$, R$^5$, R$^6$, R$^7$, R$^8$, R$^9$, R$^{12}$, R$^{13}$, R$^{14}$, R$^{15}$, R$^{16}$, R$^{17}$, R$^{18}$, R$^{19}$, R$^{20}$, R$^{21}$, R$^{22}$, R$^{23}$, R$^{24}$, R$^{25}$, R$^{26}$, R$^{27}$, R$^{28}$, R$^{29}$, R$^{30}$, R$^{31}$ and R$^{32}$ independently of one another each represent H; F; Cl; Br; I; —NO$_2$; —CN; —NH$_2$; —OH; —SH; —C(=O)—OH; —NH—R$^{33}$; —NR$^{34}$R$^{35}$; —C(=O)—R$^{36}$; —C(=O)—O—R$^{37}$; —O—R$^{45}$; —S—R$^{46}$; unsubstituted C$_{1-6}$-alkyl; or a radical selected from the group consisting of phenyl, benzyl and phenethyl, which is unsubstituted or substituted with 1, 2, 3, 4 or 5 substituents selected independently of one another from the group consisting of F, Cl, Br, I, —CN, methyl, ethyl, n-propyl, isopropyl, n-butyl, 2-butyl, isobutyl, tert-butyl, —OH, —O—CH$_3$, —O—C$_2$H$_5$ and —O—C$_3$H$_7$;

or R$^4$ and R$^5$ or R$^6$ and R$^7$ or R$^8$ and R$^9$ or R$^{12}$ and R$^{13}$ or R$^{14}$ and R$^{15}$ or R$^{16}$ and R$^{17}$ or R$^{18}$ and R$^{19}$ or R$^{20}$ and R$^{21}$ or R$^{22}$ and R$^{23}$ or R$^{24}$ and R$^{25}$ or R$^{26}$ and R$^{27}$ or R$^{28}$ and R$^{29}$ or R$^{31}$ and R$^{32}$ independently of one another represent, together in each case, a radical selected from the group consisting of an oxo group (=O) and a thioxo group (=S);

or R$^3$ and R$^4$ together with the —N—CR$^5$ group linking them form a radical selected from the group consisting of:

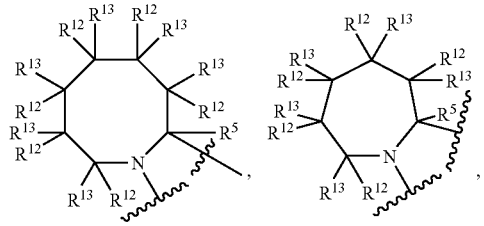

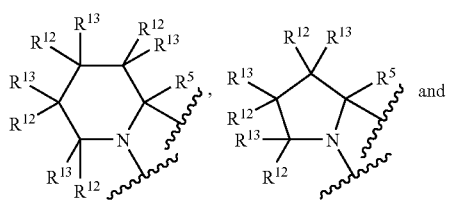

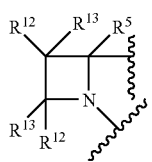

or R$^8$ and R$^{10}$ together with the —N—CR$^9$ group linking them form a radical selected from the group consisting of:

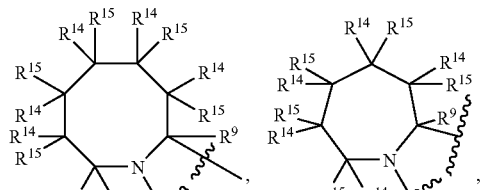

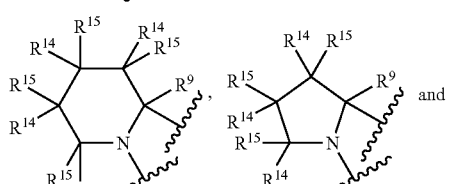

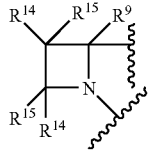

or R$^3$ and R$^6$ together with the —N—CR$^4$R$^5$—CR$^7$ group linking them form a radical selected from the group consisting of:

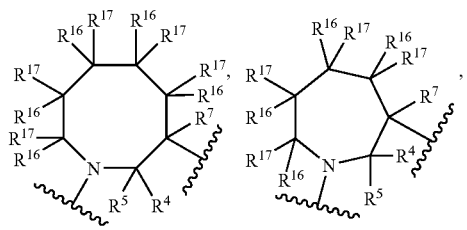

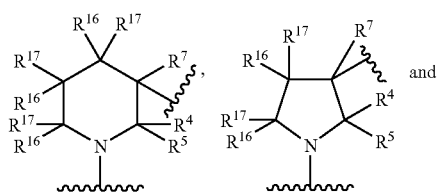

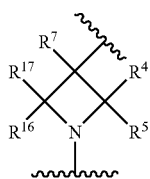

or R$^6$ and R$^{10}$ together with the —CR$^7$—CR$^8$R$^9$—N group linking them form a radical selected from the group consisting of:

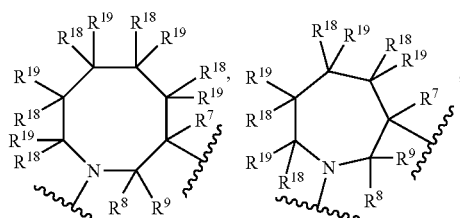

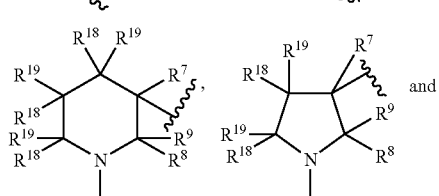

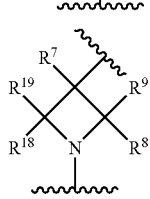

or R$^3$ and R$^8$ together with the —N—CR$^4$R$^5$—CR$^6$R$^7$—CR$^9$ group linking them form a radical selected from the group consisting of:

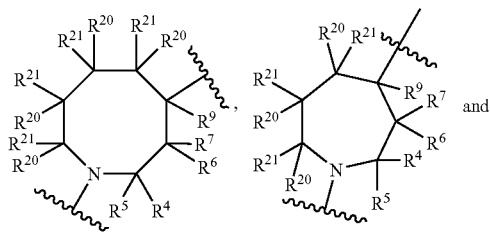

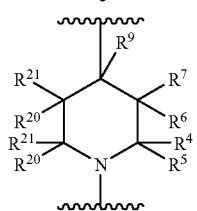

or R$^4$ and R$^{10}$ together with the —N—CR$^8$R$^9$—CR$^6$R$^7$—CR$^5$ group linking them form a radical selected from the group consisting of:

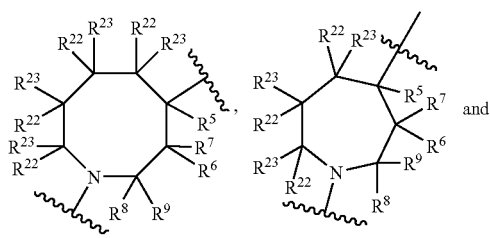

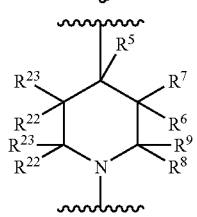

or R$^4$ and R$^8$ together with the —CR$^5$—CR$^6$R$^7$—CR$^9$ group linking them form a radical selected from the group consisting of:

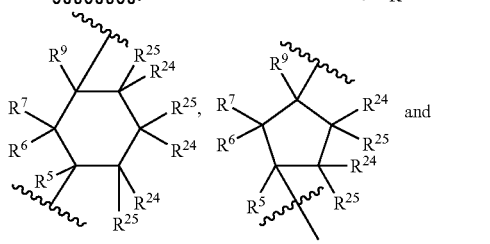

-continued

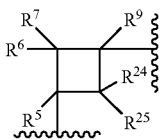

or R³ and R¹⁰ together with the —N—CR⁴R⁵—CR⁶R⁷—CR⁸R⁹—N group linking them form a radical selected from the group consisting of

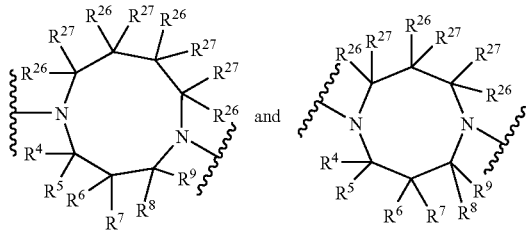

or R³ and R¹⁰ together with the —N—CR⁴R⁵—CR⁶R⁷—CR⁸R⁹—N group linking them form a bicyclic radical selected from the group consisting of:

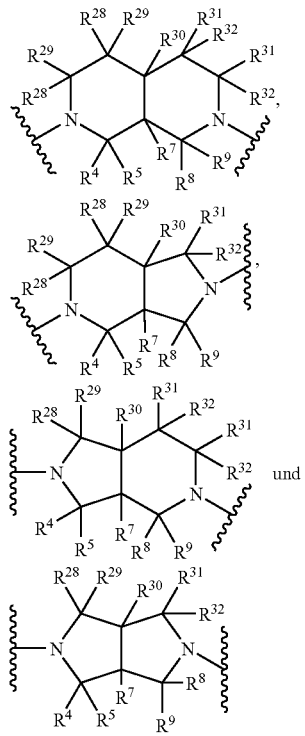

R¹¹ represents a radical selected from the group consisting of phenyl, naphthyl, anthracenyl, furyl, thienyl, pyrazolyl, pyridazinyl, pyrazinyl, pyrimidinyl, pyridinyl, pyrrolyl, oxazolyl, isoxazolyl, thiazolyl, thiadiazolyl, oxadiazolyl, triazolyl, imidazolyl, indolyl, benzo[b]thiophenyl, benzo[d]thiazolyl, benzo[b]furanyl, quinolinyl, isoquinolinyl and quinazolinyl. each of which is unsubstituted or substituted with, as appropriate, 1, 2, 3, 4 or 5 substituents selected independently of one another from the group consisting of F, Cl, Br, I, —CN, methyl, ethyl, n-propyl, isopropyl, n-butyl, 2-butyl, isobutyl, tert-butyl, ethenyl, allyl, ethynyl, propynyl, —C≡C—Si(CH₃)₃, —C≡C—Si(C₂H₅)₃, —CH₂—O—CH₃, —CH₂—O—C₂H₅, —OH, —O—CH₃, —O—C₂H₅, —O—C₃H₇, —S—CH₃, —S—C₂H₅, —S(=O)—CH₃, —S(=O)₂—CH₃, —S(=O)—C₂H₅, —S(=O)₂—C₂H₅, —NH₂, —N(CH₃)₂, —N(C₂H₅)₂, —NH—CH₃, —NH—C₂H₅, —NO₂, —CF₃, —CH₂F, —CHF₂, —O—CF₃, —S—CF₃, —SH, —NH—S(=O)₂—CH₃, —C(=O)—OH, —C(=O)—H; —C(=O)—CH₃, —C(=O)—C₂H₅, —C(=O)—NH₂, —C(=O)—N(CH₃)₂, —C(=O)—NH—CH₃, —NH—C(=O)—CH₃, —NH—C(=O)—C₂H₅, —C(=O)—O—CH₃, —C(=O)—O—C₂H₅, —C(=O)—O—C(CH₃)₃ and phenyl;

and R³³, R³⁴, R³⁵, R³⁶, R³⁷, R⁴², R⁴³, R⁴⁴, R⁴⁵, R⁴⁶, R⁴⁷ and R⁴⁸ independently of one another each represent unsubstituted $C_{1-6}$-alkyl; unsubstituted $C_{3-7}$-cycloalkyl; unsubstituted $C_{5-6}$-cycloalkenyl; unsubstituted heterocycloalkyl with 5 to 7 members or unsubstituted heterocycloalkenyl with 5 to 7 members; or represent a radical selected from the group consisting of phenyl, benzyl naphthyl, anthracenyl, pyrrolyl, indolyl, furanyl, benzo[b]furanyl, thiophenyl, benzo[b]thiophenyl, benzo[d]thiazolyl, pyrazolyl, imidazolyl, thiazolyl, thiadiazolyl, triazolyl, oxazolyl, oxadiazolyl, isoxazolyl, pyridinyl, pyridazinyl, pyrimidinyl, pyrazinyl, pyranyl, indazolyl, quinolinyl, isoquinolinyl and quinazolinyl, each of which is unsubstituted or substituted with, as appropriate, 1, 2, 3, 4 or 5 substituents selected independently of one another from the group consisting of F, Cl, Br, methyl, ethyl, n-propyl, isopropyl, n-butyl, 2-butyl, isobutyl, tert-butyl, —OH, —O—CH₃, —O—C₂H₅, —O—C₃H₇, —NH₂, —N(CH₃)₂, —N(C₂H₅)₂, —NH—CH₃, —NH—C₂H₅, —NO₂, —CF₃, —O—CF₃, —S—CF₃, —SH, —NH—S(=O)₂—CH₃, —C(=O)—OH, —C(=O)—CH₃, —C(=O)—C₂H₅, —C(=O)—N(CH₃)₂, —C(=O)—NH—CH₃, —NH—C(=O)—CH₃, —NH—C(=O)—C₂H₅, —C(=O)—O—CH₃ and —C(=O)—O—C₂H₅;

each optionally in the form of one of the pure stereoisomers, or the racemates thereof, or in the form of a mixture of stereoisomers mixed in any ratios, or each in the form of a corresponding salts.

20. The compound according to claim 1, wherein
R¹ represents H; F; Cl; Br; I; —CF₃; —NO₂; —CN; —C(=O)—OH; —C(=O)—O—R³⁷; —C(=O)—NH₂; —C(=O)—NH—R⁴²; —C(=O)—NR⁴³R⁴⁴; —O—R⁴⁵; —S—R⁴⁶; —S(=O)—R⁴⁷; —S(=O)₂—R⁴⁸;

an alkyl radical selected from the group consisting of methyl, ethyl, n-propyl, isopropyl, n-butyl, 2-butyl, isobutyl and tert-butyl; or a radical selected from the group consisting of (1,3)-dioxolan-2-yl, phenyl, benzyl, phenethyl, oxadiazolyl, 2-pyridyl, 3-pyridyl, 4-pyridyl, 2-thienyl, 3-thienyl, 2-furyl and 3-furyl, each of which is unsubstituted or substituted with, as appropriate, 1, 2, 3, 4 or 5 substituents selected independently of one another from the group consisting of F, Cl, Br, I, —CN, methyl, ethyl, n-propyl, isopropyl, n-butyl, 2-butyl, isobutyl, tert-butyl, —OH, —O—CH₃, —O—C₂H₅ and —O—C₃H₇;

R² represents H; F; Cl; Br; J; —CF₃; —NO₂; —CN; —C(=O)—OH; —C(=O)—O—R³⁷; —C(=O)—NH₂; —C(=O)—NH—R⁴²; —C(=O)—NR⁴³R⁴⁴; —O—R⁴⁵; —S—R⁴⁶; —S(=O)—R⁴⁷; —S(O)₂—R⁴⁸;

an alkyl radical selected from the group consisting of methyl, ethyl, n-propyl, isopropyl, n-butyl, 2-butyl, isobutyl and tert-butyl; or a radical selected from the group consisting of (1,3)-dioxolan-2-yl, phenyl, benzyl, phenethyl, oxadiazolyl, 2-pyridyl, 3-pyridyl, 4-pyridyl, 2-thienyl, 3-thienyl, 2-furyl and 3-furyl, each of which is unsubstituted or substituted with, as appropriate, 1, 2, 3, 4 or 5 substituents selected independently of one another from the group consisting of F, Cl, Br, I, —CN, methyl, ethyl, n-propyl, isopropyl, n-butyl, 2-butyl, isobutyl, tert-butyl, —OH, —O—$CH_3$, —O—$C_2H_5$ and —O—$C_3H_7$;

or $R^1$ and $R^2$ together with the carbon atoms linking them form a phenylene radical, which is unsubstituted or substituted with 1, 2, 3 or 4 substituents selected independently of one another from the group consisting of F, Cl, Br, I, —CN, methyl, ethyl, n-propyl, isopropyl, n-butyl, isobutyl, 2-butyl, tert-butyl, —O—$CH_3$, —O—$C_2H_5$, —O—$C_3H_7$, —$CF_3$, —$CHF_2$, —$CH_2F$ and —O—$CF_3$;

$R^3$ and $R^{10}$ independently of one another each represent H; —C(=O)—$R^{36}$; —C(=O)—O—$R^{37}$; —S(=O)—$R^{47}$; —S(=O)$_2$—$R^{48}$; an alkyl radical selected from the group consisting of methyl, ethyl, n-propyl, isopropyl, n-butyl, 2-butyl, isobutyl, tert-butyl, n-pentyl and n-hexyl; a cycloalkyl radical selected from the group consisting of cyclopropyl, cyclobutyl, cyclopentyl and cyclohexyl; or a benzyl or phenethyl radical which is unsubstituted or substituted with 1, 2, 3, 4 or 5 substituents selected independently of one another from the group consisting of F, Cl, Br, methyl, ethyl, n-propyl, isopropyl, n-butyl, 2-butyl, isobutyl, tert-butyl, —OH, —O—$CH_3$, —O—$C_2H_5$ and —O—$C_3H_7$;

$R^4$, $R^5$, $R^6$, $R^7$, $R^8$, $R^9$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, $R^{26}$, $R^{27}$, $R^{28}$, $R^{29}$, $R^{30}$, $R^{31}$ and $R^{32}$ independently of one another each represent H; F; Cl; Br; I; —$NO_2$; —CN; —$NH_2$; —OH; —SH; —NH—$R^{33}$; —$NR^{34}R^{35}$; —O—$R^{45}$; —S—$R^{46}$; —$CF_3$; —$C_2F_5$; an alkyl radical selected from the group consisting of methyl, ethyl, n-propyl, isopropyl, n-butyl, 2-butyl, isobutyl, tert-butyl, n-pentyl and n-hexyl;

or $R^4$ and $R^5$ or $R^6$ and $R^7$ or $R^8$ and $R^9$ or $R^{12}$ and $R^{13}$ or $R^{14}$ and $R^{15}$ or $R^{16}$ and $R^{17}$ or $R^{18}$ and $R^{19}$ or $R^{20}$ and $R^{21}$ or $R^{22}$ and $R^{23}$ or $R^{24}$ and $R^{25}$ or $R^{26}$ and $R^{27}$ or $R^{28}$ and $R^{29}$ or $R^{31}$ and $R^{32}$ independently of one another represent, together in each case, a radical selected from the group consisting of an oxo group (=O) and a thioxo group (=S);

or $R^3$ and $R^4$ together with the —N—$CR^5$ group linking them form a radical selected from the group consisting of:

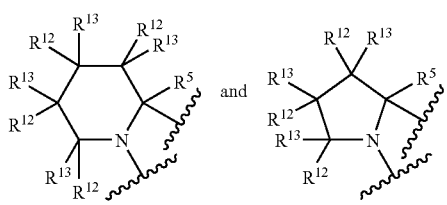

or $R^8$ and $R^{10}$ together with the —N—$CR^9$ group linking them form a radical selected from the group consisting of:

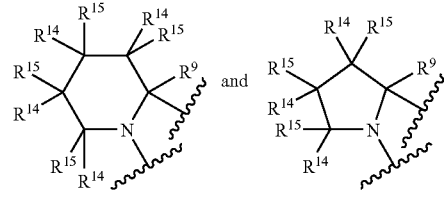

or $R^3$ and $R^6$ together with the —N—$CR^4R^5$—$CR^7$ group linking them form a radical selected from the group consisting of:

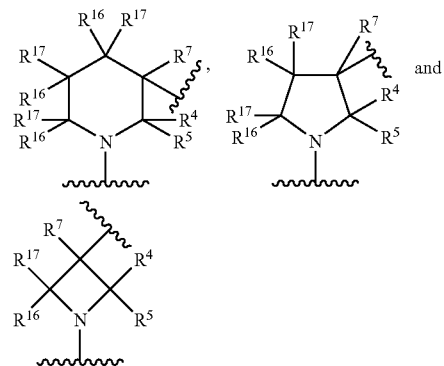

or $R^6$ and $R^{10}$ together with the —$CR^7$—$CR^8CR^9$—N group linking them form a radical selected from the group consisting of:

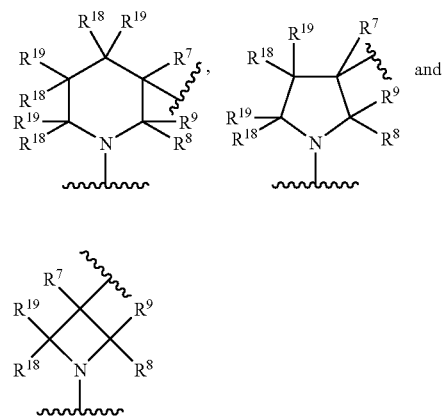

or $R^3$ and $R^8$ together with the —N—$CR^4R^5$—$CR^6R^7$—$CR^9$ group linking them form the following radical:

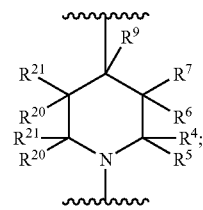

or R$^4$ and R$^{10}$ together with the —N—CR$^8$R$^9$—CR$^6$R$^7$—CR$^5$ group linking them form the following radical:

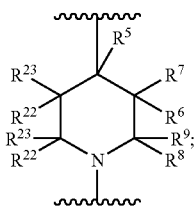

or R$^4$ and R$^8$ together with the —CR$^5$—CR$^6$R$^7$—CR$^9$ group linking them form a radical selected from the group consisting of:

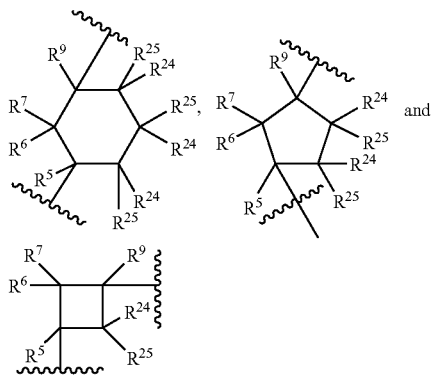

or R$^3$ and R$^{10}$ together with the —N—CR$^4$R$^5$—CR$^6$R$^7$—CR$^8$R$^9$—N group linking them form the following radical:

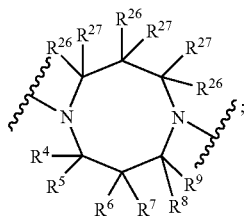

or R$^3$ and R$^{10}$ together with the —N—CR$^4$R$^5$—CR$^6$R$^7$—CR$^8$R$^9$—N group linking them form a bicyclic radical selected from the group consisting of:

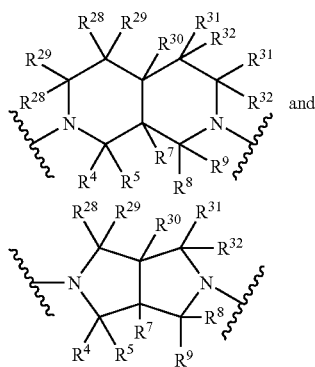

R$^{11}$ represents a radical selected from the group consisting of phenyl, naphthyl, anthracenyl, furyl, pyridazinyl, thienyl, pyrazolyl, pyrazinyl, pyrimidinyl, pyridinyl, pyrrolyl, oxazolyl, isoxazolyl, thiazolyl, thiadiazolyl, oxadiazolyl, triazolyl, imidazolyl, indolyl, benzo[b]thiophenyl, benzo[d]thiazolyl, benzo[b]furanyl, quinolinyl, isoquinolinyl and quinazolinyl, each of which is unsubstituted or substituted with, as appropriate, 1, 2, 3, 4 or 5 substituents selected independently of one another from the group consisting of F, Cl, Br, I, —CN, methyl, ethyl, n-propyl, isopropyl, n-butyl, 2-butyl, isobutyl, tert-butyl, ethenyl, allyl, ethynyl, propynyl, —C≡C—Si(CH$_3$)$_3$, —C≡C—Si(C$_2$H$_5$)$_3$, —CH$_2$—O—CH$_3$, —CH$_2$—O—C$_2$H$_5$, —OH, —O—CH$_3$, —O—C$_2$H$_5$, —O—C$_3$H$_7$, —S—CH$_3$, —S—C$_2$H$_5$, —S(=O)—CH$_3$, —S(=O)$_2$—CH$_3$, —S(=O)—C$_2$H$_5$, —S(=O)$_2$—C$_2$H$_5$, —NH$_2$, —N(CH$_3$)$_2$, —N(C$_2$H$_5$)$_2$, —NH—CH$_3$, —NH—C$_2$H$_5$, —NO$_2$, —CF$_3$, —CH$_2$F, —CHF$_2$, —O—CF$_3$, —S—CF$_3$, —SH, —NH—S(=O)$_2$—CH$_3$, —C(=O)—OH, —C(=O)—H; —C(=O)—CH$_3$, —C(=O)—C$_2$H$_5$, —C(=O)—NH$_2$, —C(=O)—N(CH$_3$)$_2$, —C(=O)—NH—CH$_3$, —NH—C(=O)—CH$_3$, —NH—C(=O)—C$_2$H$_5$, —C(=O)—O—CH$_3$, —C(=O)—O—C$_2$H$_5$, —C(=O)—O—C(CH$_3$)$_3$ and phenyl;

and R$^{33}$, R$^{34}$, R$^{35}$, R$^{36}$, R$^{37}$, R$^{42}$R$^{43}$, R$^{44}$, R$^{45}$, R$^{46}$, R$^{47}$ and R$^{48}$ independently of one another each represent an alkyl radical selected from the group consisting of methyl, ethyl, n-propyl, isopropyl, n-butyl, 2-butyl, isobutyl, tert-butyl, n-pentyl and n-hexyl; or a phenyl, benzyl or phenethyl radical which is unsubstituted or substituted with 1, 2, 3, 4 or 5 substituents selected independently of one another from the group consisting of F, Cl, Br, methyl, ethyl, n-propyl, isopropyl, n-butyl, 2-butyl, isobutyl, tert-butyl, OH, —O—CH$_3$, —O—C$_2$H$_5$ and —O—C$_3$H$_7$;

each optionally in the form of one of the pure stereoisomers, or the racemates thereof, or in the form of a mixture of stereoisomers mixed in any ratios, or each in the form of a corresponding salts.

21. The compound according to claim 1, wherein

R$^1$ represents H; F; Cl; Br; J; —CF$_3$; —NO$_2$; —CN; —C(=O)—OH; —C(=O)—O—R$^{37}$; —C(=O)—NH$_2$; —C(=O)—NH—R$^{42}$; —C(=O)—NR$^{43}$R$^{44}$; —O—R$^{45}$; —S—R$^{46}$; —S(=O)—R$^{47}$; —S(=O)$_2$—R$^{48}$; an alkyl radical selected from the group consisting of methyl, ethyl, n-propyl, isopropyl, n-butyl, 2-butyl, isobutyl and tert-butyl; or a radical selected from the group consisting of (1,3)-dioxolan-2-yl, phenyl, benzyl, phenethyl, oxadiazolyl, 2-pyridyl, 3-pyridyl, 4-pyridyl, 2-thienyl, 3-thienyl, 2-furyl and 3-furyl, each of which is unsubstituted or substituted with, as appropriate, 1, 2, 3, 4 or 5 substituents selected independently of one another from the group consisting of F, Cl, Br, I, —CN, methyl, ethyl, n-propyl, isopropyl, n-butyl, 2-butyl, isobutyl, tert-butyl, —OH, —O—CH$_3$, —O—C$_2$H$_5$ and —O—C$_3$H$_7$;

R$^2$ represents H; F; Cl; Br; I; —CF$_3$; —NO$_2$; —CN; —C(=O)—OH; —C(=O)—O—R$^{37}$; —C(=O)—NH$_2$; —C(=O)—NH—R$^{42}$; —C(=O)—NR$^{43}$R$^{44}$; —O—R$^{45}$; —S—R$^{46}$; —S(=O)—R$^{47}$; —S(=O)$_2$—R$^{48}$; an alkyl radical selected from the group consisting of methyl, ethyl, n-propyl, isopropyl, n-butyl, 2-butyl, isobutyl and tert-butyl; or a radical selected from the group consisting of (1,3)-dioxolan-2-yl, phenyl, benzyl, phenethyl, oxadiazolyl, 2-pyridyl, 3-pyridyl, 4-pyridyl, 2-thienyl, 3-thienyl, 2-furyl and 3-furyl, each of which is unsubstituted or substituted with, as appropriate, 1, 2, 3, 4 or 5 substituents selected independently of one another from the group consisting of F, Cl, Br, I, —CN, methyl, ethyl, n-propyl, isopropyl, n-butyl, 2-butyl, isobutyl, tert-butyl, —OH, —O—CH$_3$, —O—C$_2$H$_5$ and —O—C$_3$H$_7$;

or R$^1$ and R$^2$ together with the carbon atoms linking them form a phenylene radical, which is unsubstituted or substituted with 1, 2, 3 or 4 substituents selected independently of one another from the group consisting of F, Cl, Br, I, —CN, methyl, ethyl, n-propyl, isopropyl, n-butyl, isobutyl, 2-butyl, tert-butyl, —O—CH$_3$, —O—C$_2$H$_5$, —O—C$_3$H$_7$, —CF$_3$, —CHF$_2$, —CH$_2$F and —O—CF$_3$;

R$^3$ and R$^{10}$ independently of one another each represent H; —C(=O)—R$^{36}$; —C(=O)—O—R$^{37}$; —S(=O)—R$^{47}$; —S(=O)$_2$—R$^{48}$; an alkyl radical selected from the group consisting of methyl, ethyl, n-propyl, isopropyl, n-butyl, 2-butyl, isobutyl, tert-butyl, n-pentyl and n-hexyl; a cycloalkyl radical selected from the group consisting of cyclopropyl, cyclobutyl, cyclopentyl and cyclohexyl; or a benzyl or phenethyl radical which is unsubstituted or substituted with 1, 2, 3, 4 or 5 substituents selected independently of one another from the group consisting of F, Cl, Br, methyl, ethyl, n-propyl, isopropyl, n-butyl, 2-butyl, isobutyl, tert-butyl, —OH, —O—CH$_3$, —O—C$_2$H$_5$ and —O—C$_3$H$_7$;

R$^4$, R$^5$, R$^6$, R$^7$, R$^8$, R$^9$, R$^{20}$, R$^{21}$, R$^{22}$, R$^{23}$, R$^{26}$, R$^{27}$, R$^{28}$, R$^{29}$, R$^{30}$, R$^{31}$ and R$^{32}$ independently of one another each represent H; F; Cl; Br; I; —NO$_2$; —CN; —NH$_2$; —OH; —SH; —NH—R$^{33}$; —NR$^{34}$R$^{35}$; —O—R$^{45}$; —S—R$^{46}$; —CF$_3$; —C$_2$F$_5$; or an alkyl radical selected from the group consisting of methyl, ethyl, n-propyl, isopropyl, n-butyl, 2-butyl, isobutyl, tert-butyl, n-pentyl and n-hexyl;

or R$^4$ and R$^5$ or R$^6$ and R$^7$ or R$^8$ and R$^9$ or R$^{20}$ and R$^{21}$ or R$^{22}$ and R$^{23}$ or R$^{26}$ and R$^{27}$ or R$^{28}$ and R$^{29}$ or R$^{31}$ and R$^{32}$ independently of one another represent, together in each case, a radical selected from the group consisting of an oxo group (=O) and a thioxo group (=S);

or R$^3$ and R$^8$ together with the —N—CR$^4$R$^5$—CR$^6$R$^7$—CR$^9$ group linking them form the following radical:

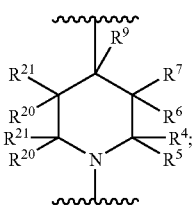

or R$^4$ and R$^{10}$ together with the —N—CR$^8$R$^9$—CR$^6$R$^7$—CR$^5$ group linking them form the following radical:

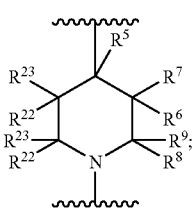

or R$^3$ and R$^{10}$ together with the —N—CR$^4$R$^5$—CR$^6$R$^7$—CR$^8$R$^9$—N group linking them form the following radical:

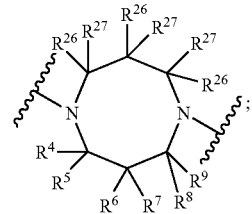

or R$^3$ and R$^{10}$ together with the —N—CR$^4$R$^5$—CR$^6$R$^7$—CR$^8$R$^9$—N group linking them form the following bicyclic radical:

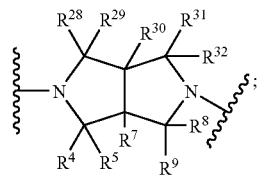

R$^{11}$ represents a radical selected from the group consisting of phenyl, naphthyl, furyl, thienyl, pyrazolyl, pyridazinyl, pyrazinyl, pyrimidinyl, pyridinyl, pyrrolyl, oxazolyl, isoxazolyl, thiazolyl, thiadiazolyl, oxadiazolyl, triazolyl, imidazolyl, indolyl, benzo[b]thiophenyl, benzo[d]thiazolyl, benzo[b]furanyl, quinolinyl, isoquinolinyl and quinazolinyl, each of which is unsubstituted or substituted with, as appropriate, 1, 2, 3, 4 or 5 substituents selected independently of one another from the group consisting of F, Cl, Br, I, —CN, methyl, ethyl, n-propyl, isopropyl, n-butyl, 2-butyl, isobutyl, tert-butyl, ethenyl, allyl, ethynyl, propynyl, —O—CH$_3$, —O—C$_2$H$_5$, —NO$_2$, —CF$_3$, —CH$_2$F, —CHF$_2$, —O—CF$_3$ and —S—CF$_3$;

and R$^{33}$, R$^{34}$, R$^{35}$, R$^{36}$, R$^{37}$, R$^{42}$, R$^{43}$, R$^{44}$, R$^{45}$, R$^{46}$, R$^{47}$ and R$^{48}$ independently of one another each represent an alkyl radical selected from the group consisting of methyl, ethyl, n-propyl, isopropyl, n-butyl, 2-butyl, isobutyl, tert-butyl, n-pentyl and n-hexyl; or a phenyl, benzyl or phenethyl radical which is unsubstituted or substituted with 1, 2, 3, 4 or 5 substituents selected independently of one another from the group consisting of F, Cl, Br, methyl, ethyl, n-propyl, isopropyl, n-butyl, 2-butyl, isobutyl, tert-butyl, OH, —O—CH$_3$, —O—C$_2$H$_5$ and —O—C$_3$H$_7$;

each optionally in the form of one of the pure stereoisomers, or the racemates thereof, or in the form of a mixture of stereoisomers mixed in any ratios, or each in the form of a corresponding salts.

22. The compound according to claim 1, wherein

R$^1$ represents H; F; Cl; Br; I; —CF$_3$; —NO$_2$; —C(=O)—O—R$^{37}$; an alkyl radical selected from the group consisting of methyl, ethyl, n-propyl, isopropyl, n-butyl, 2-butyl, isobutyl and tert-butyl; or a radical selected from the group consisting of (1,3)-dioxolan-2-yl, phenyl, benzyl, phenethyl, oxadiazolyl, 2-pyridyl, 3-pyridyl, 4-pyridyl, 2-thienyl, 3-thienyl, 2-furyl and 3-furyl;

R$^2$ represents H; F; Cl; Br; I; —CF$_3$; —NO$_2$; —C(=O)—O—R$^{37}$; an alkyl radical selected from the group consisting of methyl, ethyl, n-propyl, isopropyl, n-butyl, 2-butyl, isobutyl and tert-butyl; or a radical selected from the group consisting of (1,3)-dioxolan-2-yl, phenyl, benzyl, phenethyl, oxadiazolyl, 2-pyridyl, 3-pyridyl, 4-pyridyl, 2-thienyl, 3-thienyl, 2-furyl and 3-furyl;

or $R^1$ and $R^2$ together with the carbon atoms linking them form a phenylene radical;

$R^3$ and $R^{10}$ independently of one another each represent H; —C(=O)—$R^{36}$; —C(=O)—O—$R^{37}$; an alkyl radical selected from the group consisting of methyl, ethyl, n-propyl, isopropyl, n-butyl, 2-butyl, isobutyl, tert-butyl, n-pentyl and n-hexyl; a cycloalkyl radical selected from the group consisting of cyclopropyl, cyclobutyl, cyclopentyl and cyclohexyl; or a benzyl or phenethyl radical which is unsubstituted or substituted with 1, 2, 3, 4 or 5 substituents selected independently of one another from the group consisting of F, Cl, Br, methyl, ethyl, n-propyl, isopropyl, n-butyl, 2-butyl, isobutyl, tert-butyl, —OH, —O—$CH_3$, —O—$C_2H_5$ and —O—$C_3H_7$;

$R^4$, $R^5$, $R^6$, $R^7$, $R^8$, $R^9$, $R^{20}$, $R^{21}$, $R^{22}$, $R^{23}$, $R^{26}$, $R^{27}$, $R^{28}$, $R^{29}$, $R^{30}$, $R^{31}$ and $R^{32}$ independently of one another each represent H; F; Cl; Br; I; —OH; —SH; —NH—$R^{33}$; —N$R^{34}R^{35}$; —O—$R^{45}$; —S—$R^{46}$; —$CF_3$; —$C_2F_5$; or an alkyl radical selected from the group consisting of methyl, ethyl, n-propyl, isopropyl, n-butyl, 2-butyl, isobutyl, tert-butyl, n-pentyl and n-hexyl;

or $R^3$ and $R^8$ together with the —N—$CR^4R^5$—$CR^6R^7$—$CR^9$ group linking them form the following radical:

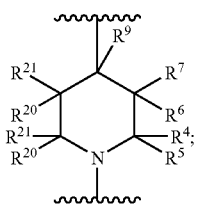

or $R^4$ and $R^{10}$ together with the —N—$CR^8R^9$—$CR^6R^7$—$CR^5$ group linking them form the following radical:

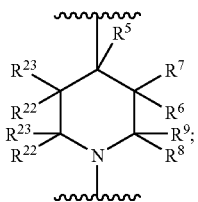

or $R^3$ and $R^{10}$ together with the —N—$CR^4R^5$—$CR^6R^7$—$CR^8R^9$—N group linking them form the following radical:

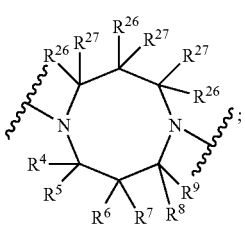

or $R^3$ and $R^{10}$ together with the —N—$CR^4R^5$—$CR^6R^7$—$CR^8R^9$—N group linking them form the following bicyclic radical:

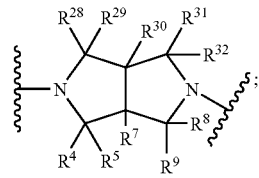

$R^{11}$ represents a radical selected from the group consisting of phenyl, furyl, thienyl, pyrazolyl, pyrazinyl, pyridazinyl, pyrimidinyl, pyridinyl, pyrrolyl, oxazolyl, isoxazolyl, thiazolyl, thiadiazolyl, oxadiazolyl, triazolyl, and imidazolyl, each of which is unsubstituted or substituted with, as appropriate, 1, 2, 3, 4 or 5 substituents selected independently of one another from the group consisting of F, Cl, Br, I, —CN, methyl, ethyl, n-propyl, isopropyl, n-butyl, 2-butyl, isobutyl, tert-butyl, ethenyl, allyl, ethynyl, propynyl, —O—$CH_3$, —O—$C_2H_5$, —$NO_2$, —$CF_3$, —$CH_2F$, —$CHF_2$, —O—$CF_3$ and —S—$CF_3$;

and $R^{33}$, $R^{34}$, $R^{35}$, $R^{36}$, $R^{37}$, $R^{45}$ and $R^{46}$ independently of one another each represent an alkyl radical selected from the group consisting of methyl, ethyl, n-propyl, isopropyl, n-butyl, 2-butyl, isobutyl, tert-butyl, n-pentyl and n-hexyl;

each optionally in the form of one of the pure stereoisomers, or the racemates thereof, or in the form of a mixture of stereoisomers mixed in any ratios, or each in the form of a corresponding salts.

23. The compound according to claim 1, wherein $R^1$ represents H, methyl, ethyl, n-propyl, —C(=O)—O—$CH_3$, —C(=O)—O—$C_2H_5$ or —C(=O)—O—C($CH_3$)$_3$;

$R^2$ represents H, methyl, ethyl, n-propyl, —C(=O)—O—$CH_3$, —C(=O)—O—$C_2H_5$ or —C(=O)—O—C($CH_3$)$_3$;

or $R^1$ and $R^2$ together with the carbon atoms linking them form a phenylene radical;

$R^3$ and $R^{10}$ independently of one another each represent H; an alkyl radical selected from the group consisting of methyl, ethyl, n-propyl, isopropyl, n-butyl, 2-butyl, isobutyl and tert-butyl; or cyclopropyl;

$R^4$, $R^5$, $R^6$, $R^7$, $R^8$ and $R^9$ each represent H;

or $R^3$ and $R^8$ together with the —N—$CH_2$—$CH_2$—CH group linking them form the following radical:

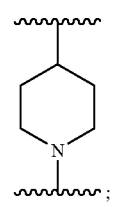

or $R^4$ and $R^{10}$ together with the —N—CH$_2$—CH$_2$—CH group linking them form the following radical:

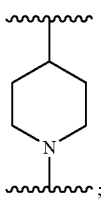

or $R^3$ and $R^{10}$ together with the —N—CH$_2$—CH$_2$—CH$_2$—N group linking them form the following radical:

or $R^3$ and $R^{10}$ together with the group linking them form the following bicyclic radical:

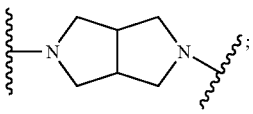

and $R^{11}$ represents a radical selected from the group consisting of 2-trifluoromethyl-phenyl, 3,4-dimethyl-phenyl, 3-methoxy-phenyl, 2-methoxy-phenyl, 4-methoxyphenyl, 4-fluoro-phenyl, 2-methyl-phenyl, 4-methylphenyl, 2-fluoro-phenyl, 2,4-difluoro-phenyl, 4-trifluoromethyl-phenyl, 3-fluoro-4-methyl-phenyl, pyrid-2-yl, pyrid-3-yl, pyrid-4-yl, phenyl, 3-methylphenyl, 3-fluoro-phenyl, 3-cyano-phenyl, 3-chloro-phenyl, 3-trifluoromethyl-phenyl, 3-difluoromethyl-phenyl, 3-fluoromethyl-phenyl, 3-nitro-phenyl, 3-ethenylphenyl, 3-ethynyl-phenyl, 3-allyl-phenyl, 3-bromophenyl and 3-trifluoromethoxy-phenyl;

each optionally in the form of one of the pure stereoisomers, or the racemates thereof, or in the form of a mixture of stereoisomers mixed in any ratios, or each in the form of a corresponding salts.

24. The compound according to claim 1, which is selected from the group consisting of:

[1] N-(3-((thiazol-2-yl)amino)propyl)-3-phenylpropiolamide
[2] 4-(thiazol-2-yl-amino)-1-(3-phenyl-propiolyl)piperidine,
[3] 3-(thiazol-2-yl)-7-(3-phenyl)-propiolyl-3,7-diaza-bicyclo[3.3.0]octane,
[4] 4-(methyl-thiazol-2-yl-amino)-1-(3-phenyl-propiolyl) piperidine,
[5] 3-phenyl-N-(1-(thiazol-2-yl)piperidin-4-yl)propiolamide,
[6] N-methyl-3-phenyl-N-(1-(thiazol-2-yl)piperidin-4-yl) propiolamide,
[7] 4-(benzothiazol-2-yl-amino)-1-(3-(3-trifluormethyl-phenyl)-propiolyl)piperidine,
[8] 1-((3,4-dimethyl-phenyl)-propiolyl)-4-(thiazol-2-yl-amino)-piperidine,
[9] 4-(benzothiazol-2-yl-amino)-1-(3,4-dimethyl-phenyl)-propiolyl)piperidine,
[10] N-(1-(4-methyl-thiazol-2-yl)piperidin-4-yl)-3-phenyl-propiolamide,
[11] N-(1-(4-methyl-thiazol-2-yl)piperidin-4-yl)-3-(3-methoxyphenyl)-propiolamide,
[12] N-(1-(4-methyl-thiazol-2-yl)piperidin-4-yl)-3-(2-methoxyphenyl)-propiolamide,
[13] N-(1-(4-Methyl-thiazol-2-yl)piperidin-4-yl)-3-(4-methoxyphenyl)-propiolamide,
[14] 3-(4-fluoro-phenyl)-N-(1-(4-methyl-thiazol-2-yl)piperidin-4-yl)-propiolamide,
[15] N-(1-(4-methyl-thiazol-2-yl)piperidin-4-yl)-3-(4-tolyl)-propiolamide,
[16] 3-(2-fluoro-phenyl)-N-(1-(4-methyl-thiazol-2-yl)piperidin-4-yl)-propiolamide,
[17] 3-(2,4-difluoro-phenyl)-N-(1-(4-methyl-thiazol-2-yl) piperidin-4-yl)-propiolamide,
[18] N-(1-(4-methyl-thiazol-2-yl)piperidin-4-yl)-3-(4-trifluoromethyl-phenyl)-propiolamide,
[19] 3-(3-fluoro-phenyl)-N-(1-(4-methyl-thiazol-2-yl)piperidin-4-yl)-propiolamide,
[20] 3-(3-fluoro-4-methyl-phenyl)-N-(1-(4-methyl-thiazol-2-yl)piperidin-4-yl)-propiolamide,
[21] N-(1-(4-methyl-thiazol-2-yl)piperidin-4-yl)-3-(3-trifluoromethyl-phenyl)-propiolamide,
[22] N-(1-(4-methyl-thiazol-2-yl)piperidin-4-yl)-3-(3-tolyl)-propiolamide, and
[23] N-(1-(4-methyl-thiazol-2-yl)piperidin-4-yl)-3-(2-tolyl)-propiolamide;

each optionally in the form of a corresponding salts.

25. The compound according to claim 1, which, after 60 minutes of incubation, in 450 µg protein from pig brain homogenate, at a temperature between 20° C. and 25° C. at a concentration less than 2000 nM, brings about a 50 percent displacement of [$^3$H]-2-methyl-6-(3-methoxyphenyl)-ethynylpyridine which is present in a concentration of 5 nM.

26. A method for producing a compound of formula I according to claim 1, wherein at least one compound of formula II,

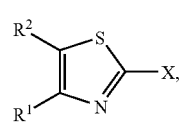

in which X represents a leaving group, together with at least one compound of formula III,

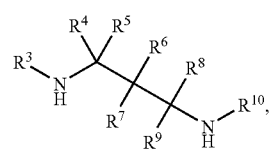

optionally in a reaction medium, optionally in the presence of at least one base or at least one organometallic compound or at least one metal hydride reagent or in the presence of at least one copper salt and optionally in the presence of at least one metal, is converted into at least one corresponding compound of formula IV, optionally in the form of a corresponding salt,

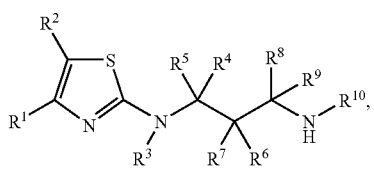

IV and this is optionally purified or isolated;
or at least one compound of formula II, together with at least one compound of formula V,

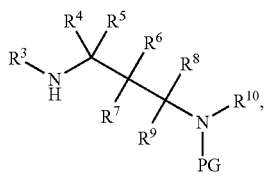

V

PG represents a protecting group,
optionally in a reaction medium, optionally in the presence of at least one base or at least one organometallic compound or at least one metal hydride reagent, is converted into at least one corresponding compound of formula VI,

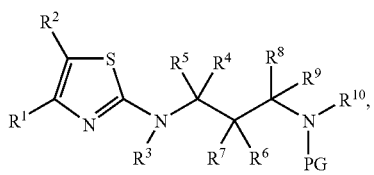

VI in which PG has the meaning given above, and this is optionally purified or isolated;
or at least one compound of formula XIII,

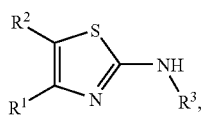

XIII together with at least one compound of formula XIV,

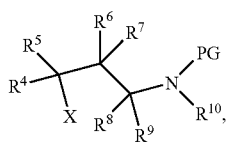

XIV in which PG has the meaning given above and X represents a leaving group, optionally in a reaction medium, optionally in the presence of at least one base, or optionally in the presence of at least one organometallic compound, or optionally in the presence of at least one metal hydride compound, is converted into at least one corresponding compound of formula VI and this is optionally purified or isolated;

or at least one compound of formula VII,

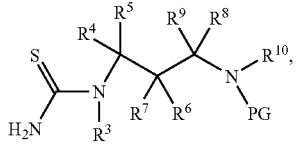

VII by reaction with at least one compound of formula $R^1$—C(=O)—$CH_2$—X or $(C_{1-5}$-alkyl-0$)_2$—CH—$CH_2$—X, in which X represents a leaving group, in a reaction medium, optionally in the presence of at least one organic base or in the presence of at least one acid, is converted into at least one corresponding compound of formula VI, optionally in the form of a corresponding salt, and this is optionally purified or isolated;

and at least one compound of formula VI, when PG represents a tert-butoxycarbonyl or 9-fluorenylmethyloxycarbonyl group, in a reaction medium in the presence of at least one acid, or when PG represents a benzyl or benzyloxycarbonyl group, in a reaction medium in the presence of hydrogen and in the presence of at least one catalyst, is converted into at least one corresponding compound of formula IV, optionally in the form of a corresponding salt, and this is optionally purified or isolated;

and at least one compound of formula IV, by reaction with at least one compound of formula $R^{11}$—C≡C—C(=O)—OH, in a reaction medium, optionally in the presence of at least one suitable coupling agent, optionally in the presence of at least one base, or by reaction with at least one compound of formula $R^{11}$—C≡C—C(=O)—X, in which X represents a leaving group, in a reaction medium, optionally in the presence of at least one base, is converted into at least one corresponding compound of formula I, optionally in the form of a corresponding salt,

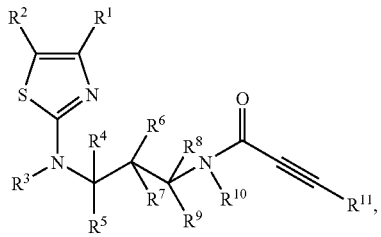

I and this is optionally purified or isolated;
or at least one compound of formula IV, by reaction with propiolic acid [HC≡C—C(=O)—OH] in a reaction medium, optionally in the presence of at least one suitable coupling agent, optionally in the presence of at least one base, or by reaction with at least one compound of formula HC≡C—C(=O)—X, in which X represents a leaving group, in a reaction medium, optionally in the presence of at least one base, is converted into at least one corresponding compound of formula VIII, optionally in the form of a corresponding salt,

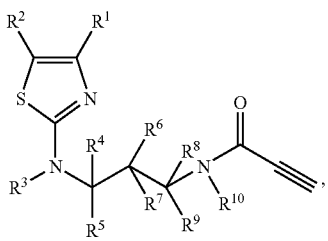

and this is optionally purified or isolated, and at least one compound of formula VIII, by reaction with at least one compound of formula $R^{11}$—X, in which X represents a leaving group, in a reaction medium, optionally in the presence of at least one catalyst, optionally in the presence of at least one ligand, optionally in the presence of at least one inorganic salt, optionally in the presence of at least one copper salt, optionally in the presence of at least one organic or inorganic base, is converted into at least one corresponding compound of formula I, optionally in the form of a corresponding salt, and this is optionally purified or isolated.

27. A method for the production of a compound of formula I according to claim 1, wherein at least one compound of formula III,

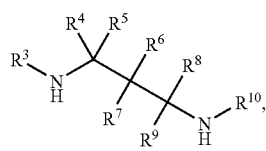

by reaction with at least one compound of formula $R^{11}$—C≡C—C(=O)—OH, in a reaction medium, optionally in the presence of a suitable coupling agent, optionally in the presence of at least one base, or by reaction with at least one compound of formula $R^{11}$—C≡C—C(=O)—X, in which X represents a leaving group, in a reaction medium, optionally in the presence of at least one base, is converted into at least one corresponding compound of formula IX, optionally in the form of a corresponding salt,

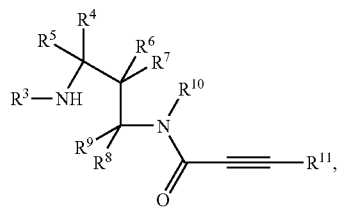

and this is optionally purified or isolated;
or at least one compound of formula V,

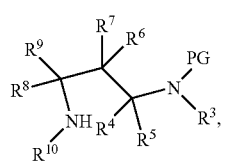

in which and PG represents a protecting group, by reaction with at least one compound of formula $R^{11}$—C≡C—C(=O)—OH, in a reaction medium, optionally in the presence of a suitable coupling agent, optionally in the presence of at least one base, or by reaction with at least one compound of formula $R^{11}$—C≡C—C(=O)—X, in which X represents a leaving group, in a reaction medium, optionally in the presence of at least one base, is converted into at least one corresponding compound of formula XI, optionally in the form of a corresponding salt,

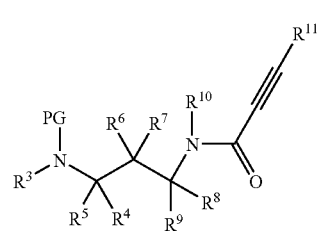

and this is optionally purified or isolated;

and at least one compound of formula XI, when PG represents a tert-butoxycarbonyl or 9-fluorenylmethyloxycarbonyl group, in a reaction medium in the presence of at least one acid, or when PG represents a benzyl or benzyloxycarbonyl group, in a reaction medium in the presence of hydrogen and in the presence of at least one catalyst, is converted into at least one corresponding compound of formula IX, optionally in the form of a corresponding salt, and this is optionally purified or isolated;

and at least one compound of formula IX, by reaction with at least one compound of formula II,

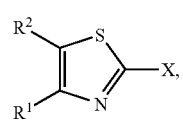

in which X represents a leaving group, in a reaction medium, optionally in the presence of at least one base or at least one organometallic compound or at least one metal hydride reagent, is converted into at least one corresponding compound of formula I, optionally in the form of a corresponding salt, and this is optionally purified or isolated;

or optionally at least one compound of formula IX, by reaction with potassium thiocyanate and ethyl chloroformate or ammonium thiocyanate or trimethylsilylisothiocyanate or thiophosgene and ammoniac or bromocyan and hydrogen sulphide, in a reaction medium, optionally in the presence of at least one acid, or optionally in the presence of at least one base, or optionally in the presence of at least one organometallic compound, or optionally in the presence of at least one metal hydride compound, is converted into at least one corresponding compound of formula XII, optionally in the form of a corresponding salt,

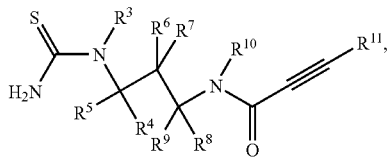 XII and this is optionally purified or isolated;

and at least one compound of formula XII by reaction with at least one compound of formula $R^1$—C(=O)—$CH_2$—X or $(C_{1-5}\text{-alkyl-O})_2$—CH—$CH_2$—X, in which X represents a leaving group, in a reaction medium, optionally in the presence of at least one organic base or in the presence of at least one acid, is converted into at least one corresponding compound of formula I, optionally in the form of a corresponding salt, and this is optionally purified or isolated.

28. A pharmaceutical composition comprising at least one compound according to claim 1 and optionally one or more physiologically acceptable excipients.

29. A method for inhibiting the mGluR5 receptor comprising administering to a patient an inhibitory amount therefor of at least one compound according to claim 1.

* * * * *